United States Patent
Snyder et al.

(10) Patent No.: US 11,761,043 B2
(45) Date of Patent: Sep. 19, 2023

(54) MACHINE ASSAY AND ANALYSIS FOR SELECTING ANTIHYPERTENSIVE DRUGS

(71) Applicant: Geneticure Inc., Minnetonka, MN (US)

(72) Inventors: Eric Snyder, Rochester, MN (US);
Ryan Sprissler, Tucson, AZ (US);
Scott C. Snyder, Minnetonka, MN (US)

(73) Assignee: Geneticure Inc., Minnetonka, MN (US)

( * ) Notice: Subject to any disclaimer, the term of this patent is extended or adjusted under 35 U.S.C. 154(b) by 691 days.

(21) Appl. No.: 16/795,060

(22) Filed: Feb. 19, 2020

(65) Prior Publication Data

US 2020/0299771 A1 Sep. 24, 2020

Related U.S. Application Data

(63) Continuation-in-part of application No. 16/789,383, filed on Feb. 12, 2020, which is a continuation of
(Continued)

(51) Int. Cl.
| | | |
|---|---|---|
| *G01N 33/68* | (2006.01) | |
| *C12Q 1/6883* | (2018.01) | |
| *G16B 20/20* | (2019.01) | |
| G16B 20/00 | (2019.01) | |
| G16B 40/10 | (2019.01) | |
| G16B 50/00 | (2019.01) | |

(Continued)

(52) U.S. Cl.
CPC ....... *C12Q 1/6883* (2013.01); *G01N 33/6893* (2013.01); *G16B 20/20* (2019.02); C12Q 2600/106 (2013.01); C12Q 2600/156 (2013.01); G01N 2800/321 (2013.01); G16B 20/00 (2019.02); G16B 40/10 (2019.02); *G16B 50/00* (2019.02); G16H 20/00 (2018.01); G16H 20/10 (2018.01)

(58) Field of Classification Search
CPC ............ C12Q 1/6883; C12Q 2600/106; C12Q 2600/156; G01N 33/6893; G01N 2800/321; G16B 20/20; G16B 20/00; G16B 40/10; G16B 50/00; G16H 20/00; G16H 20/10
See application file for complete search history.

(56) References Cited

U.S. PATENT DOCUMENTS

| 6,316,196 B1 | 11/2001 | Morten |
| 6,376,182 B1 | 4/2002 | Chao et al. |

(Continued)

FOREIGN PATENT DOCUMENTS

| EP | 3149487 B1 | 2/2020 |
| WO | WO-02/071070 A2 | 9/2002 |

(Continued)

OTHER PUBLICATIONS

U.S. Appl. No. 15/314,641 U.S. Pat. No. 10,590,485, filed Nov. 29, 2016, Improved Therapeutic Regimen for Hypertension.
(Continued)

*Primary Examiner* — Maroun P Kanaan
(74) *Attorney, Agent, or Firm* — Schwegman Lundberg & Woessner, P.A.

(57) ABSTRACT

The invention relates to improved methods, devices, and kits for identifying and implementing an appropriate treatment regimen for subjects suffering from hypertension.

20 Claims, 10 Drawing Sheets

Specification includes a Sequence Listing.

Related U.S. Application Data application No. 15/314,641, filed as application No. PCT/US2015/032651 on May 27, 2015, now Pat. No. 10,590,485.

(60) Provisional application No. 62/004,460, filed on May 29, 2014.

(51) Int. Cl.
*G16H 20/00* (2018.01)
*G16H 20/10* (2018.01)

(56) References Cited

U.S. PATENT DOCUMENTS

| | | | |
|---|---|---|---|
| 10,465,246 B2 | 11/2019 | Snyder et al. | |
| 10,590,485 B2 | 3/2020 | Snyder et al. | |
| 2007/0092888 A1 | 4/2007 | Diamond et al. | |
| 2009/0215042 A1* | 8/2009 | Sella-Tavor | C07K 14/47 435/7.1 |
| 2015/0337388 A1* | 11/2015 | Garner, Jr. | G16B 35/00 506/8 |
| 2017/0175193 A1 | 6/2017 | Snyder et al. | |
| 2018/0195128 A1 | 7/2018 | Snyder et al. | |
| 2020/0263253 A1 | 8/2020 | Snyder et al. | |

FOREIGN PATENT DOCUMENTS

| | | |
|---|---|---|
| WO | WO-2011/048033 A2 | 4/2011 |
| WO | WO-2015/183938 A1 | 12/2015 |

OTHER PUBLICATIONS

U.S. Appl. No. 15/894,546 U.S. Pat. No. 10,465,246, filed Feb. 12, 2018, Improved Therapeutic Regimen for Hypertension.
U.S. Appl. No. 16/789,383, filed Feb. 12, 2020, Therapeutic Regimen for Hypertension.
"U.S. Appl. No. 15/314,641, Preliminary Amendment filed Jan. 30, 2017", 4 pgs.
"U.S. Appl. No. 15/314,641, Advisory Action dated Aug. 20, 2019", 3 pgs.
"U.S. Appl. No. 15/314,641, Examiner Interview Summary dated Sep. 5, 2019", 2 pgs.
"U.S. Appl. No. 15/314,641, Final Office Action dated May 3, 2019", 10 pgs.
"U.S. Appl. No. 15/314,641, Non-Final Office Action dated Oct. 5, 2018", 13 pgs.
"U.S. Appl. No. 15/314,641, Notice of Allowance dated Nov. 5, 2019", 15 pgs.
"U.S. Appl. No. 15/314,641, Preliminary Amendment filed Nov. 29, 2016", 17 pgs.
"U.S. Appl. No. 15/314,641, Response filed Jan. 7, 2019 to Non-Final Office Action dated Oct. 5, 2018", 20 pgs.
"U.S. Appl. No. 15/314,641, Response filed Jul. 31, 2019 to Final Office Action dated May 3, 2019", 25 pgs.
"U.S. Appl. No. 15/314,641, Response filed Sep. 3, 2019 to Advisory Action dated Aug. 20, 2019", 13 pgs.
"U.S. Appl. No. 15/314,641, Resposne filed Jun. 28, 2018 to Restriction Requirement dated May 25, 2018", 9 pgs.
"U.S. Appl. No. 15/314,641, Restriction Requirement dated May 25, 2018", 7 pgs.
"U.S. Appl. No. 15/314,641, Second Supplemental Preliminary Amendment filed Jan. 19, 2018", 17 pgs.
"U.S. Appl. No. 15/314,641, Supplemental Preliminary Amendment filed Jul. 25, 2017", 25 pgs.
"U.S. Appl. No. 15/894,546, Advisory Action dated Jul. 22, 2019", 3 pgs.
"U.S. Appl. No. 15/894,546, Advisory Action dated Aug. 20, 2019", 5 pgs.
"U.S. Appl. No. 15/894,546, Final Office Action dated Apr. 16, 2019", 11 pgs.
"U.S. Appl. No. 15/894,546, Non-Final Office Action dated Oct. 5, 2018", 15 pgs.
"U.S. Appl. No. 15/894,546, Notice of Non-Compliant Amendment dated Jul. 22, 2019", 3 pgs.
"U.S. Appl. No. 15/894,546, Response filed Jan. 7, 2019 to Non-Final Office Action dated Oct. 5, 2018", 20 pgs.
"U.S. Appl. No. 15/894,546, Response filed Jun. 25, 2018 to Restriction Requirement dated May 18, 2018", 13 pgs.
"U.S. Appl. No. 15/894,546, Response filed Jun. 11, 2019 to Final Office Action dated Apr. 16, 2019", 25 pgs.
"U.S. Appl. No. 15/894,546, Response filed Aug. 7, 2019 to Advisory Action dated Jul. 22, 2019", 27 pgs.
"U.S. Appl. No. 15/894,546, Restriction Requirement dated May 18, 2018", 8 pgs.
"U.S. Appl. No. 15/894,546, Notice of Allowance dated Sep. 3, 2019", 15 pgs.
"U.S. Appl. No. 15/894,546, Preliminary Amendment filed Feb. 12, 2018", 16 pgs.
"U.S. Appl. No. 16/789,383, Preliminary Amendment filed Feb. 12, 2020", 10 pgs.
"U.S. Appl. No. 16/789,383, Supplemental Preliminary Amendment filed May 21, 2020", 7 pgs.
"European Application Serial No. 15728326.8, Communication Pursuant to Article 94(3) EPC dated Feb. 8, 2019", 5 pgs.
"European Application Serial No. 15728326.8, Communication Pursuant to Article 94(3) EPC dated Jan. 24, 2018", 6 pgs.
"European Application Serial No. 15728326.8, Communication Pursuant to Article 94(3) EPC dated Sep. 6, 2018", 5 pgs.
"European Application Serial No. 15728326.8, Response Filed Jan. 11, 2019 to Communication Pursuant to Article 94(3) EPC dated Sep. 6, 2018", 48 pgs.
"European Application Serial No. 15728326.8, Response filed Jun. 4, 2018 to Communication Pursuant to Article 94(3) EPC dated Jan. 24, 2018", 58 pgs.
"European Application Serial No. 15728326.8, Response filed Jun. 12, 2019 to Communication Pursuant to Article 94(3) EPC dated Feb. 8, 2019", 21 pgs.
"European Patent Application Serial No. 15728326.8, Voluntary Amendment filed on Aug. 1, 2017", 22 pgs.
"International Application Serial No. PCT/US2015/032651, International Preliminary Report on Patentability dated Dec. 8, 2016", 15 pgs.
"International Application Serial No. PCT/US2015/032651, International Search Report dated Oct. 21, 2015", 8 pgs.
"International Application Serial No. PCT/US2015/032651, Invitation to Pay Additional Fees and Partial Search Report dated Aug. 11, 2015", 8 pgs.
"International Application Serial No. PCT/US2015/032651, Written Opinion dated Oct. 21, 2015", 13 pgs.
"Notice of Intent to Grant", EPO Form 2004C—Communication Under Rule 71(3) EPC, Intention to Grant, 163.
Baudin, B., et al., "Angiotensin II receptor polymorphisms in hypertension. Pharmacogenomic considerations", Pharmacogenomics 2002;3, (2002), 65-73.
Bengtsson, K, et al., "Polymorphism in the beta1-adrenergic receptor gene and hypertension", Circulation, Lippincott Williams & Wilkins, US, vol. 104, No. 2, (Jul. 10, 2001), 187-190.
Brodde, Otto-Erich, "The functional importance of beta1 and beta2 adrenoceptors in the human heart", The American Journal of Cardiology, 62(5), (Aug. 11, 1988), 24C-29C.
Calhoun, David A., et al., "Resistant Hypertension: Diagnosis, Evaluation, and Treatment", Circulation. 2008;117: e510-e526, (2008), 18 pgs.
Chobanian, Aram V., et al., "The Seventh Report of the Joint National Committee on Prevention, Detection, Evaluation, and Treatment of High Blood Pressure", American Medical Association; vol. 289, No. 19; 2560-2572, (2003), 14 pgs.
Hesse, C, et al., "Genetic Variation in the [beta]2-Adrenergic Receptor: Impact on Intermediate Cardiovascular Phenotypes", Current Pharmacogenomics and Personalized Medicine, vol. 6, No. 3, (Sep. 1, 2008), 160-170.

(56) References Cited

OTHER PUBLICATIONS

Jin, Hyun-Seok, et al., "Genetic Variations in the Sodium Balance-Regulating Genes ENaC, NEDD4L, NDFIP2 and USP2 Influence Blood Pressure and Hypertension", Kidney Blood Press Res 2010;33:15-23, (2010), 9 pgs.

Johnson, J.A., et al., "Hypertension pharmacogenomics: Current status and future directions", Current Opinion in Molecular Therapeutics, 7(3), (2005), 218-225.

Kearney, P.M., et al., "Global burden of hypertension: analysis of worldwide data", The Lancet, 365(9455), (Jan. 15, 2005), 217-223.

La Rosee, Karl, et al., "The ARG389GLY Beta1-Adrenoceptor Gene Polymorphism Determines Contractile Response to Catecholamines", Pharmacogenetics, 14(11), (Nov. 2004), 711-716.

Liu, Jie, et al., "Gly389arg polymorphism of [beta] 1-adrenergic receptor is associated with the cardiovascular response to metoprolol", Clin Pharmacol Ther 2003;74, (2003), 372-379.

McNamara, Dennis M., et al., "Pharmacogenetic Interactions Between Angiotensin-Converting Enzyme Inhibitor Therapy and the Angiotensin-Converting Enzyme Deletion Polymorphism in Patients With Congestive Heart Failure", J Am Coll Cardiol 2004;44, (2004), 2019-2026.

Meisler, MH, et al., "SCNN1, an Epithelial Cell Sodium Channel Gene in the Conserved Linkage Group on Mouse Chromosome 6 and Human Chromosome 12", Genomics 1994;24, (1994), 185-186.

Miller, Judith A., et al., "Angiotensin II type 1 receptor gene polymorphism predicts response to losartan and angiotensin II", Kidney International, vol. 56 (1999), (1999), 2173-2180.

Patel, et al., "Genome Medicine", vol. 5:58, (2013), 14 pgs.

Pilati, Mara, et al., "The role of angiotensin-converting enzyme polymorphism in congestive heart failure", Congest Heart Fail 2004;10:87-93,quiz 94-95, (2004), 9 pgs.

Pilbrow, Anna P., "Angiotensinogen M235T and T174M Gene Polymorphisms in Combination Doubles the Risk of Mortality in Heart Failure", Hypertension 2007;49:322-327, (2007), 7 pgs.

Pratt, J. Howard, "Central Role for ENaC in Development of Hypertension", J Am Soc Nephrol 16:, (2005), 3154-3159.

Psaty, Bruce M., et al., "Diuretic therapy, the alpha-adducin gene variant, and the risk of myocardial infarction or stroke in persons with treated hypertension", JAMA 2002;287, (2002), 1680-1689.

Reddy, Sushma, et al., "Adrenergic receptor genotype influences heart failure severity and [beta]-blocker response in children with dilated cardiomyopathy", Pediatric Research, vol. 77, No. 2, (Nov. 19, 2014), 363-369.

Snyder, EM, et al., "Blood pressure variation in healthy humans: A possible interaction with ß-2 adrenergic receptor genotype and renal epithelial sodium channels", Med Hypotheses 2005;65, (2005), 296-299.

Snyder, EM, et al., "Genotype related differences in beta2 adrenergic receptor density and cardiac function", Med Sci Sports Exerc 2006;38, (2006), 882-886.

Snyder, Eric M., et al., "Effects of an inhaled beta2-agonist on cardiovascular function and sympathetic activity in healthy subjects", Pharmacotherapy 2011;31, (2011), 748-756.

Snyder, Eric M., et al., "Genetics of 261 2-Adrenergic Receptors and the Cardiopulmonary Response to Exercise", Exerc Sport Sci Rev. Apr. 2008 ; 36(2): 98-105, (2008), 16 pgs.

Snyder, Eric M, et al., "The Arg16Gly polymorphism of the [beta] 2-adrenergic receptor and the natriuretic response to rapid saline infusion in humans", The Journal of Physiology, vol. 574, No. 3, (Jul. 21, 2006), 947-954.

Tang, W., et al., "Associations between angiotensinogen gene variants and left ventricular mass and function in the HyperGEN study", Am Heart J 2002;143, (2002), 854-860.

Turner, Stephen T., et al., "WNK1 Kinase Polymorphism and Blood Pressure Response to a Thiazide Diuretic", Hypertension 2005;46:758-765, (2005), 9 pgs.

Ulgren, MS, et al., "The relationship between angiotensin-converting enzyme (insertion/deletion) gene polymorphism and left ventricular remodeling in acute myocardial infarction", Coron Artery Dis 2007;18, (2007), 153-157.

Vangjeli, Ciara, et al., "Confirmation that the renin gene distal enhancer polymorphism ren-5312c/t is associated with increased blood pressure", Circulation Cardiovascular genetics 2010;3:53-59, (2010), 17 pgs.

Zhang, Li-Na, et al., "Association between polymorphisms of alpha-adducin gene and essential hypertension in Chinese population", BioMed research international 2013:2013:451094, (2013), 5 pgs.

"U.S. Appl. No. 16/789,383, Final Office Action dated Dec. 5, 2022", 7 pgs.

"U.S. Appl. No. 16/789,383, Non Final Office Action dated May 25, 2022", 8 pgs.

"U.S. Appl. No. 16/789,383, Notice of Allowance dated Jan. 25, 2023", 8 pgs.

"U.S. Appl. No. 16/789,383, Response filed Jan. 6, 2023 to Final Office Action dated Dec. 5, 2022", 6 pgs.

"U.S. Appl. No. 16/789,383, Response filed Feb. 2, 2022 to Restriction Requirement dated Dec. 10, 2021", 4 pgs.

"U.S. Appl. No. 16/789,383, Response filed Sep. 22, 2022 to Non Final Office Action dated May 25, 2022", 6 pgs.

"U.S. Appl. No. 16/789,383, Restriction Requirement dated Dec. 10, 2021", 6 pgs.

"U.S. Appl. No. 16/789,383, Supplemental Amendment filed Jan. 10, 2023", 7 pgs.

\* cited by examiner

SEQUENCE LISTING

<160> NUMBER OF SEQ ID NOS: 85

<210> SEQ ID NO 1
<211> LENGTH: 2862
<212> TYPE: DNA
<213> ORGANISM: Homo sapiens

<400> SEQUENCE: 1

| | | | | | |
|---|---|---|---|---|---|
| gcaccacgcc | gcccgggctt | ctggggtgtt | ccccaaccac | ggcccagccc | tgccacaccc | 60 |
| cccgccccg | gcctccgcag | ctcggcatgg | gcgcggggt | gctcgtcctg | ggcgcctccg | 120 |
| agcccggtaa | cctgtcgtcg | gccgcaccgc | tccccgacgg | cgcggccacc | gcggcgcggc | 180 |
| tgctggtgcc | cgcgtcgccg | cccgcctcgt | tgctgcctcc | cgccagcgaa | agccccgagc | 240 |
| cgctgtctca | gcagtggaca | gcgggcatgg | gtctgctgat | ggcgctcatc | gtgctgctca | 300 |
| tcgtggcggg | caatgtgctg | gtgatcgtgg | ccatcgccaa | gacgccgcgg | ctgcagacgc | 360 |
| tcaccaacct | cttcatcatg | tccctggcca | gcgccgacct | ggtcatgggg | ctgctggtgg | 420 |
| tgccgttcgg | ggccaccatc | gtggtgtggg | gccgctggga | gtacggctcc | ttcttctgcg | 480 |
| agctgtggac | ctcagtggac | gtgctgtgcg | tgacggccag | catcgagacc | ctgtgtgtca | 540 |
| ttgccctgga | ccgctacctc | gccatcacct | cgcccttccg | ctaccagagc | ctgctgacgc | 600 |
| gcgcgcgggc | gcggggcctc | gtgtgcaccg | tgtgggccat | ctcggccctg | gtgtccttcc | 660 |
| tgcccatcct | catgcactgg | tggcgggcgg | agagcgacga | ggcgcgccgc | tgctacaacg | 720 |
| accccaagtg | ctgcgacttc | gtcaccaacc | gggcctacgc | catcgcctcg | tccgtagtct | 780 |
| ccttctacgt | gccctgtgc | atcatggcct | tcgtgtacct | gcgggtgttc | cgcgaggccc | 840 |
| agaagcaggt | gaagaagatc | gacagctgcg | agcgccgttt | cctcggcggc | ccagcgcggc | 900 |
| cgccctcgcc | ctcgccctcg | cccgtccccg | cgcccgcgcc | gccgccgga | ccccgcgcc | 960 |
| ccgccgccgc | cgccgccacc | gccccgctgg | ccaacgggcg | tgcgggtaag | cggcggcct | 1020 |
| cgcgcctcgt | ggccctgcgc | gagcagaagg | cgctcaagac | gctgggcatc | atcatgggcg | 1080 |
| tcttcacgct | ctgctggctg | ccttcttcc | tggcaacgt | ggtgaaggcc | ttccaccgcg | 1140 |
| agctggtgcc | cgaccgcctc | ttcgtcttct | tcaactggct | gggctacgcc | aactcggcct | 1200 |
| tcaaccccat | catctactgc | cgcagcccg | acttccgcaa | ggccttccag | ggactgctct | 1260 |
| gctgcgcgcg | cagggctgcc | cgccggcgcc | acgcgaccca | cggagaccgg | ccgcgcgcct | 1320 |
| cgggctgtct | ggcccggccc | ggacccccgc | catcgcccgg | ggccgcctcg | gacgacgacg | 1380 |
| acgacgatgt | cgtcggggcc | acgccgcccg | cgcgcctgct | ggagccctgg | gccggctgca | 1440 |
| acggcggggc | ggcggcggac | agcgactcga | gcctggacga | gccgtgccgc | cccggcttcg | 1500 |
| cctcggaatc | caaggtgtag | ggcccggcgc | ggggcgcgga | ctccgggcac | ggcttcccag | 1560 |
| gggaacgagg | agatctgtgt | ttacttaaga | ccgatagcag | gtgaactcga | agcccacaat | 1620 |
| cctcgtctga | atcatccgag | gcaaagaaa | aagccacgga | ccgttgcaca | aaaaggaaag | 1680 |
| tttgggaagg | gatgggagag | tggcttgctg | atgttccttg | ttgtttttt | tttctttct | 1740 |
| tttctttctt | cttcttttt | tttttttt | tttttctgt | ttgtggtccg | gccttctttt | 1800 |
| gtgtgtgcgt | gtgatgcatc | tttagatttt | ttccccac | caggtggttt | ttgacactct | 1860 |

```
ctgagaggac cggagtggaa gatgggtggg ttaggggaag ggagaagcat taggagggga    1920
ttaaaatcga tcatcgtggc tcccatccct ttcccgggaa caggaacaca ctaccagcca    1980
gagagaggag aatgacagtt tgtcaagaca tatttccttt tgctttccag agaaatttca    2040
ttttaatttc taagtaatga tttctgctgt tatgaaagca aagagaaagg atggaggcaa    2100
aataaaaaaa aatcacgttt caagaaatgt taagctcttc ttggaacaag ccccaccttg    2160
ctttccttgt gtagggcaaa cccgctgtcc cccgcgcgcc tgggtggtca ggctgaggga    2220
tttctacctc acactgtgca tttgcacagc agatagaaag acttgtttat attaaacagc    2280
ttatttatgt atcaatatta gttggaagga ccaggcgcag agcctctctc tgtgacatgt    2340
gactctgtca attgaagaca ggacattaaa agagagcgag agagagaaac agttcagatt    2400
actgcacatg tggataaaaa caaaaacaaa aaaaaggagt ggttcaaaat gccattttg     2460 cacagtgtta ggaattacaa aatccacaga agatgttact tgcacaaaaa gaaattaaat    2520 atttttaaa gggagagggg ctgggcagat cttaaataaa attcaaactc tacttctgtt     2580
gtctagtatg ttattgagct aatgattcat tgggaaaata cctttttata ctcctttatc    2640
atggtactgt aactgtatcc atattataaa tataattatc ttaaggattt tttattttt     2700 tttatgtcca agtgcccacg tgaatttgct ggtgaaagtt agcacttgtg tgtaaattct    2760
acttcctctt gtgtgttta ccaagtattt atactctggt gcaactaact actgtgtgag     2820
gaattggtcc atgtgcaata aataccaatg aagcacaatc aa                      2862

<210> SEQ ID NO 2
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = A or G

<400> SEQUENCE: 2
ctcgttgctg cctcccgcca gcgaangccc cgagccgctg tctcagcagt g             51

<210> SEQ ID NO 3
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or G

<400> SEQUENCE: 3
ccccgacttc cgcaaggcct tccagngact gctctgctgc gcgcgcaggg c             51

<210> SEQ ID NO 4
<211> LENGTH: 477
<212> TYPE: PRT
<213> ORGANISM: Homo sapiens

<400> SEQUENCE: 4

Met Gly Ala Gly Val Leu Val Leu Gly Ala Ser Glu Pro Gly Asn Leu
1               5                   10                  15

Ser Ser Ala Ala Pro Leu Pro Asp Gly Ala Ala Thr Ala Ala Arg Leu
            20                  25                  30

Leu Val Pro Ala Ser Pro Pro Ala Ser Leu Leu Pro Pro Ala Ser Glu
        35                  40                  45
```

```
Ser Pro Glu Pro Leu Ser Gln Gln Trp Thr Ala Gly Met Gly Leu Leu
    50                  55                  60

Met Ala Leu Ile Val Leu Ile Val Ala Gly Asn Val Leu Val Ile
65                  70                  75                  80

Val Ala Ile Ala Lys Thr Pro Arg Leu Gln Thr Leu Thr Asn Leu Phe
                85                  90                  95

Ile Met Ser Leu Ala Ser Ala Asp Leu Val Met Gly Leu Leu Val Val
            100                 105                 110

Pro Phe Gly Ala Thr Ile Val Val Trp Gly Arg Trp Glu Tyr Gly Ser
        115                 120                 125

Phe Phe Cys Glu Leu Trp Thr Ser Val Asp Val Leu Cys Val Thr Ala
    130                 135                 140

Ser Ile Glu Thr Leu Cys Val Ile Ala Leu Asp Arg Tyr Leu Ala Ile
145                 150                 155                 160

Thr Ser Pro Phe Arg Tyr Gln Ser Leu Leu Thr Arg Ala Arg Ala Arg
                165                 170                 175

Gly Leu Val Cys Thr Val Trp Ala Ile Ser Ala Leu Val Ser Phe Leu
            180                 185                 190

Pro Ile Leu Met His Trp Trp Arg Ala Glu Ser Asp Glu Ala Arg Arg
        195                 200                 205

Cys Tyr Asn Asp Pro Lys Cys Cys Asp Phe Val Thr Asn Arg Ala Tyr
    210                 215                 220

Ala Ile Ala Ser Ser Val Val Ser Phe Tyr Val Pro Leu Cys Ile Met
225                 230                 235                 240

Ala Phe Val Tyr Leu Arg Val Phe Arg Glu Ala Gln Lys Gln Val Lys
                245                 250                 255

Lys Ile Asp Ser Cys Glu Arg Arg Phe Leu Gly Gly Pro Ala Arg Pro
            260                 265                 270

Pro Ser Pro Ser Pro Ser Pro Val Pro Ala Pro Ala Pro Pro Pro Gly
        275                 280                 285

Pro Pro Arg Pro Ala Ala Ala Ala Thr Ala Pro Leu Ala Asn Gly
290                 295                 300

Arg Ala Gly Lys Arg Arg Pro Ser Arg Leu Val Ala Leu Arg Glu Gln
305                 310                 315                 320

Lys Ala Leu Lys Thr Leu Gly Ile Ile Met Gly Val Phe Thr Leu Cys
                325                 330                 335

Trp Leu Pro Phe Phe Leu Ala Asn Val Val Lys Ala Phe His Arg Glu
            340                 345                 350

Leu Val Pro Asp Arg Leu Phe Val Phe Phe Asn Trp Leu Gly Tyr Ala
        355                 360                 365

Asn Ser Ala Phe Asn Pro Ile Ile Tyr Cys Arg Ser Pro Asp Phe Arg
370                 375                 380

Lys Ala Phe Gln Gly Leu Leu Cys Cys Ala Arg Arg Ala Ala Arg Arg
385                 390                 395                 400

Arg His Ala Thr His Gly Asp Arg Pro Arg Ala Ser Gly Cys Leu Ala
                405                 410                 415

Arg Pro Gly Pro Pro Ser Pro Gly Ala Ala Ser Asp Asp Asp Asp
            420                 425                 430

Asp Asp Val Val Gly Ala Thr Pro Pro Ala Arg Leu Leu Glu Pro Trp
        435                 440                 445

Ala Gly Cys Asn Gly Gly Ala Ala Ala Asp Ser Asp Ser Ser Leu Asp
450                 455                 460
```

Glu Pro Cys Arg Pro Gly Phe Ala Ser Glu Ser Lys Val
465                 470                 475

<210> SEQ ID NO 5
<211> LENGTH: 2058
<212> TYPE: DNA
<213> ORGANISM: Homo sapiens

<400> SEQUENCE: 5

| | | | | | |
|---|---|---|---|---|---|
| gcacataacg | ggcagaacgc | actgcgaagc | ggcttcttca | gagcacgggc | tggaactggc | 60 |
| aggcaccgcg | agcccctagc | acccgacaag | ctgagtgtgc | aggacgagtc | cccaccacac | 120 |
| ccacaccaca | gccgctgaat | gaggcttcca | ggcgtccgct | cgcggcccgc | agagccccgc | 180 |
| cgtgggtccg | cccgctgagg | cgcccccagc | cagtgcgctc | acctgccaga | ctgcgcgcca | 240 |
| tggggcaacc | cgggaacggc | agcgccttct | tgctggcacc | caatagaagc | catgcgccgg | 300 |
| accacgacgt | cacgcagcaa | agggacgagg | tgtgggtggt | gggcatgggc | atcgtcatgt | 360 |
| ctctcatcgt | cctggccatc | gtgtttggca | atgtgctggt | catcacagcc | attgccaagt | 420 |
| tcgagcgtct | gcagacggtc | accaactact | tcatcacttc | actggcctgt | gctgatctgg | 480 |
| tcatgggcct | ggcagtggtg | cccttttgggg | ccgcccatat | tcttatgaaa | atgtggactt | 540 |
| ttggcaactt | ctggtgcgag | ttttggactt | ccattgatgt | gctgtgcgtc | acggccagca | 600 |
| ttgagaccct | gtgcgtgatc | gcagtggatc | gctactttgc | cattacttca | cctttcaagt | 660 |
| accagagcct | gctgaccaag | aataaggccc | gggtgatcat | tctgatggtg | tggattgtgt | 720 |
| caggccttac | ctccttcttg | cccattcaga | tgcactggta | ccgggccacc | caccaggaag | 780 |
| ccatcaactg | ctatgccaat | gagacctgct | gtgacttctt | cacgaaccaa | gcctatgcca | 840 |
| ttgcctcttc | catcgtgtcc | ttctacgttc | cctggtgat | catggtcttc | gtctactcca | 900 |
| gggtctttca | ggaggccaaa | aggcagctcc | agaagattga | caaatctgag | ggccgcttcc | 960 |
| atgtccagaa | ccttagccag | gtggagcagg | atgggcggac | ggggcatgga | ctccgcagat | 1020 |
| cttccaagtt | ctgcttgaag | gagcacaaag | ccctcaagac | gttaggcatc | atcatgggca | 1080 |
| ctttcacccct | ctgctggctg | cccttcttca | tcgttaacat | tgtgcatgtg | atccaggata | 1140 |
| acctcatccg | taaggaagtt | tacatcctcc | taaattggat | aggctatgtc | aattctggtt | 1200 |
| tcaatcccct | tatctactgc | cggagcccag | atttcaggat | tgccttccag | gagcttctgt | 1260 |
| gcctgcgcag | gtcttctttg | aaggcctatg | ggaatggcta | ctccagcaac | ggcaacacag | 1320 |
| gggagcagag | tggatatcac | gtggaacagg | agaaagaaaa | taaactgctg | tgtgaagacc | 1380 |
| tcccaggcac | ggaagacttt | gtgggccatc | aaggtactgt | gcctagcgat | aacattgatt | 1440 |
| cacaagggag | gaattgtagt | acaaatgact | cactgctgta | aagcagtttt | tctacttta | 1500 |
| aagaccccc | ccccaacag | aacactaaac | agactattta | acttgagggt | aataaactta | 1560 |
| gaataaaatt | gtaaaattgt | atagagatat | gcagaaggaa | gggcatcctt | ctgccttttt | 1620 |
| tattttttta | agctgtaaaa | agagagaaaa | cttatttgag | tgattatttg | ttatttgtac | 1680 |
| agttcagttc | ctctttgcat | ggaatttgta | agtttatgtc | taaagagctt | tagtcctaga | 1740 |
| ggacctgagt | ctgctatatt | ttcatgactt | ttccatgtat | ctacctcact | attcaagtat | 1800 |
| taggggtaat | atattgctgc | tggtaatttg | tatctgaagg | agattttcct | tcctacaccc | 1860 |
| ttggacttga | ggattttgag | tatctcggac | cttttcagctg | tgaacatgga | ctcttccccc | 1920 |
| actcctctta | tttgctcaca | cggggtattt | taggcaggga | tttgaggagc | agcttcagtt | 1980 |
| gttttcccga | gcaaagtcta | aagtttacag | taaataaatt | gtttgaccat | gccttcattg | 2040 | caaaaaaaaa aaaaaaaa                                                   2058

<210> SEQ ID NO 6
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = A or G

<400> SEQUENCE: 6
cagcgccttc ttgctggcac ccaatngaag ccatgcgccg gaccacgacg t          51

<210> SEQ ID NO 7
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or G

<400> SEQUENCE: 7
tgcgccggac cacgacgtca cgcagnaaag gacgaggtg tgggtggtgg g            51

<210> SEQ ID NO 8
<211> LENGTH: 413
<212> TYPE: PRT
<213> ORGANISM: Homo sapiens

<400> SEQUENCE: 8

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

```
Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
            245                 250                 255

Gly Leu Arg Arg Ser Ser Lys Phe Cys Leu Lys Glu His Lys Ala Leu
        260                 265                 270

Lys Thr Leu Gly Ile Ile Met Gly Thr Phe Thr Leu Cys Trp Leu Pro
    275                 280                 285

Phe Phe Ile Val Asn Ile Val His Val Ile Gln Asp Asn Leu Ile Arg
290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
            325                 330                 335

Gln Glu Leu Leu Cys Leu Arg Arg Ser Ser Leu Lys Ala Tyr Gly Asn
        340                 345                 350

Gly Tyr Ser Ser Asn Gly Asn Thr Gly Glu Gln Ser Gly Tyr His Val
    355                 360                 365

Glu Gln Glu Lys Glu Asn Lys Leu Leu Cys Glu Asp Leu Pro Gly Thr
370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
            405                 410

<210> SEQ ID NO 9
<211> LENGTH: 1673
<212> TYPE: DNA
<213> ORGANISM: Homo sapiens

<400> SEQUENCE: 9
gtgctgagag tgtcctgcct ggtcctctgt gcctggtggg gtggggtgc caggtgtgtc      60 cagaggagcc catttggtag tgaggcaggt atggggctag aagcactggt gccctggcc    120 gtgatagtgg ccatcttcct gctcctggtg gacctgatgc accggcgcca acgctgggct    180
gcacgctacc caccaggccc cctgccactg cccgggctgg caacctgct gcatgtggac     240 ttccagaaca caccatactg cttcgaccag ttgcggcgcc gcttcgggga cgtgttcagc    300
ctgcagctgg cctggacgcc ggtggtcgtg ctcaatgggc tggcggccgt gcgcgaggcg    360
ctggtgaccc acggcgagga caccgccgac cgcccgcctg tgcccatcac ccagatcctg    420
ggtttcgggc gcgttcccca agggtgttc ctggcgcgct atgggcccgc gtggcgcgag     480
cagaggcgct tctccgtgtc caccttgcgc aacttgggcc tgggcaagaa gtcgctggag    540
cagtgggtga ccgaggaggc cgcctgcctt tgtgccgcct cgccaacca ctccggacgc     600 cccttcgcc caacggtct cttggacaaa gccgtgagca acgtgatcgc ctccctcacc      660
tgcgggcgcc gcttcgagta cgacgaccct cgcttcctca ggctgctgga cctagctcag    720
gagggactga aggaggagtc gggctttctg cgcgaggtgc tgaatgctgt ccccgtcctc    780
ctgcatatcc cagcgctggc tggcaaggtc ctacgcttcc aaaaggcttt cctgacccag    840
ctggatgagc tgctaactga gcacaggatg acctgggacc cagcccagcc ccccgagac    900 ctgactgagg cctccctggc agagatggag aaggccaagg ggaaccctga gagcagcttc    960
aatgatgaga acctgcgcat agtggtggct gacctgttct ctgccgggat ggtgaccacc   1020
```

-continued

```
tcgaccacgc tggcctgggg cctcctgctc atgatcctac atccggatgt gcagcgccgt    1080
gtccaacagg agatcgacga cgtgataggg caggtgcggc gaccagagat gggtgaccag    1140
gctcacatgc cctacaccac tgccgtgatt catgaggtgc agcgctttgg ggacatcgtc    1200
cccctgggtg tgacccatat gacatcccgt gacatcgaag tacagggctt ccgcatccct    1260
aagggaacga cactcatcac caacctgtca tcggtgctga aggatgaggc cgtctgggag    1320
aagcccttcc gcttccaccc cgaacacttc ctggatgccc agggccactt tgtgaagccg    1380
gaggccttcc tgcctttctc agcaggccgc cgtgcatgcc tcggggagcc cctggcccgc    1440
atggagctct cctcttcttc cacctccctg ctgcagcact tcagcttctc ggtgcccact    1500
ggacagcccc ggcccagcca ccatggtgtc tttgctttcc tggtgagccc atcccctat    1560 gagctttgtg ctgtgccccg ctagaatggg gtacctagtc cccagcctgc tccctagcca    1620
gaggctctaa tgtacaataa agcaatgtgg tagttccaaa aaaaaaaaaa aaa            1673
```

```
<210> SEQ ID NO 10
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = A or G

<400> SEQUENCE: 10
cccttacccg catctcccac ccccangacg cccctttcgc cccaacggtc t              51

<210> SEQ ID NO 11
<211> LENGTH: 497
<212> TYPE: PRT
<213> ORGANISM: Homo sapiens

<400> SEQUENCE: 11

Met Gly Leu Glu Ala Leu Val Pro Leu Ala Val Ile Val Ala Ile Phe
1               5                   10                  15

Leu Leu Leu Val Asp Leu Met His Arg Arg Gln Arg Trp Ala Ala Arg
                20                  25                  30

Tyr Pro Pro Gly Pro Leu Pro Leu Pro Gly Leu Gly Asn Leu Leu His
            35                  40                  45

Val Asp Phe Gln Asn Thr Pro Tyr Cys Phe Asp Gln Leu Arg Arg Arg
    50                  55                  60

Phe Gly Asp Val Phe Ser Leu Gln Leu Ala Trp Thr Pro Val Val Val
65                  70                  75                  80

Leu Asn Gly Leu Ala Ala Val Arg Glu Ala Leu Val Thr His Gly Glu
                85                  90                  95

Asp Thr Ala Asp Arg Pro Pro Val Pro Ile Thr Gln Ile Leu Gly Phe
            100                 105                 110

Gly Pro Arg Ser Gln Gly Val Phe Leu Ala Arg Tyr Gly Pro Ala Trp
        115                 120                 125

Arg Glu Gln Arg Arg Phe Ser Val Ser Thr Leu Arg Asn Leu Gly Leu
    130                 135                 140

Gly Lys Lys Ser Leu Glu Gln Trp Val Thr Glu Glu Ala Ala Cys Leu
145                 150                 155                 160

Cys Ala Ala Phe Ala Asn His Ser Gly Arg Pro Phe Arg Pro Asn Gly
                165                 170                 175

Leu Leu Asp Lys Ala Val Ser Asn Val Ile Ala Ser Leu Thr Cys Gly
            180                 185                 190
```

```
Arg Arg Phe Glu Tyr Asp Asp Pro Arg Phe Leu Arg Leu Leu Asp Leu
        195                 200                 205

Ala Gln Glu Gly Leu Lys Glu Glu Ser Gly Phe Leu Arg Glu Val Leu
    210                 215                 220

Asn Ala Val Pro Val Leu Leu His Ile Pro Ala Leu Ala Gly Lys Val
225                 230                 235                 240

Leu Arg Phe Gln Lys Ala Phe Leu Thr Gln Leu Asp Glu Leu Leu Thr
                245                 250                 255

Glu His Arg Met Thr Trp Asp Pro Ala Gln Pro Pro Arg Asp Leu Thr
                260                 265                 270

Glu Ala Phe Leu Ala Glu Met Glu Lys Ala Lys Gly Asn Pro Glu Ser
                275                 280                 285

Ser Phe Asn Asp Glu Asn Leu Arg Ile Val Val Ala Asp Leu Phe Ser
    290                 295                 300

Ala Gly Met Val Thr Thr Ser Thr Thr Leu Ala Trp Gly Leu Leu Leu
305                 310                 315                 320

Met Ile Leu His Pro Asp Val Gln Arg Arg Val Gln Gln Glu Ile Asp
                325                 330                 335

Asp Val Ile Gly Gln Val Arg Arg Pro Glu Met Gly Asp Gln Ala His
                340                 345                 350

Met Pro Tyr Thr Thr Ala Val Ile His Glu Val Gln Arg Phe Gly Asp
                355                 360                 365

Ile Val Pro Leu Gly Val Thr His Met Thr Ser Arg Asp Ile Glu Val
                370                 375                 380

Gln Gly Phe Arg Ile Pro Lys Gly Thr Thr Leu Ile Thr Asn Leu Ser
385                 390                 395                 400

Ser Val Leu Lys Asp Glu Ala Val Trp Glu Lys Pro Phe Arg Phe His
                405                 410                 415

Pro Glu His Phe Leu Asp Ala Gln Gly His Phe Val Lys Pro Glu Ala
                420                 425                 430

Phe Leu Pro Phe Ser Ala Gly Arg Arg Ala Cys Leu Gly Glu Pro Leu
                435                 440                 445

Ala Arg Met Glu Leu Phe Leu Phe Phe Thr Ser Leu Leu Gln His Phe
    450                 455                 460

Ser Phe Ser Val Pro Thr Gly Gln Pro Arg Pro Ser His His Gly Val
465                 470                 475                 480

Phe Ala Phe Leu Val Ser Pro Ser Pro Tyr Glu Leu Cys Ala Val Pro
                485                 490                 495

Arg

<210> SEQ ID NO 12
<211> LENGTH: 100
<212> TYPE: DNA
<213> ORGANISM: Artificial Sequence
<220> FEATURE:
<223> OTHER INFORMATION: A synthetic oligonucleotide

<400> SEQUENCE: 12
tcccatttct ctagacctgc tgcctataca gtcactttt  tttttttttt gagacggagt      60
ctcgctctgt cgcccataca gtcactttta tgtggtttcg                           100

<210> SEQ ID NO 13
<211> LENGTH: 2587
<212> TYPE: DNA
<213> ORGANISM: Homo sapiens
```

<400> SEQUENCE: 13

```
atcccatgag cgggcagcag ggtcagaagt ggcccccgtg ttgcctaagc aagactctcc      60
cctgccctct gccctctgca cctccggcct gcatgtccct gtggcctctt gggggtacat    120
ctcccggggc tgggtcagaa ggcctggggtg gttggcctca ggctgtcaca cacctaggga    180
gatgctcccg tttctgggaa ccttggcccc gactcctgca aacttcggta aatgtgtaac    240
tcgaccctgc accggctcac tctgttcagc agtgaaactc tgcatcgatc actaagactt    300
cctggaagag gtcccagcgt gagtgtcgct tctggcatct gtccttctgg ccagcctgtg    360
gtctggccaa gtgatgtaac cctcctctcc agcctgtgca caggcagcct gggaacagct    420
ccatccccac ccctcagcta taaatagggc atcgtgaccc ggccggggga agaagctgcc    480
gttgttctgg gtactacagc agaagggtat gcggaagcga gcaccccagt ctgagatggc    540
tcctgccggt gtgagcctga gggccaccat cctctgcctc ctggcctggg ctggcctggc    600
tgcaggtgac cgggtgtaca tacacccctt ccacctcgtc atccacaatg agagtacctg    660
tgagcagctg gcaaaggcca atgccgggaa gcccaaagac cccaccttca tacctgctcc    720
aattcaggcc aagacatccc ctgtggatga aaaggcccta caggaccagc tggtgctagt    780
cgctgcaaaa cttgacaccg aagacaagtt gagggccgca atggtcggga tgctggccaa    840
cttcttgggc ttccgtatat atggcatgca cagtgagcta tggggcgtgg tccatggggc    900
caccgtcctc tccccaacgg ctgtctttgg caccctggcc tctctctatc tgggagcctt    960
ggaccacaca gctgacaggc tacaggcaat cctgggtgtt ccttggaagg acaagaactg   1020
cacctcccgg ctgatgcgc acaaggtcct gtctgccctg caggctgtac agggcctgct   1080
agtggcccag gcagggctg atagccagcc cagctgctg ctgtccacgg tggtgggcgt   1140
gttcacagcc ccaggcctgc acctgaagca gccgtttgtg cagggcctgg ctctctatac   1200
ccctgtggtc ctcccacgct ctctggactt cacagaactg gatgttgctg ctgagaagat   1260
tgacaggttc atgcaggctg tgacaggatg gaagactggc tgctccctga tgggagccag   1320
tgtggacagc accctggctt tcaacaccta cgtccacttc caaggaagga tgaagggctt   1380
ctccctgctg gccgagcccc aggagttctg ggtggacaac agcacctcag tgtctgttcc   1440
catgctctct ggcatgggca ccttccagca ctggagtgac atccaggaca acttctcggt   1500
gactcaagtg cccttcactg agagcgcctg cctgctgctg atccagcctc actatgcctc   1560
tgacctggac aagtggagg tctcactttt ccagcaaaac tccctcaact ggatgaagaa   1620
actatctccc cggaccatcc acctgaccat gccccaactg gtgctgcaag atcttatga   1680
cctgcaggac ctgctcgccc aggctgagct gcccgccatt ctgcacaccg agctgaacct   1740
gcaaaaattg agcaatgacc gcatcagggt ggggaggtg ctgaacagca tttttttga   1800
gcttgaagcg gatgagagag agcccacaga gtctacccaa cagcttaaca agcctgaggt   1860
cttggaggtg accctgaacc gcccattcct gtttgctgtg tatgatcaaa gcgccactgc   1920
cctgcacttc ctgggccgcg tggccaaccc gctgagcaca gcatgaggcc agggcccag   1980
aacacagtgc ctggcaaggc ctctgccccct ggctttgag gcaaaggcca gcagcagata   2040
acaaccccgg acaaatcagc gatgtgtcac ccccagtctc ccacctttc ttctaatgag   2100
tcgactttga gctggaaagc agccgtttct ccttggtcta agtgtgctgc atggagtgag   2160
cagtagaagc ctgcagcggc acaaatgcac ctcccagttt gctgggttta ttttagaaa   2220
tgggggtggg gaggcaagaa ccagtgttta gcgcgggact actgttccaa aaagaattcc   2280
```

```
aaccgaccag cttgtttgtg aaacaaaaaa gtgttcccct ttcaagttga gaacaaaaat    2340
tgggttttaa aattaaagta tacattttg cattgccttc ggtttgtatt tagtgtcttg    2400
aatgtaagaa catgacctcc gtgtagtgtc tgtaatacct tagttttttc cacagatgct    2460
tgtgattttt gaacaatacg tgaaagatgc aagcacctga atttctgttt gaatgcggaa    2520
ccatagctgg ttatttctcc cttgtgttag taataaacgt cttgccacaa taagcctcca    2580
aaaaaaa                                                              2587
```

```
<210> SEQ ID NO 14
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or T

<400> SEQUENCE: 14
ggatggaaga ctggctgctc cctganggga gccagtgtgg acagcaccct g             51

<210> SEQ ID NO 15
<211> LENGTH: 485
<212> TYPE: PRT
<213> ORGANISM: Homo sapiens

<400> SEQUENCE: 15
```

| | | | | | | | | | | | | | | | |
|---|---|---|---|---|---|---|---|---|---|---|---|---|---|---|---|
| Met | Arg | Lys | Arg | Ala | Pro | Gln | Ser | Glu | Met | Ala | Pro | Ala | Gly | Val | Ser |
| 1 | | | | 5 | | | | | 10 | | | | | 15 | |
| Leu | Arg | Ala | Thr | Ile | Leu | Cys | Leu | Leu | Ala | Trp | Ala | Gly | Leu | Ala | Ala |
| | | | 20 | | | | | 25 | | | | | 30 | | |
| Gly | Asp | Arg | Val | Tyr | Ile | His | Pro | Phe | His | Leu | Val | Ile | His | Asn | Glu |
| | | | 35 | | | | 40 | | | | | 45 | | | |
| Ser | Thr | Cys | Glu | Gln | Leu | Ala | Lys | Ala | Asn | Ala | Gly | Lys | Pro | Lys | Asp |
| | 50 | | | | | 55 | | | | | 60 | | | | |
| Pro | Thr | Phe | Ile | Pro | Ala | Pro | Ile | Gln | Ala | Lys | Thr | Ser | Pro | Val | Asp |
| 65 | | | | | 70 | | | | | 75 | | | | | 80 |
| Glu | Lys | Ala | Leu | Gln | Asp | Gln | Leu | Val | Leu | Val | Ala | Ala | Lys | Leu | Asp |
| | | | | 85 | | | | | 90 | | | | | 95 | |
| Thr | Glu | Asp | Lys | Leu | Arg | Ala | Ala | Met | Val | Gly | Met | Leu | Ala | Asn | Phe |
| | | | 100 | | | | | 105 | | | | | 110 | | |
| Leu | Gly | Phe | Arg | Ile | Tyr | Gly | Met | His | Ser | Glu | Leu | Trp | Gly | Val | Val |
| | | | 115 | | | | 120 | | | | | 125 | | | |
| His | Gly | Ala | Thr | Val | Leu | Ser | Pro | Thr | Ala | Val | Phe | Gly | Thr | Leu | Ala |
| | 130 | | | | | 135 | | | | | 140 | | | | |
| Ser | Leu | Tyr | Leu | Gly | Ala | Leu | Asp | His | Thr | Ala | Asp | Arg | Leu | Gln | Ala |
| 145 | | | | | 150 | | | | | 155 | | | | | 160 |
| Ile | Leu | Gly | Val | Pro | Trp | Lys | Asp | Lys | Asn | Cys | Thr | Ser | Arg | Leu | Asp |
| | | | | 165 | | | | | 170 | | | | | 175 | |
| Ala | His | Lys | Val | Leu | Ser | Ala | Leu | Gln | Ala | Val | Gln | Gly | Leu | Leu | Val |
| | | | 180 | | | | | 185 | | | | | 190 | | |
| Ala | Gln | Gly | Arg | Ala | Asp | Ser | Gln | Ala | Gln | Leu | Leu | Leu | Ser | Thr | Val |
| | | | 195 | | | | 200 | | | | | 205 | | | |
| Val | Gly | Val | Phe | Thr | Ala | Pro | Gly | Leu | His | Leu | Lys | Gln | Pro | Phe | Val |
| | 210 | | | | | 215 | | | | | 220 | | | | |
| Gln | Gly | Leu | Ala | Leu | Tyr | Thr | Pro | Val | Val | Leu | Pro | Arg | Ser | Leu | Asp |
| 225 | | | | | 230 | | | | | 235 | | | | | 240 |

Phe Thr Glu Leu Asp Val Ala Ala Glu Lys Ile Asp Arg Phe Met Gln
            245                 250                 255

Ala Val Thr Gly Trp Lys Thr Gly Cys Ser Leu Met Gly Ala Ser Val
        260                 265                 270

Asp Ser Thr Leu Ala Phe Asn Thr Tyr Val His Phe Gln Gly Lys Met
        275                 280                 285

Lys Gly Phe Ser Leu Leu Ala Glu Pro Gln Glu Phe Trp Val Asp Asn
        290                 295                 300

Ser Thr Ser Val Ser Val Pro Met Leu Ser Gly Met Gly Thr Phe Gln
305                 310                 315                 320

His Trp Ser Asp Ile Gln Asp Asn Phe Ser Val Thr Gln Val Pro Phe
                325                 330                 335

Thr Glu Ser Ala Cys Leu Leu Leu Ile Gln Pro His Tyr Ala Ser Asp
                340                 345                 350

Leu Asp Lys Val Glu Gly Leu Thr Phe Gln Gln Asn Ser Leu Asn Trp
        355                 360                 365

Met Lys Lys Leu Ser Pro Arg Thr Ile His Leu Thr Met Pro Gln Leu
    370                 375                 380

Val Leu Gln Gly Ser Tyr Asp Leu Gln Asp Leu Leu Ala Gln Ala Glu
385                 390                 395                 400

Leu Pro Ala Ile Leu His Thr Glu Leu Asn Leu Gln Lys Leu Ser Asn
                405                 410                 415

Asp Arg Ile Arg Val Gly Glu Val Leu Asn Ser Ile Phe Phe Glu Leu
                420                 425                 430

Glu Ala Asp Glu Arg Glu Pro Thr Glu Ser Thr Gln Gln Leu Asn Lys
        435                 440                 445

Pro Glu Val Leu Glu Val Thr Leu Asn Arg Pro Phe Leu Phe Ala Val
    450                 455                 460

Tyr Asp Gln Ser Ala Thr Ala Leu His Phe Leu Gly Arg Val Ala Asn
465                 470                 475                 480

Pro Leu Ser Thr Ala
            485

<210> SEQ ID NO 16
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = A or C

<400> SEQUENCE: 16
tgcagcactt cactaccaaa tgagcnttag ctactttca gaattgaagg a          51

<210> SEQ ID NO 17
<211> LENGTH: 720
<212> TYPE: DNA
<213> ORGANISM: Homo sapiens

<400> SEQUENCE: 17
attcaactag gcatcatacg tgactgtaga attgcagata ttgtggacac ggccatgcct    60
atcaccattt gtatagctta ttttaacaat tgcctgaatc ctcttttta tggctttctg   120 gggaaaaaat ttaaaagata ttttctccag cttctaaaat atattccccc aaaagccaaa   180
tcccactcaa acctttcaac aaaaatgagc acgctttcct accgcccctc agataatgta   240
agctcatcca ccaagaagcc tgcaccatgt tttgaggttg agtgacatgt tcgaaacctg   300

-continued

| | |
|---|---|
| tccataaagt aattttgtga aagaaggagc aagagaacat tcctctgcag cacttcacta | 360 |
| ccaaatgagc attagctact tttcagaatt gaaggagaaa atgcattatg tggactgaac | 420 |
| cgacttttct aaagctctga acaaaagctt ttctttcctt ttgcaacaag acaaagcaaa | 480 |
| gccacatttt gcattagaca gatgacggct gctcgaagaa caatgtcaga aactcgatga | 540 |
| atgtgttgat ttgagaaatt ttactgacag aaatgcaatc tccctagcct gcttttgtcc | 600 |
| tgttattttt tatttccaca taaaggtatt tagaatatat aaatcgtta gaggagcaac | 660 |
| aggagatgag agttccagat tgttctgtcc agtttccaaa gggcagtaaa gttttcgtgc | 720 |

<210> SEQ ID NO 18
<211> LENGTH: 2185
<212> TYPE: DNA
<213> ORGANISM: Homo sapiens

<400> SEQUENCE: 18

| | |
|---|---|
| ggcagcagcg agtgacagga cgtctggacc ggcgcgccgc tagcagctct gccgggccgc | 60 |
| ggcggtgatc gatgggagcg gctggagcgg acccagcgag tgagggcgca cagccggacg | 120 |
| ccgaggcggc gggcgggaga ccgcaccgcg acgccggccc tcggcggacg agtcgagcgc | 180 |
| ccgggcgcgg gtgtatttga tatagtgttt gcaacaaatt cgacccaggt gatcaaaatg | 240 |
| attctcaact cttctactga agatggtatt aaaagaatcc aagatgattg tcccaaagct | 300 |
| ggaaggcata attacatatt tgtcatgatt cctactttat acagtatcat ctttgtggtg | 360 |
| ggaatatttg gaaacagctt ggtggtgata gtcatttact tttatatgaa gctgaagact | 420 |
| gtggccagtg ttttttcttt gaatttagca ctggctgact tatgcttttt actgactttg | 480 |
| ccactatggg ctgtctacac agctatggaa taccgctggc cctttggcaa ttacctatgt | 540 |
| aagattgctt cagccagcgt cagtttcaac ctgtacgcta gtgtgtttct actcacgtgt | 600 |
| ctcagcattg atcgatacct ggctattgtt cacccaatga agtcccgcct tcgacgcaca | 660 |
| atgcttgtag ccaaagtcac ctgcatcatc atttggctgc tggcaggctt ggccagtttg | 720 |
| ccagctataa tccatcgaaa tgtatttttc attgagaaca ccaatattac agtttgtgct | 780 |
| ttccattatg agtcccaaaa ttcaaccctc ccgatagggc tgggcctgac caaaaatata | 840 |
| ctgggttttc tgtttccttt tctgatcatt cttacaagtt atactcttat ttggaaggcc | 900 |
| ctaaagaagg cttatgaaat tcagaagaac aaaccaagaa atgatgatat ttttaagata | 960 |
| attatggcaa ttgtgctttt cttttttcttt tcctggattc cccaccaaat attcactttt | 1020 |
| ctggatgtat tgattcaact aggcatcata cgtgactgta aattgcaga tattgtggac | 1080 |
| acggccatgc ctatcaccat ttgtatagct tattttaaca attgcctgaa tcctctttt | 1140 |
| tatgcctttc tgggaaaaaa atttaaaaga tattttctcc agcttctaaa atatattccc | 1200 |
| ccaaaagcca atcccactc aaacctttca acaaaaatga gcacgctttc ctaccgcccc | 1260 |
| tcagataatg taagctcatc caccaagaag cctgcaccat gttttgaggt tgagtgacat | 1320 |
| gttcgaaacc tgtccataaa gtaattttgt gaaagaagga gcaagagaac attcctctgc | 1380 |
| agcacttcac taccaaatga gcattagcta cttttcagaa ttgaaggaga aatgcatta | 1440 |
| tgtggactga accgactttt ctaaagctct gaacaaaagc ttttctttcc ttttgcaaca | 1500 |
| agacaaagca aagccacatt ttgcattaga cagatgacgg ctgctcgaag aacaatgtca | 1560 |
| gaaactcgat gaatgtgttg atttgagaaa ttttactgac agaaatgcaa tctccctagc | 1620 |
| ctgcttttgt cctgttattt tttatttcca cataaaggta tttagaatat attaactcgt | 1680 |

| | |
|---|---|
| tagaggagca acaggagatg agagttccag attgttctgt ccagtttcca aagggcagta | 1740 |
| aagttttcgt gcctgttttc agctattagc aactgtgcct acacttgcac ctggtctgca | 1800 |
| cattttgtac aaagatatgc ttaagcagta gtcgtcaagt tgcagatctt tgttgtgaaa | 1860 |
| ttcaacctgt gtcttatagg tttacactgc caaaacaatg cccgtaagat ggcttatttg | 1920 |
| tataatggtg ttacctaaag tcacatataa aagttaaact acttgtaaag gtgctgcact | 1980 |
| ggtcccaagt agtagtgtct tcctagtata ttagtttgat ttaatatctg agaagtgtat | 2040 |
| atagtttgtg gtaaaaagat tatatatcat aaagtatgcc ttcctgttta aaaaaagtat | 2100 |
| atattctaca catatatgta tatgtatatc tatatctcta aactgctgtt aattgattaa | 2160 |
| aatctggcaa agttatattt acccc | 2185 |

```
<210> SEQ ID NO 19
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = A or G

<400> SEQUENCE: 19
```

| | |
|---|---|
| agaacaccaa agcaggctta atctgngggc acttacagag actgctttaa a | 51 |

```
<210> SEQ ID NO 20
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or T

<400> SEQUENCE: 20
```

| | |
|---|---|
| tttaaagcag tctctgtaag tgcccncaga ttaagcctgc tttggtgttc t | 51 |

```
<210> SEQ ID NO 21
<211> LENGTH: 3497
<212> TYPE: DNA
<213> ORGANISM: Homo sapiens

<400> SEQUENCE: 21
```

| | |
|---|---|
| aaacagaagg cagatagaga gggagtgaga ggcaggagct gagacacaga tcctggagga | 60 |
| agaagaccaa aggaaggggg cagagacaga aagggaggtg ctaggacaaa actcgaaagg | 120 |
| tggccctatc agggaagcag aggagaggcc gttctaggga agcccagctc cggcactttt | 180 |
| ggccccaact cccgcaggtc tgctggctcc aggaaaggtg gaggagggag ggaggagtgg | 240 |
| gagaatgtgg gcgcagggtg ggacatgggc atggccaggg gcagcctcac tcgggttcca | 300 |
| ggggtgatgg gagagggcac tcagggccca gagctcagcc ttgaccctga cccttgctct | 360 |
| ccccaatcca ctccggggct catgaagggg aacaagctgg aggagcagga ccctagacct | 420 |
| ctgcagccca taccaggtct catggagggg aacaagctgg aggagcagga ctctagccct | 480 |
| ccacagtcca ctccagggct catgaagggg aacaagcgtg aggagcaggg gctgggcccc | 540 |
| gaacctgcgg cgccccagca gcccacggcg gaggaggagg ccctgatcga gttccaccgc | 600 |
| tcctaccgag agctcttcga gttcttctgc aacaacacca ccatccacgg cgccatccgc | 660 |
| ctggtgtgct cccagcacaa ccgcatgaag acggccttct gggcagtgct gtggctctgc | 720 |
| acctttggca tgatgtactg gcaattcggc ctgcttttcg gagagtactt cagctacccc | 780 |

-continued

```
gtcagcctca acatcaacct caactcggac aagctcgtct tccccgcagt gaccatctgc    840
accctcaatc cctacaggta cccggaaatt aagaggagc tggaggagct ggaccgcatc    900
acagagcaga cgctctttga cctgtacaaa tacagctcct tcaccactct cgtggccggc    960
tcccgcagcc gtcgcgacct gcgggggact ctgccgcacc ccttgcagcg cctgagggtc   1020
ccgcccccgc ctcacggggc ccgtcgagcc cgtagcgtgg cctccagctt gcgggacaac   1080 aaccccagg tggactggaa ggactggaag atcggcttcc agctgtgcaa ccagaacaaa   1140
tcggactgct tctaccagac atactcatca ggggtggatg cggtgaggga gtggtaccgc   1200
ttccactaca tcaacatcct gtcgaggctg ccagagactc tgccatccct ggaggaggac   1260
acgctgggca acttcatctt cgcctgccgc ttcaaccagg tctcctgcaa ccaggcgaat   1320
tactctcact ccaccaccc gatgtatgga aactgctata ctttcaatga caagaacaac   1380
tccaacctct ggatgtcttc catgcctgga atcaacaacg gtctgtccct gatgctgcgc   1440
gcagagcaga atgacttcat tcccctgctg tccacagtga ctggggcccg ggtaatggtg   1500
cacgggcagg atgaacctgc ctttatggat gatggtggct ttaacttgcg gcctggcgtg   1560
gagacctcca tcagcatgag gaaggaaacc ctggacagac ttgggggcga ttatggcgac   1620
tgcaccaaga atggcagtga tgttcctgtt gagaaccttt acccttcaaa gtacacacag   1680
caggtgtgta ttcactcctg cttccaggag agcatgatca aggagtgtgg ctgtgcctac   1740
atcttctatc cgcggcccca gaacgtggag tactgtgact acagaaagca cagttcctgg   1800
gggtactgct actataagct ccaggttgac ttctcctcag accacctggg ctgtttcacc   1860
aagtgccgga agccatgcag cgtgaccagc taccagctct ctgctggtta ctcacgatgg   1920
ccctcggtga catcccagga atgggtcttc cagatgctat cgcgacagaa caattcacc   1980 gtcaacaaca agagaaatgg agtggccaaa gtcaacatct tcttcaagga gctgaactac   2040
aaaaccaatt ctgagtctcc ctctgtcacg atggtcaccc tcctgtccaa cctgggcagc   2100
cagtggagcc tgtggttcgg ctcctcggtg ttgtctgtgg tggagatggc tgagctcgtc   2160
tttgacctgc tggtcatcat gttcctcatg ctgctccgaa ggttccgaag ccgatactgg   2220
tctccaggcc gagggggcag gggtgctcag gaggtagcc ccaccctggc atcctcccct   2280
ccttcccact tctgccccca ccccatgtct ctgtccttgt cccagccagg ccctgctccc   2340
tctccagcct tgacagcccc tcccctgcc tatgccaccc tgggccccg cccatctcca   2400 ggggctctg cagggccag ttcctccacc tgtcctctgg ggggccctg agaggaagg    2460 agaggtttct cacaccaagg cagatgctcc tctggtggga gggtgctggc cctggcaaga   2520
ttgaaggatg tgcagggctt cctctcagag ccgcccaaac tgccgttgat gtgtggaggg   2580
gaagcaagat gggtaagggc tcaggaagtt gctccaagaa cagtagctga tgaagctgcc   2640
cagaagtgcc ttggctccag ccctgtaccc cttggtactg cctctgaaca ctctggtttc   2700
cccacccaac tgcggctaag tctctttttc ccttggatca gccaagcgaa acttggagct   2760
ttgacaagga actttcctaa gaaaccgctg ataaccagga caaaacacaa ccaagggtac   2820
acgcaggcat gcacgggttt cctgcccagc gacggcttaa gccagccccc gactggcctg   2880
gccacactgc tctccagtag cacagatgtc tgctcctcct cttgaacttg ggtgggaaac   2940
cccacccaaa agccccttt gttacttagg caattcccct tccctgactc ccgagggcta   3000
gggctagagc agacccgggt aagtaaaggc agacccaggg ctcctctagc ctcatacccg   3060
tgccctcaca gagccatgcc ccggcacctc tgccctgtgt ctttcatacc tctacatgtc   3120
```

-continued

```
tgcttgagat atttcctcag cctgaaagtt tccccaacca tctgccagag aactcctatg    3180
catcccttag aaccctgctc agacaccatt acttttgtga acgcttctgc cacatcttgt    3240
cttccccaaa attgatcact ccgccttctc ctgggctccc gtagcacact ataacatctg    3300
ctggagtgtt gctgttgcac catactttct tgtacatttg tgtctccctt cccaactaga    3360
ctgtaagtgc cttgcggtca gggactgaat cttgcccgtt tatgtatgct ccatgtctag    3420
cccatcatcc tgcttggagc aagtaggcag gagctcaata aatgtttgtt gcatgaagga    3480
aaaaaaaaaa aaaaaa                                                    3497
```

<210> SEQ ID NO 22
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = A or G

<400> SEQUENCE: 22

```
gggctctgca ggggccagtt cctccncctg tcctctgggg gggccctgag a             51
```

<210> SEQ ID NO 23
<211> LENGTH: 728
<212> TYPE: PRT
<213> ORGANISM: Homo sapiens

<400> SEQUENCE: 23

```
Met Gly Met Ala Arg Gly Ser Leu Thr Arg Val Pro Gly Val Met Gly
1               5                   10                  15

Glu Gly Thr Gln Gly Pro Glu Leu Ser Leu Asp Pro Asp Pro Cys Ser
                20                  25                  30

Pro Gln Ser Thr Pro Gly Leu Met Lys Gly Asn Lys Leu Glu Glu Gln
            35                  40                  45

Asp Pro Arg Pro Leu Gln Pro Ile Pro Gly Leu Met Glu Gly Asn Lys
        50                  55                  60

Leu Glu Glu Gln Asp Ser Ser Pro Pro Gln Ser Thr Pro Gly Leu Met
65                  70                  75                  80

Lys Gly Asn Lys Arg Glu Glu Gln Gly Leu Gly Pro Glu Pro Ala Ala
                85                  90                  95

Pro Gln Gln Pro Thr Ala Glu Glu Ala Leu Ile Glu Phe His Arg
            100                 105                 110

Ser Tyr Arg Glu Leu Phe Glu Phe Phe Cys Asn Asn Thr Thr Ile His
            115                 120                 125

Gly Ala Ile Arg Leu Val Cys Ser Gln His Asn Arg Met Lys Thr Ala
        130                 135                 140

Phe Trp Ala Val Leu Trp Leu Cys Thr Phe Gly Met Met Tyr Trp Gln
145                 150                 155                 160

Phe Gly Leu Leu Phe Gly Glu Tyr Phe Ser Tyr Pro Val Ser Leu Asn
                165                 170                 175

Ile Asn Leu Asn Ser Asp Lys Leu Val Phe Pro Ala Val Thr Ile Cys
            180                 185                 190

Thr Leu Asn Pro Tyr Arg Tyr Pro Glu Ile Lys Glu Glu Leu Glu Glu
        195                 200                 205

Leu Asp Arg Ile Thr Glu Gln Thr Leu Phe Asp Leu Tyr Lys Tyr Ser
    210                 215                 220

Ser Phe Thr Thr Leu Val Ala Gly Ser Arg Ser Arg Arg Asp Leu Arg
```

```
              225                 230                 235                 240
Gly Thr Leu Pro His Pro Leu Gln Arg Leu Arg Val Pro Pro Pro
                245                 250                 255

His Gly Ala Arg Arg Ala Arg Ser Val Ala Ser Ser Leu Arg Asp Asn
                260                 265                 270

Asn Pro Gln Val Asp Trp Lys Asp Trp Lys Ile Gly Phe Gln Leu Cys
                275                 280                 285

Asn Gln Asn Lys Ser Asp Cys Phe Tyr Gln Thr Tyr Ser Ser Gly Val
            290                 295                 300

Asp Ala Val Arg Glu Trp Tyr Arg Phe His Tyr Ile Asn Ile Leu Ser
305                 310                 315                 320

Arg Leu Pro Glu Thr Leu Pro Ser Leu Glu Glu Asp Thr Leu Gly Asn
                325                 330                 335

Phe Ile Phe Ala Cys Arg Phe Asn Gln Val Ser Cys Asn Gln Ala Asn
                340                 345                 350

Tyr Ser His Phe His His Pro Met Tyr Gly Asn Cys Tyr Thr Phe Asn
            355                 360                 365

Asp Lys Asn Asn Ser Asn Leu Trp Met Ser Ser Met Pro Gly Ile Asn
        370                 375                 380

Asn Gly Leu Ser Leu Met Leu Arg Ala Glu Gln Asn Asp Phe Ile Pro
385                 390                 395                 400

Leu Leu Ser Thr Val Thr Gly Ala Arg Val Met Val His Gly Gln Asp
                405                 410                 415

Glu Pro Ala Phe Met Asp Asp Gly Gly Phe Asn Leu Arg Pro Gly Val
                420                 425                 430

Glu Thr Ser Ile Ser Met Arg Lys Glu Thr Leu Asp Arg Leu Gly Gly
                435                 440                 445

Asp Tyr Gly Asp Cys Thr Lys Asn Gly Ser Asp Val Pro Val Glu Asn
            450                 455                 460

Leu Tyr Pro Ser Lys Tyr Thr Gln Gln Val Cys Ile His Ser Cys Phe
465                 470                 475                 480

Gln Glu Ser Met Ile Lys Glu Cys Gly Cys Ala Tyr Ile Phe Tyr Pro
                485                 490                 495

Arg Pro Gln Asn Val Glu Tyr Cys Asp Tyr Arg Lys His Ser Ser Trp
                500                 505                 510

Gly Tyr Cys Tyr Tyr Lys Leu Gln Val Asp Phe Ser Ser Asp His Leu
            515                 520                 525

Gly Cys Phe Thr Lys Cys Arg Lys Pro Cys Ser Val Thr Ser Tyr Gln
        530                 535                 540

Leu Ser Ala Gly Tyr Ser Arg Trp Pro Ser Val Thr Ser Gln Glu Trp
545                 550                 555                 560

Val Phe Gln Met Leu Ser Arg Gln Asn Asn Tyr Thr Val Asn Asn Lys
                565                 570                 575

Arg Asn Gly Val Ala Lys Val Asn Ile Phe Phe Lys Glu Leu Asn Tyr
                580                 585                 590

Lys Thr Asn Ser Glu Ser Pro Ser Val Thr Met Val Thr Leu Leu Ser
                595                 600                 605

Asn Leu Gly Ser Gln Trp Ser Leu Trp Phe Gly Ser Ser Val Leu Ser
            610                 615                 620

Val Val Glu Met Ala Glu Leu Val Phe Asp Leu Leu Val Ile Met Phe
625                 630                 635                 640

Leu Met Leu Leu Arg Arg Phe Arg Ser Arg Tyr Trp Ser Pro Gly Arg
                645                 650                 655
```

```
Gly Gly Arg Gly Ala Gln Glu Val Ala Ser Thr Leu Ala Ser Ser Pro
            660                 665                 670

Pro Ser His Phe Cys Pro His Pro Met Ser Leu Ser Leu Ser Gln Pro
        675                 680                 685

Gly Pro Ala Pro Ser Pro Ala Leu Thr Ala Pro Pro Ala Tyr Ala
    690                 695                 700

Thr Leu Gly Pro Arg Pro Ser Pro Gly Gly Ser Ala Gly Ala Ser Ser
705                 710                 715                 720

Ser Thr Cys Pro Leu Gly Gly Pro
                725

<210> SEQ ID NO 24
<211> LENGTH: 3345
<212> TYPE: DNA
<213> ORGANISM: Homo sapiens

<400> SEQUENCE: 24
```

| | | | | | |
|---|---|---|---|---|---|
| cttgcctgtc | tgcgtctaaa | gccctgccc | agagtccgcc | ttctcaggtc | cagtactccc     60 |
| agttcacctg | ccctcgggag | ccctccttcc | ttcggaaaac | tcccggctct | gactcctcct    120 |
| cagcccctcc | ccccgccctg | ctcacctta | attgagatgc | taatgagatt | cctgtcgctt    180 |
| ccatccctgg | ccggccagcg | ggcgggctcc | ccagccaggc | cgctgcacct | gtcaggggaa    240 |
| caagctggag | gagcaggacc | ctagacctct | gcagcccata | ccaggtctca | tggaggggaa    300 |
| caagctggag | gagcaggact | ctagccctcc | acagtccact | ccagggctca | tgaaggggaa    360 |
| caagcgtgag | gagcaggggc | tgggccccga | acctgcggcg | ccccagcagc | ccacggcgga    420 |
| ggaggaggcc | ctgatcgagt | tccaccgctc | ctaccgagag | ctcttcgagt | tcttctgcaa    480 |
| caacaccacc | atccacggcg | ccatccgcct | ggtgtgctcc | cagcacaacc | gcatgaagac    540 |
| ggccttctgg | gcagtgctgt | ggctctgcac | ctttggcatg | atgtactggc | aattcggcct    600 |
| gcttttcgga | gagtacttca | gctaccccgt | cagcctcaac | atcaacctca | actcggacaa    660 |
| gctcgtcttc | cccgcagtga | ccatctgcac | cctcaatccc | tacaggtacc | cggaaattaa    720 |
| agaggagctg | gaggagctgg | accgcatcac | agagcagacg | ctctttgacc | tgtacaaata    780 |
| cagctccttc | accactctcg | tggccggctc | ccgcagccgt | cgcgacctgc | ggggactct    840 |
| gccgcaccc | ttgcagcgcc | tgaggtccc | gccccgcct | cacggggccc | gtcgagcccg    900 |
| tagcgtggcc | tccagcttgc | gggacaacaa | ccccaggtg | gactggaagg | actggaagat    960 |
| cggcttccag | ctgtgcaacc | agaacaaatc | ggactgcttc | taccagacat | actcatcagg   1020 |
| ggtggatgcg | gtgagggagt | ggtaccgctt | ccactacatc | aacatcctgt | cgaggctgcc   1080 |
| agagactctg | ccatccctgg | aggaggacac | gctgggcaac | ttcatcttcg | cctgccgctt   1140 |
| caaccaggtc | tcctgcaacc | aggcgaatta | ctctcacttc | caccacccga | tgtatggaaa   1200 |
| ctgctatact | ttcaatgaca | gaacaactc | caacctctgg | atgtcttcca | tgcctggaat   1260 |
| caacaacggt | ctgtccctga | tgctgcgcgc | agagcagaat | gacttcattc | ccctgctgtc   1320 |
| cacagtgact | ggggcccggg | taatggtgca | cgggcaggat | gaacctgcct | tatggatga   1380 |
| tggtggcttt | aacttgcggc | ctggcgtgga | gacctccatc | agcatgagga | aggaaaccct   1440 |
| ggacagactt | gggggcgatt | atggcgactg | caccaagaat | ggcagtgatg | ttcctgttga   1500 |
| gaacctttac | ccttcaaagt | acacacagca | ggtgtgtatt | cactcctgct | tccaggagag   1560 |
| catgatcaag | gagtgtggct | gtgcctacat | cttctatccg | cggccccaga | acgtggagta   1620 |
| ctgtgactac | agaaagcaca | gttcctgggg | gtactgctac | tataagctcc | aggttgactt   1680 |

```
ctcctcagac cacctgggct gtttcaccaa gtgccggaag ccatgcagcg tgaccagcta    1740
ccagctctct gctggttact cacgatggcc ctcggtgaca tcccaggaat gggtcttcca    1800
gatgctatcg cgacagaaca attacaccgt caacaacaag agaaatggag tggccaaagt    1860
caacatcttc ttcaaggagc tgaactacaa aaccaattct gagtctccct ctgtcacgat    1920
ggtcaccctc ctgtccaacc tgggcagcca gtggagcctg tggttcggct cctcggtgtt    1980
gtctgtggtg gagatggctg agctcgtctt tgacctgctg gtcatcatgt tcctcatgct    2040
gctccgaagg ttccgaagcc gatactggtc tccaggccga gggggcaggg gtgctcagga    2100
ggtagcctcc accctggcat cctcccctcc ttcccacttc tgcccccacc ccatgtctct    2160
gtccttgtcc cagccaggcc ctgctccctc tccagccttg acagcccctc ccctgccta    2220
tgccaccctg ggccccgcc catctccagg gggctctgca ggggcagtt cctccacctg    2280
tcctctgggg gggcctgag agggaaggag aggtttctca caccaaggca gatgctcctc    2340
tggtgggagg gtgctggccc tggcaagatt gaaggatgtg cagggcttcc tctcagagcc    2400
gcccaaactg ccgttgatgt gtggagggga agcaagatgg gtaagggctc aggaagttgc    2460
tccaagaaca gtagctgatg aagctgccca gaagtgcctt ggctccagcc ctgtacccct    2520
tggtactgcc tctgaacact ctggtttccc cacccaactg cggctaagtc tcttttttcc    2580
ttggatcagc caagcgaaac ttggagcttt gacaaggaac tttcctaaga aaccgctgat    2640
aaccaggaca aaacacaacc aagggtacac gcaggcatgc acgggtttcc tgcccagcga    2700
cggcttaagc cagcccccga ctggcctggc cacactgctc tccagtagca cagatgtctg    2760
ctcctcctct tgaacttggg tgggaaaccc cacccaaaag cccccttttgt tacttaggca    2820
attccccttc cctgactccc gagggctagg gctagagcag accgggtaa gtaaaggcag    2880
acccagggct cctctagcct catacccgtg ccctcacaga gccatgcccc ggcacctctg    2940
ccctgtgtct ttcatacctc tacatgtctg cttgagatat ttcctcagcc tgaaagtttc    3000
cccaaccatc tgccagagaa ctcctatgca tcccttagaa ccctgctcag acaccattac    3060
ttttgtgaac gcttctgcca catcttgtct tccccaaaat tgatcactcc gccttctcct    3120
gggctcccgt agcacactat aacatctgct ggagtgttgc tgttcacca tactttcttg    3180
tacatttgtg tctcccttcc caactagact gtaagtgcct tgcggtcagg gactgaatct    3240
tgcccgttta tgtatgctcc atgtctagcc catcatcctg cttggagcaa gtaggcagga    3300
gctcaataaa tgtttgttgc atgaaggaaa aaaaaaaaa aaaaa                    3345
```

<210> SEQ ID NO 25
<211> LENGTH: 669
<212> TYPE: PRT
<213> ORGANISM: Homo sapiens

<400> SEQUENCE: 25

Met Glu Gly Asn Lys Leu Glu Glu Gln Asp Ser Ser Pro Pro Gln Ser
1               5                   10                  15

Thr Pro Gly Leu Met Lys Gly Asn Lys Arg Glu Glu Gln Gly Leu Gly
            20                  25                  30

Pro Glu Pro Ala Ala Pro Gln Gln Pro Thr Ala Glu Glu Glu Ala Leu
        35                  40                  45

Ile Glu Phe His Arg Ser Tyr Arg Glu Leu Phe Glu Phe Phe Cys Asn
    50                  55                  60

Asn Thr Thr Ile His Gly Ala Ile Arg Leu Val Cys Ser Gln His Asn
65                  70                  75                  80

```
Arg Met Lys Thr Ala Phe Trp Ala Val Leu Trp Leu Cys Thr Phe Gly
                85                  90                  95

Met Met Tyr Trp Gln Phe Gly Leu Leu Phe Gly Glu Tyr Phe Ser Tyr
                100                 105                 110

Pro Val Ser Leu Asn Ile Asn Leu Asn Ser Asp Lys Leu Val Phe Pro
                115                 120                 125

Ala Val Thr Ile Cys Thr Leu Asn Pro Tyr Arg Tyr Pro Glu Ile Lys
    130                 135                 140

Glu Glu Leu Glu Glu Leu Asp Arg Ile Thr Glu Gln Thr Leu Phe Asp
145                 150                 155                 160

Leu Tyr Lys Tyr Ser Ser Phe Thr Thr Leu Val Ala Gly Ser Arg Ser
                165                 170                 175

Arg Arg Asp Leu Arg Gly Thr Leu Pro His Pro Leu Gln Arg Leu Arg
                180                 185                 190

Val Pro Pro Pro His Gly Ala Arg Arg Ala Arg Ser Val Ala Ser
                195                 200                 205

Ser Leu Arg Asp Asn Asn Pro Gln Val Asp Trp Lys Asp Trp Lys Ile
    210                 215                 220

Gly Phe Gln Leu Cys Asn Gln Asn Lys Ser Asp Cys Phe Tyr Gln Thr
225                 230                 235                 240

Tyr Ser Ser Gly Val Asp Ala Val Arg Glu Trp Tyr Arg Phe His Tyr
                245                 250                 255

Ile Asn Ile Leu Ser Arg Leu Pro Glu Thr Leu Pro Ser Leu Glu Glu
                260                 265                 270

Asp Thr Leu Gly Asn Phe Ile Phe Ala Cys Arg Phe Asn Gln Val Ser
                275                 280                 285

Cys Asn Gln Ala Asn Tyr Ser His Phe His His Pro Met Tyr Gly Asn
    290                 295                 300

Cys Tyr Thr Phe Asn Asp Lys Asn Asn Ser Asn Leu Trp Met Ser Ser
305                 310                 315                 320

Met Pro Gly Ile Asn Asn Gly Leu Ser Leu Met Leu Arg Ala Glu Gln
                325                 330                 335

Asn Asp Phe Ile Pro Leu Leu Ser Thr Val Thr Gly Ala Arg Val Met
                340                 345                 350

Val His Gly Gln Asp Glu Pro Ala Phe Met Asp Asp Gly Gly Phe Asn
    355                 360                 365

Leu Arg Pro Gly Val Glu Thr Ser Ile Ser Met Arg Lys Glu Thr Leu
    370                 375                 380

Asp Arg Leu Gly Gly Asp Tyr Gly Asp Cys Thr Lys Asn Gly Ser Asp
385                 390                 395                 400

Val Pro Val Glu Asn Leu Tyr Pro Ser Lys Tyr Thr Gln Gln Val Cys
                405                 410                 415

Ile His Ser Cys Phe Gln Glu Ser Met Ile Lys Glu Cys Gly Cys Ala
                420                 425                 430

Tyr Ile Phe Tyr Pro Arg Pro Gln Asn Val Glu Tyr Cys Asp Tyr Arg
    435                 440                 445

Lys His Ser Ser Trp Gly Tyr Cys Tyr Tyr Lys Leu Gln Val Asp Phe
    450                 455                 460

Ser Ser Asp His Leu Gly Cys Phe Thr Lys Cys Arg Lys Pro Cys Ser
465                 470                 475                 480

Val Thr Ser Tyr Gln Leu Ser Ala Gly Tyr Ser Arg Trp Pro Ser Val
                485                 490                 495
```

Thr Ser Gln Glu Trp Val Phe Gln Met Leu Ser Arg Gln Asn Asn Tyr
            500                 505                 510

Thr Val Asn Asn Lys Arg Asn Gly Val Ala Lys Val Asn Ile Phe Phe
        515                 520                 525

Lys Glu Leu Asn Tyr Lys Thr Asn Ser Glu Ser Pro Ser Val Thr Met
    530                 535                 540

Val Thr Leu Leu Ser Asn Leu Gly Ser Gln Trp Ser Leu Trp Phe Gly
545                 550                 555                 560

Ser Ser Val Leu Ser Val Val Glu Met Ala Glu Leu Val Phe Asp Leu
                565                 570                 575

Leu Val Ile Met Phe Leu Met Leu Leu Arg Arg Phe Arg Ser Arg Tyr
            580                 585                 590

Trp Ser Pro Gly Arg Gly Gly Arg Gly Ala Gln Glu Val Ala Ser Thr
        595                 600                 605

Leu Ala Ser Ser Pro Pro Ser His Phe Cys Pro His Pro Met Ser Leu
    610                 615                 620

Ser Leu Ser Gln Pro Gly Pro Ala Pro Ser Pro Ala Leu Thr Ala Pro
625                 630                 635                 640

Pro Pro Ala Tyr Ala Thr Leu Gly Pro Arg Pro Ser Pro Gly Gly Ser
                645                 650                 655

Ala Gly Ala Ser Ser Ser Thr Cys Pro Leu Gly Gly Pro
            660                 665

<210> SEQ ID NO 26
<211> LENGTH: 3970
<212> TYPE: DNA
<213> ORGANISM: Homo sapiens

<400> SEQUENCE: 26

| | | |
|---|---|---|
| gcacccaggt cgggcggtgg gggcgagcgg aggggctgag gggcggagag gcctggcggg | 60 |
| ccgctgctgc gggccagggg acggggcgg agcggagcc ggagccgacg ggcggtggcc | 120 |
| gcactgggac cccggaatcc cgcgcgctgc ccacgattcg cttctgagga acctagaaag | 180 |
| attgtacaat gaatggtgat ctcgtgctg cggtggtgac ctcaccaccc ccgaccacag | 240 |
| cccctcacaa ggagaggtac ttcgaccgag tagatgagaa caacccagag tacttgaggg | 300 |
| agaggaacat ggcaccagac cttcgccagg acttcaacat gatggagcaa agaagagggg | 360 |
| tgtccatgat tctgcaaagc cctgctttct gtgaagaatt ggaatcaatg atacaggagc | 420 |
| aatttaagaa ggggaagaac cccacaggcc tattggcatt acagcagatt gcagatttta | 480 |
| tgaccacgaa tgtaccaaat gtctacccag cagctccgca aggagggatg gctgccttaa | 540 |
| acatgagtct tggtatggtg actcctgtga acgatcttag aggatctgat tctattgcgt | 600 |
| atgacaaagg agagaagtta ttacggtgta aattggcagc gttttataga ctagcagatc | 660 |
| tcttttgggtg gtctcagctt atctacaatc atatcacaac cagagtgaac tccgagcagg | 720 |
| aacacttcct cattgtccct tttgggcttc tttacagtga agtgactgca tccagtttgg | 780 |
| ttaagatcaa tctacaagga gatatagtag atcgtggaag cactaatctg ggagtgaatc | 840 |
| aggccggctt caccttacac tctgcaattt atgctgcacg cccggacgtg aagtgcgtcg | 900 |
| tgcacattca caccccagca ggggctgcgg tctctgcaat gaatgtggc ctcttgccaa | 960 |
| tctcccgga ggcgctttcc cttggagaag tggcttatca tgactaccat ggcattctgg | 1020 |
| ttgatgaaga ggaaaaagtt ttgattcaga aaaatctggg gcctaaaagc aaggttctta | 1080 |
| ttctccggaa ccatgggctc gtgtcagttg gagagagcgt tgaggaggcc ttctattaca | 1140 |

```
tccataacct tgtggttgcc tgtgagatcc aggttcgaac tctggccagt gcaggaggac    1200
cagacaactt agtcctgctg aatcctgaga agtacaaagc caagtcccgt tccccagggt    1260
ctccggtagg ggaaggcact ggatcgcctc ccaagtggca gattggtgag caggaatttg    1320
aagccctcat gcggatgctc gataatctgg gctacagaac tggctaccct tatcgatacc    1380
ctgctctgag agagaagtct aaaaaataca gcgatgtgga ggttcctgct agtgtcacag    1440
gttactcctt tgctagtgac ggtgattcgg gcacttgctc cccactcaga cacagttttc    1500
agaagcagca gcgggagaag acaagatggc tgaactctgg ccggggcgac gaagcttccg    1560
aggaagggca gaatggaagc agtcccaagt cgaagactaa gtggactaaa gaggatggac    1620
atagaacttc cacctctgct gtccctaacc tgtttgttcc attgaacact aacccaaaag    1680
aggtccagga gatgaggaac aagatccgag agcagaattt acaggacatt aagacggctg    1740
gccctcagtc ccaggttttg tgtggtgtag tgatggacag gagcctcgtc cagggagagc    1800
tggtgacggc ctccaaggcc atcattgaaa aggagtacca gccccacgtc attgtgagca    1860
ccacgggccc caacccctcc accacactca cagaccgtga gctggaggag taccgcaggg    1920
aggtggagag gaagcagaag ggctctgaag agaatctgga cgaggctaga aacagaaag    1980 aaaagagtcc tccagaccag cctgcggtcc ccacccgcc tcccagcact cccatcaagc    2040
tggaggaaga ccttgtgccg gagccgacta ctggagatga cagtgatgct gccacctta    2100 agccaactct ccccgatctg tccctgatg aaccttcaga agcactcggc ttcccaatgt    2160
tagagaagga ggaggaagcc catagacccc caagccccac tgaggcccct actgaggcca    2220
gccccgagcc agccccagac ccagcccgg tggctgaaga ggctgccccc tcagctgtcg    2280
aggagggggc cgccgcggac cctggcagcg atgggtctcc aggcaagtcc ccgtccaaaa    2340
agaagaagaa gttccgtacc ccgtcctttc tgaagaagag caagaagaag agtgactcct    2400
gaaagccctg cgctaacact gtcctgtccg gagcgaccct ggctctgcca gcgtccccgg    2460
ccacgtctgt gctctgtcct tgtgtaatgg aatgcaaaaa agccaagccc tccgcctaga    2520
ggtcccctca cgtgaccagc cccgtgtagc cccgggctga cccagtgtgt gctcagcagc    2580 cccacccac cctgccccctt gtcctctcag agcctcagct tctggggag acatgctctc    2640 cccacagggg ggaggcacta agtcatggtc ctggctggaa ggtactgaag gcttctgcag    2700
ctttggctgc acgtcaccct cctgagcctc acctttcctg ccgtccctcc tgttgtgaaa    2760
tcaccacatt ctgtctctgc ttggcttccc ctccacccta aagtctcagg tgacggactc    2820
agactcctgg cttcatgtgg cattctctct gctcagtgat ctcacttaaa tctatataca    2880
aagccttggt cccgtgaaaa cactcgtgtg cccaccagcg gccttgaaga ggcaggtctg    2940
ggccagatgc tgggcaggaa accccagcgg cagatgggcc tgtgtgcacc caacgtgatg    3000
ctatgcatgt ctgaccgacg atccctcgac cagaatcaga ttcaggagct cagtttcttt    3060
ttcacttggg tctctggatt cctgtcatag ggaaggtata tcaggagggg aagaggcctt    3120
tctagaattt tctttgagca ggtttacaat ttagcttaca ttttttcgact gtgaacgtga    3180 ataggctgct ttttgctttc ttcttttccag accccacagt agagcacttt tcacttattt    3240
gggggaggct tcagggggact gttctcacct taactcagcc agaaagatgc cctagttgtg    3300
atcaaaggta actcgaggtg gagggtagcc ctggggcccc tcgacatcac cgtcattgat    3360
ggagcctgaa ccgtgtgctc ctcggcagat gctgttgttg ttacttccct ccaagaggct    3420
ggaaaagggc tcagagctgc tgagcaggaa ccggagggtg acccatttca ggaggtgccg    3480
gtaccagcct gactaggtac aggcaagctt gtgtgggccc aacaggccct tggtagagct    3540
```

```
ggtgccagat gtgggctcag atcctgggca tgatgggccg agccacctcg gatcccactg    3600
attggccagc cgagcgagaa ccaggctgct gcatggcact gaccgccgct tccagcttcc    3660
tctgagccgc agggcctgct acgcgggcaa gcgtgctgcc tctcttctgt gtcgttttgt    3720
tgccaaggca gaatgaaaag tccttaaccg tggactcttc ctttatcccc tcctttaccc    3780
cacatatgca atgactttta attttcactt ttgtagttta atcctttgta ttacaacatg    3840
aaatatagtt gcatatatgg acaccgactt gggaggacag gtcctgaatg tcctttctcc    3900
agtgtaacat gttttactca caaataaaat tctttcagca agttccttgt ctaaaaaaaa    3960
aaaaaaaaaa                                                           3970
```

<210> SEQ ID NO 27
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = G or T

<400> SEQUENCE: 27

```
ccggggcgac gaagcttccg aggaanggca gaatggaagc agtcccaagt c             51
```

<210> SEQ ID NO 28
<211> LENGTH: 737
<212> TYPE: PRT
<213> ORGANISM: Homo sapiens

<400> SEQUENCE: 28

```
Met Asn Gly Asp Ser Arg Ala Ala Val Val Thr Ser Pro Pro Pro Thr
1               5                   10                  15

Thr Ala Pro His Lys Glu Arg Tyr Phe Asp Arg Val Asp Glu Asn Asn
            20                  25                  30

Pro Glu Tyr Leu Arg Glu Arg Asn Met Ala Pro Asp Leu Arg Gln Asp
        35                  40                  45

Phe Asn Met Met Glu Gln Lys Lys Arg Val Ser Met Ile Leu Gln Ser
    50                  55                  60

Pro Ala Phe Cys Glu Glu Leu Glu Ser Met Ile Gln Glu Gln Phe Lys
65                  70                  75                  80

Lys Gly Lys Asn Pro Thr Gly Leu Leu Ala Leu Gln Gln Ile Ala Asp
                85                  90                  95

Phe Met Thr Thr Asn Val Pro Asn Val Tyr Pro Ala Ala Pro Gln Gly
            100                 105                 110

Gly Met Ala Ala Leu Asn Met Ser Leu Gly Met Val Thr Pro Val Asn
        115                 120                 125

Asp Leu Arg Gly Ser Asp Ser Ile Ala Tyr Asp Lys Gly Glu Lys Leu
    130                 135                 140

Leu Arg Cys Lys Leu Ala Ala Phe Tyr Arg Leu Ala Asp Leu Phe Gly
145                 150                 155                 160

Trp Ser Gln Leu Ile Tyr Asn His Ile Thr Thr Arg Val Asn Ser Glu
                165                 170                 175

Gln Glu His Phe Leu Ile Val Pro Phe Gly Leu Leu Tyr Ser Glu Val
            180                 185                 190

Thr Ala Ser Ser Leu Val Lys Ile Asn Leu Gln Gly Asp Ile Val Asp
        195                 200                 205

Arg Gly Ser Thr Asn Leu Gly Val Asn Gln Ala Gly Phe Thr Leu His
```

```
            210                 215                 220
Ser Ala Ile Tyr Ala Ala Arg Pro Asp Val Lys Cys Val Val His Ile
225                 230                 235                 240

His Thr Pro Ala Gly Ala Ala Val Ser Ala Met Lys Cys Gly Leu Leu
                245                 250                 255

Pro Ile Ser Pro Glu Ala Leu Ser Leu Gly Glu Val Ala Tyr His Asp
                260                 265                 270

Tyr His Gly Ile Leu Val Asp Glu Glu Lys Val Leu Ile Gln Lys
                275                 280                 285

Asn Leu Gly Pro Lys Ser Lys Val Leu Ile Leu Arg Asn His Gly Leu
                290                 295                 300

Val Ser Val Gly Glu Ser Val Glu Glu Ala Phe Tyr Tyr Ile His Asn
305                 310                 315                 320

Leu Val Val Ala Cys Glu Ile Gln Val Arg Thr Leu Ala Ser Ala Gly
                325                 330                 335

Gly Pro Asp Asn Leu Val Leu Leu Asn Pro Glu Lys Tyr Lys Ala Lys
                340                 345                 350

Ser Arg Ser Pro Gly Ser Pro Val Gly Glu Gly Thr Gly Ser Pro Pro
                355                 360                 365

Lys Trp Gln Ile Gly Glu Gln Glu Phe Glu Ala Leu Met Arg Met Leu
                370                 375                 380

Asp Asn Leu Gly Tyr Arg Thr Gly Tyr Pro Tyr Arg Tyr Pro Ala Leu
385                 390                 395                 400

Arg Glu Lys Ser Lys Lys Tyr Ser Asp Val Glu Val Pro Ala Ser Val
                405                 410                 415

Thr Gly Tyr Ser Phe Ala Ser Asp Gly Asp Ser Gly Thr Cys Ser Pro
                420                 425                 430

Leu Arg His Ser Phe Gln Lys Gln Gln Arg Glu Lys Thr Arg Trp Leu
                435                 440                 445

Asn Ser Gly Arg Gly Asp Glu Ala Ser Glu Glu Gly Gln Asn Gly Ser
                450                 455                 460

Ser Pro Lys Ser Lys Thr Lys Trp Thr Lys Glu Asp Gly His Arg Thr
465                 470                 475                 480

Ser Thr Ser Ala Val Pro Asn Leu Phe Val Pro Leu Asn Thr Asn Pro
                485                 490                 495

Lys Glu Val Gln Glu Met Arg Asn Lys Ile Arg Glu Gln Asn Leu Gln
                500                 505                 510

Asp Ile Lys Thr Ala Gly Pro Gln Ser Gln Val Leu Cys Gly Val Val
                515                 520                 525

Met Asp Arg Ser Leu Val Gln Gly Glu Leu Val Thr Ala Ser Lys Ala
530                 535                 540

Ile Ile Glu Lys Glu Tyr Gln Pro His Val Ile Val Ser Thr Thr Gly
545                 550                 555                 560

Pro Asn Pro Phe Thr Thr Leu Thr Asp Arg Glu Leu Glu Glu Tyr Arg
                565                 570                 575

Arg Glu Val Glu Arg Lys Gln Lys Gly Ser Glu Glu Asn Leu Asp Glu
                580                 585                 590

Ala Arg Glu Gln Lys Glu Lys Ser Pro Pro Asp Gln Pro Ala Val Pro
                595                 600                 605

His Pro Pro Ser Thr Pro Ile Lys Leu Glu Glu Asp Leu Val Pro
                610                 615                 620

Glu Pro Thr Thr Gly Asp Asp Ser Asp Ala Ala Thr Phe Lys Pro Thr
625                 630                 635                 640
```

```
Leu Pro Asp Leu Ser Pro Asp Glu Pro Ser Glu Ala Leu Gly Phe Pro
                645                 650                 655
Met Leu Glu Lys Glu Glu Ala His Arg Pro Ser Pro Thr Glu
            660                 665                 670
Ala Pro Thr Glu Ala Ser Pro Glu Pro Ala Pro Asp Pro Ala Pro Val
            675                 680                 685
Ala Glu Glu Ala Ala Pro Ser Ala Val Glu Glu Gly Ala Ala Ala Asp
        690                 695                 700
Pro Gly Ser Asp Gly Ser Pro Gly Lys Ser Pro Ser Lys Lys Lys Lys
705                 710                 715                 720
Lys Phe Arg Thr Pro Ser Phe Leu Lys Lys Ser Lys Lys Lys Ser Asp
                725                 730                 735
Ser
```

<210> SEQ ID NO 29
<211> LENGTH: 5582
<212> TYPE: DNA
<213> ORGANISM: Homo sapiens

<400> SEQUENCE: 29

```
ctggcccctc cctggacacc caggcgacaa tggcagaact gcccacaaca gagacgcctg      60
gggacgccac tttgtgcagc gggcgcttca ccatcagcac actgctgagc agtgatgagc     120
cctctccacc agctgcctat gacagcagcc accccagcca cctgacccac agcagcacct     180
tctgcatgcg caccttgcc tacaaacacga tcgatgtggt gcccacatat gagcactatg     240
ccaacagcac ccagcctggt gagccccgga aggtccggcc cacactggct gacctgcact     300
ccttcctcaa gcaggaaggc agacacctgc atgcccctggc ctttgacagc cggcccagcc     360
acgagatgac tgatgggctg gtggagggcg aggcaggcac cagcagcgag aagaaccccg     420
aggagccagt gcgcttcggc tgggtcaagg gggtgatgat tcgttgcatg ctcaacattt     480
ggggcgtgat cctctacctg cggctgccct ggattacggc ccaggcaggc atcgtcctga     540
cctggatcat catcctgctg tcggtcacgg tgacctccat acaggcctc tccatctcag     600
ccatctccac caatggcaag gtcaagtcag gtggcaccta cttcctcatc tcccggagtc     660
tgggcccaga gcttggggc tccatcggcc tcattttcgc tttcgccaat gccgtgggtg     720
tggccatgca cacggtgggc tttgcagaga ccgtgcggga cctgctccag gagtatgggg     780
cacccatcgt ggaccccatt aacgacatcc gcatcattgg cgtggtctcg gtcactgtgc     840
tgctggccat ctccctggct ggcatggagt gggagtccaa ggcccaggtg ctgttcttcc     900
ttgtcatcat ggtctccttt gccaactatt agtggggac gctgatcccc ccatctgagg     960
acaaggcctc caaggcttc ttcagctacc gggcggacat ttttgtccag aacttggtgc    1020
ctgactggcg gggtccagat ggcaccttct tcggaatgtt ctccatcttc ttcccctcgg    1080
ccacaggcat cctggcaggg gccaacatat ctggtgacct caaggaccct gctatagcca    1140
tccccaaggg gaccctcatg gccatttttct ggacgaccat ttcctacctg gccatctcag    1200
ccaccattgg ctcctgcgtg gtgcgtgatg cctctggggt cctgaatgac acagtgaccc    1260
ctgggctggg tgcctgcgag gggctggcct gcagctatgg ctggaacttc accgagtgca    1320
cccagcagca cagctgccac tacggcctca tcaactatta ccagaccatg agcatggtgt    1380
caggcttcgc gccctgatc acggctggca tcttcgggc cacctctcc ctgccctgg    1440
cctgccttgt ctctgctgcc aaagtcttcc agtgcctttg cgaggaccag ctgtacccac    1500
```

```
tgatcggctt cttcggcaaa ggctatggca agaacaagga gcccgtgcgt ggctacctgc   1560
tggcctacgc catcgctgtg gccttcatca tcatcgctga gctcaacacc atagccccca   1620
tcatttccaa cttcttcctc tgctcctatg ccctcatcaa cttcagctgc ttccacgcct   1680
ccatcaccaa ctcgcctggg tggagacctt cattccaata ctacaacaag tgggcggcgc   1740
tgtttgggge tatcatctcc gtggtcatca tgttcctcct cacctggtgg gcggccctca   1800
tcgccattgg cgtggtgctc ttcctcctgc tctatgtcat ctacaagaag ccagaggtaa   1860
attgggcte ctcggtacag gctggctcct acaacctggc cctcagctac tcggtgggcc    1920
tcaatgaggt ggaagaccac atcaagaact accgccccca gtgcctggtg ctcacggggc   1980
cccccaactt ccgcccggcc ctggtggact tgtgggcac cttcacccgg aacctcagcc    2040
tgatgatctg tggccacgtg ctcatcggac cccacaagca gaggatgcct gagctccagc   2100
tcatcgccaa cgggcacacc aagtggctga acaagaggaa gatcaaggcc ttctactcgg   2160
atgtcattgc cgaggacctc cgcagaggcg tccagatcct catgcaggcc gcaggtctcg   2220
ggagaatgaa gcccaacatt ctggtggttg ggttcaagaa gaactggcag tcggctcacc   2280
cggccacagt ggaagactac attggcatcc tccatgatgc ctttgatttc aactatggcg   2340
tgtgtgtcat gaggatgcgg gagggactca acgtgtccaa gatgatgcag cgcacatta    2400
accccgtgtt tgacccagcg gaggacggga aggaagccag cgccagaggt gccaggccat   2460
cagtctctgg cgcttttggac cccaaggccc tggtgaagga ggagcaggcc accaccatct   2520
tccagtcgga gcagggcaag aagaccatag acatctactg gctctttgac gatggaggcc   2580
tcaccctcct cattccctat ctccttggcc gcaagaggag gtggagcaaa tgcaagatcc   2640
gtgtgttcgt aggcggccag attaacagga tggaccagga gagaaaggcg atcatttctc   2700
tgctgagcaa gttccgactg ggattccatg aagtccacat cctccctgac atcaaccaga   2760
accctcgggc tgagcacacc aagaggtttg aggacatgat tgcacccttc cgtctgaatg   2820
atggcttcaa ggatgaggcc actgtcaacg agatgcggcg ggactgcccc tggaagatct   2880
cagatgagga gattacgaag aacagagtca agtcccttcg gcaggtgagg ctgaatgaga   2940
ttgtgctgga ttactcccga gacgctgctc tcatcgtcat cactttgccc ataggggaga   3000
agggaagtg ccccagctcg ctgtacatgg cctggctgga gaccctgtcc caggacctca    3060
gacctccagt catcctgatc cgaggaaacc aggaaaacgt gctccacctt tactgccagt   3120
aactccaggc tttgacatcc ctgtccacag ctctgagtgt gtgggataag ttggaacttg   3180
attgcctcta gtccacaggg atgagactca tgttctgttg cactttaagt ggcagcatct   3240
gatgatctca ccgaaaaaga tggtagattt ccaaatctgg ctggactcca cttccatggg   3300
acacattccc tgggtcttgt gtttataggc tagagaaata gcagatggag ctgcaaggaa   3360
aactctctaa agcatcctat tccttttaaa ggatttcttt tgattttgat gaccattaat   3420
taagagttca gtctttgatt tgtatgcaaa ttggagtccc aatgctgggc gtgaatcttg   3480
acagtttcta cagaccttcc tgggtgaaag ttcctaaatc atgccctgct tcctccaata   3540
ggagaatggg agcctcacct gtaggaccta caggctctct aaggaatgca ggtctctctc   3600
tgagcctcca cagccaggca aatacatata tatatatttt tttttagat gaagtttttt    3660
ctcttgttgc ccaggctagg gtgtaatggc atgatctcag gtcactgcaa cctcctcccg   3720
ggttcaagca tttcttctgt ctcagcctcc cgaatagctg ggattacagg cacctgccat   3780
cacacgagct aattttttgta ttttttagtag agatgggggtt tcaccatgtt gaccaggctg   3840
gtgttgagct cctgacctca ggtgatccac ccacctcggt ctcccaaagt gctggggtta   3900
```

-continued

```
caggcctgag ccactgcgcc cggcccaggc aaatttcttg aaccacttct cactcccgtc   3960
actttcaata aggggtcttt gatgtcttca ctggttcttt ggacgaggga cttttcgaac   4020
ttttttggtt gcaacacaca gtaagaaata tacttcacac tgagacttgc agcgcacaca   4080
cacggaaacg accaaaacaa aaatgtcaca aaacaatact tacccttccc tggggacgt   4140 cctccagtat gttctgttct gtttattttt cactgttggt tgcaatccaa taaaatgact   4200
ttgggatcca ctcatgggtg gggacccaca catttgaaag gcatggccac cttctgttg   4260 tgccttgcat ttgtccacac acagggagtc tggctgagct ggggaaaggc cacggctggg   4320
tgtcattgcc atttcccag ctcatctcac cgggaagaaa agcagattga cagaacacgt   4380
gaggaggggt attgatggca ggagagtcaa aaaagagttt taagaaggg gcaaggttga   4440 aggagtctag tggcaagggt aagatttcag gcatggttaa gaacagacga caaggatgtc   4500
aggaatgaag atgtggagag gggtgtagag atggcaaggt tggcaaggaa cagataggca   4560
ggagcaggtc caagccaagc ctagcccaag accaggtgaa aggagagggg aggaggagcc   4620
acctgcaaga gatggaaaga gcaggcggca gaggggctg gcagggaggg gctgttaaga   4680
gtggggttgg aggtgggaga gaagctagga caagggagat ggagaaagga cctatacctg   4740
gctcacggaa ggccttcagg tcactacacg ttgaacatcc ccagtgtttg agccccaaa   4800 gctagggtgc aagagcactg ccatcgaatg ccagtgggtg aggccaagtg agggtatttg   4860
cagctctaga cataaccaag aagcgtaaag gtgagttgtt tggtggtacg actgcctgtg   4920
ccttcttccg atggcactgg ggtggctgaa ggaacagaca tctttgggtt tcatcagcct   4980
cctccaagac tgctgcagtg cctacacttt agacttcaga aggagactaa agacttctag   5040
aatttagaag gagatctgaa gtctcctttc tggagttaca acccaaagga tgttagcatt   5100
tctcaggtca tcccactgca aagcccagaa ggcttgggc tcccaggctg ctctgaagcc   5160
ccactgtctg accgcctcag ggcttgctac gagggactgg ggcacggcca agctgactag   5220
gaacagctct cgtgctcctg agggacctgg aggatgggcc tgcctcccag ccattgagct   5280
ggattctggg ataattctta actcgaaata aggggaagca tccatcaggg aatgctggcc   5340
tttctagagc cacgtagaaa acaattttct ggttcttcaa acctcaaaga gtccttggtc   5400
caaaaaacag aatgttttgg cttcgggtgt caaaaaaaaa attttcacga tgtcagaaat   5460
agtatgtttt taacaatagt aatagctttg taaaaaaata aaaagcttta acagcgaggc   5520
cataaacaat gaaatgaata aaaacggtgg tcattcagtc aacggaaaaa aaaaaaaaa   5580 aa                                                                 5582
```

<210> SEQ ID NO 30
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or G

<400> SEQUENCE: 30

```
cccattaacg acatccgcat cattgncgtg gtctcggtca ctgtgctgct g            51
```

<210> SEQ ID NO 31
<211> LENGTH: 1030
<212> TYPE: PRT
<213> ORGANISM: Homo sapiens

```
<400> SEQUENCE: 31

Met Ala Glu Leu Pro Thr Thr Glu Thr Pro Gly Asp Ala Thr Leu Cys
1               5                   10                  15

Ser Gly Arg Phe Thr Ile Ser Thr Leu Leu Ser Ser Asp Glu Pro Ser
                20                  25                  30

Pro Pro Ala Ala Tyr Asp Ser Ser His Pro Ser His Leu Thr His Ser
            35                  40                  45

Ser Thr Phe Cys Met Arg Thr Phe Gly Tyr Asn Thr Ile Asp Val Val
        50                  55                  60

Pro Thr Tyr Glu His Tyr Ala Asn Ser Thr Gln Pro Gly Glu Pro Arg
65                  70                  75                  80

Lys Val Arg Pro Thr Leu Ala Asp Leu His Ser Phe Leu Lys Gln Glu
                85                  90                  95

Gly Arg His Leu His Ala Leu Ala Phe Asp Ser Arg Pro Ser His Glu
            100                 105                 110

Met Thr Asp Gly Leu Val Glu Gly Ala Gly Thr Ser Ser Glu Lys
        115                 120                 125

Asn Pro Glu Glu Pro Val Arg Phe Gly Trp Val Lys Gly Val Met Ile
130                 135                 140

Arg Cys Met Leu Asn Ile Trp Gly Val Ile Leu Tyr Leu Arg Leu Pro
145                 150                 155                 160

Trp Ile Thr Ala Gln Ala Gly Ile Val Leu Thr Trp Ile Ile Ile Leu
                165                 170                 175

Leu Ser Val Thr Val Thr Ser Ile Thr Gly Leu Ser Ile Ser Ala Ile
            180                 185                 190

Ser Thr Asn Gly Lys Val Lys Ser Gly Gly Thr Tyr Phe Leu Ile Ser
        195                 200                 205

Arg Ser Leu Gly Pro Glu Leu Gly Gly Ser Ile Gly Leu Ile Phe Ala
210                 215                 220

Phe Ala Asn Ala Val Gly Val Ala Met His Thr Val Gly Phe Ala Glu
225                 230                 235                 240

Thr Val Arg Asp Leu Leu Gln Glu Tyr Gly Ala Pro Ile Val Asp Pro
                245                 250                 255

Ile Asn Asp Ile Arg Ile Ile Gly Val Val Ser Val Thr Val Leu Leu
            260                 265                 270

Ala Ile Ser Leu Ala Gly Met Glu Trp Glu Ser Lys Ala Gln Val Leu
        275                 280                 285

Phe Phe Leu Val Ile Met Val Ser Phe Ala Asn Tyr Leu Val Gly Thr
290                 295                 300

Leu Ile Pro Pro Ser Glu Asp Lys Ala Ser Lys Gly Phe Phe Ser Tyr
305                 310                 315                 320

Arg Ala Asp Ile Phe Val Gln Asn Leu Val Pro Asp Trp Arg Gly Pro
                325                 330                 335

Asp Gly Thr Phe Phe Gly Met Phe Ser Ile Phe Phe Pro Ser Ala Thr
            340                 345                 350

Gly Ile Leu Ala Gly Ala Asn Ile Ser Gly Asp Leu Lys Asp Pro Ala
        355                 360                 365

Ile Ala Ile Pro Lys Gly Thr Leu Met Ala Ile Phe Trp Thr Thr Ile
370                 375                 380

Ser Tyr Leu Ala Ile Ser Ala Thr Ile Gly Ser Cys Val Val Arg Asp
385                 390                 395                 400

Ala Ser Gly Val Leu Asn Asp Thr Val Thr Pro Gly Trp Gly Ala Cys
                405                 410                 415
```

```
Glu Gly Leu Ala Cys Ser Tyr Gly Trp Asn Phe Thr Glu Cys Thr Gln
            420                 425                 430

Gln His Ser Cys His Tyr Gly Leu Ile Asn Tyr Tyr Gln Thr Met Ser
        435                 440                 445

Met Val Ser Gly Phe Ala Pro Leu Ile Thr Ala Gly Ile Phe Gly Ala
450                 455                 460

Thr Leu Ser Ser Ala Leu Ala Cys Leu Val Ser Ala Ala Lys Val Phe
465                 470                 475                 480

Gln Cys Leu Cys Glu Asp Gln Leu Tyr Pro Leu Ile Gly Phe Phe Gly
                485                 490                 495

Lys Gly Tyr Gly Lys Asn Lys Glu Pro Val Arg Gly Tyr Leu Leu Ala
                500                 505                 510

Tyr Ala Ile Ala Val Ala Phe Ile Ile Ile Ala Glu Leu Asn Thr Ile
            515                 520                 525

Ala Pro Ile Ile Ser Asn Phe Phe Leu Cys Ser Tyr Ala Leu Ile Asn
530                 535                 540

Phe Ser Cys Phe His Ala Ser Ile Thr Asn Ser Pro Gly Trp Arg Pro
545                 550                 555                 560

Ser Phe Gln Tyr Tyr Asn Lys Trp Ala Ala Leu Phe Gly Ala Ile Ile
                565                 570                 575

Ser Val Val Ile Met Phe Leu Leu Thr Trp Trp Ala Ala Leu Ile Ala
            580                 585                 590

Ile Gly Val Val Leu Phe Leu Leu Tyr Val Ile Tyr Lys Lys Pro
            595                 600                 605

Glu Val Asn Trp Gly Ser Ser Val Gln Ala Gly Ser Tyr Asn Leu Ala
            610                 615                 620

Leu Ser Tyr Ser Val Gly Leu Asn Glu Val Glu Asp His Ile Lys Asn
625                 630                 635                 640

Tyr Arg Pro Gln Cys Leu Val Leu Thr Gly Pro Pro Asn Phe Arg Pro
                645                 650                 655

Ala Leu Val Asp Phe Val Gly Thr Phe Thr Arg Asn Leu Ser Leu Met
                660                 665                 670

Ile Cys Gly His Val Leu Ile Gly Pro His Lys Gln Arg Met Pro Glu
            675                 680                 685

Leu Gln Leu Ile Ala Asn Gly His Thr Lys Trp Leu Asn Lys Arg Lys
        690                 695                 700

Ile Lys Ala Phe Tyr Ser Asp Val Ile Ala Glu Asp Leu Arg Arg Gly
705                 710                 715                 720

Val Gln Ile Leu Met Gln Ala Ala Gly Leu Gly Arg Met Lys Pro Asn
                725                 730                 735

Ile Leu Val Val Gly Phe Lys Lys Asn Trp Gln Ser Ala His Pro Ala
            740                 745                 750

Thr Val Glu Asp Tyr Ile Gly Ile Leu His Asp Ala Phe Asp Phe Asn
            755                 760                 765

Tyr Gly Val Cys Val Met Arg Met Arg Glu Gly Leu Asn Val Ser Lys
        770                 775                 780

Met Met Gln Ala His Ile Asn Pro Val Phe Asp Pro Ala Glu Asp Gly
785                 790                 795                 800

Lys Glu Ala Ser Ala Arg Gly Ala Arg Pro Ser Val Ser Gly Ala Leu
                805                 810                 815

Asp Pro Lys Ala Leu Val Lys Glu Glu Gln Ala Thr Thr Ile Phe Gln
            820                 825                 830
```

```
Ser Glu Gln Gly Lys Lys Thr Ile Asp Ile Tyr Trp Leu Phe Asp Asp
        835                 840                 845
Gly Gly Leu Thr Leu Leu Ile Pro Tyr Leu Leu Gly Arg Lys Arg Arg
    850                 855                 860
Trp Ser Lys Cys Lys Ile Arg Val Phe Val Gly Gly Gln Ile Asn Arg
865                 870                 875                 880
Met Asp Gln Glu Arg Lys Ala Ile Ile Ser Leu Leu Ser Lys Phe Arg
                885                 890                 895
Leu Gly Phe His Glu Val His Ile Leu Pro Asp Ile Asn Gln Asn Pro
                900                 905                 910
Arg Ala Glu His Thr Lys Arg Phe Glu Asp Met Ile Ala Pro Phe Arg
                915                 920                 925
Leu Asn Asp Gly Phe Lys Asp Glu Ala Thr Val Asn Glu Met Arg Arg
    930                 935                 940
Asp Cys Pro Trp Lys Ile Ser Asp Glu Glu Ile Thr Lys Asn Arg Val
945                 950                 955                 960
Lys Ser Leu Arg Gln Val Arg Leu Asn Glu Ile Val Leu Asp Tyr Ser
                965                 970                 975
Arg Asp Ala Ala Leu Ile Val Ile Thr Leu Pro Ile Gly Arg Lys Gly
                980                 985                 990
Lys Cys Pro Ser Ser Leu Tyr Met Ala Trp Leu Glu Thr Leu Ser Gln
                995                 1000                1005
Asp Leu Arg Pro Pro Val Ile Leu Ile Arg Gly Asn Gln Glu Asn Val
        1010                1015                1020
Leu Thr Phe Tyr Cys Gln
1025                1030

<210> SEQ ID NO 32

<400> SEQUENCE: 32

000

<210> SEQ ID NO 33
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or T

<400> SEQUENCE: 33
cacttcctcc aaaaaaaaag aaaacnccat ttcccctcaa ctcttccagt t          51

<210> SEQ ID NO 34
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = C or G

<400> SEQUENCE: 34
aatgttaaca gtatagaaaa ttttanctca acaaatagag aatatcagta a           51

<210> SEQ ID NO 35
<211> LENGTH: 50
<212> TYPE: DNA
<213> ORGANISM: Artificial Sequence
```

```
<220> FEATURE:
<223> OTHER INFORMATION: A synthetic oligonucleotide

<400> SEQUENCE: 35
tcccatttct ctagacctgc tgcctataca gtcactttta tgtggtttcg        50

<210> SEQ ID NO 36
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 36
acgttggatg agacatgacg atgcccatgc                              30

<210> SEQ ID NO 37
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 37
acgttggatg agcgccttct tgctggcac                               29

<210> SEQ ID NO 38
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 38
acgttggatg ctgtgacagg atggaagact                              30

<210> SEQ ID NO 39
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 39
acgttggatg tggacgtagg tgttgaaagc                              30

<210> SEQ ID NO 40
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 40
acgttggatg tgttcgtcca caccttagtc                              30

<210> SEQ ID NO 41
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 41
acgttggatg acaagatggc tgaactctgg                              30
```

<210> SEQ ID NO 42
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 42
acgttggatg ggaatccagg agaataggtc                                30

<210> SEQ ID NO 43
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 43
acgttggatg acaggctacc tggctttaac                                30

<210> SEQ ID NO 44
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 44
acgttggatg gcctcgttgc tgcctcccg                                 29

<210> SEQ ID NO 45
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 45
acgttggatg atcagcagac ccatgcccg                                 29

<210> SEQ ID NO 46
<211> LENGTH: 28
<212> TYPE: DNA
<213> ORGANISM: Artificial Sequence
<220> FEATURE:
<223> OTHER INFORMATION: A synthetic oligonucleotide

<400> SEQUENCE: 46
acgttggatg agccctgcgc gcgcagca                                  28

<210> SEQ ID NO 47
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 47
acgttggatg tcaaccccat catctactgc                                30

<210> SEQ ID NO 48
<211> LENGTH: 30
<212> TYPE: DNA
<213> ORGANISM: Artificial Sequence
<220> FEATURE:
<223> OTHER INFORMATION: A synthetic oligonucleotide -continued

<400> SEQUENCE: 48
acgttggatg ctgacattgc cagctgtatc                                              30

<210> SEQ ID NO 49
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 49
acgttggatg gtagtggcac tggcatattc                                              30

<210> SEQ ID NO 50
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 50
acgttggatg gcaaccatca cagtactaag                                              30

<210> SEQ ID NO 51
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 51
acgttggatg cacaactgga agagttgagg                                              30

<210> SEQ ID NO 52
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 52
acgttggatg tggaccccat taacgacatc                                              30

<210> SEQ ID NO 53
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 53
acgttggatg tcaccttgga ctcccactc                                               29

<210> SEQ ID NO 54
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 54
acgttggatg cactttccat aaaagcaagg                                              30

<210> SEQ ID NO 55

<210> SEQ ID NO 55
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 55
acgttggatg gcaataattt tcccactatc                                              30

<210> SEQ ID NO 56
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 56
acgttggatg atgagagaca tgacgatgcc                                              30

<210> SEQ ID NO 57
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 57
acgttggatg gaacggcagc gccttcttg                                               29

<210> SEQ ID NO 58
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 58
acgttggatg gaaacagtga cagccaaatg                                              30

<210> SEQ ID NO 59
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 59
acgttggatg gtttttcagt tcctgaattt g                                            31

<210> SEQ ID NO 60
<211> LENGTH: 15
<212> TYPE: DNA
<213> ORGANISM: Artificial Sequence
<220> FEATURE:
<223> OTHER INFORMATION: A synthetic oligonucleotide

<400> SEQUENCE: 60
acacctcgtc cctttt                                                             15

<210> SEQ ID NO 61
<211> LENGTH: 15
<212> TYPE: DNA
<213> ORGANISM: Artificial Sequence
<220> FEATURE:
<223> OTHER INFORMATION: A synthetic oligonucleotide

<400> SEQUENCE: 61
ctggctgctc cctga                                                15

<210> SEQ ID NO 62
<211> LENGTH: 17
<212> TYPE: DNA
<213> ORGANISM: Artificial Sequence
<220> FEATURE:
<223> OTHER INFORMATION: A synthetic oligonucleotide

<400> SEQUENCE: 62
actgcttcca ttctgcc                                              17

<210> SEQ ID NO 63
<211> LENGTH: 17
<212> TYPE: DNA
<213> ORGANISM: Artificial Sequence
<220> FEATURE:
<223> OTHER INFORMATION: A synthetic oligonucleotide

<400> SEQUENCE: 63
agtctctgta agtgccc                                              17

<210> SEQ ID NO 64
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 64
gtgcctcccg ccagcgaa                                             18

<210> SEQ ID NO 65
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 65
cgcgcgcagc agagcagt                                             18

<210> SEQ ID NO 66
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 66
agctgtatct gctccattca                                           20

<210> SEQ ID NO 67
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 67
tcctccaaaa aaaagaaaa c                                          21

<210> SEQ ID NO 68
<211> LENGTH: 22
<212> TYPE: DNA

<213> ORGANISM: Artificial Sequence
<220> FEATURE:
<223> OTHER INFORMATION: A synthetic oligonucleotide

<400> SEQUENCE: 68
gttaccgaca tccgcatcat tg                                    22

<210> SEQ ID NO 69
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 69
taagtaattt gttatgggtt cc                                    22

<210> SEQ ID NO 70
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 70 ggagggtcc ggcgcatggc ttc                                    23

<210> SEQ ID NO 71
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 71
caaatgttaa cagtatagaa aatttta                               27

<210> SEQ ID NO 72
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 72
ttcagtccct cctgagcta                                        19

<210> SEQ ID NO 73
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 73
aaggtggatg cacaaagag                                        19

<210> SEQ ID NO 74
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 74
gtgcatctgt agcagtcctc                                       20

<210> SEQ ID NO 75
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 75
ccaaactgga atcaacagaa					20

<210> SEQ ID NO 76
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 76
gaagtggtct cgtctagcaa					20

<210> SEQ ID NO 77
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 77
cagagagaga ggtcccattt					20

<210> SEQ ID NO 78
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 78
ccactcaaac ctttcaacaa					20

<210> SEQ ID NO 79
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 79
tggacagaac aatctggaac					20

<210> SEQ ID NO 80
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 80
cccatttctc tagacctgct					20

<210> SEQ ID NO 81
<211> LENGTH: 20
<212> TYPE: DNA
<213> ORGANISM: Artificial Sequence
<220> FEATURE:

```
<223> OTHER INFORMATION: A synthetic oligonucleotide

<400> SEQUENCE: 81
gggatggtgt ctcgtacata                                                    20

<210> SEQ ID NO 82
<211> LENGTH: 46
<212> TYPE: DNA
<213> ORGANISM: Artificial Sequence
<220> FEATURE:
<223> OTHER INFORMATION: A synthetic oligonucleotide

<400> SEQUENCE: 82
gaagagattg aacgtgtcgt tggcagaaac cggagcccct gcatgc                       46

<210> SEQ ID NO 83
<211> LENGTH: 46
<212> TYPE: DNA
<213> ORGANISM: Artificial Sequence
<220> FEATURE:
<223> OTHER INFORMATION: A synthetic oligonucleotide

<400> SEQUENCE: 83
gaagagattg aacgtgtcgt tggcagaaac cggagcccct gcatgc                       46

<210> SEQ ID NO 84
<211> LENGTH: 46
<212> TYPE: DNA
<213> ORGANISM: Artificial Sequence
<220> FEATURE:
<223> OTHER INFORMATION: A synthetic oligonucleotide
<221> NAME/KEY: misc_feature
<222> LOCATION: (1)...(46)
<223> OTHER INFORMATION: n = A,T,C or G

<400> SEQUENCE: 84
gaagagattg aacgtgtngt tggcagaaac cggagcccct gcatgc                       46

<210> SEQ ID NO 85
<211> LENGTH: 46
<212> TYPE: DNA
<213> ORGANISM: Artificial Sequence
<220> FEATURE:
<223> OTHER INFORMATION: A synthetic oligonucleotide
<221> NAME/KEY: misc_feature
<222> LOCATION: (1)...(46)
<223> OTHER INFORMATION: n = A,T,C or G

<400> SEQUENCE: 85
gaagagattg aacgtgtcnt tggcagaaac cggagcccct gcatgc                       46
```

MACHINE ASSAY AND ANALYSIS FOR SELECTING ANTIHYPERTENSIVE DRUGS

CROSS REFERENCE TO RELATED APPLICATIONS

This application is a continuation-in-part of U.S. patent application Ser. No. 16/789,383, filed Feb. 12, 2020, which is a continuation of U.S. patent application Ser. No. 15/314,641, filed Nov. 29, 2016, which is a U.S. National Stage Filing under 35 U.S.C. § 371 from International Application No. PCT/US2015/032651, filed May 27, 2015, and published as WO 2015/183938 on Dec. 3, 2015, which application claims benefit of the priority filing date of United States Provisional Application Ser. No. 62/004,460, filed May 29, 2014, the contents of which applications are specifically incorporated herein by reference in their entireties.

BACKGROUND

Hypertension (high blood pressure) is one of the most significant preventable contributors to disease and death in the world and represents the most common condition seen in the primary care setting (Kearney et al., *Lancet* 365:217-223 (2005)). According to the American Heart Association, approximately 78 million adults (1 in 3) living in the United States have hypertension with more than 5 million new diagnoses made each year. Of these individuals, 82% are aware they have it, 75% are currently being treated for it, but only 52% have their blood pressure under control (thus, ~48% do not have adequate blood pressure control).

Hypertension can lead to myocardial infarction (heart attack), stroke, renal failure, and death if not detected early and treated appropriately. In 2009, high blood pressure was listed as a primary or contributing cause of death in about 350.000 of the approximate 2.4 million U.S. deaths (14% of all deaths). From 1999-2009 the number of deaths attributable to hypertension increased by 44%.

Refractory (or resistant) hypertension is defined as blood pressure that remains above clinical guideline goals in spite of concurrent use of three antihypertensive agents of different classes. Critically, refractory hypertension is noted in approximately 25-30% of all individuals being treated for hypertension. Refractory hypertension is a common clinical problem which contributes to the high levels of morbidity and mortality. In 2009, the direct and indirect economic burden on the United States health care system associated with hypertension was estimated at $51 billion.

Globally, nearly 1 billion individuals have been diagnosed with hypertension, with an estimate of an additional 400 million living with undiagnosed hypertension. Hypertension is the leading cause of premature death and the leading cause of cardiovascular disease worldwide. Similar to the continued upward trend in prevalence as seen in the United States, it is estimated that in 2025 about 1.56 billion adults will be living with hypertension. Because nearly two-thirds of the people living with hypertension worldwide reside in developing countries, providing optimal treatment at the lowest cost is critically important.

Unfortunately, despite a significant impulse in the medical community to move towards an "individualized medicine" approach to patient centered treatment, the current clinical treatment strategy is based on a set algorithm which does not take into account individual patient differences. Rather, physicians are guided to choose a drug (one out of many options) in a given class of drugs and use that specific drug as a "first line therapy" (typically initiating with the diuretic class) and titrate that specific drug of choice to therapeutic dosage regardless of efficacy. It is only after a prolonged course of treatment with that specific class of drug that clinical efficacy is determined (typically three months). At this stage, if clinical guideline goals for blood pressure have not been met, it is often recommended that the patient remain on the "first line therapy" whilst an additional drug from a different class of drugs (typically an Angiotensin converting enzyme inhibitor (ACE inhibitor) or Angiotensin II receptor blocker (ARB)) is added to the pharmacologic regimen. Again, this drug is titrated to recommended therapeutic dosage and another prolonged course of treatment is initiated before clinical efficacy is determined (an additional three months—six months since initiation of treatment). If at this point, clinical guideline goals for blood pressure have not been met, a third drug from a third class of drugs (typically a beta-blocker) is added and the process is repeated (another three months—nine months from initiation of treatment). Further, if clinical guideline goals have continued to be elusive, the diagnosis of refractory hypertension is added and the process is reinitiated with a different combination of drugs, different classes of drugs, different drug options within a given class of drugs, different dosages, or all of the above. Thus, from the time of initial diagnosis and the start of treatment to the point in which blood pressure is adequately controlled may take anywhere from three months to well over one year. This trial-and-error standard of care is clearly not optimal.

SUMMARY

The invention relates to improved methods, devices, and kits for identifying and implementing an appropriate treatment regimen for subjects suffering from hypertension. The methods, devices, and kits comprehensively assess common genetic variants in the cardiac, vascular, and renal systems in an effort to improve therapeutic guidance for high blood pressure treatment. Detection of an individual's genetic variants permits selection appropriate drug classes for that individual. Clinicians can then guide blood pressure therapy using knowledge that is specific to their individual patient, rather than the currently employed "trial-and-error" procedures that are based on population data and use of drugs with the least initial side effects.

One aspect of the invention is a method that includes:
(a) administering a loop diuretic to a subject as a first line therapy, without a beta blocker and without a vasodilator, if the subject's genome comprises a WNK1 nucleic acid with a cytosine at the variable position of rs1159744 or rs2107614;
(b) administering a hydrochlorothiazide to a subject as a first line therapy, without a beta blocker and without a vasodilator, if the subject's genome comprises an ADD1 nucleic acid with a thymine at the variable position of rs4961, or if the test sample comprises a SLC12A3 nucleic acid with a thymine at the variable position of rs1529927; or
(c) administering a hydrochlorothiazide to a subject as a first line therapy, without a beta blocker and without a vasodilator, if the subject's genome comprises an ADD1 nucleic acid with a thymine at the variable position of rs4961, or if the test sample comprises a SLC12A3 nucleic acid with a thymine at the variable position of rs1529927.

Another aspect of the invention is a method that includes: administering a beta-blocker drug to a subject as a first line therapy, without a diuretic and without a hydrochlorothiazide, if the subject's genome does not comprise:
  (a) a WNK1 nucleic acid with a cytosine at the variable position of rs1159744;
  (b) a WNK1 nucleic acid with a cytosine at the variable position of rs2107614;
  (c) an ADD1 nucleic acid with a thymine at the variable position of rs4961; or
  (d) a SLC12A3 nucleic acid with a thymine at the variable position of rs1529927
but the subject's genome does comprise:
  1. a CYP2D6 nucleic acid with an adenine at the variable position of Rs3892097;
  2. an ADRB1 nucleic acid with a cytosine at the variable position of rs1801253;
  3. an ADRB1 nucleic acid with an adenine at the variable position of rs1801252;
  4. an ADRB2 nucleic acid with a guanine at the variable position of rs1042714; or
  5. an ADRB2 nucleic acid with a guanine at the variable position of rs1042713.

Another aspect of the invention is a method that includes: administering an angiotensin II receptor blocker to a subject as a first line therapy, without a diuretic, without a hydrochlorothiazide, and without a beta-blocker, if the subject's genome does not comprise:
  (a) a WNK1 nucleic acid with a cytosine at the variable position of rs1159744;
  (b) a WNK1 nucleic acid with a cytosine at the variable position of rs2107614;
  (c) an ADD1 nucleic acid with a thymine at the variable position of rs4961; or
  (d) a SLC12A3 nucleic acid with a thymine at the variable position of rs1529927
but the subject's genome does comprise:
  1. a renin nucleic acid with a cytosine at the variable position of rs12750834; or
  2. an AGT1R nucleic acid with a cytosine at the variable position of rs5186.

Another aspect of the invention is a method that includes: administering an ACE inhibitor to a subject without an angiotensin II receptor blocker as a first line therapy, without a diuretic, without a hydrochlorothiazide, and without a beta-blocker, if the subject's genome does not comprise:
  (a) WNK1 nucleic acid with a cytosine at the variable position of rs1159744;
  (b) a WNK1 nucleic acid with a cytosine at the variable position of rs2107614;
  (c) an ADD1 nucleic acid with a thymine at the variable position of rs4961; or
  (d) a SLC12A3 nucleic acid with a thymine at the variable position of rs1529927
but the subject's genome does comprise:
  1. an ACE nucleic acid with a deletion in rs1799752; or
  2. an AGT nucleic acid with a cytosine at the variable position of rs699.

Another aspect of the invention is a method that includes: administering an amiloride as a first line therapy to a subject without an ACE inhibitor, without an angiotensin II receptor blocker, without a diuretic, without a hydrochlorothiazide, and without a beta-blocker, if the subject's genome does not comprise:
  1. a WNK1 nucleic acid with a cytosine at the variable position of rs1159744;
  2. a WNK1 nucleic acid with a cytosine at the variable position of rs2107614;
  3. an ADD1 nucleic acid with a thymine at the variable position of rs4961; or
  4. a SLC12A3 nucleic acid with a thymine at the variable position of rs1529927.
  but if the subject's genome does comprise a SCNN1A nucleic acid with an adenine at the variable position of rs2228576.

The methods can also include administering a second line therapy drug after administration of the first line therapy for at least 1 month, wherein the second line therapy drug is selected from the group consisting of diuretic, a beta-blocker, an ACE inhibitor, a vasodilator, and a combination thereof.

The methods can include providing a therapy recommendation according to a mathematical algorithm that includes: 1.) computing a weighted score for each genetic variant identified in an individual subject; 2.) calculating values for variables pertaining to each organ or system (e.g., cardiac, renal and vascular system) based on the weighted scores for each genetic variant; and 3.) determining recommendations based on the values for each of the variables pertaining to each organ or system.

Devices, compositions, methods, and kits are also described herein for identifying and implementing an appropriate treatment regimen for subjects suffering from hypertension.

DESCRIPTION OF THE FIGURES

FIG. 3B shows the same process but without the steps of DNA Stocks Storage and Future Testing if the sample Passes Yield and Purity Assays.

DETAILED DESCRIPTION

Methods, devices, and kits are described herein for selecting individualized hypertension treatment regimens that are more effective than currently available regimens. The methods, devices, and kits include assays for identifying genetic variants in individual subjects that make the individual more or less responsive to specific medications. When the appropriate medication is administered, the subject's blood pressure is appropriately controlled, and side effects are avoided. Genetic variants present in genes such as ADRB1, ADRB2, CYP2D6, angiotensin converting enzyme (ACE), angiotensinogen, angiotensin receptor, renin. $Na^+$ channels (such as SCNN1A), adducin, sodium ($Na^+$) chloride ($Cl^-$) co-transporters (such as SLC12A3), and/or WNK1 genes are correlated with heightened or reduced responsiveness to various blood pressure medications. Although there are a number of hypertension drugs available on the market, subjects react differently to such drugs. The kits, methods, and devices described herein are useful for detecting which subjects benefit from which therapeutic regimen.

High Blood Pressure (Hypertension)

The development of high blood pressure in humans is the result of one or more of three physiologic maladaptations: 1) elevated cardiac output (liters of blood ejected from the heart per minute) that increases the amount of blood pressing against the vessels, 2) relatively narrow blood vessels that results in increased pressure towards the lumen of the blood vessel due to Poiseuille's Law (which describes the inverse relationship between the diameter of a tube (vessel) and the pressure against the walls of the tube (vessel), all else being equal), or 3) increased sodium ($Na^+$) absorption in the kidney which results in increased blood volume (and the amount of blood pumped per minute, cardiac output) and subsequently increased outward pressure against the tubes (vessels).

Figure 1:
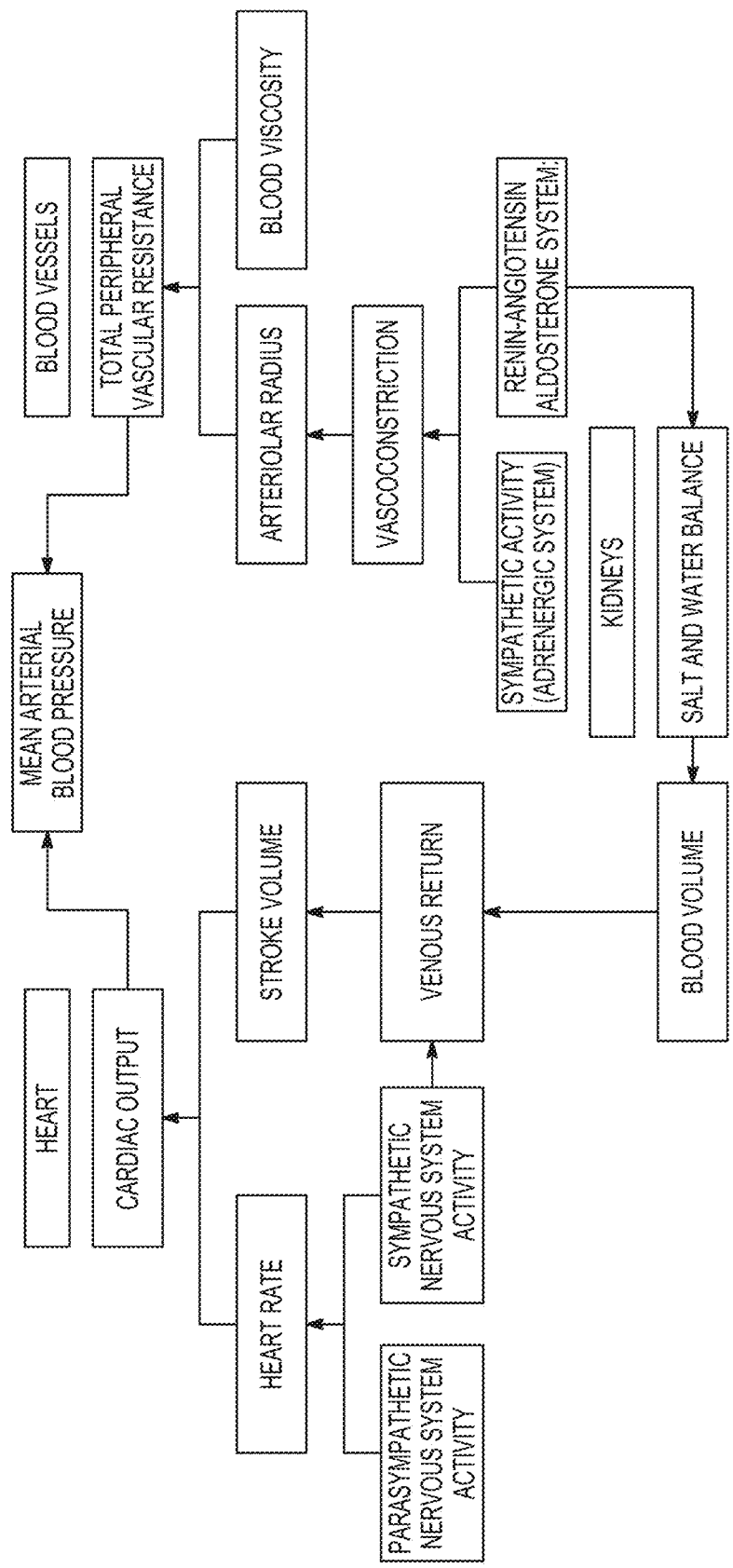
FIG. 1 is a schematic diagram illustrating the interplay between the heart, blood vessels, and kidney in blood pressure regulation.
Figure 2:
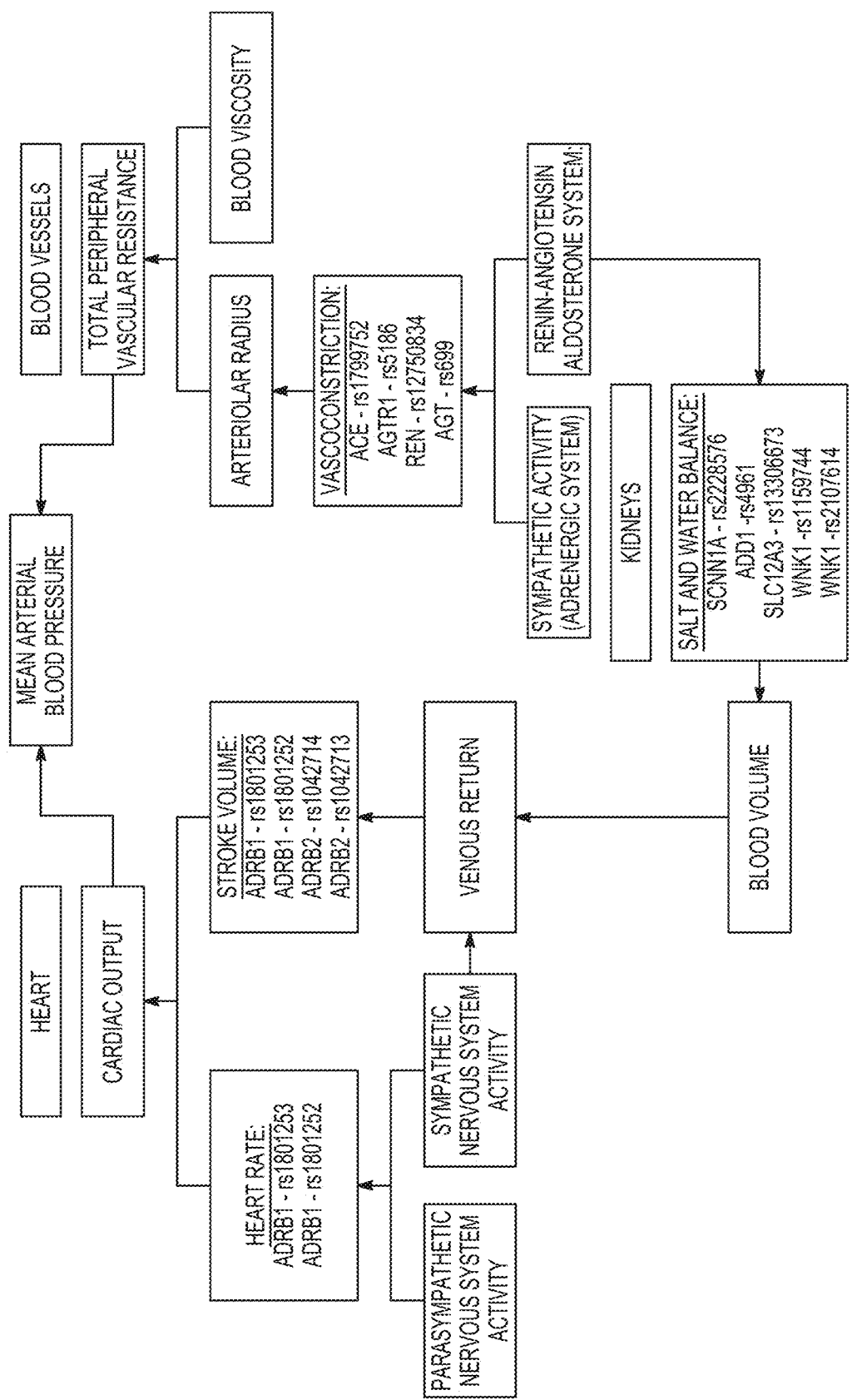
FIG. 2 is a schematic diagram illustrating of the types of genes useful for evaluating hypertension, and representative single nucleotide polymorphisms that are correlated with blood pressure drug responses.

Blood pressure is highly regulated and tightly controlled in humans, such that in the event of a drop in cardiac output, the heart sends a signal to the kidneys (via the proteins atrial natriuretic peptide and brain-type natriuretic peptide, among others) and vessels with the ultimate function of increasing $Na^+$ reabsorption to increase plasma volume and vasoconstriction to increase blood pressure. Similarly, if there is a drop in blood pressure, there is an increase in cardiac output (primarily via an immediate increase in heart rate through inhibition of the parasympathetic nervous system) to compensate and an increase in the renin-angiotensin aldosterone system which results in both constriction of blood vessels (which increases blood pressure) and an increase in $Na^+$ and, therefore, fluid retention in the kidney, which increases plasma volume and can increase blood pressure. Hence, the human body provides redundant functions to maintain blood pressure both in the short-term and in the long-term, by regulating the interplay between the heart, blood vessels, and kidney. FIG. 1 is a schematic diagram illustrating the interplay between the heart, blood vessels, and kidneys involved in regulating blood pressure.

Blood pressure therapy following diagnosis traditionally follows a regimented algorithm based on therapies effective across the general population. Currently, clinicians start a patient who has been diagnosed with high blood pressure on a diuretic (to reduce renal $Na^+$ reabsorption). If such a diuretic does not work within a period of time, the clinician next tries a vasodilator, and if this is not effective, then a clinician will lastly prescribe a beta-blocker. This trial-and-error process to lower a patient's blood pressure can take several months, is costly, and threatens the health of the patient because the patient's hypertension is frequently not adequately controlled in a timely manner.

Such currently available methods are in stark contrast to the methods, devices, and kits described herein that involve specifically testing an individual's genetic profile and, as illustrated herein, basing therapeutic treatment on the results of such testing. Hence, the methods, devices, and kits described herein for evaluating a blood pressure genetic panel to improve treatment of hypertensive subjects, by quickly identifying more effective medications, thereby avoiding side effects and delays in treatment. Applicants' methods are therefore an improvement over the currently available trial-and-error procedures that frequently result in side effects and delays in effective treatment.

Ranking of Genotypes that Affect Therapy

The genotype of a subject can significantly affect the response of the subject to blood pressure medications because certain functional polymorphisms have greater effects on the physiology of a subject than others. The following is a summary of polymorphisms in order of their impact on blood pressure and which drugs should be employed by subjects with such genetic variations.

1. Subjects with the WNK1 polymorphism defined by rs1159744 (SEQ ID NO:34, with cytosine at the variable position), benefit more from loop diuretics.
2. Subjects with the WNK1 polymorphism defined by rs2107614 (SEQ ID NO:33, with cytosine at the variable position), benefit more from loop diuretics.
3. Subjects with the ADD1 polymorphism defined by rs4961 (SEQ ID NO:27, with thymine at the variable position), benefit more from hydrochlorothiazides.
4. Subjects with the SLC12A3 polymorphism defined by rs1529927 (SEQ ID NO:30, with thymine at the variable position), benefit more from hydrochlorothiazides.

Any homozygous combination at one or more of the WNK1 Rs1159744, WNK1 Rs2107614, ADD1 Rs4961, and SLC12A3 rs1529927 polymorphisms means that diuretics should be the first-line therapy, especially if the patient is heterozygous for polymorphisms in genes responsive to beta-blockers or vasodilators.

5. Subjects with the CYP2D6 polymorphism defined by Rs3892097 (SEQ ID NO: 10, with adenine at the variable position), plus the ADRB1 polymorphism defined by rs1801253 (SEQ ID NO:3, with cytosine as the variable nucleotide), plus the ADRB1 polymorphism defined by rs1801252 (SEQ ID NO:2, with adenine as the variable nucleotide) benefit from beta-blockade classes of drugs.
6. Subjects with the renin polymorphism defined by rs12750834 (SEQ ID NO:20, with cytosine as the variable nucleotide) plus the AGT1R polymorphism defined by rs5186 (SEQ ID NO:16, with cytosine as the variable nucleotide), which affect responses to angiotensin II receptor blockers.

7. Subjects with the ACE deletion defined by Rs1799752 (SEQ ID NO:35) and the AGT polymorphism defined by rs699 (SEQ ID NO:14, with cytosine as the variable nucleotide) can benefit from the combination of an angiotensin II receptor blocker and an ACE inhibitor.
8. Subjects with the SCNN1A polymorphism defined by rs2228576 (SEQ ID NO:22, with adenine as the variable position) can benefit from administration of amiloride.
9. Subjects with the ADRB2 polymorphism defined by rs1042714 (SEQ ID NO:7, with guanine as the variable nucleotide) can benefit from administration of a non-selective beta-blockade.
10. Subjects with the ADRB2 polymorphism defined by s1042713 (SEQ ID NO:6, with guanine as the variable nucleotide) can benefit from administration of a non-selective beta-blockade.

All patients do not respond to same. Some subjects have genotypes that can significantly affect their response to medications. When clinicians employ currently available procedures (diuretic first, then vasodilator, then beta blocker), some patients will benefit but others will not respond or will respond negatively. Hence, some patients would benefit from initial administration of a vasodilator or a beta-blocker, rather than a diuretic.

Beta-Blocker Responsive Polypeptides and Nucleic Acids

There are two primary receptors within the heart that influence both heart rate (chronotropic effect) and heart contractility (inotropic effect) (Brodde. *Am J Cardiol* 62:24C-29C (1988), the beta-1 adrenergic receptors ($\beta_1$AR, encoded by the ADRB1 gene) and the beta-2 adrenergic receptors ($\beta_2$AR, encoded by the ADRB2 gene).

The heart is primary comprised of beta-1 adrenergic receptors, which are located on 80% of the ventricular wall surface, 70% of the atrial wall surface, and 95% of the sino-atrial (SA) node. The atria of the heart receive blood that returns from the body (right atria) of lungs (left atria) whereas the ventricles pump blood to the lungs (right ventricle) and body (left ventricle). The sino-atrial node primarily controls heart rate.

Although heart rate and cardiac contractility are primarily regulated by $\beta_1$AR, the $\beta_2$AR also play a role, primarily in cardiac contractility. Stimulation of either $\beta_1$AR or $\beta_2$AR can influence heart rate and cardiac contractility through increases in intracellular c-AMP and protein kinase A (PKA) which, ultimately, alter $Ca^+$-channel sensitivity and reduce the threshold needed for an action potential. Therefore, cardiac output (and blood pressure) can be increased through increases in $\beta_1$AR and/or $\beta_2$AR activities. If a variant $\beta_1$AR or $\beta_2$AR gene encodes a more functional receptor, cardiac output is increased.

$\beta_1$AR and $\beta_2$AR activities can be modulated through the use of selective (e.g., atenolol and metoprolol) and non-selective (e.g., propranolol and carvedilol) beta-blockers. The selective beta-blockers are selective for inhibiting the $\beta_1$AR. The non-selective beta-blockers inhibit both $\beta_1$AR and $\beta_2$AR. Both types of beta-blockers tend to decrease blood pressure through a decrease in heart rate and cardiac contractility, which ultimately results in a decrease in cardiac output. Similarly, the administration of a $\beta_2$AR-agonist (e.g., albuterol sulfate) tends to increase cardiac output and heart rate (Snyder et al., *Pharmacotherapy* 31:748-756 (2011)). Thus, both $\beta_1$AR and $\beta_2$AR are important in the regulation of cardiac output.

Just as stimulation of these receptors can elevate cardiac output and increase blood pressure, so too can genetic variation of the genes that encode $\beta_1$AR and $\beta_2$AR (ADRB1 and ADRB2) elevate receptor activity and increase blood pressure. Conversely, some ADRB1 and ADRB2 genetic variants encode receptors with reduced activity. In addition, some ADRB1 and ADRB2 genetic variants exhibit reduced, or enhanced, responsiveness to blood pressure medications such as beta-blockers. Not all individuals respond similarly to beta-blockade, despite similar clinical and environmental conditions. As described herein, the effectiveness of beta-blockers is dependent to some extent upon the genetic make-up of the subjects to which the beta-blockers are administered.

Sequences for various adrenergic receptors are available, for example, from the National Center for Biotechnology Information (see website at ncbi.nlm.nih.gov).

For example, a full length human ADRB1 cDNA nucleotide sequence is available from the database maintained by the National Center for Biotechnology Information (see website at ncbi.nlm.nih.gov), which has accession number NM_00064 (GI:110349783), and is shown below as SEQ ID NO: 1.

```
   1  GCACCACGCC GCCCGGGCTT CTGGGGTGTT CCCCAACCAC
  41  GGCCCAGCCC TGCCACACCC CCCGCCCCCG GCCTCCGCAG
  81  CTCGGCATGG GCGCGGGGGT GCTCGTCCTG GGCGCCTCCG
 121  AGCCCGGTAA CCTGTCGTCG GCCGCACCGC TCCCCGACGG
 161  CGCGGCCACC GCGGCGCGGC TGCTGGTGCC CGCGTCGCCG
 201  CCCGCCTCGT TGCTGCCTCC CGCCAGCGAA AGCCCCGAGC
 241  CGCTGTCTCA GCAGTGGACA GCGGGCATGG GTCTGCTGAT
 281  GGCGCTCATC GTGCTGCTCA TCGTGGCGGG CAATGTGCTG
 321  GTGATCGTGG CCATCGCCAA GACGCCGCGG CTGCAGACGC
 361  TCACCAACCT CTTCATCATG TCCCTGGCCA GCGCCGACCT
 401  GGTCATGGGG CTGCTGGTGG TGCCGTTCGG GGCCACCATC
 441  GTGGTGTGGG GCCGCTGGGA GTACGGCTCC TTCTTCTGCG
 481  AGCTGTGGAC CTCAGTGGAC GTGCTGTGCG TGACGGCCAG
 521  CATCGAGACC CTGTGTGTCA TTGCCCTGGA CCGCTACCTC
 561  GCCATCACCT CGCCCTTCCG CTACCAGAGC CTGCTGACGC
 601  GCGCGCGGGC GCGGGGCCTC GTGTGCACCG TGTGGGCCAT
 641  CTCGGCCCTG GTGTCCTTCC TGCCCATCCT CATGCACTGG
 681  TGGCGGGCGG AGAGCGACGA GGCGCGCCGC TGCTACAACG
 721  ACCCCAAGTG CTGCGACTTC GTCACCAACC GGGCCTACGC
 761  CATCGCCTCG TCCGTAGTCT CCTTCTACGT GCCCCTGTGC
 801  ATCATGGCCT TCGTGTACCT GCGGGTGTTC CGCGAGGCCC
 841  AGAAGCAGGT GAAGAAGATC GACAGCTGCG AGCGCCGTTI
 881  CCTCGGCGGC CAGCGCGGC CGCCCTCGCC CTCGCCCTCG
 921  CCCGTCCCCG CGCCCGCGCC GCCGCCCGGA CCCCCGCGCC
 961  CCGCCGCCGC CGCCGCCACC GCCCCGCTGG CCAACGGGCG
1001  TGCGGGTAAG CGGCGGCCCT CGCGCCTCGT GGCCCTGCGC
1041  GAGCAGAAGG CGCTCAAGAC GCTGGGCATC ATCATGGGCG
1081  TCTTCACGCT CTGCTGGCTG CCCTTCTTCC TGGCCAACGT
```

-continued

```
1121 GGTGAAGGCC TTCCACCGCG AGCTGGTGCC CGACCGCCTC
1161 TTCGTCTTCT TCAACTGGCT GGGCTACGCC AACTCGGCCT
1201 TCAACCCCAT CATCTACTGC CGCAGCCCCG ACTTCCGCAA
1241 GGCCTTCCAG GGACTGCTCT GCTGCGCGCG CAGGGCTGCC
1281 CGCCGGCGCC ACGCGACCCA CGGAGACCGG CCGCGCGCCT
1321 CGGGCTGTCT GGCCCGGCCC GGACCCCCGC CATCGCCCGG
1361 GGCCGCCTCG GACGACGACG ACGACGATGT CGTCGGGGCC
1401 ACGCCGCCCG CGCGCCTGCT GGAGCCCTGG GCCGGCTGCA
1441 ACGGCGGGGC GGCGGCGGAC AGCGACTCGA GCCTGGACGA
1481 GCCGTGCCGC CCCGGCTTCG CCTCGGAATC CAAGGTGTAG
1521 GGCCCGGCGC GGGGCGCGGA CTCCGGGCAC GGCTTCCCAG
1561 GGGAACGAGG AGATCTGTGT TTACTTAAGA CCGATAGCAG
1601 GTGAACTCGA AGCCCACAAT CCTCGTCTGA ATCATCCGAG
1641 GCAAAGAGAA AAGCCACGGA CCGTTGCACA AAAAGGAAAG
1681 TTTGGGAAGG GATGGGAGAG TGGCTTGCTG ATGTTCCTTG
1721 TTGTTTTTTT TTTCTTTTCT TTTCTTTCTT CTTCTTTTTT
1741 TTTTTTTTTT TTTTTTCTGT TTGTGGTCCG GCCTTCTTTT
1801 GTGTGTGCGT GTGATGCATC TTTAGATTTT TTTCCCCCAC
1841 CAGGTGGTTT TTGACACTCT CTGAGAGGAC CGGAGTGGAA
1881 GATGGGTGGG TTAGGGGAAG GGAGAAGCAT TAGGAGGGGA
1921 TTAAAATCGA TCATCGTGGC TCCCATCCCT TTCCCGGGAA
1961 CAGGAACACA CTACCAGCCA GAGAGAGGAG AATGACAGTT
2001 TGTCAAGACA TATTTCCTTT TGCTTTCCAG AGAAATTTCA
2041 TTTTAATTTC TAAGTAATGA TTTCTGCTGT TATGAAAGCA
2081 AAGAGAAAGG ATGGAGGCAA AATAAAAAAA AATCACGTTT
2121 CAAGAAATGT TAAGCTCTTC TTGGAACAAG CCCCACCTTG
2161 CTTTCCTTGT GTAGGGCAAA CCCGCTGTCC CCCGCGCGCC
2201 TGGGTGGTCA GGCTGAGGGA TTTCTACCTC ACACTGTGCA
2241 TTTGCACAGC AGATAGAAAG ACTTGTTTAT ATTAAACAGC
2281 TTATTTATGT ATCAATATTA GTTGGAAGGA CCAGGCGCAG
2321 AGCCTCTCTC TGTGACATGT GACTCTGTCA ATTGAAGACA
2361 GGACATTAAA AGAGAGCGAG AGAGAGAAAC AGTTCAGATT
2401 ACTGCACATG TGGATAAAAA CAAAAACAAA AAAAAGGAGT
2441 GGTTCAAAAT GCCATTTTTG CACAGTGTTA GGAATTACAA
2481 AATCCACAGA AGATGTTACT TGCACAAAAA GAATTAAAT
2521 ATTTTTTAAA GGGAGAGGGG CTGGGCAGAT CTTAAATAAA
2561 ATTCAAACTC TACTTCTGTT GTCTAGTATG TTATTGAGCT
2601 AATGATTCAT TGGGAAAATA CCTTTTTATA CTCCTTTATC
2641 ATGGTACTGT AACTGTATCC ATATTATAAA TATAATTATC
2681 TTAAGGATTT TTTATTTTTT TTTATGTCCA AGTGCCCACG
2721 TGAATTTGCT GGTGAAAGTT AGCACTTGTG TGTAAATTCT
2761 ACTTCCTCTT GTGTGTTTTA CCAAGTATTT ATACTCTGGT
2801 GCAACTAACT ACTGTGTGAG GAATTGGTCC ATGTGCAATA
2841 AATACCAATG AAGCACAATC AA
```

The rs1801252 single nucleotide polymorphism (SNP) is present in the ADRB1 gene, where the variable nucleotide at about position 231 (underlined) can be adenine in some individuals and guanine in others. The rs1801252 sequence (SEQ ID NO:2) is shown below, where the underlined A/G is the SNP.

CTCGTTGCTGCCTCCCGCCAGCGAA[A/G]GCCCCGAGCCGCTGTCTCAG

CAGTG.

The rs1801253 single nucleotide polymorphism (SNP) is also present in the ADRB1 gene, where the variable nucleotide at about position 1251 (underlined) can be guanine in some individuals and cytosine in others. The rs1801253 sequence (SEQ ID NO:3) is shown below, where the underlined C/G is the SNP.

CCCCGACTTCCGCAAGGCCTTCCAG[C/G]GACTGCTCTGCTGCGCGCGC

AGGGC.

The $\beta_1$AR polypeptide encoded by the ADRB1 cDNA with SEQ ID NO:1 has the following sequence (SEQ ID NO:4).

```
  1  MGAGVLVLGA SEPGNLSSAA PLPDGAATAA RLLVPASPPA
 41  SLLPPASESP EPLSQQWTAG MGLLMALIVL LIVAGNVLVI
 81  VAIAKTPRLQ TLTNLFIMSL ASADLVMGLL VVPFGATIVV
121  WGRWEYGSFF CELWTSVDVL CVTASIETLC VIALDRYLAI
161  TSPFRYQSLL TRARARGLVC TVWAISALVS FLPILMHWWR
201  AESDEARRCY NDPKCCDFVT NRAYAIASSV VSFYVPLCIM
241  AFVYLRVFRE AQKQVKKIDS CERRFLGGPA RPPSPSPSPV
281  PAPAPPPGPP RPAAAAATAP LANGRAGKRR PSRLVALREQ
321  KALKTLGIIM GVFTLCWLPF FLANVVKAFH RELVPDRLFV
361  FFNWLGYANS AFNPIIYCRS PDFRKAFQGL LCCARRAARR
401  RHATHGDRPR ASGCLARPGP PPSPGAASDD DDDDVVGATP
441  PARLLEPWAG CNGGAAADSD SSLDEPCRPG FASESKV
```

Note that the underlined amino acid at position 49 is serine because some individuals have SEQ ID NO:1 or 2, where the variable nucleotide at about position 231 of SEQ ID NO: 1 is adenine. However, position 49 of SEQ ID NO:4 can be glycine in some individuals because those individual have guanine at nucleotide position 231 in SEQ ID NO:1.

Note also that the glycine at position 389 is an arginine (instead of glycine) as shown for SEQ ID NO:4 when position 1251 of SEQ ID NO:1 is a cytosine.

Individuals with serine at $\beta_1$AR amino acid position 49 and/or arginine at position 389 are more responsive to beta-blockers than those with glycines at these positions. Hence, for example, an individual who expresses the $\beta_1$AR polypeptide with SEQ ID NO:4, will be more responsive to beta-blockers than an individual who expresses the β₁AR polypeptide with glycines at both positions 49 and 389.

A full length human ADRB2 cDNA nucleotide sequence is available from the database maintained by the National Center for Biotechnology Information (see website at ncbi.nlm.nih.gov), which has accession number NM_000024 (GI:283483994), and is shown below as SEQ ID NO:5.

```
   1  GCACATAACG GGCAGAACGC ACTGCGAAGC GGCTTCTTCA
  41  GAGCACGGGC TGGAACTGGC AGGCACCGCG AGCCCCTAGC
  81  ACCCGACAAG CTGAGTGTGC AGGACGAGTC CCCACCACAC
 121  CCACACCACA GCCGCTGAAT GAGGCTTCCA GGCGTCCGCT
 161  CGCGGCCCGC AGAGCCCCGC CGTGGGTCCG CCCGCTGAGG
 201  CGCCCCCAGC CAGTGCGCTC ACCTGCCAGA CTGCGCGCCA
 241  TGGGGCAACC CGGGAACGGC AGCGCCTTCT TGCTGGCACC
 281  CAATAGAAGC CATGCGCCGG ACCACGACGT CACGCAGCAA
 321  AGGGACGAGG TGTGGGTGGT GGGCATGGGC ATCGTCATGT
 361  CTCTCATCGT CCTGGCCATC GTGTTTGGCA ATGTGCTGGT
 401  CATCACAGCC ATTGCCAAGT TCGAGCGTCT GCAGACGGTC
 441  ACCAACTACT TCATCACTTC ACTGGCCTGT GCTGATCTGG
 481  TCATGGGCCT GGCAGTGGTG CCCTTTGGGG CCGCCCATAT
 521  TCTTATGAAA ATGTGGACTT TTGGCAACTT CTGGTGCGAG
 561  TTTTGGACTT CCATTGATGT GCTGTGCGTC ACGGCCAGCA
 601  TTGAGACCCT GTGCGTGATC GCAGTGGATC GCTACTTTGC
 641  CATTACTTCA CCTTTCAAGT ACCAGAGCCT GCTGACCAAG
 681  AATAAGGCCC GGGTGATCAT TCTGATGGTG TGGATTGTGT
 721  CAGGCCTTAC CTCCTTCTTG CCCATTCAGA TGCACTGGTA
 761  CCGGGCCACC CACCAGGAAG CCATCAACTG CTATGCCAAT
 801  GAGACCTGCT GTGACTTCTT CACGAACCAA GCCTATGCCA
 841  TTGCCTCTTC CATCGTGTCC TTCTACGTTC CCCTGGTGAT
 881  CATGGTCTTC GTCTACTCCA GGGTCTTTCA GGAGGCCAAA
 921  AGGCAGCTCC AGAAGATTGA CAAATCTGAG GGCCGCTTCC
 961  ATGTCCAGAA CCTTAGCCAG GTGGAGCAGG ATGGGCGGAC
1001  GGGGCATGGA CTCCGCAGAT CTTCCAAGTT CTGCTTGAAG
1041  GAGCACAAAG CCCTCAAGAC GTTAGGCATC ATCATGGGCA
1081  CTTTCACCCT CTGCTGGCTG CCCTTCTTCA TCGTTAACAT
1121  TGTGCATGTG ATCCAGGATA ACCTCATCCG TAACGAAGTT
1161  TACATCCTCC TAAATTGGAT AGGCTATGTC AATTCTGGTT
1201  TCAATCCCCT TATCTACTGC CGGAGCCCAG ATTTCAGGAT
1241  TGCCTTCCAG GAGCTTCTGT GCCTGCGCAG GTCTTCTTTG
1281  AAGGCCTATG GAATGGCTA CTCCAGCAAC GGCAACACAG
1321  GGGAGCAGAG TGGATATCAC GTGGAACAGG AGAAAGAAAA
1361  TAAACTGCTG TGTGAAGACC TCCCAGGCAC GGAAGACTTT
1401  GTGGGCCATC AAGGTACTGT GCCTAGCGAT AACATTGATT
1441  CACAAGGGAG GAATTGTAGT ACAAATGACT CACTGCTGTA
1481  AAGCAGTTTT TCTACTTTTA AAGACCCCCC CCCCCAACAG
1521  AACACTAAAC AGACTATTTA ACTTGAGGGT AATAAACTTA
1561  GAATAAAATT GTAAAATTGT ATAGAGATAT GCAGAAGGAA
1601  GGGCATCCTT CTGCCTTTTT TATTTTTTTA AGCTGTAAAA
1641  AGAGAGAAAA CTTATTTGAG TGATTATTTG TTATTTGTAC
1681  AGTTCAGTTC CTCTTTGCAT GGAATTTGTA AGTTTATGTC
1721  TAAAGAGCTT TAGTCCTAGA GGACCTGAGT CTGCTATATT
1761  TTCATGACTT TTCCATGTAT CTACCTCACT ATTCAAGTAT
1801  TAGGGGTAAT ATATTGCTGC TGGTAATTTG TATCTGAAGG
1841  AGATTTTCCT TCCTACACCC TTGGACTTGA GGATTTTGAG
1881  TATCTCGGAC CTTTCAGGTG TGAACATGGA CTCTTCCCCC
1921  ACTCCTCTTA TTTGCTCACA CGGGGTATTT TAGGCAGGGA
1961  TTTGAGGAGC AGCTTCAGTT GTTTTCCCGA GCAAAGTCTA
2001  AAGTTTACAG TAAATAAATT GTTTGACCAT GCCTTCATTG
2041  CAAAAAAAAA AAAAAAA
```

The rs1042713 single nucleotide polymorphism (SNP) is present in the ADRB2 gene, where the variable nucleotide at about position 285 (underlined) can be in adenine some individuals and guanine in others. The rs1042713 sequence (SEQ ID NO:6) is shown below, where the underlined A/G is the SNP.

CAGCGCCTTCTTGCTGGCACCCAAT[A/G]GAAGCCATGCGCCGGACCAC CACGT.

The rs1042714 single nucleotide polymorphism (SNP) is also present in the ADRB2 gene, where the variable nucleotide at about position 318 (underlined) can be cytosine in some individuals and guanine in others. The rs1042714 sequence (SEQ ID NO:7) is shown below, where the underlined C/G is the SNP.

TGCGCCGGACCACGACGTCACGCAG[C/G]AAAGGGACGAGGTGTGGGTG GTGGG.

The β₂AR polypeptide encoded by the ADRB2 cDNA with SEQ ID NO:5 has the following sequence (SEQ ID NO:8).

```
   1  MGQPGNGSAF LLAPNRSHAP DHDVTQQRDE VWVVGMGIVM
  41  SLIVLAIVFG NVLVITAIAK FERLQTVTNY FITSLACADL
  81  VMGLAVVPFG AAHILMKMWT FGNFWCEFWT SIDVLCVTAS
 121  IETLCVIAVD RYFAITSPFK YQSLLTKNKA RVIILMVWIV
 161  SGLTSFLPIQ MHWYRATHQE AINCYANETC CDFFTNQAYA
 201  IASSIVSFYV PLVIMVFVYS RVFQEAKRQL QKIDKSEGRF
 241  HVQNLSQVEQ DGRTGHGLRR SSKFCLKEHK ALKTLGIIMG
```

```
281  TFTLCWLPFF IVNIVHVIQD NLIRKEVYIL LNWIGYVNSG
321  FNPLIYCRSP DFRIAFQELL CLRRSSLKAY GNGYSSNGNT
361  GEQSGYHVEQ EKENKLLCED LPGTEDFVGH QGTVPSDNID
401  SQGRNCSTND SLL
```

Note that the underlined arginine at position 16 of SEQ ID NO:8 is arginine because some individuals have nucleotide sequence SEQ ID NO:5, where the nucleotide at about position 285 is adenine. However, position 16 of SEQ ID NO:8 can be glycine in some individuals because those individuals have guanine at nucleotide position 285 in SEQ ID NO:5.

Note also that the glutamine at position 27 of SEQ ID NO:8 is a glutamic acid when position 318 of nucleotide sequence SEQ ID NO:5 is a guanine.

Individuals with glycine at position 16 and/or glutamic acid at β$_2$AR position 27 are more responsive to beta-blockers than those with arginine and glutamine, respectively, at these positions. Hence, for example, an individual who expresses the β$_2$AR polypeptide with SEQ ID NO:5, will be more responsive to beta-blockers than an individual who expresses the β$_2$AR polypeptide with arginine and glutamine at positions 16 and 27.

The gene that encodes cytochrome P450 2D6 (CYP2D6) has been shown to alter the metabolism of the drugs in the beta-blocker class. This alteration in drug metabolism can alter the amount of bioavailable drug. Poor drug metabolizers tend to have more drugs available in the body for longer and will, therefore, have a greater response to therapy. In contrast, active metabolizers of a drug will have less of the drug available in their system and will respond poorly to therapy.

Because of the importance of CYP2D6 on beta-blocker metabolism, this gene is a useful marker of responsive to beta-blocker therapy.

A full length human CYP2D6 cDNA nucleotide sequence is available from the database maintained by the National Center for Biotechnology Information (see website at ncbi.nlm.nih.gov), which has accession number NM_000106.5 GI:392513720), and is shown below as SEQ ID NO:9.

```
   1  GTGCTGAGAG TGTCCTGCCT GGTCCTCTGT GCCTGGTGGG
  41  GTGGGGGTGC CAGGTGTGTC CAGAGGAGCC CATTTGGTAG
  81  TGAGGCAGGT ATGGGGCTAG AAGCACTGGT GCCCCTGGCC
 121  GTGATAGTGG CCATCTTCCT GCTCCTGGTG GACCTGATGC
 161  ACCGGCGCCA ACGCTGGGCT GCACGCTACC CACCAGGCCC
 201  CCTGCCACTG CCCGGGCTGG GCAACCTGCT GCATGTGGAC
 241  TTCCAGAACA CACCATACTG CTTCGACCAG TTGCGGCGCC
 281  GCTTCGGGGA CGTGTTCAGC CTGCAGCTGG CCTGGACGCC
 321  GGTGGTCGTG CTCAATGGGC TGGCGGCCGT GCGCGAGGCG
 361  CTGGTGACCC ACGGCGAGGA CACCGCCGAC CGCCCGCCTG
 401  TGCCCATCAC CCAGATCCTG GGTTTCGGGC GCGTTCCCA
 441  AGGGGTGTTC CTGGCGCGCT ATGGGCCCGC GTGGCGCGAG
 481  CAGAGGCGCT TCTCCGTGTC CACCTTGCGC AACTTGGGCC
 521  TGGGCAAGAA GTCGCTGGAG CAGTGGGTGA CCGAGGAGGC
 561  CGCCTGCCTT TGTGCCGCCT TCGCCAACCA CTCCGGACGC
 601  CCCTTTCGCC CCAACGGTCT CTTGGACAAA GCCGTGAGCA
 641  ACGTGATCGC CTCCCTCACC TGCGGGCGCC GCTTCGAGTA
 681  CGACGACCCT CGCTTCCTCA GGCTGCTGGA CCTAGCTCAG
 721  GAGGGACTGA AGGAGGAGTC GGGCTTTCTG CGCGAGGTGC
 761  TGAATGCTGT CCCCGTCCTC CTGCATATCC CAGCGCTGGC
 801  TGGCAAGGTC CTACGCTTCC AAAAGGCTTT CCTGACCCAG
 841  CTGGATGAGC TGCTAACTGA GCACAGGATG ACCTGGGACC
 881  CAGCCCAGCC CCCCCGAGAC CTGACTGAGG CCTTCCTGGC
 921  AGAGATGGAG AAGGCCAAGG GGAACCCTGA GAGCAGCTTC
 961  AATGATGAGA ACCTGCGCAT AGTGGTGGCT GACCTGTTCT
1001  CTGCCGGGAT GGTGACCACC TCGACCACGC TGGCCTGGGG
1041  CCTCCTGCTC ATGATCCTAC ATCCGGATGT GCAGCGCCGT
1081  GTCCAACAGG AGATCGACGA CGTGATAGGG CAGGTGCGGC
1121  GACCAGAGAT GGGTGACCAG GCTCACATGC CCTACACCAC
1161  TGCCGTGATT CATGAGGTGC AGCGCTTTGG GGACATCGTC
1201  CCCCTGGGTG TGACCCATAT GACATCCCGT GACATCGAAG
1241  TACACGGCTT CCGCATCCCT AAGGGAACGA CACTCATCAC
1281  CAACCTGTCA TCGGTGCTGA AGGATGAGGC CGTCTGGGAG
1321  AAGCCCTTCC GCTTCCACCC CGAACACTTC CTGGATGCCC
1361  AGGGCCACTT TGTGAAGCCG GAGGCCTTCC TGCCTTTCTC
1401  AGCAGGCCGC CGTGCATGCC TCGGGGAGCC CCTGGCCCGC
1441  ATGGAGCTCT TCCTCTTCTT CACCTCCCTG CTGCAGCACT
1481  TCAGCTTCTC GGTGCCCACT GGACAGCCCC GGCCCAGCCA
1521  CCATGGTGTC TTTGCTTTCC TGGTGAGCCC ATCCCCCTAT
1561  GAGCTTTGTG CTGTGCCCCG CTAGAATGGG GTACCTAGTC
1601  CCCAGCCTGC TCCCTAGCCA GAGGCTCTAA TGTACAATAA
1641  AGCAATGTGG TAGTTCCAAA AAAAAAAAA AAA
```

The rs3892097 single nucleotide polymorphism (SNP) is present in the CYP2D6 gene, where the variable nucleotide at a splice site at about position 595 in SEQ ID NO:9 (underlined), which can be in adenine some individuals and guanine in others.

The rs3892097 sequence (SEQ ID NO: 10) of the CYP2D6 gene is shown below, where the underlined A/G is the SNP.

```
CCCTTACCCGCATCTCCCACCCCCA[A/G]GACGCCCCTTTCGCCCCAA
CGGTCT.
```

Because the SNP occurs near a splice site, the sequences to the left of the SNP site in SEQ ID NO: 10 do not appear in the SEQ ID NO:9 nucleotide CYP2D6 cDNA sequence.

The cytochrome P450 2D6 polypeptide encoded by the CYP2D6 cDNA with SEQ ID NO:9 has the following sequence (SEQ ID NO: 11).

```
  1    MGLEALVPLA VIVAIFILLV DLMHRRQRWA ARYPPGPLPL
 41    PGLGNLLHVD FQNTPYCFDQ LRRRFGDVFS LQLAWTPVVV
 81    LNGLAAVREA LVTHGEDTAD RPPVPITQIL GFGPRSQGVF
121    LARYGPAWRE QRRFSVSTLR NLGLGKKSLE QWVTEEAACL
161    CAAFANHSGR PFRPNGLLDK AVSNVIASLT CGRRFEYDDP
201    RFLRLLDLAQ EGLKEESGFL REVLNAVPVL LHIPALAGKV
241    LRFQKAFLTQ LDELLTEHRM TWDPAQPPRD LTEAFLAEME
281    KAKGNPESSF NDENLRIVVA DLFSAGMVTT STTLAWGLLL
321    MILHPDVQRR VQQEIDDVIG QVRRPEMGDQ AHMPYTTAVI
361    HEVQRFGDIV PLGVTHMTSR DIEVQGFRIP KGTTLITNLS
401    SVLKDEAVWE KPFRFHPEHF LDAQGHFVKP EAFLPFSAGR
441    RACLGEPLAR MELFLFFTSL LQHFSFSVPT GQPRPSHHGV
481    FAFLVSPSPY ELCAVPR
```

Note that the underlined glycine at position 169 of SEQ ID NO: 11 is glycine because some individuals have nucleotide sequence SEQ ID NO:9, where the nucleotide at about position 595 is guanine. However, position 169 of SEQ ID NO: 11 can be arginine in some individuals because those individuals have adenine at nucleotide position 295 in SEQ ID NO:9.

A patient with that is homozygous for adenine (AA) at the rs3892097 variable site will express CYP2D6 with arginine at position 169 and will not metabolize metoprolol and propranolol as quickly as those with guanine (glycine). Hence, homozygous individuals with adenine (AA) at the rs3892097 variable site have higher plasma levels of metoprolol and propranolol after taking these drugs than subjects that are not homozygous for adenine (AA) at the rs3892097 variable site. Homozygous individuals with adenine (AA) at the rs3892097 variable site would respond more normally to atenolol and carvedilol, which do not require CYP2D6 for their metabolism.

Vasodilation Therapy

Dilation of blood vessels results in decreases in blood pressure, whereas constriction of blood vessels results in increases in blood pressure. The blood vessels are controlled through local neural signaling that is largely under parasympathetic control, and circulating hormones that are largely under sympathetic control, as well as other circulating proteins. Blood pressure increases following stimulation of the angiotensin receptors, which results in vasoconstriction. Angiotensin receptors are stimulated by angiotensin II, which is converted from angiotensin I through the angiotensin converting enzyme (ACE). Angiotensin II is a potent vasoconstrictor and actively inhibits bradykinin, which is a potent vasodilator.

Therefore, angiotensin converting enzyme is a common target of blood pressure therapy. ACE inhibitors such as lisinopril promote vasodilation which, ultimately, reduces the bioavailability of angiotensin-II. Similarly, angiotensin II receptor antagonists such as losartan act as competitive inhibitors, which decrease the number of receptors that are available to bind to angiotensin-II. Despite the method used for promoting vasodilation (through reductions in ACE or receptor inhibition) the end result, on average in the population, is vasodilation which results in a drop in blood pressure due to the inverse relationship between the size of the vessel and the pressure exerted on the vessel all else being equal. Despite this benefit there is a "bell-curve" response to these therapies in humans. Not all individuals are responsive to vasodilator therapy.

Several functional polymorphisms of the genes that encode for ACE and angiotensin-II receptors exist, which can affect how a subject responds to vasodilation.

Examples of functional ACE polymorphisms include the insertion or deletion polymorphisms such as a 287 base pair fragment (Ulgen et al., *Coron Artery Dis* 18:153-157 (2007)). The rs1799752 polymorphism is an insertion/deletion in an intron of the ACE gene, and with the sequence (SEQ ID NO:12) shown below, where sequences in the bracket are the insertion/deletion.

TCCCATTTCTCTAGACCTGCTGCCT[-/ATACAGTCACTTTTTTTTTT

TTTTGAGACGGAGTCTCGCTCTGTCGCCC]ATACAGTCACTTTTATGTG

GTTTCG.

The deletion removes the bracketed nucleic acid segment so that the rs1799752 polymorphism will have the following sequence (SEQ ID NO:35).

TCCCATTTCTCTAGACCTGCTGCCTATACAGTCACTTTTATGTGGTTTCG.

Research indicates that such an ACE deletion polymorphism results in higher ACE plasma levels and greater reduction in ejection fraction in patients following myocardial infraction (likely from elevations in blood pressure) (McNamara et al., *J Am Coll Cardiol* 44:2019-2026 (2004), Pilati et al., *Congest Heart Fail* 10:87-93 (2004). In addition, patients with the deletion polymorphism are more likely to have left-ventricular hypertrophy when compared to patients with the insertion polymorphism (left-ventricular hypertrophy results secondary to prolonged exposure to high blood pressure). Subjects with the deletion polymorphism would therefore be most responsive to ACE-inhibition or angiotensin-II receptor inhibition.

At least one functional variant of angiotensin has been found in humans: a cytosine to threonine substitution at nucleotide 4072 (Pilbrow et al., *Hypertension* 49:322-327 (2007); Tang et al., *Am Heart J* 143:854-860 (2002)). Human angiotensinogen is expressed from the AGT gene. A cDNA nucleotide sequence for human angiotensinogen is provided below as SEQ ID NO: 13 (accession number NM_000029.3 GI:188595658, from the NCBI database).

```
  1    ATCCCATGAG CGGGCAGCAG GGTCAGAAGT GGCCCCCGTG
 41    TTGCCTAAGC AAGACTCTCC CCTGCCCTCT GCCCTCTGCA
 81    CCTCCGGCCT GCATGTCCCT GTGGCCTCTT GGGGGTACAT
121    CTCCCGGGGC TGGGTCAGAA GGCCTGGGTG GTTGGCCTCA
161    GGCTGTCACA CACCTAGGGA GATGCTCCCG TTTCTGGGAA
201    CCTTGGCCCC GACTCCTGCA AACTTCGGTA AATGTGTAAC
241    TCGACCCTGC ACCGGCTCAC TCTGTTCAGC AGTGAAACTC
281    TGCATCGATC ACTAAGACTT CCTGGAAGAG GTCCCAGCGT
```

```
 321  GAGTGTCGCT TCTGGCATCT GTCCTTCTGG CCAGCCTGTG
 361  GTCTGGCCAA GTGATGTAAC CCTCCTCTCC AGCCTGTGCA
 401  CAGGCAGCCT GGGAACAGCT CCATCCCCAC CCCTCAGCTA
 441  TAAATAGGGC ATCGTGACCC GGCCGGGGGA AGAAGCTGCC
 481  GTTGTTCTGG GTACTACAGC AGAAGGGTAT GCGGAAGCGA
 521  GCACCCCAGT CTGAGATGGC TCCTGCCGGT GTGAGCCTGA
 561  GGGCCACCAT CCTCTGCCTC CTGGCCTGGG CTGGCCTGGC
 601  TGCAGGTGAC CCGGTGTACA TACACCCCTT CCACCTCGTC
 641  ATCCACAATG ACAGTACCTG TGAGCAGCTG GCAAAGGCCA
 681  ATGCCGGGAA GCCCAAAGAC CCCACCTTCA TACCTGCTCC
 721  AATTCAGGCC AAGACATCCC CTGTGGATGA AAAGGCCCTA
 761  CAGGACCAGC TGGTGCTAGT CGCTGCAAAA CTTGACACCG
 801  AAGACAAGTT GAGGGCCGCA ATGGTCGGGA TGCTGGCCAA
 841  CTTCTTGGGC TTCCGTATAT ATGGCATGCA CAGTGAGCTA
 881  TGGGGCGTGG TCCATGGGGC CACCGTCCTC TCCCCAACGG
 921  CTGTCTTTGG CACCCTGGCC TCTCTCTATC TGGGAGCCTT
 961  GGACCACACA GCTGACAGGC TACAGGCAAT CCTGGGTGTT
1001  CCTTGGAAGG ACAAGAACTG CACCTCCCGG CTGGATGCGC
1041  ACAAGGTCCT GTCTGCCCTG CAGGCTGTAC AGGGCCTGCT
1081  AGTGGCCCAG GGCAGGGCTG ATAGCCAGGC CCAGCTGCTG
1121  CTGTCCACGG TGGTGGGCGT GTTCACAGCC CCAGGCCTGC
1161  ACCTGAAGCA GCCGTTTGTG CAGGGCCTGG CTCTCTATAC
1201  CCCTGTGGTC CTCCCACGCT CTCTGGACTT CACAGAACTG
1241  GATGTTGCTG CTGAGAAGAT TGACAGGTTC ATGCAGGCTG
1281  TGACAGGATG GAAGACTGGC TGCTCCCTGA TGGGAGCCAG
1321  TGTGGACAGC ACCCTGGCTT TCAACACCTA CGTCCACTTC
1361  CAAGGAAGA TGAAGGGCTT CTCCCTGCTG GCCGAGCCCC
1401  AGGAGTTCTG GGTGGACAAC AGCACCTCAG TGTCTGTTCC
1441  CATGCTCTCT GGCATGGGCA CCTTCCAGCA CTGGAGTGAC
1481  ATCCAGGACA ACTTCTCGGT GACTCAAGTG CCCTTCACTG
1521  AGAGCGCCTG CCTGCTGCTG ATCCAGCCTC ACTATGCCTC
1561  TGACCTGGAC AAGGTGGAGG GTCTCACTTT CCAGCAAAAC
1601  TCCCTCAACT GGATGAAGAA ACTATCTCCC CGGACCATCC
1641  ACCTGACCAT GCCCCAACTG GTGCTGCAAG GATCTTATGA
1681  CCTGCAGGAC TGCTCGCCCC AGGCTGAGCT GCCCGCCATT
1721  CTGCACACCG AGCTGAACCT GCAAAAATTG AGCAATGACC
1761  GCATCAGGGT GGGGGAGGTG CTGAACAGCA TTTTTTTTGA
1801  GCTTGAAGCG GATGAGAGAG AGCCCACAGA GTCTACCCAA
1841  CAGCTTAACA AGCCTGAGGT CTTGGAGGTG ACCCTGAACC
1881  GCCCATTCCT GTTTGCTGTG TATGATCAAA GCGCCACTGC
1921  CCTGCACTTC CTGGGCCGCG TGGCCAACCC GCTGAGCACA
1961  GCATGAGGCC AGGGCCCCAG AACACAGTGC CTGGCAAGGC
2001  CTCTGCCCCT GGCCTTTGAG GCAAAGGCCA GCAGCAGATA
2041  ACAACCCCGG ACAAATCAGC GATGTGTCAC CCCCAGTCTC
2081  CCACCTTTTC TTCTAATGAG TCGACTTTGA GCTGGAAAGC
2121  AGCCGTTTCT CCTTGGTCTA AGTGTGCTGC ATGGAGTGAG
2161  CAGTAGAAGC CTGCAGCGGC ACAAATGCAC CTCCCAGTTT
2201  GCTGGGTTTA TTTTAGAGAA TGGGGGTGGG GAGGCAAGAA
2241  CCAGTGTTTA GCGCGGGACT ACTGTTCCAA AAAGAATTCC
2281  AACCGACCAG CTTGTTTGTG AAACAAAAAA GTGTTCCCTT
2321  TTCAAGTTGA GAACAAAAAT TGGGTTTTAA AATTAAAGIA
2361  TACATTTTTG CATTGCCTTC GGTTTGTATT TAGTGTCTTG
2401  AATGTAAGAA CATGACCTCC GTGTAGTGTC TGTAATACCT
2441  TAGTTTTTTC CACAGATGCT TGTGATTTTT GAACAATACG
2481  TGAAAGATGC AAGCACCTGA ATTTCTGTTT GAATGCGGAA
2521  CCATAGCTGG TTATTTCTCC CTTGTGTTAG TAATAAACGT
2561  CTTGCCACAA TAAGCCTCCA
2581  AAAAAAA
```

The rs699 single nucleotide polymorphism (SNP) is present in the AGT gene, where the variable nucleotide is at about position 1311 in SEQ ID NO: 13 (underlined), which can be in thymine some individuals and cytosine in others. The rs699 sequence (SEQ ID NO: 14) is shown below, where the underlined C/T is the SNP.

GGATGGAAGACTGGCTGCTCCCTGA[C/T]GGGAGCCAGTGTGGACAGCA CCCTG.

The human angiotensinogen polypeptide encoded by the AGT cDNA with SEQ ID NO:13 has the following sequence (SEQ ID NO:15).

```
  1  MRKRAPQSEM APAGVSLRAT ILCLLAWAGL AAGDRVYIHP
 41  FHLVIHNEST CEQLAKANAG KPKDPTFIPA PIQAKTSPVD
 81  EKALQDQLVL VAAKLDTEDK LRAAMVGMLA NFLGFRIYGM
121  HSELWGVVHG ATVLSPTAVF GTLASLYLGA LDHTADRLQA
161  ILGVPWKDKN CTSRLDAHKV LSALQAVQGL LVAQGRADSQ
201  AQLLLSTVVG VFTAPGLHLK QPFVQGLALY TPVVLPRSLD
241  FTELDVAAEK IDRFMQAVTG WKTGCSLMGA SVDSTLAFNT
281  YVHFQGKMKG FSLLAEPQEF WVDNSTSVSV PMLSGMGTFQ
321  HWSDIQDNFS VTQVPFTESA CLLLIQPHYA SDLDKVEGLT
361  FQQNSLNWMK KLSPRTIHLT MPQLVLQGSY DLQDLLAQAE
401  LPAILHTELN LQKLSNDRIR VGEVLNSIFF ELEADEREPT
441  ESTQQLNKPE VLEVTLNRPF LFAVYDQSAT ALHFLGRVAN
481  PLSTA
```

Note that the underlined methionine at position 268 of SEQ ID NO:15 is methionine because some individuals have nucleotide sequence SEQ ID NO: 13, where the nucleotide at about position 1311 is thymine. However, position 268 of SEQ ID NO: 15 can be threonine in some individuals because those individuals have cytosine at nucleotide position 1311 in SEQ ID NO: 13.

The threonine polymorphism of angiotensin results in higher angiotensin levels and higher resting blood pressure values. Therefore, patients with the threonine genetic variant will benefit primarily from an ACE inhibitor (preventing the conversion of the higher levels of angiotensin I to angiotensin II) or an angiotensin receptor inhibitor.

An example of a functional polymorphism of an angiotensin II receptor type-1 involves an adenine to cytosine substitution at nucleotide 1166 (Miller et al. *Kidney Int* 56:2173-2180 (1999); Baudin. *Pharmacogenomics* 3:65-73 (2002)). Human angiotensin II receptor type-1 is expressed from the AGT1R gene. One example of an AGT1R single nucleotide polymorphism is the so-called A1166→C polymorphism, which is in the 3' untranslated region of the AGT1R gene. This A1166→C polymorphism is also identified as the rs5186 single nucleotide polymorphism (SNP), which has the following sequence (SEQ ID NO: 16) where the underlined A/C is the variable SNP site.

TGCAGCACTTCACTACCAAATGAGC[A/C]TTAGCTACTTTTCAGAATTG

AAGGA.

A portion of a 3' untranslated region of the AGT1R gene with NCBI accession number NG_008468.1 (GI: 198041751) is shown below (SEQ ID NO:17) that contains the rs5186 SNP with the variant nucleotide (adenine) identified below in bold and with underlining.

```
48961  ATTCAACTAG GCATCATACG TGACTGTAGA ATTGCAGATA
49001  TTGTGGACAC GGCCATGCCT ATCACCATTT GTATAGCTTA
49041  TTTTAACAAT TGCCTGAATC CTCTTTTTTA TGGCTTTCTG
49081  GGGAAAAAAT TTAAAAGATA TTTTCTCCAG CTTCTAAAAT
49121  ATATTCCCCC AAAAGCCAAA TCCCACTCAA ACCTTTCAAC
49181  AAAAATGAGC ACGCTTTCCT ACCGCCCCTC AGATAATGTA
49201  AGCTCATCCA CCAAGAAGCC TGCACCATGT TTTGAGGTTG
49241  AGTGACATGT TCGAAACCTG TCCATAAAGT AATTTTGTGA
49301  AAGAAGGAGC AAGAGAACAT TCCTCTGCAG CACTTCACTA
49321  CCAAATGAGC ATTAGCTACT TTTCAGAATT GAAGGAGAAA
49361  ATGCATTATG TGGACTGAAC CGACTTTTCT AAAGCTCTGA
49401  ACAAAAGCTT TTCTTTCCTT TTGCAACAAG ACAAAGCAAA
49441  GCCACATTTT GCATTAGACA GATGACGGCT GCTCGAAGAA
49481  CAATGTCAGA AACTCGATGA ATGTGTTGAT TTGAGAAATT
49521  TTACTGACAG AAATGCAATC TCCCTAGCCT GCTTTTGTCC
49561  TGTTATTTTT TATTTCCACA TAAAGGTATT TAGAATATAT
49601  TAAATCGTTA GAGGAGCAAC AGGAGATGAG AGTTCCAGAT
49641  TGTTCTGTCC AGTTTCCAAA GGGCAGTAAA GTTTTCGTGC
```

This polymorphism has been shown to influence resting blood pressure values which suggest which patients may benefit more from angiotensin-II receptor inhibition. Specifically, patients with the C variant of the angiotensin receptor type I tend to demonstrate higher resting blood pressure values, have more detrimental cardiovascular events, and have a greater chance of developing high blood pressure during pregnancy, when compared to the A variant. Subjects with the C variant will therefore be more responsive to angiotensin receptor blockers.

A cDNA sequence for human angiotensin II receptor is provided in the NCBI database as accession number X65699.1 (GI:510983), which has the following sequence (SEQ ID NO:18).

```
   1  GGCAGCAGCG AGTGACAGGA CGTCTGGACC GGCGCGCCGC
  41  TAGCAGCTCT GCCGGGCCGC GGCGGTGATC GATGGGAGCG
  81  GCTGGAGCGG ACCCAGCGAG TGAGGGCGCA CAGCCGGACG
 121  CCGAGGCGGC GGGCGGGAGA CCGCACCGCG ACGCCGGCCC
 161  TCGGCGGACG AGTCGAGCGC CCGGGCGCGG GTGTATTTGA
 201  TATAGTGTTT GCAACAAATT CGACCCAGGT GATCAAAATG
 241  ATTCTCAACT CTTCTACTGA AGATGGTATT AAAAGAATCC
 281  AAGATGATTG TCCCAAAGCT GGAAGGCATA ATTACATATT
 321  TGTCATGATT CCTACTTTAT ACAGTATCAT CTTTGTGGTG
 361  GGAATATTTG GAAACAGCTT GGTGGTGATA GTCATTTACT
 401  TTTATATGAA GCTGAAGACT GTGGCCAGTG TTTTTCTTTT
 441  GAATTTAGCA CTGGCTGACT TATGCTTTTT ACTGACTTTG
 481  CCACTATGGG CTGTCTACAC AGCTATGGAA TACCGCTGGC
 521  CCTTTGGCAA TTACCTATGT AAGATTGCTT CAGCCAGCGT
 561  CAGTTTCAAC CTGTACGCTA GTGTGTTTCT ACTCACGTGT
 601  CTCAGCATTG ATCGATACCT GGCTATTGTT CACCCAATGA
 641  AGTCCCGCCT TCGACGCACA ATGCTTGTAG CCAAAGTCAC
 681  CTGCATCATC ATTTGGCTGC TGGCAGGCTT GGCCAGTTTG
 721  CCAGCTATAA TCCATCGAAA TGTATTTTTC ATTGAGAACA
 761  CCAATATTAC AGTTTGTGCT TTCCATTATG AGTCCCAAAA
 801  TTCAACCCTC CCGATAGGGC TGGGCCTGAC CAAAAATATA
 841  CTGGGTTTCC TGTTTCCTTT TCTGATCATT CTTACAAGTT
 881  ATACTCTTAT TTGGAAGGCC CTAAAGAAGG CTTATGAAAT
 921  TCAGAAGAAC AAACCAAGAA ATGATGATAT TTTTAAGATA
 961  ATTATGGCAA TTGTGCTTTT CTTTTTCTTT TCCTGGATTC
1001  CCCACCAAAT ATTCACTTTT CTGGATGTAT TGATTCAACT
1041  AGGCATCATA CGTGACTGTA GAATTGCAGA TATTGTGGAC
1081  ACGGCCATGC CTATCACCAT TTGTATAGCT TATTTTAACA
1121  ATTGCCTGAA TCCTCTTTTT TATGGCTTTC TGGGGAAAAA
1161  ATTTAAAAGA TATTTTCTCC AGCTTCTAAA ATATATTCCC
1201  CCAAAAGCCA AATCCCACTC AAACCTTTCA ACAAAAATGA
1241  GCACGCTTTC CTACCGCCCC TCAGATAATG TAAGCTCATC
1281  CACCAAGAAG CCTGCACCAT GTTTTGAGGT TGAGTGACAT
```

```
1321  GTTCGAAACC TGTCCATAAA GTAATTTTGT GAAAGAAGGA

1361  GCAAGAGAAC ATTCCTCTCC AGCACTTCAC TACCAAATGA

1401  GCATTAGCTA CTTTTCAGAA TTGAAGGAGA AAATGCATTA

1441  TGTGGACTGA ACCGACTTTT CTAAAGCTCT GAACAAAAGC

1481  TTTTCTTTCC TTTTGCAACA AGACAAAGCA AAGCCACATT

1521  TTGCATTAGA CAGATGACGG CTGCTCGAAG AACAATGTCA

1561  GAAACTCGAT GAATGTGTTG ATTTGAGAAA TTTTACTGAC

1601  AGAAATGCAA TCTCCCTAGC CTGCTTTTGT CCTGTTATTT

1641  TTTATTTCCA CATAAAGGTA TTTAGAATAT ATTAACTCGT

1681  TAGAGGAGCA ACAGGAGATG AGAGTTCCAG ATTGTTCTGT

1721  CCAGTTTCCA AAGGGCAGTA AAGTTTTCGT GCCTGTTTTC

1761  AGCTATTAGC AACTGTGCCT ACACTTGCAC CTGGTCTGCA

1801  CATTTTGTAC AAAGATATGC TTAAGCAGTA GTCGTCAAGT

1841  TGCAGATCTT TGTTGTGAAA TTCAACCTGT GTCTTATAGG

1881  TTTACACTGC CAAAACAATG CCCGTAAGAT GGCTTATTTG

1921  TATAATGGTG TTACCTAAAG TCACATATAA AAGTTAAACT

1961  ACTTGTAAAG GTGCTGCACT GGTCCCAAGT AGTAGTGTCT

2001  TCCTAGTATA TTAGTTTGAT TTAATATCTG AGAAGTGTAT

2041  ATAGTTTGTG GTAAAAAGAT TATATATCAT AAAGTATGCC

2081  TTCCTGTTTA AAAAAAGTAT ATATTCTACA CATATATGTA

2121  TATGTATATC TATATCTCTA AACTGCTGTT AATTGATTAA

2161  AATCTGGCAA AGTTATATTT ACCCC
```

In addition to angiotensin, angiotensin II receptors and ACE, renin has been shown to be a potent vasoconstrictor that can result in high blood pressure. Renin converts angiotensinogen to angiotensin I which can result in vasoconstriction due to the down-stream effects (angiotensin-I conversion to angiotensin II through ACE). One example of a functional and common renin polymorphism (Vangjeli et al., *Circulation Cardiovascular genetics* 3:53-59 (2010)) can influence the blood pressure response to vasodilator therapy. This renin polymorphism is present in rs12750834. The nucleotide sequence surrounding the renin rs12750834 single nucleotide polymorphism is shown below, where the underlined A/G in the sequence (SEQ ID NO:19) is the SNP.

AGAACACCAAAGCAGGCTTAATCTG[A/G]GGGCACTTACAGAGACTGC

TTTAAA.

The complementary sequence of SEQ ID NO:19 is the following sequence (SEQ ID NO:20).

TTTAAAGCAGTCTCTGTAAGTGCCC[C/T]CAGATTAAGCCTGCTTTGG

TGTTCT.

Note that the cytosine to thymine substitution is a guanine to adenine substitution in the opposite strand.

The rs12750834 SNP contains a cytosine to thymine substitution, or a guanine to adenine substitution depending upon the DNA strand, at about nucleotide position 5312 upstream of the renin start site. The cytosine (guanine) variant of renin has been shown to correlate with greater reduction in blood pressure upon administration of angiotensin II receptor blockers such as valsartan.

Sodium/Diuretic Regulation of Blood Pressure

The kidneys are the center of long-term blood pressure regulation. Alterations in $Na^+$ reabsorption in the kidneys result in alterations in fluid retention, which leads to increases or decreases in blood plasma volume as well as to changes in the pressure against the vessels. There are several proteins that are important in renal $Na^+$ handling and in the response to diuretic therapy including the epithelial $Na^+$ channels, alpha-adducin, the $Na^+Cl^-$ co-transporter, and lysine deficient protein kinase-1 (WNK).

The epithelial sodium ($Na^+$) channel is responsible for $Na^+$ reabsorption on the apical portion of epithelial cells in the kidneys. The $Na^+$ channel is made up of three different subunits: the alpha, beta, and gamma. The alpha subunit of the epithelial $Na^+$ channel is highly functional and removal of this subunit abolishes channel activity in cell and animal models. The gamma subunit is also extremely important in channel function. Functional gamma genetic variants result in pseudohypoaldosteronism type-I and Liddle's syndrome, two severe genetic diseases resulting in salt wasting and high salt conservation (salt sensitivity), respectively. Adducin is made up of an alpha, beta, and gamma subunit. The alpha subunit increases sodium ($Na^+$) reabsorption in the kidneys through the activity of $Na^+K^+$ ATPase (which moves $Na^+$ and potassium into and out of cells). The sodium ($Na^+$) chloride ($Cl^-$) co-transporter is important in regulating $Na^+$ and $Cl^-$ movement between the kidney and the rest of the body. Active $Na^+$—$Cl^-$ transport results in $Na^+$ reabsorption and can, therefore, result in higher blood pressure. The WNK1 protein is a key regulator of long-term $Na^+$ and chloride $Cl^-$ reabsorption in the kidneys. WNK1 regulates the activity of $Na^+$—$Cl^-$ co-transporters. If a patient has a more active WNK1 genotype, they likely have greater $Na^+$ and $Cl^-$ reabsorption in the kidneys which can increase blood volume and, therefore, pressure on the vessels.

A functional and common polymorphism of the gene that encodes the epithelial Na+channel (SCNN1A) has been identified, where the polymorphism is an alanine to threonine substitution at about position 663-722. A cDNA sequence for the human SCNN1A gene is available from the NCBI database as accession number NM_001159576.1 (GI: 227430288). This sequence is provided below as SEQ ID NO:21.

```
  1   AAACAGAAGG CAGATAGAGA GGGAGTGAGA GGCAGGAGCT

41   GAGACACAGA TCCTGGAGGA AGAAGACCAA AGGAAGGGGG

81   CAGAGACAGA AAGGGAGGTG CTAGGACAAA ACTCGAAAGG

121   TGGCCCTATC AGGGAAGCAG AGGAGAGGCC GTTCTAGGGA

161   AGCCCAGCTC CGGCACTTTT GGCCCCAACT CCCGCAGGTC

201   TGCTGGCTCC AGGAAAGGTG GAGGAGGGAG GGAGGAGTGG

241   GAGAATGTGG GCGCAGGGTG GGACATGGGC ATGGCCAGGG

281   GCAGCCTCAC TCGGGTTCCA GGGGTGATGG GAGAGGGCAC

321   TCAGGGCCCA GAGCTCAGCC TTGACCCTGA CCCTTGCTCT

361   CCCCAATCCA CTCCGGGGCT CATGAAGGGG AACAAGCTGG

401   AGGAGCAGGA CCCTAGACCT CTGCAGCCCA TACCAGGTCT
```

```
 441 CATGGAGGGG AACAAGCTGG AGGAGCAGGA CTCTAGCCCT
 481 CCACAGTCCA CTCCAGGGCT CATGAAGGGG AACAAGCGTG
 521 AGGAGCAGGG GCTGGGCCCC GAACCTGCGG CGCCCCAGCA
 561 GCCCACGGCG GAGGAGGAGG CCCTGATCGA GTTCCACCGC
 601 TCCTACCGAG AGCTCTTCGA GTTCTTCTGC AACAACACCA
 641 CCATCCACGG CGCCATCCGC CTGGTGTGCT CCCAGCACAA
 681 CCGCATGAAG ACGGCCTTCT GGGCAGTGCT GTGGCTCTGC
 721 ACCTTTGGCA TGATGTACTG GCAATTCGGC CTGCTTTTCG
 761 GAGAGTACTT CAGCTACCCC GTCAGCCTCA ACATCAACCT
 801 CAACTCGGAC AAGCTCGTCT TCCCCGCAGT GACCATCTGC
 841 ACCCTCAATC CCTACAGGTA CCCGGAAATT AAAGAGGAGC
 881 TGGAGGAGCT GGACCGCATC ACAGAGCAGA CGCTCTTTGA
 921 CCTGTACAAA TACAGCTCCT TCACCACTCT CGTGGCCGGC
 961 TCCCGCAGCC GTCGCGACCT GCGGGGGACT CTGCCGCACC
1001 CCTTGCAGCG CCTGAGGGTC CCGCCCCCGC CTCACGGGGC
1041 CCGTCGAGCC CGTAGCGTGG CCTCCAGCTT GCGGGACAAC
1081 AACCCCCAGG TGGACTGGAA GGACTGGAAG ATCGGCTTCC
1121 AGCTGTGCAA CCAGAACAAA TCGGACTGCT TCTACCAGAC
1161 ATACTCATCA GGGGTGGATG CGGTGAGGGA GTGGTACCGC
1201 TTCCACTACA TCAACATCCT GTCGAGGCTG CGAGAGACTC
1241 TGCCATCCCT GGAGGAGGAC ACGCTGGGCA ACTTCATCTT
1281 CGCCTGCCGC TTCAACCAGG TCTCCTGCAA CCAGGCGAAT
1321 TACTCTCACT TCCACCACCC GATGTATGGA AACTGCTATA
1361 CTTTCAATGA CAAGAACAAC TCCAACCTCT GGATGTCTTC
1401 CATGCCTGGA ATCAACAACG GTCTCTCCCT GATGCTGCGC
1441 GCAGAGCAGA ATGACTTCAT TCCCCTGCTG TCCACAGTGA
1481 CTGGGGCCCG GGTAATGGTG CACGGGCAGG ATGAACCTGC
1521 CTTTATGGAT GATGGTGGCT TTAACTTGCG GCCTGGCGTG
1561 GAGACCTCCA TCAGCATGAG GAAGGAAACC CTGGACAGAC
1601 TTGGGGGCGA TTATGGCGAC TGCACCAAGA ATGGCAGTGA
1641 TGTTCCTGTT GAGAACCTTT ACCCTTCAAA GTACACACAG
1681 CAGGTGTGTA TTCACTCCTG CTTCCAGGAG AGCATGATCA
1721 AGGAGTGTGG CTGTGCCTAC ATCTTCTATC CGCGGCCCCA
1761 GAACGTGGAG TACTGTGACT ACAGAAAGCA CAGTTCCTGG
1801 GGGTACTGCT ACTATAAGCT CCAGGTTGAC TTCTCCTCAG
1841 ACCACCTGGG CTGTTTCACC AAGTGCCGGA AGCCATGCAG
1881 CGTGACCAGC TACCAGCTCT CTGCTGGTTA CTCACGATGG
1921 CCCTCGGTGA CATCCCAGGA ATGGGTCTTC CAGATGCTAT
1961 CGCGACAGAA CAATTACACC GTCAACAACA AGAGAAATGG
2001 AGTGGCCAAA GTCAACATCT TCTTCAAGGA GCTGAACTAC
2041 AAAACCAATT CTGAGTCTCC CTCTGTCACG ATGGTCACCC
2081 TCCTGTCCAA CCTGGGCAGC CAGTGGAGCC TGTGGTTCGG
2121 CTCCTCGGTG TTGTCTGTGG TGGAGATGGC TGAGCTCGTC
2161 TTTGACCTGC TGGTCATCAT GTTCCTCATG CTGCTCCGAA
2201 GGTTCCGAAG CCGATACTGG TCTCCAGGCC GAGGGGGCAG
2241 GGGTGCTCAG GAGGTAGCCT CCACCCTGGC ATCCTCCCCT
2281 CCTTCCCACT TCTGCCCCCA CCCCATGTCT CTGTCCTTGT
2321 CCCAGCCAGG CCCTGCTCCC TCTCCAGCCT TGACAGCCCC
2361 TCCCCCTGCC TATGCCACCC TGGGCCCCCG CCCATCTCCA
2401 GGGGGCTCTG CAGGGGCCAG TTCCTCCACC TGTCCTCTGG
2441 GGGGGCCCTG AGAGGGAAGG AGAGGTTTCT CACACCAAGG
2481 CAGATGCTCC TCTGGTGGGA GGGTGCTGGC CCTGGCAAGA
2521 TTGAAGGATG TGCAGGGCTT CCTCTCAGAG CCGCCCAAAC
2561 TGCCGTTGAT GTGTGGAGGG GAAGCAAGAT GGGTAAGGGC
2601 TCAGGAAGTT GCTCCAAGAA CAGTAGCTGA TGAAGCTGCC
2641 CAGAAGTGCC TTGGCTCCAG CCCTGTACCC CTTGGTACTG
2681 CCTCTGAACA CTCTGGTTTC CCCACCCAAC TGCGGCTAAG
2721 TCTCTTTTTC CCTTGGATCA GCCAAGCGAA ACTTGGAGCT
2761 TTGACAAGGA ACTTTCCTAA GAAACCGCTG ATAACCAGGA
2801 CAAAACACAA CCAAGGGTAC ACGCAGGCAT GCACGGGTTT
2841 CCTGCCCAGC GACGGCTTAA GCCAGCCCCC GACTGGCCTG
2881 GCCACACTGC TCTCCAGTAG CACAGATGTC TGCTCCTCCT
2921 CTTGAACTTG GGTGGGAAAC CCCACCCAAA GCCCCCTTT
2961 GTTACTTAGG CAATTCCCCT TCCCTGACTC CCGAGGGCTA
3001 GGGCTAGAGC AGACCCGGGT AAGTAAAGGC AGACCCAGGG
3041 CTCCTCTAGC CTCATACCCG TGCCCTCACA GAGCCATGCC
3081 CCGGCACCTC TGCCCTGTGT CTTTCATACC TCTACATGTC
3121 TGCTTGAGAT ATTTCCTCAG CCTGAAAGTT TCCCCAACCA
3161 TCTGCCAGAG AACTCCTATG CATCCCTTAG AACCCTGCTC
3201 AGACACCATT ACTTTTGTGA ACGCTTCTGC CACATCTTGT
3241 CTTCCCCAAA ATTGATCACT CCGCCTTCTC CTGGGCTCCC
3281 GTAGCACACT ATAACATCTG CTGGAGTGTT GCTGTTGCAC
3321 CATACTTTCT TGTACATTTG TGTCTCCCTT CCCAACTAGA
3361 CTGTAAGTGC CTTGCGGTCA GGGACTGAAT CTTGCCCGTT
3401 TATGTATGCT CCATGTCTAG CCCATCATCC TGCTTGGAGC
3441 AAGTAGGCAG GAGCTCAATA AATGTTTGTT GCATGAAGGA
3481 AAAAAAAAAA AAAAAA
```

The rs2228576 single nucleotide polymorphism (SNP) is present in the SCNN1A gene, where the variable nucleotide is at about position 2428 in SEQ ID NO:21 (underlined), which can be adenine in some individuals and guanine in others. The rs2228576 sequence (SEQ ID NO:22) is shown below, where the underlined A/G is the SNP.

GGGCTCTGCAGGGGCCAGTTCCTCC[A/G]CCTGTCCTCTGGGGGGC

CCTGAGA

The human the epithelial Na+channel encoded by the SCNN1A cDNA with SEQ ID NO:21 has the following sequence (SEQ ID NO:23).

```
  1 MGMARGSLTR VPGVMGEGTQ GPELSLDPDP CSPQSTPGLM
 41 KGNKLEEQDP RPLQPIPGLM EGNKLEEQDS SPPQSTPGLM
 81 KGNKREEQGL GPEPAAPQQP TAEEEALIEF HRSYRELFEF
121 FCNNTTIHGA IRLVCSQHNR MKTAFWAVLW LCTFGMMYWQ
161 FGLLFGEYFS YPVSLNINLN SDKLVFPAVT ICTLNPYRYP
201 EIKEELEELD RITEQTLFDL YKYSSFTTLV AGSRSRRDLR
241 GTLPHPLQRL RVPPPPHGAR RARSVASSLR DNNPQVDWKD
281 WKIGFQLCNQ NKSDCFYQTY SSGVDAVREW YRFHYINILS
321 RLPETLPSLE EDTLGNFIFA CRFNQVSCNQ ANYSHFHHPM
361 YGNCYTFNDK NNSNLWMSSM PGINNGLSLM LRAEQNDFIP
401 LLSTVTGARV MVHGQDEPAF MDDGGFNLRP GVETSISMRK
441 ETLDRLGGDY GDCTKNGSDV PVENLYPSKY TQQVCIHSCF
481 QESMIKECGC AYIFYPRPQN VEYCDYRKHS SWGYCYYKLQ
521 VDFSSDHLGC FTKCRKPCSV TSYQLSAGYS RWPSVTSQEW
561 VFQMLSRQNN YTVNNKRNGV AKVNIFFKEL NYKTNSESPS
601 VTMVTLLSNL GSQWSLWFGS SVLSVVEMAE LVFDLLVIMF
641 LMLLRRFRSR YWSPGRGGRG AQEVASTLAS SPPSHFCPHP
681 MSLSLSQPGP APSPALTAPP PAYATLGPRP SPGGSAGASS
721 STCPLGGP
```

Another cDNA sequence for the human SCNN1A gene with the same SNP is available from the NCBI database as accession number NM_001038.5 (GI:227430285). This sequence is provided below as SEQ ID NO:24.

```
   1 CTTGCCTGTC TGCGTCTAAA GCCCCTGCCC AGAGTCCGCC
  41 TTCTCAGGTC CAGTACTCCC AGTTCACCTG CCCTCGGGAG
  81 CCCTCCTTCC TTCGGAAAAC TCCCGGCTCT GACTCCTCCT
 121 CAGCCCCTCC CCCCGCCCTG CTCACCTTTA ATTGAGATGC
 161 TAATGAGATT CCTGTCGCTT CCATCCCTGG CCGGCCAGCG
 201 GGCGGGCTCC CCAGCCAGGC CGCTGCACCT GTCAGGGGAA
 241 CAAGCTGGAG GAGCAGGACC CTAGACCTCT GCAGCCCATA
 281 CCAGGTCTCA TGGAGGGGAA CAAGCTGGAG GAGCAGGACT
 321 CTAGCCCTCC ACAGTCCACT CCAGGGCTCA TGAAGGGGAA
 361 CAAGCGTGAG GAGCAGGGGC TGGGCCCCGA ACCTGCGGCG
 401 CCCCAGCAGC CCACGGCGGA GGAGGAGGCC CTGATCGAGT
 441 TCCACCGCTC CTACCGAGAG CTCTTCGAGT TCTTCTGCAA
 481 CAACACCACC ATCCACGGCG CCATCCGCCT GGTGTGCTCC
 521 CAGCACAACC GCATGAAGAC GGCCTTCTGG GCAGTGCTGT
 561 GGCTCTGCAC CTTTGGCATG ATGTACTGGC AATTCGGCCT
 601 GCTTTTCGGA GAGTACTTCA GCTACCCCGT CAGCCTCAAC
 641 ATCAACCTCA ACTCGGACAA GCTCGTCTTC CCCGCAGTGA
 681 CCATCTGCAC CCTCAATCCC TACAGGTACC CGGAAATTAA
 721 AGAGGAGCTG GAGGAGCTGG ACCGCATCAC AGAGCAGACG
 761 CTCTTTGACC TGTACAAATA CAGCTCCTTC ACCACTCTCG
 801 TGGCCGGCTC CCGCAGCCGT CGCGACCTGC GGGGGACTCT
 841 GCCGCACCCC TTGCAGCGCC TGAGGGTCCC GCCCCCGCCT
 881 CACGGGGCCC GTCGAGCCCG TAGCGTGGCC TCCAGCTTGC
 921 GGGACAACAA CCCCCAGGTG GACTGGAAGG ACTGGAAGAT
 961 CGGCTTCCAG CTGTGCAACC AGAACAAATC GGACTGCTTC
1001 TACCAGACAT ACTCATCAGG GGTGGATGCG GTGAGGGAGT
1041 GGTACCGCTT CCACTACATC AACATCCTGT CGAGGCTGCC
1081 AGAGACTCTG CCATCCCTGG AGGAGGACAC GCTGGGCAAC
1121 TTCATCTTCG CCTGCCGCTT CAACCAGGTC TCCTGCAACC
1161 AGGCGAATTA CTCTCACTTC CACCACCCGA TGTATGGAAA
1201 CTGCTATACT TTCAATGACA AGAACAACTC CAACCTCTGG
1241 ATGTCTTCCA TGCCTGGAAT CAACAACGGT CTGTCCCTGA
1281 TGCTGCGCGC AGAGCAGAAT GACTTCATTC CCCTGCTGTC
1321 CACAGTGACT GGGGCCCGGG TAATGGTGCA CGGGCAGGAT
1361 GAACCTGCCT TTATGGATGA TGGTGGCTTT AACTTGCGGC
1401 CTGGCGTGGA GACCTCCATC AGCATGAGGA AGGAAACCCT
1441 GGACAGACTT GGGGGCGATT ATGGCGACTG CACCAAGAAT
1481 GGCAGTGATG TTCCTGTTGA GAACCTTTAC CCTTCAAAGT
1521 ACACACAGCA GGTGTGTATT CACTCCTGCT TCCAGGAGAG
1561 CATGATCAAG GAGTGTGGCT GTGCCTACAT CTTCTATCCG
1601 CGGCCCCAGA ACGTGGAGTA CTGTGACTAC AGAAAGCACA
1641 GTTCCTGGGG GTACTGCTAC TATAAGCTCC AGGTTGACTT
1681 CTCCTCAGAC CACCTGGGCT GTTTCACCAA GTGCCGGAAG
1721 CCATGCAGCG TGACCAGCTA CCAGCTCTCT GCTGGTTACT
1761 CACGATGGCC CTCGGTGACA TCCCAGGAAT GGGTCTTCCA
1801 GATGCTATCG CGACAGAACA ATTACACCGT CAACAACAAG
1841 AGAAATGGAG TGGCCAAAGT CAACATCTTC TTCAAGGAGC
1881 TGAACTACAA AACCAATTCT GAGTCTCCCT CTGTCACGAT
1921 GGTCACCCTC CTGTCCAACC TGGGCAGCCA GTGGAGCCTG
1961 TGGTTCGGCT CCTCGGTGTT GTCTGTGGTG GAGATGGCTG
2001 AGCTCGTCTT TGACCTGCTG GTCATCATGT TCCTCATGCT
2041 GCTCCGAAGG TTCCGAAGCC GATACTGGTC TCCAGGCCGA
2081 GGGGGCAGGG GTGCTCAGGA GGTAGCCTCC ACCCTGGCAT
2121 CCTCCCCTCC TTCCCACTTC TGCCCCCACC CCATGTCTCT
```

-continued

```
2161 GTCCTTGTCC CAGCCAGGCC CTGCTCCCTC TCCAGCCTTG
2201 ACAGCCCCTC CCCCTGCCTA TGCCACCCTG GGCCCCCGCC
2241 CATCTCCAGG GGGCTCTGCA GGGGCCAGTT CCTCCACCTG
2281 TCCTCTGGGG GGGCCCTGAG AGGGAAGGAG AGGTTTCTCA
2321 CACCAAGGCA GATGCTCCTC TGGTGGGAGG GTGCTGGCCC
2361 TGGCAAGATT GAAGGATGTG CAGGGCTTCC TCTCAGAGCC
2401 GCCCAAACTG CCGTTGATGT GTGGAGGGGA AGCAAGATGG
2441 GTAAGGGCTC AGGAAGTTGC TCCAAGAACA GTAGCTGATG
2481 AAGCTGCCCA GAAGTGCCTT GGCTCCAGCC CTGTACCCCT
2521 TGGTACTGCC TCTGAACACT CTGGTTTCCC CACCCAACTG
2561 CGGCTAAGTC TCTTTTTCCC TTGGATCAGC CAAGCGAAAC
2601 TTGGAGCTTT GACAAGGAAC TTTCCTAAGA AACCGCTGAT
2641 AACCAGGACA AAACACAACC AAGGGTACAC GCAGGCATGC
2681 ACGGGTTTCC TGCCCAGCGA CGGCTTAAGC CAGCCCCCGA
2721 CTGGCCTGGC CACACTGCTC TCCAGTAGCA CAGATGTCTG
2761 CTCCTCCTCT TGAACTTGGG TGGGAAACCC CACCCAAAAG
2801 CCCCCTTTGT TACTTAGGCA ATTCCCCTTC CCTGACTCCC
2841 GAGGGCTAGG GCTAGAGCAG ACCCGGGTAA GTAAAGGCAG
2881 ACCCAGGGCT CCTCTAGCCT CATACCCGTG CCCTCACAGA
2921 GCCATGCCCC GGCACCTCTG CCCTGTGTCT TTCATACCTC
2961 TACATGTCTG CTTGAGATAT TTCCTCAGCC TGAAAGTTTC
3001 CCCAACCATC TGCCAGAGAA CTCCTATGCA TCCCTTAGAA
3041 CCCTGCTCAG ACACCATTAC TTTTGTGAAC GCTTCTGCCA
3081 CATCTTGTCT TCCCCAAAAT TGATCACTCC GCCTTCTCCT
3121 GGGCTCCCGT AGCACACTAT AACATCTGCT GGAGTGTTGC
3161 TGTTGCACCA TACTTTCTTG TACATTTGTG TCTCCCTTCC
3201 CAACTAGACT GTAAGTGCCT TGCGGTCAGG GACTGAATCT
3241 TGCCCGTTTA TGTATGCTCC ATGTCTAGCC CATCATCCTG
3281 CTTGGAGCAA GTAGGCAGGA GCTCAATTTA TGTTTGTTGC
3321 ATGAAGGAAA AAAAAAAAAA AAAAA
```

The human epithelial Na+ channel encoded by the SCNN1A cDNA with SEQ ID NO:24 has the following sequence (SEQ ID NO:25).

```
  1 MEGNKLLQED SSPPQSTPGL MKGNKREEQG LGPEPAAPQQ
 41 PTAEEEALIE FHRSYRELFE FFCNNTTIHG AIRLVCSQHN
 81 RMKTAFWAVL WLCTFGMMYW QFGLLFGEYF SYPVSLNINL
121 NSDKLVFPAV TICTLNPYRY PEIKEELEEL DRITEQTLFD
161 LYKYSSFTTL VAGSRSRRDL RGTLPHPLQR LRVPPPPHGA
201 RRARSVASSL RDNNPQVDWK DWKIGFQLCN QNKSDCFYQT
241 YSSGVDAVRE WYRFHYINIL SRLPETLPSL EEDTLGNFIF
281 ACRFNQVSCN QANYSHFHHP MYGNCYTFND KNNSNLWMSS
321 MPGINNGLSL MLRAEQNDFI PLLSTVTGAR VMVHGQDEPA
361 FMDDGGFNLR PGVETSISMR KETLDRLGGD YGDCTKNGSD
401 VPVENLYPSK YTQQVCIHSC FQESMIKECS CAYIFYPRPQ
441 NVEYCDYRKH SSWGYCYYKL QVDFSSDHLG CFTKCRKPCS
481 VTSYQLSAGY SRWPSVTSQE WVFQMLSRQN NYTVNNKRNG
521 VAKVNIFFKE LNYKTNSESP SVTMVTLLSN LGSQWSLWFG
561 SSVLSVVEMA ELVFDLLVIM FLMLLRRFRS RYWSPGRGGR
601 GAQEVASTLA SSPPSHFCPH PMSLSLSQPG PAPSPALTAP
641 PPAYATLGPR PSPGGSAGAS SST̲CPLGGP
```

Note that the underlined threonine at position 722 of the SEQ ID NO:23 SCNN1A protein, and the underlined threonine at position 663 of the SEQ ID NO:25 SCNN1A protein, is threonine because some individuals have nucleotide sequence SEQ ID NO:22, where the variable nucleotide is adenine. However, position 722 of SEQ ID NO:23 and position 663 of SEQ ID NO:25 can be alanine in some individuals because those individuals have guanine as the variable nucleotide in sequence SEQ ID NO:22.

Patients with the threonine substitution in SCNN1A (adenine in rs2228576) have more functional $Na^+$ channels and consequently higher activity higher voltage currents across the cells. Hence, patients with such a threonine at the variable site in SCNN1A are more susceptible to hypertension than SCNNIA proteins with alanine at that position. Patients with the threonine substitution in SCNN1A can benefit from administration of amiloride.

Common and functional genetic variation of alpha adducin at amino acid 460 has also been identified where some individuals have glycine and others have tryptophan. A cDNA sequence for the human alpha adducin gene (ADD1) is available from the NCBI database as accession number NM_001119.4 (GI:346644753). This ADD1 sequence is provided below as SEQ ID NO:26.

```
  1 GCACCCAGGT CGGGCGGTGG GGGCGAGCGG AGGGGCTGAG
 41 GGGCGGAGAG GCCTGGCGGG CCGCTGCTGC GGGCCAGGGG
 81 ACGGGGCGG AGCCGGAGCC GGAGCCGACG GGCGGTGGCC
121 GCACTGGGAC CCCGGAATCC CGCGCGCTGC CCACGATTCG
161 CTTCTGAGGA ACCTAGAAAG ATTGTACAAT GAATGGTGAT
201 TCTCGTGCTG CGGTGGTGAC CTCACCACCC CCGACCACAG
241 CCCCTCACAA GGAGAGGTAC TTCGACCGAG TAGATGAGAA
281 CAACCCAGAG TACTTGAGGG AGAGGAACAT GGCACCAGAC
321 CTTCGCCAGG ACTTCAACAT GATGGAGCAA AAGAAGAGGG
361 TGTCCATGAT TCTGCAAAGC CCTGCTTTCT GTGAAGAATT
401 GGAATCAATG ATACAGGAGC AATTTAAGAA GGGGAAGAAC
441 CCCACAGGCC TATTGGCATT ACAGCAGATT GCAGATTTTA
481 TGACCACGAA TGTACCAAAT GTCTACCCAG CAGCTCCGCA
521 AGGAGGGATG GCTGCCTTAA ACATGAGTCT TGGTATGGTG
```

```
 561 ACTCCTGTGA ACGATCTTAG AGGATCTGAT TCTATTGCGT
 601 ATGACAAAGG AGAGAAGTTA TTACGGTGTA AATTGGCAGC
 641 GTTTTATAGA CTAGCAGATC TCTTTGGGTG GTCTCAGCTT
 681 ATCTACAATC ATATCACAAC CAGAGTGAAC TTTACAGTGA
 721 AACACTTCCT CATTGTCCCT TTTGGGCTTC TTTACAGTGA
 761 AGTGACTGCA TCCAGTTTGG TTAAGATCAA TCTACAAGGA
 801 GATATAGTAG ATCGTGGAAG CACTAATCTG GGAGTGAATC
 841 AGGCCGGCTT CACCTTACAC TCTGCAATTT ATGCTGCACG
 881 CCCGGACGTG AAGTGCGTCG TGCACATTCA CACCCCAGCA
 921 GGGGCTGCGG TCTCTGCAAT GAAATGTGGC CTCTTGCCAA
 961 TCTCCCCGGA GGCGCTTTCC CTTGGAGAAG TGGCTTATCA
1001 TGACTACCAT GGCATTCTGG TTGATGAAGA GGAAAAAGTT
1041 TTGATTCAGA AAAATCTGGG GCCTAAAAGC AAGGTTCTTA
1081 TTCTCCGGAA CCATGGGCTC GTGTCAGTTG GAGAGAGCGT
1121 TGAGGAGGCC TTCTATTACA TCCATAACCT TGTGGTTGCC
1161 TGTGAGATCC AGGTTCGAAC TCTGGCCAGT GCAGGAGGAC
1201 CAGACAACTT AGTCCTGCTG AATCCTGAGA AGTACAAAGC
1241 CAAGTCCCGT TCCCCAGGGT CTCCGGTAGG GGAAGGCACT
1281 GGATCGCCTC CCAAGTGGCA GATTGGTGAG CAGGAATTTG
1321 AAGCCCTCAT GCGGATGCTC GATAATCTGG GCTACAGAAC
1361 TGGCTACCCT TATCGATACC CTGCTCTGAG AGAGAAGTCT
1401 AAAAAATACA GCGATGTGGA GGTTCCTGCT AGTGTCACAG
1441 GTTACTCCTT TGCTAGTGAC GGTGATTCGG GCACTTGCTC
1481 CCCACTCAGA CACAGTTTTC AGAAGCAGCA GCGGGAGAAG
1521 ACAAGATGGC TGAACTCTGG CCGGGGCGAC GAAGCTTCCG
1561 AGGAAGGGCA GAATGGAAGC AGTCCCAAGT CGAAGACTAA
1601 GTGGACTAAA GAGGATGGAC ATAGAACTTC CACCTCTGCT
1641 GTCCCTAACC TGTTTGTTCC ATTGAACACT AACCCAAAAG
1681 AGGTCCAGGA GATGAGGAAC AAGATCCGAG AGCAGAATTT
1721 ACAGGACATT AAGACGGCTG GCCCTCAGTC CCAGGTTTTG
1761 TGTGGTGTAG TGATGGACAG GAGCCTCGTC CAGGGAGAGC
1801 TGGTGACGGC CTCCAAGGCC ATCATTGAAA AGGAGTACCA
1841 GCCCCACGTC ATTGTGAGCA CCACGGGCCC CAACCCCTTC
1881 ACCACACTCA CAGACCGTGA GCTGGAGGAG TACCGCAGGG
1921 AGGTGGAGAG GAAGCAGAAG GGCTCTGAAG AGAATCTGGA
1961 CGAGGCTAGA GAACAGAAAG AAAAGAGTCC TCCAGACCAG
2001 CCTGCGGTCC CCACCCGCC TCCCAGCACT CCCATCAAGC
2041 TGGAGGAAGA CCTTGTGCCG GAGCCGACTA CTGGAGATGA
2081 CAGTGATGCT GCCACCTTTA AGCAACTCT CCCCGATCTG
2121 TCCCCTGATG AACCTTCAGA AGCACTCGGC TTCCCAATGT
2161 TAGAGAAGGA GGAGGAAGCC CATAGACCCC CAAGCCCCAC
2201 TGAGGCCCCT ACTGAGGCCA GCCCCGAGCC AGCCCCAGAC
2241 CCAGCCCCGG TGGCTGAAGA GGCTGCCCCC TCAGCTGTCG
2281 AGGAGGGGGC CGCCGCGGAC CCTGGCAGCG ATGGGTCTCC
2321 AGGCAAGTCC CCGTCCAAAA GAAGAAGAA GTTCCGTACC
2361 CCGTCCTTTC TGAAGAAGAG CAAGAAGAAG AGTGACTCCT
2401 GAAAGCCCTG CGCTAACACT GTCCTGTCCG GAGCGACCCT
2441 GGCTCTGCCA GCGTCCCCGG CCACGTCTGT GCTCTGTCCT
2481 TGTGTAATGG AATGCAAAAA AGCCAAGCCC TCCGCCTAGA
2521 GGTCCCCTCA CGTGACCAGC CCCGTGTAGC CCCGGGCTGA
2561 CCCAGTGTGT GCTCAGCAGC CCCACCCCAC CCTGCCCCTT
2601 GTCCTCTCAG AGCCTCAGCT TCTGGGGGAG ACATGCTCTC
2641 CCCACAGGGG GGAGGCACTA AGTCATGGTC CTGGCTGGAA
2681 GGTACTGAAG GCTTCTGCAG CTTTGGCTGC ACGTCACCCT
2721 CCTGAGCCTC ACCTTTCCTG CCGTCCCTCC TGTTGTGAAA
2761 TCACCACATT CTGTCTCTGC TTGGCTTCCC CTCCACCCTA
2801 AAGTCTCAGG TGACGGACTC AGACTCCTGG CTTCATGTGG
2841 CATTCTCTCT GCTCAGTGAT CTCACTTAAA TCTATATACA
2881 AAGCCTTGGT CCCGTGAAAA CACTCGTGTG CCCACCAGCG
2921 GCCTTGAAGA GGCAGGTCTG GGCCAGATGC TGGGCAGGAA
2961 ACCCCAGCGG CAGATGGGCC TGTGTGCACC CAACGTGATG
3001 CTATGCATGT CTGACCGACG ATCCCTCGAC CAGAATCAGA
3041 TTCAGGAGCT CAGTTTCTTT TTCACTTGGG TCTCTGGATT
3081 CCTGTCATAG GGAAGGTATA TCAGGAGGGG AAGAGGCCTT
3121 TCTAGAATTT TCTTTGAGCA GGTTTACAAT TTAGCTTACA
3161 TTTTTCGACT GTGAACGTGA ATAGGCTGCT TTTTGCTTTC
3201 TTCTTTCCAG ACCCCACAGT AGAGCACTTT TCACTTATTT
3241 GGGGGAGGCT TCAGGGGACT GTTCTCACCT TAACTCAGCC
3281 AGAAAGATGC CCTAGTTGTG ATCAAAGGTA ACTCGAGGTG
3321 GAGGGTAGCC CTGGGGCCCC TCGACATCAC CGTCATTGAT
3361 GGAGCCTGAA CCGTGTGCTC CTCGGCAGAT GCTGTTGTTG
3401 TTACTTCCCT CCAAGAGGCT GGAAAAGGGC TCAGAGCTGC
3441 TGAGCAGGAA CCGGAGGGTG ACCCATTTCA GGAGGTGCCG
3481 GTACCAGCCT GACTAGGTAC AGGCAAGCTT GTGTGGGCCC
3521 AACAGGCCCT TGGTAGAGCT GGTGCCAGAT GTGGGCTCAG
3561 ATCCTGGGCA TGATGGGCCG AGCCACCTCG GATCCCACTG
3601 ATTGGCCAGC CGAGCGAGAA CCAGGCTGCT GCATGGCACT
3641 GACCGCCGCT TCCAGCTTCC TCTGAGCCGC AGGGCCTGCT
3681 ACGCGGGCAA GCGTGCTGCC TCTCTTCTGT GTCGTTTTGT
3721 TGCCAAGGCA GAATGAAAAG TCCTTAACCG TGGACTCTTC
3761 CTTTATCCCC TCCTTTACCC CACATATGCA ATGACTTTTA
```

```
3801 ATTTTCACTT TTGTAGTTTA ATCCTTTGTA TTACAACATG
3841 AAATATAGTT GCATATATGG ACACCGACTT GGGAGGACAG
3881 GTCCTGAATG TCCTTTCTCC AGTGTAACAT GTTTTACTCA
3921 CAAATAAAAT TCTTTCAGCA AGTTCCTTGT CTAAAAAAAA
3961 AAAAAAAAAA
```

The rs4961 single nucleotide polymorphism (SNP) is present in the ADD1 gene, where the variable nucleotide is at about position 1566 in SEQ ID NO:26 (underlined), which can be guanine in some individuals and thymine in others. The rs4961 sequence (SEQ ID NO:27) is shown below, where the underlined G/T is the SNP.

CCGGGGCGACGAAGCTTCCGAGGAA[G/T]GGCAGAATGGAAGCAGTCCC

AAGTC.

The human alpha adducin encoded by the ADD1 cDNA with SEQ ID NO:26 has the following sequence (SEQ ID NO:28).

```
  1 MNGDSRAAVV TSPPPTTAPH KERYFDRVDE NNPEYLRERN
 41 MAPDLRQDFN MMEQKKRVSM ILQSPAFCEE LESMIQEQFK
 81 KGKNPTGLLA LQQIADFMTT NVPNVYPAAP QGGMAALNMS
121 LGMVTPVNDL RGSDSIAYDK GEKLLRCKLA AFYRLADLFG
161 WSQLIYNHIT TRVNSEQEHF LIVPFGLLYS EVTASSLVKI
201 NLQGDIVDRG STNLGVNQAG FTLHSAIYAA RPDVKCVVHI
241 HTPAGAAVSA MKCGLLPISP EALSLGEVAY HDYHGILVDE
281 EEKVLIQKNL GPKSKVLILR NHGLVSVGES VEEAFYYIHN
321 LVVACEIQVR TLASAGGPDN LVLLNPEYK AKSRSPGSPV
361 GEGTGSPPKW QIGEQEFEAL MRMLDNLGYR TGYPYRYPAL
401 REKSKKYSDV EVPASVTGYS FASDGDSGTC SPLRHSFQKQ
441 QREKTRWLNS GRGDEASEEG QNGSSPKSKT KWTKEDGHRT
481 STSAVPNLFV PLNTNPKEVQ EMRNKIREQN LQDIKTAGPQ
521 SQVLCGVVMD RSLVQGELVT AKSAIIEKEY QPHVIVSTTG
561 PNPFTTLTDR ELEEYRREVE RKQKGSEENL DEAREQKEKS
601 PPDQPAVPHP PPSTPIKLEE DLVPEPTTGD DSDAATFKPT
641 LPDLSPDEPS EALGFPMLEK EEEAHRPPSP TEAPTEASPE
681 PAPDPAPVAE EAAPSAVEEG AAADPGSDGS PGKSPSKKKK
721 KFRTPSFLKK SKKKSDS
```

Note that the underlined glycine at position 460 of the SEQ ID NO:28 alpha adducin protein is glycine because some individuals have nucleotide sequence SEQ ID NO:26, where the variable nucleotide at position 1566 is guanine. However, position 460 of SEQ ID NO:28 can be tryptophan in some individuals because those individuals have thymine as the variable nucleotide at position 1566 in sequence SEQ ID NO:28.

Individuals with the tryptophan variant of alpha adducin are more likely to be salt sensitive, more likely to have hypertension and have a greater response to diuretics.

Genetic variation of the sodium ($Na^+$) chloride ($Cl^-$) co-transporter (SLC12A3) also has blood pressure consequences. A cDNA sequence for the sodium ($Na^+$) chloride ($Cl^+$) co-transporter (SLC12A3) is available from the NCBI database as accession number NM_000339.2 (GI: 186910314). This SLC12A3 cDNA sequence is provided below as SEQ ID NO:29.

```
   1 CTGGCCCCTC CCTGGACACC CAGGCGACAA TGGCAGAACT
  41 GCCCACAACA GAGACGCCTG GGGACGCCAC TTTGTGCAGC
  81 GGGCGCTTCA CCATCAGCAC ACTGCTGAGC AGTGATGAGC
 121 CCTCTCCACC AGCTGCCTAT GACAGCAGCC ACCCCAGCCA
 161 CCTGACCCAC AGCAGCACCT TCTGCATGCG CACCTTTGGC
 201 TACAACACGA TCGATGTGGT GCCCACATAT GAGCACTATG
 241 CCAACAGCAC CCAGCCTGGT GAGCCCCGGA AGGTCCGGCC
 281 CACACTGGCT GACCTGCACT CCTTCCTCAA GCAGGAAGGC
 321 AGACACCTGC ATGCCCTGGC CTTTGACAGC CGGCCCAGCC
 361 ACGAGATGAC TGATGGGCTG GTGGAGGGCG AGGCAGGCAC
 401 CAGCAGCGAG AAGAACCCCG AGGAGCCAGT GCGCTTCGGC
 441 TGGGTCAAGG GGGTGATGAT TCGTTGCATG CTCAACATTT
 481 GGGGCGTGAT CCTCTACCTG CGGCTGCCCT GGATTACGGC
 521 CCAGGCAGGC ATCGTCCTGA CCTGGATCAT CATCCTGCTG
 561 TCGGTCACGG TGACCTCCAT CACAGGCCTC TCCATCTCAG
 601 CCATCTCCAC CAATGGCAAG GTCAAGTCAG GTGGCACCTA
 641 CTTCCTCATC TCCCGGAGTC TGGGCCCAGA GCTTGGGGGC
 681 TCCATCGGCC TCATTTTCGC TTTCGCCAAT GCCGTGGGTC
 721 TGGCCATGCA CACGGTGGGC TTTGCAGAGA CCGTGCGGGA
 761 CCTGCTCCAG GAGTATGGGG CACCCATCGT GGACCCCATT
 801 AACGACATCC GCATCATTGG CGTGGTCTCG GTCACTGTGC
 841 TGCTGGCCAT CTCCCTGGCT GGCATGGAGT GGGAGTCCAA
 881 GGCCCAGGTG CTGTTCTTCC TTGTCATCAT GGTCTCCTTT
 921 GCCAACTATT TAGTGGGGAC GCTGATCCCC CCATCTGAGG
 961 ACAAGGCCTC CAAAGGCTTC TTCAGCTACC GGGCGGACAT
1001 TTTTGTCCAG AACTTGGTGC CTGACTGGCG GGGTCCAGAT
1041 GGCACCTTCT TCGGAATGTT CTCCATCTTC TTCCCCTCGG
1081 CCACAGGCAT CCTGGCAGGG GCCAACATAT CTGGTGACCT
1121 CAAGGACCCT GCTATAGCCA TCCCCAAGGG GACCCTCATG
1161 GCCATTTTCT GGACGACCAT TTCCTACCTG GCCATCTCAG
1201 CCACCATTGG CTCCTGCGTG GTGCGTGATG CCTCTGGGGT
1241 CCTGAATGAC ACAGTGACCC CTGGCTGGGG TGCCTGCGAG
1281 GGGCTGGCCT GCAGCTATGG CTGGAACTTC ACCGAGTGCA
1321 CCCAGCAGCA CAGCTGCCAC TACGGCCTCA TCAACTATTA
1361 CCAGACCATG AGCATGGTGT CAGGCTTCGC GCCCCTGATC
1401 ACGGCTGGCA TCTTCGGGGC CACCCTCTCC TCTGCCCTGG
```

```
1441 CCTGCCTTGT CTCTGCTGCC AAAGTCTTCC AGTGCCTTTG
1481 CGAGGACCAG CTGTACCCAC TGATCGGCTT CTTCGGCAAA
1521 GGCTATGGCA AGAACAAGGA GCCCGTGCGT GGCTACCTGC
1561 TGGCCTACGC CATCGCTGTG GCCTTCATCA TCATCGCTGA
1601 GCTCAACACC ATAGCCCCCA TCATTTCCAA CTTCTTCCTC
1641 TGCTCCTATG CCCTCATCAA CTTCAGCTGC TTCCACGCCT
1681 CCATCACCAA CTCGCCTGGG TGGAGACCTT CATTCCAATA
1721 CTACAACAAG TGGGCGGCGC TGTTTGGGGC TATCATCTCC
1761 GTGGTCATCA TGTTCCTCCT CACCTGGTGG GCGGCCCTCA
1801 TCGCCATTGG CGTGGTGCTC TTCCTCCTGC TCTATGTCAT
1841 CTACAAGAAG CCAGAGGTAA ATTGGGGCTC CTCGGTACAG
1881 GCTGGCTCCT ACAACCTGGC CCTCAGCTAC TCGGTGGGCC
1921 TCAATGAGGT GGAAGACCAC ATCAAGAACT ACCGCCCCCA
1961 GTGCCTGGTG CTCACGGGGC CCCCCAACTT CCGCCCGGCC
2001 CTGGTGGACT TTGTGGGCAC CTTCACCCGG AACCTCAGCC
2041 TGATGATCTG TGGCCACGTG CTCATCGGAC CCCACAAGCA
2081 GAGGATGCCT GAGCTCCAGC TCATCGCCAA CGGGCACACC
2121 AAGTGGCTGA ACAAGAGGAA GATCAAGGCC TTCTACTCGG
2161 ATGTCATTGC CGAGGACCTC CGCAGAGGCC TCCAGATCCT
2201 CATGCAGGCC GCAGGTCTCG GGAGAATGAA GCCCAACATT
2241 CTGGTGGTTG GGTTCAAGAA GAACTGGCAG TCGGCTCACC
2281 CGGCCACAGT GGAAGACTAC ATTGGCATCC TCCATGATGC
2321 CTTTGATTTC AACTATGGCG TGTGTGTCAT GAGGATGCGG
2361 GAGGGACTCA ACGTGTCCAA GATGATGCAG GCGCACATTA
2401 ACCCCGTGTT TGACCCAGCG GAGGACGGGA AGGAAGCCAG
2441 CGCCAGAGGT GCCAGGCCAT CAGTCTCTGG CGCTTTGGAC
2481 CCCAAGGCCC TGGTGAAGGA GGAGCAGGCC ACCACCATCT
2521 TCCAGTCGGA GCAGGGCAAG AAGACCATAG ACATCTACTG
2561 GCTCTTTGAC GATGGAGGCC TCACCCTCCT CATTCCCTAT
2601 CTCCTTGGCC GCAAGAGGAG GTGGAGCAAA TGCAAGATCC
2641 GTGTGTTCGT AGGCGGCCAG ATTAACAGGA TGGACCAGGA
2681 GAGAAAGGCG ATCATTTCTC TGCTGAGCAA GTTCCGACTG
2721 GGATTCCATG AAGTCCACAT CCTCCCTGAC ATCAACCAGA
2761 ACCCTCGGGC TGAGCACACC AAGAGGTTTG AGGACATGAT
2801 TGCACCCTTC CGTCTGAATG ATGGCTTCAA GGATGAGGCC
2841 ACTGTCAACG AGATGCGGCG GGACTGCCCC TGGAAGATCT
2881 CAGATGAGGA GATTACGAAG AACAGAGTCA AGTCCCTTCG
2921 GCAGGTGAGG CTGAATGAGA TTGTGCTGGA TTACTCCCGA
2961 GACGCTGCTC TCATCGTCAT CACTTTGCCC ATAGGGAGGA
3001 AGGGGAAGTG CCCCAGCTCG CTGTACATGG CCTGGCTGGA
3041 GACCCTGTCC CAGGACCTCA GACCTCCAGT CATCCTGATC
3081 CGAGGAAACC AGGAAAACGT GCTCACCTTT TACTGCCAGT
3121 AACTCCAGGC TTTGACATCC CTGTCCACAG CTCTGAGTGT
3161 GTGGGATAAG TTGGAACTTG ATTGCCTCTA GTCCACAGGG
3201 ATGAGACTCA TGTTCTGTTG CACTTTAAGT GGCAGCATCT
3241 GATGATCTCA CCGAAAAGA TGGTAGATTT CCAAATCTGG
3281 CTGGACTCCA CTTCCATGGG ACACATTCCC TGGGTCTTGT
3321 GTTTATAGGC TAGAGAAATA GCAGATGGAG CTGCAAGGAA
3361 AACTCTCTAA AGCATCCTAT TCCTTTTAAA GGATTTCTTT
3401 TGATTTTGAT GACCATTAAT TAAGAGTTCA GTCTTTGATT
3441 TGTATGCAAA TTGGAGTCCC AATGCTGGGC GTGAATCTTG
3481 ACAGTTTCTA CAGACCTTCC TGGGTGAAAG TTCCTAAATC
3521 ATGCCCTGCT TCCTCCAATA GGAGAATGGG AGCCTCACCT
3561 GTAGGACCTA CAGGCTCTCT AAGGAATGCA GGTCTCTCTC
3601 TGAGCCTCCA CAGCCAGGCA AATACATATA TATATATTTT
3641 TTTTTTAGAT GAAGTTTTTT CTCTTGTTGC CCAGGCTAGG
3681 GTGTAATGGC ATGATCTCAG GTCACTGCAA CCTCCTCCCG
3721 GGTTCAAGCA TTTCTTCTGT CTCAGCCTCC GAATAGCTG
3761 GGATTACAGG CACCTGCCAT CACACGAGCT AATTTTTGTA
3801 TTTTTAGTAG AGATGGGGTT TCACCATGTT GACCAGGCTG
3841 GTGTTGAGCT CCTGACCTCA GGTGATCCAC CCACCTCGGT
3881 CTCCCAAAGT GCTGGGGTTA CAGGCCTGAG CCACTGCGCC
3921 CGGCCCAGGC AAATTTCTTG AACCACTTCT CACTCCCGTC
3961 ACTTTCAATA AGGGGTCTTT GATGTCTTCA CTGGTTCTTT
4001 GGACGAGGGA CTTTTCGAAC TTTTTTGGTT GCAACACACA
4041 GTAAGAAATA TACTTCACAC TGAGACTTGC AGCGCACACA
4081 CACGGAAACG ACCAAAACAA AAATGTCACA AAACAATACT
4121 TACCCTTCCC TGGGGGACGT CCTCCAGTAT GTTCTGTTCT
4161 GTTTATTTTT CACTGTTGGT TGCAATCCAA TAAAATGACT
4201 TTGGGATCCA CTCATGGGTG GGACCCACA CATTTGAAAG
4241 GCATGGCCAC CTTTCTGTTG TGCCTTGCAT TTGTCCACAC
4281 ACAGGGAGTC TGGCTGAGCT GGGGAAAGGC CACGGCTGGG
4321 TGTCATTGCC ATTTTCCCAG CTCATCTCAC CGGGAAGAAA
4361 AGCAGATTGA CAGAACACGT GAGGAGGGGT ATTGATGGCA
4001 GGAGAGTCAA AAAAGAGTTT TAAAGAAGGG GCAAGGTTGA
4441 AGGAGTCTAG TGGCAAGGGT AAGATTTCAG GCATGGTTAA
4481 GAACAGACGA CAAGGATGTC AGGAATGAAG ATGTGGAGAG
4521 GGGTGTAGAG ATGGCAAGGT TGGCAAGGAA CAGATAGGCA
4561 GGAGCAGGTC CAAGCCAAGC CTAGCCCAAG ACCAGGTGAA
4601 AGGAGAGGGG AGGAGGAGCC ACCTGCAAGA GATGGAAAGA
4641 GCAGGCGGCA GAGGGGGCTG GCAGGGAGGG GCTGTTAAGA
```

```
4681 GTGGGGTTGG AGGTGGGAGA GAAGCTAGGA CAAGGGAGAT

4721 GGAGAAAGGA CCTATACCTG GCTCACGGAA GGCCTTCAGG

4761 TCACTACACG TTGAACATCC CCAGTGTTTG AGCCCCCAAA

4801 GCTAGGGTGC AAGAGCACTG CCATCGAATG CCAGTGGGTG

4841 AGGCCAAGTG AGGGTATTTG CAGCTCTAGA CATAACCAAG

4881 AAGCGTAAAG GTGAGTTGTT TGGTGGTACG ACTGCCTGTG

4921 CCTTCTTCCG ATGGCACTGG GGTGGCTGAA GGAACAGACA

4961 TCTTTGGGTT TCATCAGCCT CCTCCAAGAC TGCTGCAGTG

5001 CCTACACTTT AGACTTCAGA AGGAGACTAA AGACTTCTAG

5041 AATTTAGAAG GAGATCTGAA GTCTCCTTTC TGGAGTTACA

5081 ACCCAAAGGA TGTTAGCATT TCTCAGGTCA TCCCACTGCA

5121 AAGCCCAGAA GGCTTGGGGC TCCCAGGCTG CTCTGAAGCC

5161 CCACTGTCTG ACCGCCTCAG GGCTTGCTAC GAGGGACTGG

5201 GGCACGGCCA AGCTGACTAG GAACAGCTCT CGTGCTCCTG

5241 AGGGACCTGG AGGATGGGCC TGCCTCCCAG CCATTGAGCT

5281 GGATTCTGGG ATAATTCTTA ACTCGAAATA AGGGGAAGCA

5321 TCCATCAGGG AATGCTGGCC TTTCTAGAGC CACGTAGAAA

5361 ACAATTTTCT GGTTCTTCAA ACCTCAAAGA GTCCTTGGTC

5401 ATTTTCACGA TGTCAGAAAT AGTATGTTTT TAACAATAGT

5441 ATTTTCACGA TGTCAGAAAT AGTATGTTTT TAACAATAGT

5481 AATAGCTTTG TAAAAAAATA AAAAGCTTTA ACAGCGAGGC

5521 CATAAACAAT GAAATGAATA AAAACGGTGG TCATTCAGTC

5561 AACGGAAAAA AAAAAAAAAA AA
```

The rs1529927 single nucleotide polymorphism (SNP) is present in the SLC12A3 gene, where the variable nucleotide is at about position 820 in SEQ ID NO:29 (underlined), which can be guanine in some individuals and cytosine in others. The rs1529927 sequence (SEQ ID NO:30) is shown below, where the underlined C/G is the SNP.

CCCATTAACGACATCCGCATCATTG[C/G]CGTGGTCTCGGTCACTGTG

CTGCTG.

The human the sodium (Na$^+$) chloride (Cl$^-$) co-transporter encoded by the SLC12A3 cDNA with SEQ ID NO:29 has the following sequence (SEQ ID NO:31).

```
  1 MAELPTTETP GDATLCSGRF TISTLLSSDE PSPPAAYDSS

41 HPSHLTHSST FCMRTFGYNT IDVVPTYEHY ANSTQPGEPR

81 KVRPTLADLH SFLKQEGRHL HALAFDSRPS HEMTDGLVEG

121 EAGTSSEKNP EEPVRFWGVK GVMIRCMLNI WGVILYLRLP

161 WITAQAGIVL TWIIILLSVT VTSITGLSIS AISTNGKVKS

201 GGTYFLISRS LGPELGGSIG LIFAFANAVG VAMHTVGFAE

241 TVRDLLQEYG APIVDPINDI RIIGVVSVTV LLAISLAGME

281 WESKAQVLFF LVIMVSFANY LVGTLIPPSE DKASKGFFSY

321 RADIFVQNLV PDWRGPDGTF FGMFSIFFPS ATGILAGANI

361 SGDLKDPAIA IPKGTLMAIF WTTISYLAIS ATIGSCVVRD

401 ASGVLNDTVT PGWGACEGLA CSYGWNFTEC TQQHSCHYGL

441 INYYQTMSMV SGFAPLITAG IFGATLSSAL ACLVSAAKVF

481 QCLCEDQLYP LIGFFGKGYG KNKEPVRGYL LAYAIAVAFI

521 IIAELNTIAP IISNFFLCSY ALINFSCFHA SITNSPGWRP

561 SFQYYNKWAA LFGAIISVVI MFLLTWWAAL IAIGVVLFLL

601 LYVIYKKPEV NWGSSVQAGS YNLALSYSVG LNEVEDHIKN

641 YRPQCLVLTG PPNFRPALVD FVGTFTRNLS LMICGHVLIG

681 PHKQRMPELQ LIANGHTKWL NKRKIKAFYS DVIAEDLRRG

721 VQILMQAAGL GRMKPNILVV GFKKNWQSAH PATVEDYIGI

761 LHDAFDFNYG VCVMRMREGL NVSKMMQAHI NPVFDPAEDG

801 KEASARGARP SVSGALDPKA LVKEEQATTI FQSEQGKKTI

841 DIYWLFDDGG LTLLIPYLLG RKRRWSKCKQ RVFVGGQINR

881 MDQERKAIIS LLSKFRLGFH EVHILPDINQ NPRAEHTKRF

921 EDMIAPFRLN DGFKDEATVN EMRRDCPWKI SDEEITKNRV

961 KSLRQVRLNE IVLDYSRDAA LIVITLPIGR KGKCPSSLYM

1001 AWLETLSQDL RPPVILIRGN QENVLTFYCQ
```

Note that the underlined glycine at position 264 of the SEQ ID NO:31 sodium (Na$^+$) chloride (Cl$^-$) co-transporter protein is glycine because some individuals have nucleotide sequence SEQ ID NO:29, where the variable nucleotide at position 820 is guanine. However, position 264 of SEQ ID NO:29 can be alanine in some individuals because those individuals have cytosine as the variable nucleotide at position 820 in sequence SEQ ID NO:29.

Patients with the alanine variant of SLC12A3 (encoded by the rs1529927 site (SEQ ID NO:30)) exhibit a stronger diuretic effect to loop diuretics and demonstrate more excretion of Cl$^-$ and K$^+$ in response to therapy. Hence, subject with alanine or guanine at the rs1529927 site are more response to diuretics.

The WNK1 gene has functional and common polymorphisms that affect how a subject's blood pressure responds to drugs. Several cDNA sequences for the WNT1 gene are available from the NCBI database.

The rs2107614 single nucleotide polymorphism (SNP) is present in an intron of the WNK1 gene, where the variable nucleotide can be thymine in some individuals and cytosine in others. The rs2107614 sequence (SEQ ID NO:33) is shown below, where the underlined C/T is the SNP.

CACTTCCTCCAAAAAAAAAGAAAAC[C/T]CCATTTCCCCTCAACTCTT

CCAGTT.

Another SNP, rs1159744, is present an intron of the WNK1 gene, where the variable nucleotide can be guanine in some individuals and cytosine in others. The rs1159744 sequence (SEQ ID NO:34) is shown below, where the underlined C/G is the SNP.

AATGTTAACAGTATAGAAAATTTTA[C/G]CTCAACAAATAGAGAATAT
CAGTAA.

Patients with the cytosine variant of WNK1 at SNP positions rs1159744 and rs2107614 exhibit greater blood pressure reductions in response to loop diuretic therapy when compared to patients with the guanine or thymine variants at these two sites, respectively (Turner et al., *Hypertension* 46:758-765 (2005)).

Therapy

The methods, reagents, devices, and kits described herein can be used for determining whether a subject may benefit from treatment with a blood pressure medication, and which medication can be more effective for treating high blood pressure. For example, the methods described herein can be employed for determining whether a subject should be treated with a diuretic, an angiotensin converting enzyme (ACE) inhibitor, or a beta-blocker. Such determination is performed by identifying or detecting whether the subject has a genetic variant or single nucleotide polymorphism in his or her ADRB1, ADRB2. CYP2D6, angiotensin converting enzyme (ACE), angiotensinogen, angiotensin receptors, renin. $N^+$ channels (such as SCNN1A), adducin, sodium ($Na^+$) chloride ($Cl^-$) co-transporters (such as SLC12A3), and/or WNK1 polypeptides or nucleic acids. If testing of the subject's tissue sample shows that the subject has a genetic variant or single nucleotide polymorphism in his or her ADRB1, ADRB2, CYP2D6, angiotensin converting enzyme (ACE), angiotensinogen, angiotensin receptors, renin, $Na^+$ channels (such as SCNN1A), adducin, sodium ($Na^+$) chloride ($Cl^-$) co-transporters (such as SLC12A3), and/or WNK1 polypeptides or nucleic acids, a suitable therapeutic regimen can be prescribed for the subject.

A diuretic promotes the production or urine. Diuretics are sometimes grouped into three categories: thiazides, loop, and potassium-sparing diuretics. Thiazide diuretics include chlorothiazide, hydrochlorothiazide, indapamide, metolazone, and chlorthalidone. Loop diuretics include furosemide, bumetanide, ethacrynic acid, and torsemide. Examples of potassium-sparing diuretics include amiloride, eplerenone, spironolactone, and triamterene.

Examples of diuretics that can be employed also include furosemide, thiazides, carbonic anhydrase inhibitors, potassium-sparing diuretics (e.g., aldosterone antagonists, spironolactone, eplerenone, potassium canreonate, amiloride, triamterene, aldactone, and combinations thereof), calcium-sparing diuretics. For example, the diuretic can be acetazolamide, amiloride, bumetanide, chlorothalidone, chlorothiazide, ethacrynic acid, furosemide, glycerin, hydrochlorothiazide, hydroflumthiazide, indapamide, isosorbide, mannitol, methazolamide, methylchlothiazide, metolazone, dichlorphenamide, spironolactone, torsemide, triamterene, urea, and combinations thereof.

The angiotensin converting enzyme inhibitor can be selected from enalapril lisinopril, captopril alacipril, benazapril, cilazapril, delapril, fosinopril, perindopril, quinapril, ramipril, moveltipril, spirapril, ceronapril, imidapril, temocapril, trandolopril, utilbapril, zofenopril CV5975, EMD 56855, libenzapril, zalicipril, HOE065, MDL 27088, AB47, DU 1777, MDL 27467A, Equaten™, Prentyl™, Synecor™, and Y23785; and the diuretic is selected from hydrochlorothiazide (HCTZ), furosemide, altizide, trichlormethazide, triflumethazide, bemetizide, cyclothiazide, methylchlothiazide, azosemide, chlorothiazide, butizide, bendroflumethazide, cyclopenthiazide, benzclortriazide, polythiazide, hydroflumethazide, benzthiazide, ethiazide, penflutazide, and any combination thereof.

The angiotensin II receptor antagonists can, for example, be losartan, valsartan, candesartan, irbesartan, olmesartan, or any combination thereof.

The renin inhibitors can be urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren ((2S,4S,5S, 7S)—N-(2-carbamoyl-2-methylpropyl)-5-amino-4-hydroxy-2,7-diisopropyl-8-[4-methoxy-3-(3-methoxypropoxy)phenyl]-oetanamid hemifumarate) SPP600, SPP630 and SPP635), or any combination thereof.

Other therapeutic agents can also be administered including endothelin receptors antagonists, vasodilators, calcium channel blockers (e.g., amlodipine, nifedipine, veraparmil, diltiazem, gallopamil, nifedipine, nimodipins, nicardipine), potassium channel activators (e.g., nicorandil, pinacidil, cromakalim, minoxidil, aprilkalim, loprazolam), diuretics (e.g., hydrochlorothiazide), sympatholytics, beta-adrenergic blocking drugs (e.g., propranolol, atenolol, bisoprolol, carvedilol, metoprolol, or metoprolol tartrate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds (e.g., muraglitazar, glipizide, metformin, rosiglitazone) or with other drugs beneficial for the prevention or the treatment of disease including nitroprusside and diazoxide.

The therapeutic protocol can generally be conducted as follows. An assay of all sixteen genotypes (polymorphic sites) can be performed. The therapeutic decision tree of the results can be as follows.

To ascertain whether a diuretic should be administered to a subject, the following can be performed.

If the subject is (a) homozygous for cytosine at the rs1529927 (SEQ ID NO:30) variable site (expressing alanine at position 264 of the SLC12A3 gene product); (b) homozygous for adenine at the rs2228576 (SEQ ID NO:22) variable site (expressing threonine at about 663 or 722 of the SCNN1A protein); and/or (c) homozygous for thymine at the rs4961 (SEQ ID NO:27) variable site (expressing tryptophan at about position 460 of the adducin protein) then the patient should initially start with a diuretic as the first line of therapy. If the patient is heterozygous at these sites, then genetic variation within the polymorphic sites relating to vasodilator and beta-blocker drug class responses should initially be considered.

If the patient does not carry homozygous variants that are known to be functionally important within the vasodilator and beta-blocker classes, but are heterozygous at rs1529927, rs2228576, and rs4961, then diuretic therapy should initially be considered as first-line therapy.

If the subject is homozygous for cytosine at the WNK1 rs1159744 (SEQ ID NO:34) variable site and also homozygous for cytosine at the WNK1 rs2107614 (SEQ ID NO:33) variable site then the patient should start with a loop diuretic as first-line of therapy.

If the patient does not carry homozygous variants within the vasodilator and beta-blocker classes that are known to be functionally important, but are heterozygous at rs1529927, rs2228576, and rs4961, then loop diuretic therapy should initially be considered as first-line therapeutic agent.

To ascertain whether a vasodilator should be administered to a subject the following can be performed.

If the subject is homozygous for cytosine at the rs5186 (SEQ ID NO:16) variable site of AGT1R, and the subject is homozygous cytosine at the rs12750834 (SEQ ID NO:20) variable site of renin, then the patient should use an angiotensin II (AII) receptor blocker as a first line of therapy.

If the patient is heterozygous for cytosine at the rs5186 and rs12750834 variable sites, but does not present with other important functional genotypes within the diuretic and beta-blockade classes, then the patient should also use an angiotensin II receptor blocker as a first line of therapy.

If the patient is homozygous for cytosine at the rs699 (SEQ ID NO:14) variable site of AGT, or for the deletion at the rs1799752 (SEQ ID NO:12; SEQ ID NO:35) of ACE, then the patient will likely benefit most from an angiotensin-converting enzyme (ACE) inhibitor.

Patients who are homozygous for cytosine at the rs699 (SEQ ID NO: 14) will likely benefit most from BOTH ACE inhibition and angiotensin II (AII) receptor blockade.

Patients who are heterozygous for the deletion at the rs1799752 (SEQ ID NO: 12; SEQ ID NO:35) and heterozygous for cytosine at the rs699 (SEQ ID NO: 14) variable site should be administered other drug classes (e.g., diuretic initially followed by beta-blockade). Although homozygosity at other sites has a greater impact on hypertension than heterozygosity at rs1799752 and rs699, this is generally true only if the patient has combined homozygosity at sites indicating that drug classes other than vasodilators should be administered.

To ascertain whether a beta-blocker should be administered to a subject the following can be performed.

Patients homozygous for adenine at the rs3892097 (SEQ ID NO: 10) variable site of the CYP2D6 gene should initially consider the use of atenolol and carevdilol as therapy. This is PARTICULARLY important if the patient is homozygous for cytosine at the rs1801253 (SEQ ID NO:3) variable site (and expresses arginine at position 389 of the $\beta_1$AR polypeptide), or if the patient is homozygous for adenine at the rs1801252 variable position (and expresses serine at position 49 of the $\beta_1$AR polypeptide).

The rs1042713 (SEQ ID NO:6) and rs1042714 (SEQ ID NO:7) variable sites are less important of the other polymorphism sites within the beta-blocker class of drugs and generally indicate patients who will likely respond to non-selective beta-blockade. Thus, subjects who are homozygous for guanine at the rs1042713 variable site (and express glycine at about position 16 of the ADRB2 gene product) as well as subjects who are homozygous for guanine at the rs1042714 position (and express glutamic acid at $\beta_2$AR position 27) are the most responsive to beta-blocker drugs.

If subjects are non-homozygous for polymorphisms in the beta-blockade class of variants, but are homozygous for cytosine at the rs1801253 (SEQ ID NO:3) variable site (and expresses arginine at position 389 of the $\beta_1$AR polypeptide), or if subjects are homozygous for adenine at the rs1801252 variable position (and expresses serine at position 49 of the $\beta_1$AR polypeptide), the beta-blockade class should be considered a possible line of therapy if they do not carry functional mutations within the diuretic and vasodilator classes of drugs.

Polymorphism Detection

The polymorphism present in genes such as ADRB1, ADRB2, cytochrome P450 2D6 (CYP2D6), angiotensin converting enzyme (ACE), angiotensinogen, angiotensin receptors, renin. Na$^+$ channels (such as SCNN1A), adducin, sodium (Na$^+$) chloride (Cl$^-$) co-transporters (such as SLC12A3), and/or WNK1 can be detected by any available procedure. For example, samples of cDNA, genomic DNA, and/or mRNA can be obtained from a subject and the sequences of polymorphic or variant sites can be evaluated by procedures such as nucleic acid amplification (e.g., PCR), reverse transcription, insertion/deletion analysis, primer extension, probe hybridization, SNP analysis, sequencing, restriction fragment length polymorphism, Matrix-Assisted Laser Desorption/Ionization Time-Of-Flight mass spectrometry (MALDI-TOF MS), Sequenom MassArray genotyping. Sanger sequencing, polyacrylamide gel electrophoresis, agarose gel electrophoresis, probe array hybridization analysis, and combinations thereof.

The methods for detecting polymorphisms can therefore involve detecting an alteration in a nucleic acid. As used herein a "nucleic acid" is a DNA or RNA molecule. A nucleic acid can be a segment of genomic DNA (e.g., an entire gene, an intron of a gene, an exon of a gene, a segment that includes regulatory elements, a 5' non-coding segment, a 3' non-coding segment, or any combination thereof). The nucleic acid can also be a cDNA (having exons but not introns), an amplicon, an RNA, a primer, or probe.

Probes and/or primers can be used that can hybridize to nucleic acid segments flanking or including of any of SNPs, insertions, deletions, polymorphic, or other variant segments of ADRB1. ADRB2, cytochrome P450 2D6 (CYP2D6), angiotensin converting enzyme (ACE), angiotensinogen, angiotensin receptors, renin, Na$^+$ channels (such as SCNN1A), adducin, sodium (Na$^+$) chloride (Cl$^-$) co-transporters (such as SLC12A3), and/or WNK1 genes. For example, probes and/or primers can be employed that hybridize to nucleic acid segments flanking or including any of the following polymorphisms: rs1801252 (ADRB1), rs1801253 (ADRB1), rs1042713 (ADRB2), rs1042714 (ADRB2), rs3892097 (CYP2D6), rs1799752 (ACE), rs699 (AGT), rs5186 (AGT1R), rs12750834 (renin), rs2228576 (SCNN1A), rs4961 (ADD1), rs1529927 (SLC12A3), rs2107614 (WNK1), or rs1159744 (WNK1). For example, the probes and/or primers can separately hybridize to segments of any of SEQ ID NO:2, 3, 6, 7, 10, 12, 14, 16, 19, 20, 22, 27, 30, 32, 33, 34, as well as to the complementary sequences, amplicons, cDNA, cRNA, and genomic sequences thereof. The probes and/or primers can hybridize to genomic, complementary, amplicon, or cDNA sequences that flank up to 50 nucleotides of any of SEQ ID NO:2, 3, 6, 7, 10, 12, 14, 16, 19, 20, 22, 27, 30, 33, or 34, on either or both of the 5' and 3' sides of the polymorphism.

Methods and devices described herein can detect at least two of these polymorphisms, or at least three of these polymorphisms, or at least four of these polymorphisms, or at least five of these polymorphisms, or at least six of these polymorphisms, or at least seven of these polymorphisms, or at least of eight of these polymorphisms, or at least nine of these polymorphisms, or at least of ten of these polymorphisms, or at least eleven of these polymorphisms, or at least of twelve of these polymorphisms, or at least thirteen of these polymorphisms, or at least fourteen of these polymorphisms, or at least fifteen of these polymorphisms or all of these polymorphisms. In some embodiments, the methods and devices described herein detect no other polymorphisms, although such methods and devices can include steps and probes for detecting 1-4 control target nucleic acids. For example, the methods, devices, and kits described herein can detect and evaluate about sixteen polymorphisms.

The probes and primers can be of any convenient length selected by one of skill in the art such as at least 12 nucleotides long, or at least 13 nucleotides long, or at least 14 nucleotides long, or at least 15 nucleotides long, or at least 16 nucleotides long, or at least 17 nucleotides long, or at least 18 nucleotides long, or at least 19 nucleotides long, or at least 20 nucleotides long. In some embodiments, the probes and primers can be less than 150 nucleotides in length, or less than 125 nucleotides in length, or less than 100 nucleotides in length, or less than 75 nucleotides in length, or less than 65 nucleotides in length, or less than 60 nucleotides in length, or less than 55 nucleotides in length, or less than 50 nucleotides in length, or less than 45 nucleotides in length, or less than 40 nucleotides in length.

To detect hybridization, it may be advantageous to employ probes, primers and other nucleic acids in combination with an appropriate detection means. Labels incorporated into primers, incorporated into the amplified product during amplification, or attached to probes that can hybridize to the target, or its amplified product, are useful in the identification of nucleic acid molecules. A number of different labels may be used for this purpose including, but not limited to, fluorophores, chromophores, radiolabels, enzymatic tags, antibodies, chemiluminescence, electroluminescence, and affinity labels. One of skill in the art will recognize that these and other labels can be used with success in this invention.

Examples of affinity labels include, but are not limited to the following: an antibody, an antibody fragment, a receptor protein, a hormone, biotin, dinitrophenyl (DNP), or any polypeptide/protein molecule that binds to an affinity label. Examples of enzyme tags include enzymes such as urease, alkaline phosphatase or peroxidase to mention a few. Colorimetric indicator substrates can be employed to provide a detection means visible to the human eye or spectrophotometrically, to identify specific hybridization with complementary nucleic acid-containing samples. Examples of fluorophores include, but are not limited to, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5, 6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

Means of detecting such labels are well known to those of skill in the art. For example, radiolabels may be detected using photographic film or scintillation counters. In other examples, fluorescent markers may be detected using a photodetector to detect emitted light. In still further examples, enzymatic labels are detected by providing the enzyme with a substrate and detecting the reaction product produced by the action of the enzyme on the substrate, and colorimetric labels are detected by simply visualizing the colored label or by use of spectrometer.

So called "direct labels" are detectable labels that are directly attached to or incorporated into a probe or primer, or to the target (sample) nucleic acid prior to hybridization to a probe that can, for example, be present on a plate, chip, microtiter plate, or microarray. In contrast, so called "indirect labels" are joined to the hybrid duplex after hybridization. In some embodiments, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin-bearing hybrid duplexes providing a label that is easily detected. For a detailed review of methods of labeling nucleic acids and detecting labeled hybridized nucleic acids see, for example, Peter C, van der Vliet & Shiv Pillai, eds., Laboratory Techniques in Biochemistry and Molecular Biology (1993).

Probe arrays, assay plates, and gene chip technology provide a means of rapidly screening a large number of nucleic acid samples for their ability to hybridize to a variety of probes immobilized on a solid substrate that is part of the probe array, assay plate, gene chip or microarray. The technology capitalizes on the complementary binding properties of single stranded nucleic acid probe to screen nucleic acid samples by hybridization (Pease et al., Proc. Natl. Acad. Sci. U.S.A 91: 5022-5026 (1994); U.S. patent to Fodor et al. (1991)). Basically, a nucleic acid probe array or gene chip consists of a solid substrate with an attached array of single-stranded probe molecules. In some embodiments, the probes can fold back on (i.e., hybridize to) themselves to quench a signal from an attached label, but the probes unfold to hybridize to a target nucleic acid, whereupon the signal from the attached label becomes detectable. In other embodiments, the probe can be complementary to the segment of a target nucleic acid but the 3' end of the probe terminates one nucleotide short of a SNP in the target nucleic acid. The target nucleic acid can be longer than the probe. A signal can be detected upon primer extension of the probe, where the assay mixture contains just one type of labeled nucleotide that can base pair with the variant nucleotide of the SNP. After washing, the presence or absence of the SNP is detectable by incorporation or non-incorporation of the labeled SNP nucleotide into specific probes of the array or plate.

For screening, the chip, plate, or array is contacted with a nucleic acid sample (e.g., genomic DNA, cRNA, cDNA, or amplified copies thereof), which is allowed to hybridize under stringent conditions. The chip, plate, or array is then scanned to determine which targets have hybridized to which probes. The probes are arrayed in known locations so a signal detected at a specific location indicates that its target has hybridized thereto.

Methods for directly synthesizing on or attaching nucleic acid probes to solid substrates are available in the art. See, e.g., U.S. Pat. Nos. 5,837,832 and 5,837,860, both of which are expressly incorporated by reference herein in their entireties. A variety of methods have been utilized to either permanently or removably attach the probes to the substrate. Exemplary methods include: the immobilization of biotinylated nucleic acid molecules to avidin/streptavidin coated supports (Holmstrom, (Anal. Biochem. 209: 278283 (1993)), the direct covalent attachment of short, 5'-phosphorylated primers to chemically modified polystyrene plates (Rasmussen et al., Anal. Biochem. 198: 138-142 (1991)), or the precoating of the polystyrene or glass solid phases with poly-L-Lys or poly L-Lys. Phe, followed by the covalent attachment of either amino- or sulfhydryl-modified oligonucleotides using bifunctional crosslinking reagents (Running et al., BioTechniques 8: 276 277 (1990); Newton, C. R. et al., Acids Res. 21: 1155-1162 (1993)). When immobilized onto a substrate, the probes are typically stabilized and therefore can be used repeatedly.

Hybridization can performed on an immobilized probe that is attached to a solid surface such as silicon, plastic, nitrocellulose, nylon or glass by addition of one or more target molecules. In some embodiments, the target nucleic acid can be attached to a solid surface and the probe can be added to the immobilized target nucleic acids. Numerous substrate and/or matrix materials can be used, including reinforced nitrocellulose membrane, activated quartz, activated glass, polyvinylidene difluoride (PVDF) membranes, polystyrene, polyacrylamide, poly(vinyl chloride), poly(methyl methacrylate), poly(dimethyl siloxane), photopolymers (which contain photoreactive species such as nitrenes, carbenes and ketyl radicals capable of forming covalent links with target molecules), and combinations thereof.

The term "hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, primer extension, or the enzymatic cleavage of a polynucleotide by a ribozyme.

Hybridization reactions can be performed under conditions of different "stringency". The stringency of a hybridization reaction includes the difficulty with which any two nucleic acid molecules will hybridize to one another. Under low to medium stringent conditions, nucleic acid molecules at least 60%, 65%, 70%, 75% identical to each other remain hybridized to each other, whereas molecules with lower percent identity cannot remain hybridized. For detection of single base polymorphisms, higher stringency conditions can be used.

A preferred, non-limiting example of highly stringent hybridization conditions include hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65° C.

When hybridization occurs in an antiparallel configuration between two single-stranded polynucleotides, the reaction is called "annealing" and those polynucleotides are described as "complementary". A double-stranded polynucleotide can be "complementary" and/or "homologous" to another polynucleotide, if hybridization can occur between one of the strands of the first polynucleotide and the second.

Complementarity" or "homology" (the degree that one polynucleotide is identical or complementary to another) is quantifiable in terms of the proportion of bases in opposing strands that are expected to hydrogen bond with each other, according to generally accepted base-pairing rules.

Detection/Identification of Genetic Variants in Expressed Polypeptides

Genetic variants present in polypeptides such as ADRB1. ADRB2, cytochrome P450 2D6 (CYP2D6), angiotensin converting enzyme (ACE), angiotensinogen, angiotensin receptor, renin, $Na^+$ channels (such as SCNN1A), adducin, sodium ($Na^+$) chloride ($Cl^-$) co-transporters (such as SLC12A3), and/or WNK1 can be detected by use of binding entities such as antibodies. Detection of specific differences in these polypeptides can be used to evaluate which blood pressure mediation is more effective.

Altered polypeptides can be detected in a selected fluid or tissue sample (e.g., cell scrapings, saliva, hair follicle, blood, skin tissue, or any convenient sample of a subject's nucleic acids). Any available methods for detecting polypeptides can be employed. Examples of such methods include immunoassay, Western blotting, enzyme-linked immunosorbant assays (ELISAs), radioimmunoassay, immunocytochemistry, immunohistochemistry, flow cytometry, immunoprecipitation, one- and two-dimensional electrophoresis, mass spectroscopy and/or detection of enzymatic activity.

Altered polypeptides can be detected by binding entities.

Antibodies and other binding entities can be used to detect genetic variants present in ADRB1, ADRB2, cytochrome P450 2D6 (CYP2D6), angiotensin converting enzyme (ACE), angiotensinogen, angiotensin receptors, renin, $Na^+$ channels (such as SCNN1A), adducin, sodium ($Na^+$) chloride ($Cl^-$) co-transporters (such as SLC12A3), and/or WNK1 polypeptides. Such antibodies and binding entities can be prepared by available methods. For example, available amino acid sequences of non-variant and genetic variant ADRB1, ADRB2, CYP2D6, angiotensin converting enzyme (ACE), angiotensinogen, angiotensin receptors, renin, $Na^+$ channels (such as SCNN1A), adducin, sodium ($Na^+$) chloride ($Cl^-$) co-transporters (such as SLC12A3), and/or WNK1, including those illustrated herein, can be used to make antibodies and binding entities. Suitable antibodies may include polyclonal monoclonal, fragments (such as Fab fragments), single chain antibodies and other forms of specific binding molecules. Briefly, these polypeptide detection assays can include contacting a test sample with an antibody specific to the genetic variant site in the polypeptide, detecting the presence of a complex between the antibody and the polypeptide. In some embodiments, a signal from the polypeptide-antibody complex is detected.

Such antibody-based detection methods can any convenient immuno-detection method such as Western Blot, ELISA, radioimmunoassay, immunocytochemistry, immunohistochemistry, flow cytometry, and immunoprecipitation.

Antibodies can be used to detect or identify the presence of genetic variant forms of ADRB1, ADRB2, CYP2D6, angiotensin converting enzyme (ACE), angiotensinogen, angiotensin receptors, renin, $Na^+$ channels (such as SCNN1A), adducin, sodium ($Na^+$) chloride ($Cl^-$) co-transporters (such as SLC12A3), and/or WNK1 polypeptides in a sample. The antibodies are specific for sites of genetic variations, and exhibit substantially no (or significantly less) binding to similar polypeptides that do not have the same genetic variation(s).

Generally speaking, such antibodies can be employed in any type of immunoassay, so long as the genetic variations in the polypeptides are reliably identified. This includes both the two-site sandwich assay and the single site immunoassay of the non-competitive type, as well as in traditional competitive binding assays.

For example, in a typical forward sandwich assay, unlabeled antibody is immobilized on a solid substrate, e.g., within microtiter plate wells, and the sample to be tested is brought into contact with the bound molecule. After a suitable period of incubation, for a period of time sufficient to allow formation of an antibody-antigen binary complex, a second antibody, labeled with a reporter molecule capable of emitting or inducing a detectable signal, is then added and incubation is continued allowing sufficient time for binding with the antigen at a different site and the formation of a ternary complex of antibody-antigen-labeled antibody. Any unreacted material is washed away, and the presence of the antigen is determined by observation of a signal, which may be quantified by comparison with a control sample containing known amounts of antigen.

Variations on the forward sandwich assay include the simultaneous assay, in which both sample and antibody are added simultaneously to the bound antibody, or a reverse sandwich assay in which the labeled antibody and sample to be tested are first combined, incubated and added to the unlabeled surface bound antibody. These techniques are well known to those skilled in the art, and the possibility of minor variations will be readily apparent. As used herein, "sandwich assay" is intended to encompass all variations on the basic two-site technique.

For the sandwich assays, the only limiting factor is that both antibodies have different binding specificities for the genetic variant polypeptide. Thus, a number of possible combinations are possible. For example, a primary antibody can bind specifically to the variant epitope of one of the variant polypeptides. A secondary antibody can bind to a different site on the genetic variant polypeptide. As a more specific example, in a typical forward sandwich assay, a primary antibody is either covalently or passively bound to a solid support. The solid surface is usually glass or a polymer, the most commonly used polymers being cellulose, polyacrylamide, nylon, polystyrene, polyvinylchloride or polypropylene. The solid supports may be in the form of tubes, beads, discs or microplates, or any other surfaces suitable for conducting an immunoassay.

Conventional antibody binding processes can be employed. Following binding, the solid phase-antibody complex is washed in preparation for the test sample. An aliquot of the test sample is then added to the solid phase complex and incubated at about 25° C. for a period of time sufficient to allow binding of any genetic variant polypeptides present to the antibody. The primary antibody can bind specifically to the site of the genetic variant (e.g., the region of a variant amino acid and/or the structural changes associated therewith), but not to similar polypeptides that have no such genetic variant. After washing off unbound antibodies, the second antibody is then added to the solid phase complex and incubated at 25° C. for an additional period of time sufficient to allow the second antibody to bind to the primary antibody-antigen solid phase complex (e.g., to a different site on the genetic variant polypeptide than is bound by the primary antibody). The second antibody may be linked to a reporter molecule, the visible signal of which is used to indicate the binding of the second antibody to any antigen in the sample.

As used herein, a "reporter molecule" or "label" is a molecule that provides an analytically detectable signal, allowing the detection of antigen-bound antibody. In some embodiments, detection is preferably at least relatively quantifiable, to allow determination of the amount of antigen in the sample, this may be calculated in absolute terms, or may be done in comparison with a standard (or series of standards) containing a known normal level of antigen. The term "label" is used interchangeably with "reporter molecule."

Many commonly used reporter molecules in this type of assay are either enzymes or fluorophores. In the case of an enzyme immunoassay an enzyme is conjugated to the second antibody, often by means of glutaraldehyde or periodate. As will be readily recognized, however, a wide variety of different conjugation techniques exist, which are well known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates: for peroxidase conjugates, 1,2-phenylenediamine or toluidine are commonly used. It is also possible to employ fluorogenic substrates, which yield a fluorescent product rather than the chromogenic substrates noted above. In all cases, the enzyme-labeled antibody is added to the first antibody-antigen complex and allowed to bind to the complex, and then the excess reagent is washed away. A solution containing the appropriate substrate is then added to the tertiary complex of antibody-antigen-labeled antibody. The substrate reacts with the enzyme linked to the second antibody, giving a qualitative visual signal which may be further quantified, usually spectrophotometrically, to give an evaluation of the amount of antigen that is present in the serum sample.

Additionally, fluorescent compounds, such as fluorescein or rhodamine, may be chemically coupled to antibodies without altering their binding capacity. When activated by illumination with light of a particular wavelength, the fluorophore-labeled antibody absorbs the light energy, inducing a state of excitability in the molecule, followed by emission of the light at a characteristic longer wavelength. The emission appears as a characteristic color visually detectable with a light microscope. As in the enzyme immunoassay (EIA), the fluorescent-labeled antibody is allowed to bind to the first antibody-tagged polypeptide complex. After washing the unbound reagent, the remaining ternary complex is then exposed to light of the appropriate wavelength, and the fluorescence observed indicates the presence of the antigen.

Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

In another embodiment, the sample to be tested may be used in a single site immunoassay wherein it is adhered to a solid substrate either covalently or non-covalently. An unlabeled antibody is brought into contact with the sample bound on the solid substrate. After a suitable period of incubation, for a period of time sufficient to allow formation of an antibody-antigen binary complex a second antibody, labeled with a reporter molecule capable of inducing a detectable signal, is then added and incubation is continued allowing sufficient time for the formation of a ternary complex of antigen-antibody-labeled antibody. For the single site immunoassay, the second antibody may be a general antibody (i.e., xenogeneic antibody to immunoglobulin, particularly anti-(IgM and IgG) linked to a reporter molecule) that is capable of binding an antibody that is specific for the genetic variant polypeptide of interest.

Kits

Another aspect of the invention is one or more kits for evaluating blood pressure from a test sample provided by, or obtained from, a subject.

The kits can include any reagents, components and instructions useful for testing, assaying, detecting, identifying, and/or determining whether genetic variations are present in ADRB1, ADRB2, CYP2D6, angiotensin converting enzyme (ACE), angiotensinogen, angiotensin receptors, renin, $Na^+$ channels (such as SCNN1A), adducin, sodium ($Na^+$) chloride ($Cl^-$) co-transporters (such as SLC12A3), and/or WNK1 polypeptides or nucleic acids that can be present in the test samples.

The kits can include reagents, components and instructions for detecting, identifying, and/or quantifying such polypeptides or nucleic acids. For example, the kits may include primers, probes, labels, enzymes and/or other components for detecting, and/or identifying genetic variations in such polypeptides or nucleic acids.

In other embodiments, the kits may include one or more antibody preparations that selectively bind to genetic variant ADRB1, ADRB2, CYP2D6, angiotensin converting enzyme (ACE), angiotensinogen, angiotensin receptors, renin, $Na^+$ channels (such as SCNN1A), adducin, sodium ($Na^+$) chloride ($Cl^-$) co-transporters (such as SLC12A3), and/or WNK1 polypeptides, and a detection means for detecting an antibody complex that can form (e.g., a label or reporter molecule that is either bound to an antibody or is capable of binding to the antibody).

One type of kit can include components for obtaining a sample from a subject, and instructions for sample collection. For example, such a sample collection kit can include one or more containers for sample collection such as one or more vials, test tubes, or receptacles. The sample collection containers can include a solution for stabilizing samples placed in the containers. Such a stabilizing solution can include protease inhibitors, nuclease inhibitors, DNase inhibitors, RNase inhibitors, chelators, denaturants, salts, salts, and/or buffers. The sample collection kit can also include components for sample collection such as swabs, droppers, syringes, needles, scalpels, and/or catheters. The instructions can include steps for sample collection, storage of the sample, and submission of the sample.

The kits can include one or more probes and/or primers each capable of specifically binding to a nucleic acid segment of at least 13, 14, 15, 16, 17, 18, 19, 20, or 25 nucleotides. In some embodiments, probes and/or primers are each capable of specifically binding to a nucleic acid segment of 15-30, 15-40, 15-50 nucleotides, or any number of nucleotides between 13-50 nucleotides, in a target DNA or RNA. The probes may be part of an array, microarray, microchip, assay plate, or nanochip. Alternatively, the probes or primers may be packaged separately and/or individually. In some embodiments, the probes or primers may be detectably labeled. For example, labels can be included on immobilized probes, where the label signals are quenched until hybridization occurs and then, upon hybridization, the label emits a detectable signal. Alternatively, one or more labels can be included in the kit that can bind to a hybridized complex between a probe and a target DNA or RNA.

Additional reagents can be included in the kits. For example, the kits may also contain reagents for detecting or identifying a genetic variant in an ADRB1, ADRB2, CYP2D6, angiotensin converting enzyme (ACE), angiotensinogen, angiotensin receptors, renin. $Na^+$ channels (such as SCNN1A), adducin, sodium ($Na^+$) chloride ($Cl^-$) co-transporters (such as SLC12A3), and/or WNK1 nucleic acid in a test sample. Such reagents can include reagents for isolating, storing and detecting nucleic acids. For example, the kits can include reagents and enzymes for nucleic acid amplification, primer extension. RNA reverse transcription, sequencing, restriction enzyme cleavage, and/or separation of nucleic acids. The kits may also include reagents such as solutions for stabilizing nucleic acids, solutions for purifying nucleic acids, nucleotide triphosphates, buffers, and/or other reagents that can be used in in a test tissue sample.

Preservatives and/or antimicrobial agents can be included to stabilize reagents and prevent contamination, such as, for example, paraben, chlorobutanol, phenol sorbic acid, and the like.

It may also be desirable to include agents such as solvents for nucleic acids, reducing agents (e.g., beta-mercaptoethanol), stabilizing reagents (e.g., reagents for inhibiting nucleases, ribonucleases, disrupting tissues, precipitating nucleic acids, and the like).

In further embodiments, the kits can include a computer program product for use in conjunction with a computer system and the methods described herein. A computer program mechanism can be embedded in the computer program product. The computer program product can, for example, be a device with a computer program mechanism encoded thereon, where the computer program mechanism may be loaded into the memory of a computer and cause the computer to carry out at least one step of a method for assessing the malignant/benign status of a test thyroid tissue sample. For example, the device can be a computer readable storage medium, a flash memory, a compact disc (CD), a digital versatile disc, digital video disc, or an article of manufacture that tangibly includes one or more computer programs and memory storage. In some embodiments, the computer program product can be a computer readable storage medium. In such kits, the computer program mechanism can include instructions for determining, detecting, and/or identifying a genetic variant in an ADRB1, ADRB2, CYP2D6, angiotensin converting enzyme (ACE), angiotensinogen, angiotensin receptors, renin, $Na^+$ channel (such as SCNN1A), adducin, sodium ($Na^+$) chloride ($Cl^-$) co-transporter (such as SLC12A3), and/or WNK1 nucleic acid or polypeptide in a test sample.

In other embodiments, the kits can include a system, such as a computer, having a central processing unit and a memory coupled to the central processing unit. The memory may store instructions for determining, detecting, and/or identifying a genetic variant in an ADRB1, ADRB2, CYP2D6, angiotensin converting enzyme (ACE), angiotensinogen, angiotensin receptors, renin, $Na^+$ channel (such as SCNN1A), adducin, sodium ($Na^+$) chloride ($Cl^-$) co-transporter (such as SLC12A3), and/or WNK1 nucleic acid or polypeptide in a test sample. The memory can also store therapeutic options for different genotyping results.

The kits can also include one or more therapeutic agents, for example, any blood pressure medications described herein.

Definitions

Some definitions are provided below; other definitions are provided in the other sections of the applications.

As used herein. "obtaining a test sample" involves removing a sample of tissue from a patient, receiving a sample of tissue from a patient, receiving a patient's tissue sample from a physician, receiving a patient's tissue sample via mail delivery and/or removing a patient's tissue sample from a storage apparatus (e.g., a refrigerator or freezer) or a facility. Thus, obtaining a test sample can involve removal or receipt of the test sample directly from the patient, but obtaining a test sample can also include receipt of a test sample indirectly from a medical worker, from a storage apparatus/facility, from a mail delivery service after transportation from a medical facility, and any combination thereof. The test sample can therefore originate in one location, and be transported to another location where it is received and tested. Any of these activities or combinations of activities involves "obtaining a test sample."

As used herein a probe refers to a single DNA or RNA molecule (a nucleic acid oligomer) or a collection of nucleic acid molecules (nucleic acid oligomers) where the DNA molecules have at least one segment with a sequence that is complementary to a region of a target nucleic acid. The probe can hybridize with the target nucleic acid under stringent conditions. In some cases, the probe can hybridize with the target nucleic acid under highly stringent conditions. The probe is not identical to naturally available nucleic acids because has additional components such as one or more labels, one or more (engineered) restriction sites, one or more molecular barcodes, one or more tags for identification or retrieval of the probe (e.g., with or without the target hybridized thereto). In some instances the probe is attached to a solid surface such as a chip, an array, a bead, or other surface.

As used herein a primer contains a region that is designed to hybridize to a targeted locus (e.g., a targeted polymorphic locus or a nonpolymorphic locus). The primer and may contain a priming sequence designed to allow PCR amplification. The primer can have at least one segment with a sequence that is complementary to a region of a target nucleic acid. The primer can hybridize with the target nucleic acid under stringent conditions. In some cases, the primer can hybridize with the target nucleic acid under highly stringent conditions. The primer is not identical to naturally available nucleic acids because has additional components such as a molecular barcode, a tag, an engineered restriction site, or a combination thereof. A primer may contain a random region that differs for each individual molecule. The terms "test primer" and "candidate primer" are not meant to be limiting and may refer to any of the primers disclosed herein.

As used herein a "binding entity" is a molecule or molecular complex that can recognize and bind to selected target molecules. Such binding entities can be antibodies or any molecule that has a binding domain for a target molecule.

A number of proteins can serve as protein scaffolds to which binding domains for targets can be attached and thereby form a suitable binding entity. The binding domains bind or interact with the targets of the invention while the protein scaffold merely holds and stabilizes the binding domains so that they can bind. A number of protein scaffolds can be used. For example, phage capsid proteins can be used. See Review in Clackson & Wells, Trends Biotechnol. 12:173-184 (1994). Phage capsid proteins have been used as scaffolds for displaying random peptide sequences, including bovine pancreatic trypsin inhibitor (Roberts et al., PNAS 89:2429-2433 (1992)), human growth hormone (Lowman et al., Biochemistry 30:10832-10838 (1991)), Venturini et al., Protein Peptide Letters 1:70-75 (1994)), and the IgG binding domain of *Streptococcus* (O'Neil et al., Techniques in Protein Chemistry V (Crabb, L., ed.) pp. 517-524. Academic Press. San Diego (1994)). These scaffolds have displayed a single randomized loop or region that can be modified to include binding domains for selected targets.

Researchers have also used the small 74 amino acid α-amylase inhibitor Tendamistat as a presentation scaffold on the filamentous phage M13. McConnell, S. J & Hoess, R. H., J. Mol. Biol. 250:460-470 (1995). Tendamistat is a β-sheet protein from *Streptomyces tendae*. It has a number of features that make it an attractive scaffold for binding peptides, including its small size, stability, and the availability of high resolution NMR and X-ray structural data. The overall topology of Tendamistat is similar to that of an immunoglobulin domain, with two β-sheets connected by a series of loops. In contrast to immunoglobulin domains, the β-sheets of Tendamistat are held together with two rather than one disulfide bond, accounting for the considerable stability of the protein. The loops of Tendamistat can serve a similar function to the CDR loops found in immunoglobulins and can be easily randomized by in vitro mutagenesis. Tendamistat is derived from *Streptomyces tendae* and may be antigenic in humans. Hence, binding entities that employ Tendamistat are preferably employed in vitro.

Fibronectin type III domain has also been used as a protein scaffold to which binding entities can be attached. Fibronectin type III is part of a large subfamily (Fn3 family or s-type Ig family) of the immunoglobulin superfamily. Sequences, vectors and cloning procedures for using such a fibronectin type III domain as a protein scaffold for binding entities (e.g. CDR peptides) are provided, for example, in U.S. Patent Application Publication 20020019517. See also, Bork, P. & Doolittle, R. F. (1992) Proposed acquisition of an animal protein domain by bacteria. Proc. Natl. Acad. Sci. USA 89, 8990-8994; Jones. E. Y. (1993) The immunoglobulin superfamily Curr. Opinion Struct. Biol. 3, 846-852; Bork, P., Hom, L. & Sander, C. (1994) The immunoglobulin fold. Structural classification, sequence patterns and common core. J. Mol. Biol. 242, 309-320; Campbell, I. D. & Spitzfaden, C. (1994) Building proteins with fibronectin type III modules Structure 2, 233-337; Harpez, Y. & Chothia. C. (1994).

The following non-limiting examples further illustrate aspects of the invention.

Example 1: Sample Processing

Each patient is given a collection kit consisting of two buccal swabs and two uniquely barcoded tubes (termed A and B swabs) containing a proprietary lysis buffer consisting of 50 mM Tris pH 8.0, 50 mM EDTA, 25 mM Sucrose, 100 mM NaCl, and 1% SDS. The patient will use the swab to collect buccal cells by scraping the inside of their cheek and place the swab in the provided barcoded tube, one swab for each check. Once the swab has been placed into the lysis buffer the cells are no longer viable and therefore samples are now considered to be nucleic acids and safe to be shipped via standard mail. All samples are checked-in. The barcodes of the samples are scanned and their arrival in the laboratory is confirmed.

Figure 3A:
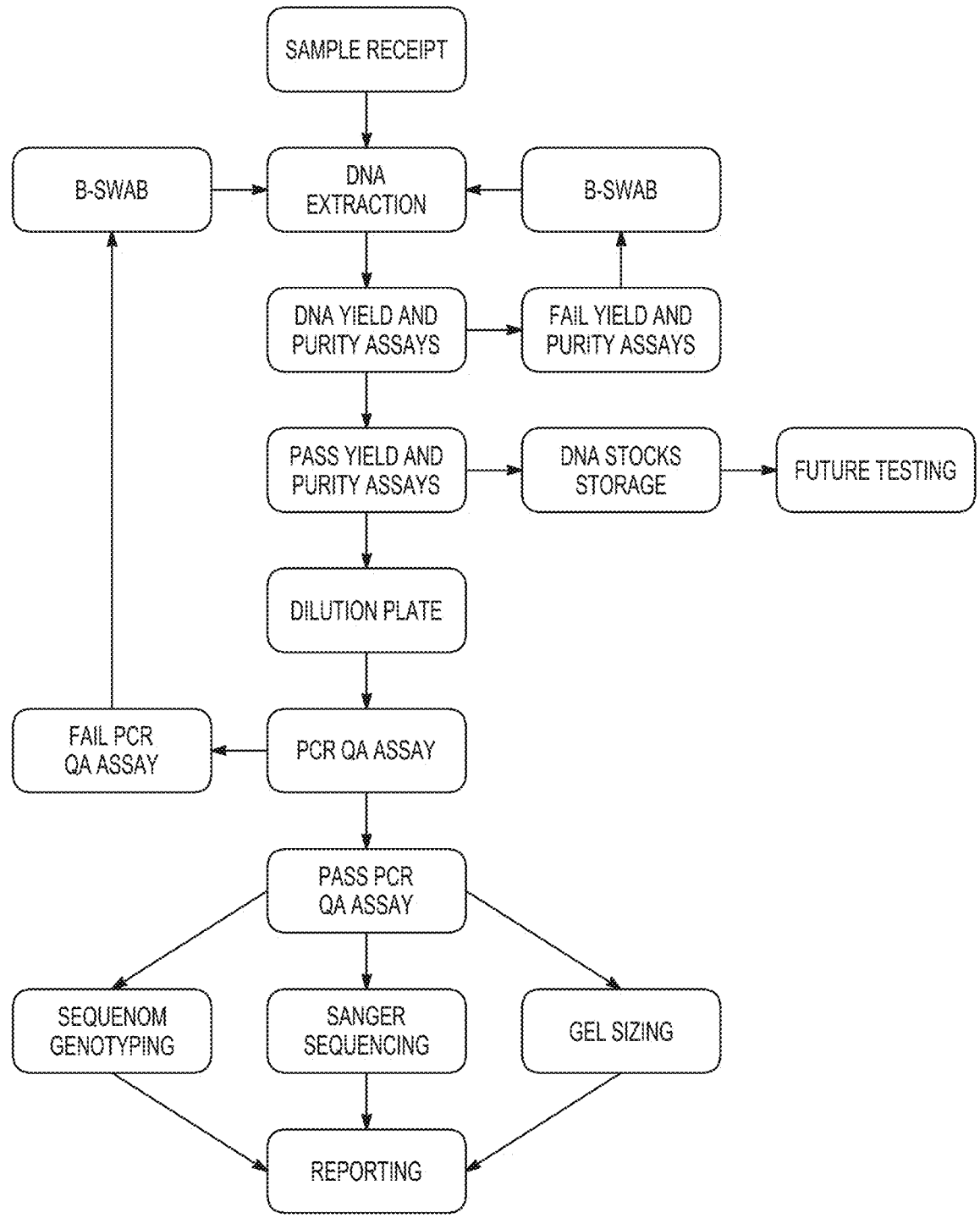
FIG. 3A-3B are schematic diagrams illustrating processing of test samples. For example, each subject can collect two swabs. The A swab can collect cell material from the inside of the right cheek, while the B swab can collect cell material from the left cheek. For FIG. 3A, the A swab can be the initial swab entered into the process (from DNA Extraction to Reporting). If the A swab fails, during DNA Yield and Purity Analysis. Genetic analysis, or the PCR QA Assay then the B swab can be entered into the system as illustrated.
Figure 3B:
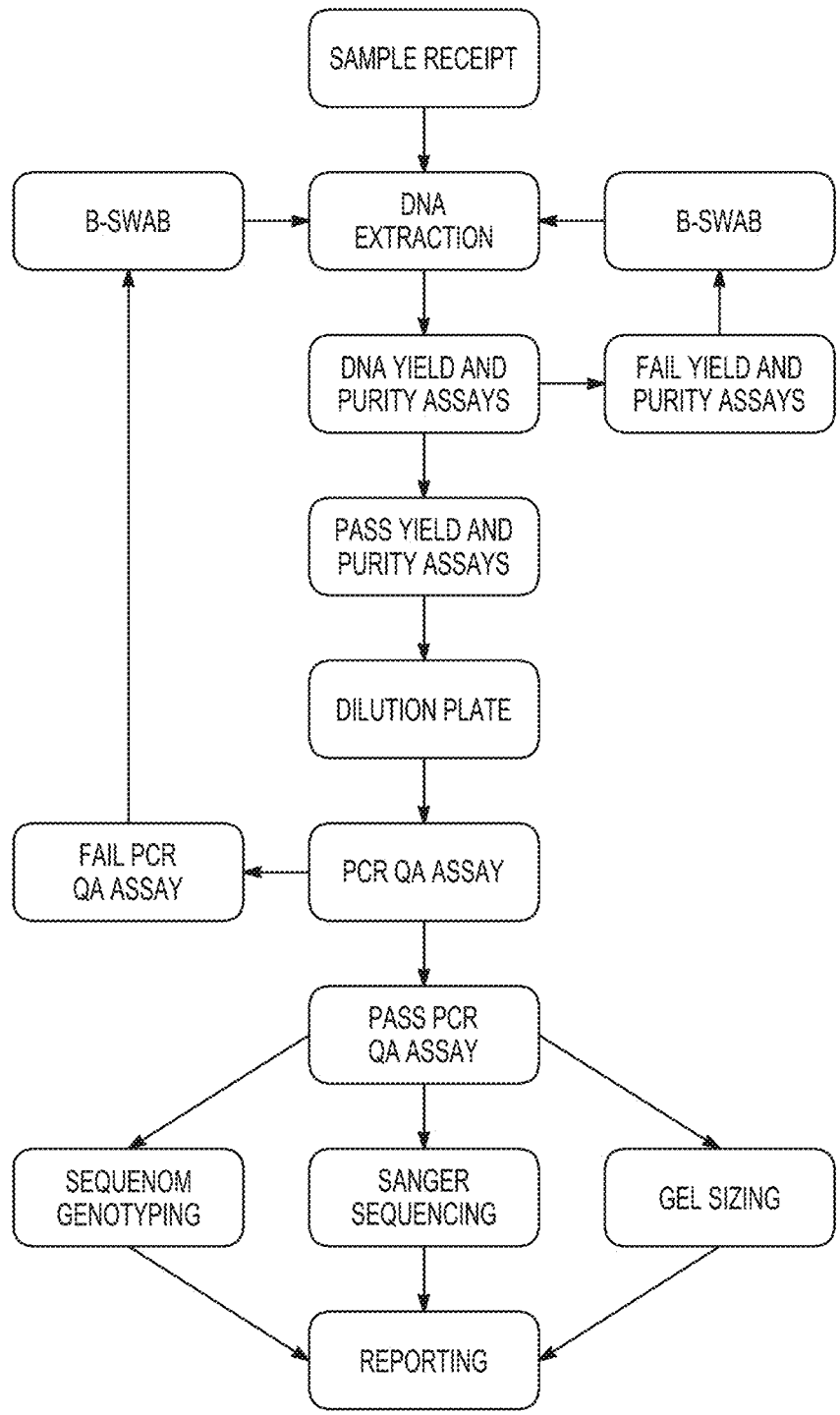
Figure 4:
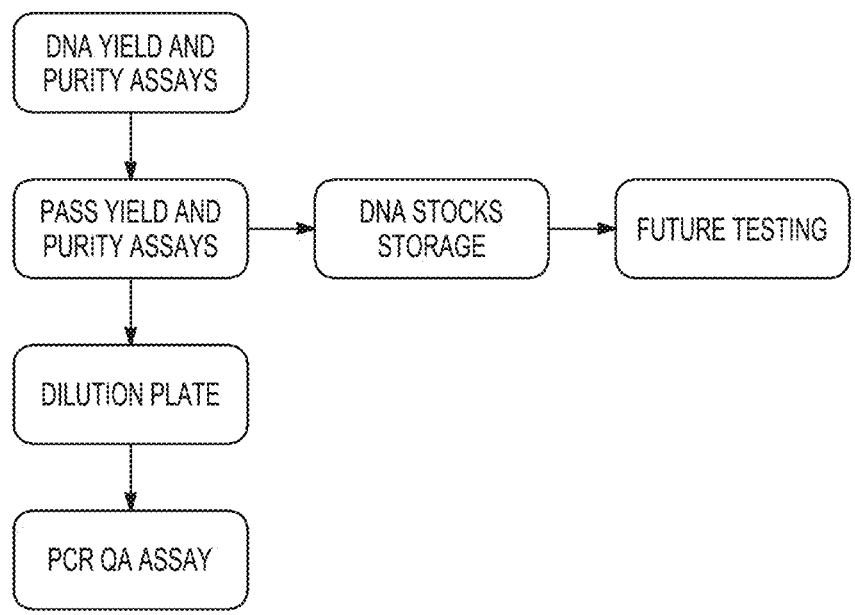
FIG. 4 is a schematic diagram illustrating handling of DNA samples.
Figure 5:
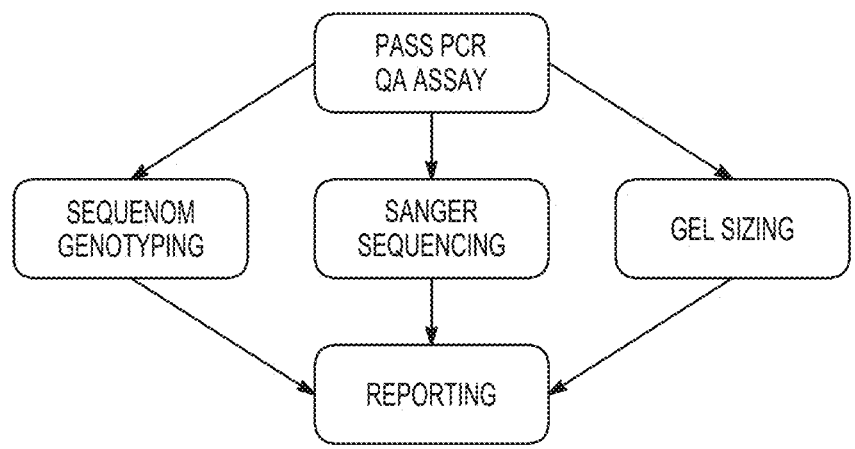
FIG. 5 is a schematic diagram illustrating processing of the sample after PCR amplification.

FIGS. 3A-3B show schematic diagrams illustrating slight variations in sample processing. In general, two samples (Swab A and Swab B) are taken. The Swab A sample is subjected to the process (DNA Extraction through Reporting) unless the Swab A sample fails either the DNA Yield and Purity Assays. Genomic Analysis, or the PCR QA Assay. If such failure occurs, then the other sample (Swab B) is subjected to the process, as illustrated in FIGS. 3A and/or 3B.

The samples are grouped into sets of 91 and assigned positions in 96 sample grids (12×8 grid layout) for DNA extraction. The remaining five positions in each grid can be extraction controls (four negative controls [H₂O] and one non-human positive). The five controls can be assigned random positions in each grid, giving each grid/plate a unique "plate fingerprint." The randomly assigned controls prevent possible plate swaps or 180° rotations as every plate is now identifiable simply by control positions. All samples are then normalized to a volume of 650 ul by addition of the above mentioned lysis buffer. Additionally, 25 ul of proteinase K (ProK) is added and each sample is incubated in a 55° C. oven for a minimum of 4 hours.

Following such incubation, the samples are extracted using a BioSprint96 (KingFisher96) Robotic workstation with magnetic-particle DNA purification chemistry to isolate genomic DNA (GenomicDNA) from tissue samples. This protocol utilizes the chemistry from the eVoMagDNA Extraction KF96 Kit (Verde Labs. Marietta, Ga.) and is run to specifications provided by the manufacturer.

Following DNA extraction and subsequent desiccation, the DNA is resuspended in HPLC water. Five microliters of each sample is then aliquoted to assay plates for the first pair of QA assays, both a PicoGreen fluorometric quantification and a spectrophotometric purity estimation. The fluorescence and absorbance data is analyzed for all samples in the 96 well plate, including the five controls. The positions of the negative controls is confirmed and accessed for possible plate contamination. The results for the positive control as well as the samples on the plate are analyzed for quality metrics using a systems analysis approach. The outliers are statistically assessed. After the quantification and purity evaluations. QA assay robotic systems are used to transfer the samples into racks of 96 sample septa sealed plates (to ensure there is no evaporative loss) and a fractional volume of each sample is used to create a daughter plate of the samples at a normalized concentration of 5 ng/µl for the PCR QA assays and subsequent genotyping. The creation of the normalized daughter plate serves two purposes. First, it allows the immediate storage of the primary stock of each sample at −80° C. avoiding the need for unnecessary freeze-thaw of samples and the potential contamination risks associated with repeated accessing of the stock. Second, it avoids unnecessary waste of the DNA associated with the use of full concentration stock for the PCR applications (this −80° C. stock DNA can be used at any time or saved for future testing).

Any samples that fail any of the QA assays can re-enter the pipeline and be sorted and re-processed from the B-swab, which is the second tube/swab in the kit sent to the customer mentioned above. By always having a backup sample it is not necessary to go back to the customer to ask for a re-swab. If the quantity and purity are still insufficient then whole genome amplification and/or organic re-extraction can be employed.

Following the passage of the QA thresholds normalized fractions of the samples are transferred to PCR plates for genotyping. Each sample is analyzed using three different methodologies, the Sequenom MassArray genotyping platform. Sanger sequencing using the ABI 3730xl genomic analyzer from Applied Biosystems, and classical PCR and gel sizing to determine insertion/deletion status. The Sequenom MassArray genotyping platform is used to analyze the following SNP sites: rs1042713, rs1042714, rs1159744, rs12750834, rs1801252, rs1801253, rs2107614, rs227869, rs4244285, rs4961, and rs699. Sanger sequencing is used to analyze the following SNPs: rs3892097, rs3758581, rs2228586, and rs5186. Finally classical gel sizing is used to determine the insertion/deletion status of the rs1799752 SNP.

Example 2: Sequenom MassArray Assay Design and Processing

The Sequenom platform is able to perform genotyping as a twelve-plex assay (testing 12 variable sites in one reaction) in a 96 well format using one aliquot of DNA. The AssayDesign software from Sequenom is used to generate both PCR and single base extension primers using the individual rs number of each variable site to create the final assay design. Table 1 shows examples of primers that can be used to detect various single nucleotide polymorphisms.

TABLE 1

Primers for Amplification of Nucleic Acid Variant Segments

| SNP ID PCRP | 2$^{nd}$ PCRP | SEQ ID 1$^{st}$ SEQ ID |
|---|---|---|
| rs1042714 | ACGTTGGATGAGACATGACGATGCCCATGC | NO: 36 |
|  | ACGTTGGATGAGCGCCTTCTTGCTGGCAC | NO: 37 |
| rs699 | ACGTTGGATGCTGTGACAGGATGGAAGACT | NO: 38 |
|  | ACGTTGGATGTGGACGTAGGTGTTGAAAGC | NO: 39 |
| rs4961 | ACGTTGGATGTGTTCGTCCACACCTTAAGT | NO: 40 |
|  | ACGTTGGATGACAAGATGGCTGAACTCTGG | NO: 41 |
| rs12750834 | ACGTTGGATGGGAATCCAGGAGAATAGGTC | NO: 42 |
|  | ACGTTGGATGACAGGCTACCTGGCTTTAAC | NO: 43 |
| rs1801252 | ACGTTGGATGGCCTCGTTGCTGCCTCCCG | NO: 44 |
|  | ACGTTGGATGATCAGCAGACCCATGCCCG | NO: 45 |
| rs1801253 | ACGTTGGATGAGCCCTGCGCGCGCAGCA | NO: 46 |
|  | ACGTTGGATGTCAACCCCATCATCTACTGC | NO: 47 |
| rs227869 | ACGTTGGATGCTGACATTGCCAGCTGTATC | NO: 48 |
|  | ACGTTGGATGGTAGTGGCACTGGCATATTC | NO: 49 |
| rs2107614 | ACGTTGGATGGCAACCATCACAGTACTAAG | NO: 50 |
|  | ACGTTGGATGCACAACTGGAAGAGTTGAGG | NO: 51 |
| rs1529927 | ACGTTGGATGTGGACCCCATTAACGACATC | NO: 52 |
|  | ACGTTGGATGTCACCTTGGACTCCCACTC | NO: 53 |

TABLE 1-continued

Primers for Amplification of Nucleic Acid Variant Segments

| SNP ID PCRP | 2nd PCRP | SEQ ID 1st SEQ ID |
|---|---|---|
| rs4244285 | ACGTTGGATGCACTTTCCATAAAAGCAAGG | NO: 54 |
|  | ACGTTGGATGGCAATAATTTTCCCACTATC | NO: 55 |
| rs1042713 | ACGTTGGATGATGAGAGACATGACGATGCC | NO: 56 |
|  | ACGTTGGATGGAACGGCAGCGCCTTCTTG | NO: 57 |
| rs1159744 | ACGTTGGATGGAAACAGTGACAGCCAAATG | NO: 58 |
|  | ACGTTGGATGGTTTTTCAGTTCCTGAATTG | NO: 59 |

DNA samples at a concentration of 5 ng/ul undergo a PCR using the above designed PCR primers and the Sequenom iPLEX Gold Reagent kit under the conditions described in Table 2.

TABLE 2

PCR Reaction Mixture

| Reagent | Final Concentration | Vol/rxn (uL) |
|---|---|---|
| Water, HPLC | N/A | 1.8 |
| 10x PCR Buffer with 20 mM MgCl$_2$ | 2mM MgCl$_2$ | 0.5 |
| 25 mM MgCl$_2$ | 2 mM | 0.4 |
| 25 mM dNTP Mix | 500 uM | 0.1 |
| 0.5 mM Primer Mix | 0.1 uM | 1 |
| 5 U/uL PCR Enzyme | 1 unit | 0.2 |
| Volume |  | 4 |
| 10 ng/uL DNA | 10 ng/rxn | 1 |
| Total Volume |  | 5 |

The PCR reaction cycling conditions can be as illustrated in Table 3.

TABLE 3

PCR Reaction Cycling
Cycler Program iPlex- PCR

| Temp (° C.) | Time (mm) | | |
|---|---|---|---|
| 95 | 2:00 | | |
| 95 | 0:30 | Repeat | |
| 56 | 0:30 | 45 | |
| 72 | 1:00 | Cycles | |
| 72 | 5:00 | | |
| 4 | ∞ | | |

Directly following PCR amplification, excess primers and deoxynucleotide triphosphates are removed via a SAP (shrimp alkaline phosphatase) reaction under the conditions described in Table 4.

TABLE 4

PCR Clean-Up

| Reagent | Final Concentration | Vol/rxn (uL) |
|---|---|---|
| Water, HPLC | N/A | 1.53 |
| SAP Buffer (10x) | 0.24x | 0.17 |
| 5 U/uL PCR Enzyme | 1 unit | 0.2 |
| Volume |  | 2 |
| PCR product |  | 5 |
| Total Volume |  | 7 |

The Shrimp Alkaline Phosphatase reaction is incubated at 37° C. for 40 min, followed by incubation at 85° C. for 5 min. The samples can be stored at 4° C. indefinitely.

After the SAP reaction is completed the samples can be subjected to single base extension reactions using the primers described in Table 5, and the conditions described in Table 6 and 7.

TABLE 5

Single Base Extension Primers

| SNP | Sequence | SEQ ID NO: |
|---|---|---|
| rs1042714 | ACACCTCGTCCCTTT | 60 |
| rs699 | CTGGCTGCTCCCTGA | 61 |
| rs4961 | ACTGCTTCCATTCTGCC | 62 |
| rs12750834 | AGTCTCTGTAAGTGCCC | 63 |
| rs1801252 | GTGCCTCCCGCCAGCGAA | 64 |
| rs1801253 | CGCGCGCAGCAGAGCAGT | 65 |
| rs227869 | AGCTGTATCTGCTCCATTCA | 66 |
| rs2107614 | TCCTCCAAAAAAAAGAAAAC | 67 |
| rs1529927 | GTTACCGACATCCGCATCATTG | 68 |
| rs4244285 | TAAGTAATTTGTTATGGGTTCC | 69 |
| rs1042713 | GGAGGGGTCCGGCGCATGGCTTC | 70 |
| rs1159744 | CAAATGTTAACAGTATAGAAAATTTTA | 71 |

TABLE 6

Single Base Extension Reaction Conditions

| Reagents | Final Concentration | Vol/rxn (uL) |
|---|---|---|
| Water HPLC | N/A | 0.619 |
| iPlex Gold Buffer | 0.222x | 0.200 |
| iPlex Termination Mix | 1x | 0.200 |
| iPlex Extend Primer Mix | varies | 0.940 |
| iPlex Enzyme | 1x | 0.041 |
| Volume |  | 2.000 |
| PCR product |  | 7 |
| Total Volume |  | 9 |

TABLE 7

Single Base Extension Reaction Cycling conditions

| Temp (∞ C.) | Time | | |
|---|---|---|---|
| 94 | 0:30 | | |
| 94 | 0:05 | | 40 cycles |
| 52 | 0:05 | 5 cycles | ↓ |
| 80 | 0:05 | ↓ | |
| 72 | 3:00 | | |
| 4 | forever | | |

After completion of all of the above reactions, the samples are run through resin based clean-up to remove excess salts according to standard Sequenom protocols. The samples are then spotted onto the Sequenom provided SpectroChip using the Sequenom Nanodispenser according to manufacturer protocols and subsequently processed on the Sequenom MALDI-TOF platform.

A sample results report is provided in Table 7. The two letters for each polymorphism type are for the two alleles present in the subjects, illustrating that the subjects are homozygous for some polymorphisms (e.g., subject GCE0104 is homozygous (G/G) for the variable site in the rs1042713 polymorphism, but subject GCE0120 is heterozygous (GA) for that site).

TABLE 8

Results

| SNP | GCE0120 | GCE0104 |
|---|---|---|
| rs1042713 | GA | GG |
| rs1042714 | GC | GG |
| rs1159744 | AA | AT |
| rs12750834 | GA | GG |
| rs1529927 | GG | GG |
| rs1801252 | AA | AA |
| rs1801253 | GG | GG |
| rs2107614 | CT | TT |
| rs227869 | AA | AG |
| rs4244285 | GG | GA |
| rs4961 | GG | GG |
| rs699 | CG | GG |

Practice of the foregoing methods can be accomplished with a PCR thermocycler instrument such as an MJ Research Tetrad 2 thermocycler for PCR amplification and an instrument for identification of the amplified DNA fragments such as an Agena MassArray® system or a Sequenom MALDI-TOF system which utilize the function of a time-of-flight mass spectrometer. A patient's DNA is first extracted as described above and the PCR reaction conducted in the MJ thermocycler to amplify only DNA fragments corresponding substantially to the patient's genomic SNP's described above. The amplified genomic material is then introduced into the detection and identification instrument such as an Agena or Sequenom automated DNA fragment identification system. This system enables identification of multiples of PCR amplified DNA fragments and provides identification of the patient's 14 genotype SNP's in accordance with embodiments of the invention.

Example 3: Sanger Sequencing Primer Design and Workflow

All primers for Sanger sequencing were designed using the free, web-based primer design tool Primer3. 500 base pairs of flanking sequence for each SNP (single nucleotide polymorphism) were entered into Primer3. The top primer candidate for each site was chosen and optimized using a buffer panel with varying MgCl concentrations and a temperature gradient to determine the optimal cycling conditions for each primer pair.

TABLE 9

Primers for Sequencing of SNPs

| Primer Name | Sequence | SEQ ID | Purpose |
|---|---|---|---|
| rs3892097_F | TTCAGTCCCTCCTGAGCTA | NO: 72 | SNP |
| rs3892097_R | AAGGTGGATGCACAAAGAG | NO: 73 | SNP |
| rs3758581_F | GTGCATCTGTAGCAGTCCTC | NO: 74 | SNP |
| rs3758581_R | CCAAACTGGAATCAACAGAA | NO: 75 | SNP |
| rs2228586_F | GAAGTGGTCTCGTCTAGCAA | NO: 76 | SNP |
| rs2228586_R | CAGAGAGAGAGGTCCCATTT | NO: 77 | SNP |
| rs5186_F | CCACTCAAACCTTTCAACAA | NO: 78 | SNP |
| rs5186_R | TGGACAGAACAATCTGGAAC | NO: 79 | SNP |

The region encompassing the SNP was amplified from sample nucleic acids by PCR using optimized individual cycling conditions for each SNP site. Directly after PCR amplification each sample is cleaned up using a size exclusion micro-filtration plate from Millipore and entered into the Sanger sequencing reaction. Each sample is sequenced in both the forward (3') and reverse (5') direction giving double conformation of the allelic state. These forward and reverse sequences from each patient are then aligned to the human reference sequence using the CLC DNA workbench program creating an alignment file from which the allele call is made and added to the final SNP call report.

Figure 6:
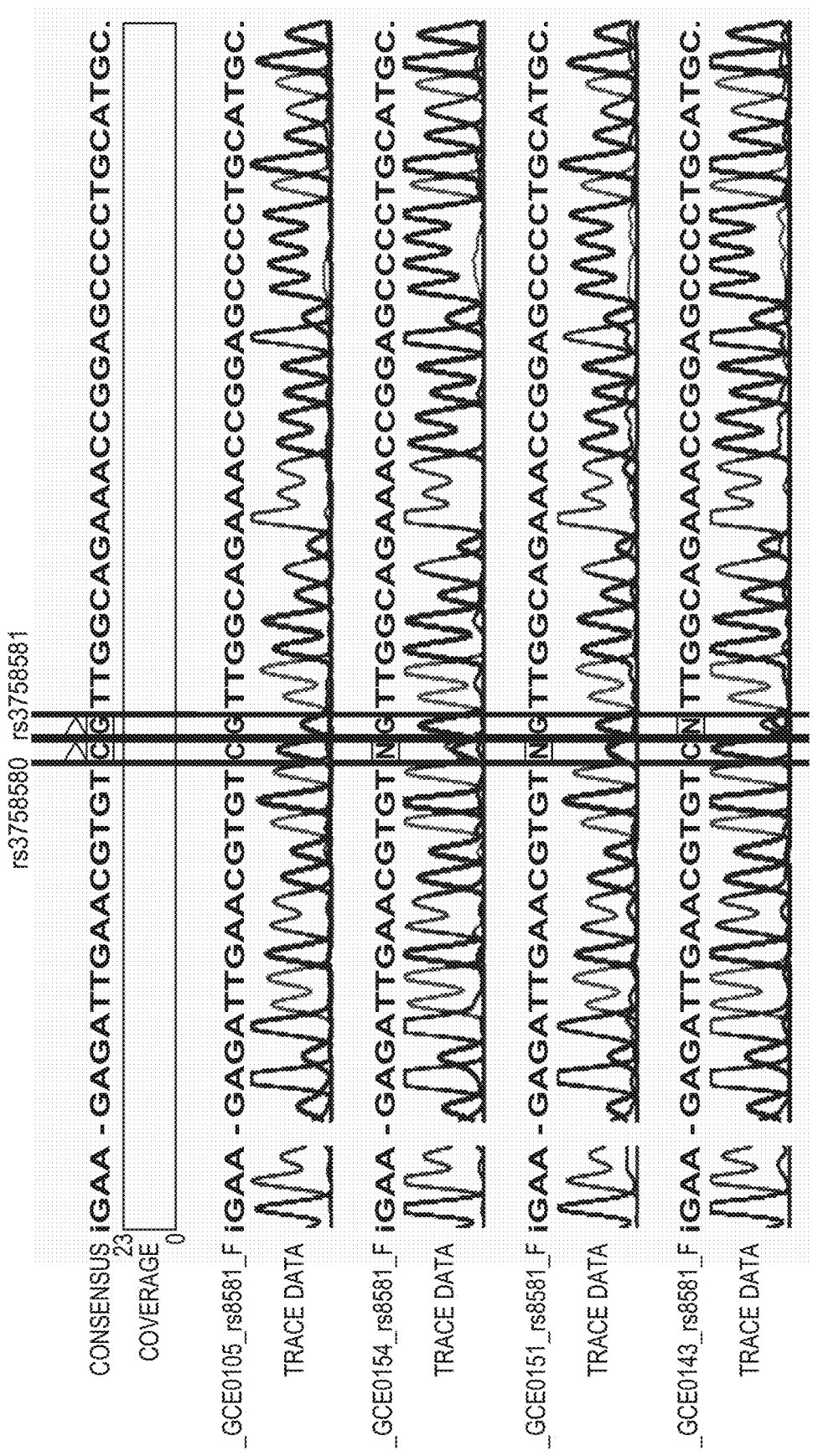
FIG. 6 illustrates alignment of sample results to a human reference sequence using the CLC DNA workbench program for creating an alignment file from which the allele call is made and added to the final SNP call report (SEQ ID NOs:82-85).

FIG. 6 illustrates the results from one such alignment.

Example 4: Gel Sizing Primer Design and Workflow

To accurately call the insertion/deletion status for site rs1799752, PCR amplification of sample nucleic acids is performed followed by gel electrophoresis. The PCR primers for this site were also designed and optimized using Primer3 and the above mentioned buffer and temperature gradient. The following primer sequences and PCR conditions were ultimately chosen:

TABLE 10

Primer Sequences for PCR of rs1799752 Insertion/Deletion

| Primer Name | Sequence | SEQ ID | Purpose |
|---|---|---|---|
| rs1799752_F-2 | CCCATTTCTCTAGACCTGCT | NO: 80 | INDEL |
| rs1799752_R-2 | GGGATGGTGTCTCGTACATA | NO: 81 | INDEL |

Figure 7:
FIG. 7 is an example of 2% agarose gel used to score the presence or absence of a 288 bp ALU by visually examining the gel for either the higher molecular weight band (indicating the presence of the 288 bp ALU), the lower molecular weight band (indicating the absence of the 288 bp ALU), or both (indicating a heterozygous state).

Following PCR amplification, each sample is loaded into its own well of a 2% agarose gel and run at 150 mV for approximately 45 min and stained in a bath of GelRed for 2 hours prior to imaging with UV light. The resulting image is used to score the presence or absence of a 288 bp ALU visually by examining the gel for either the higher molecular weight band (indicating the presence of the 288 bp ALU), the lower molecular weight band (indicating the absence of the 288 bp ALU) or both (indicating a heterozygous state. A sample image of the gel is provided in FIG. 7.

Example 5: Genotyping Reports

Once all tests are performed a report is generated containing all results for each tested patient. One example of a report for subjects GCE0120 and GCE0104, is shown below. The two letters for each polymorphism type are for the two alleles present in the subjects, illustrating that the subjects are homozygous whereas other subjects are heterozygous for the variable site of each polymorphism.

TABLE 11

Results from Analysis of Polymorphisms

| Polymorphism type | GCE0120 | GCE0104 |
|---|---|---|
| Sequenom Results | | |
| rs1042713 | GA | GG |
| rs1042714 | GC | GG |
| rs1159744 | CG | CG |
| rs12750834 | GA | GG |
| rs1529927 | GG | GG |
| rs1801252 | AA | AA |
| rs1801253 | GG | GG |
| rs2107614 | CT | TT |
| rs227869 | AA | AG |
| rs4244285 | GG | GA |
| rs4961 | GG | GG |
| rs699 | TT | TT |
| Sanger Sequencing Results | | |
| rs3892097 | CC | CC |
| rs3758581 | GG | GG |
| rs3758580 | CC | CT |
| rs2228586 | TT | TT |
| rs5186 | AC | AA |
| Gel Results | | |
| rs1799752 | +/+ | +/− |

Example 6: Clinical Study Protocol

Clinical Protocol Summary

| | |
|---|---|
| Study Title: | Assessment of the Relationship between Genes that Encode Proteins Important in Blood Pressure Regulation and Blood Pressure Therapy in Patients with Hypertension. |
| Study Device: | The Geneticure Pharmacogenetic Testing Kit. The kit contains two buccal swabs with two buffer solution vials to stabilize DNA. These buccal swabs are used for DNA collection which is then extracted for analysis of genes important in high blood pressure. |
| Target Indication for Use: | The Geneticure Pharmacogenetic Testing Kit is a pharmacogenomic treatment decision support product that tests for clinically important genetic variants affecting a patient's response to antihypertensive medications. |
| Study Design: | This is a post-hoc association study of patients who have been diagnosed with high blood pressure and have been stable on medication treatment for at least 6 months. |
| Study Population: | To be enrolled in this study, subjects must meet ALL of the inclusion criteria and NONE of the exclusion criteria: Inclusion Criteria<br>1. Subject is able and willing to provide informed consent<br>2. Subject is ≥30 and ≤70 years of age<br>3. Subject with diagnosis of Hypertension for a minimum of 1 year<br>4. Subject has been on the same class/classes of blood pressure medication for a minimum of 6 months. Note: A change in dosage, frequency, or specific medication is acceptable as long as there have been no changes to the class/classes of medications prescribed.<br>5. Subject with a Body Mass Index (BMI) ≥19 and ≤35<br>6. Subject is currently prescribed and taking one of the following classes of medications alone or in combination with each other or a Ca+ channel blocker.<br>    Diuretics<br>    ACE Inhibitors<br>    Angiotensin Receptor Blocker (ARB)<br>    Beta-blockers<br>Exclusion Criteria<br>1. Subject has clinically significant kidney disease as determined by the investigator.<br>2. Subject has clinically significant cardiac disease as determined by the investigator.<br>3. Subject has clinically significant vascular disease as determined by the investigator.<br>4. Subject has a diagnosis of secondary hypertension or is experiencing a complication of pregnancy.<br>5. Subject is currently prescribed and taking any additional class of medication(s) for high blood pressure not included in the list above, with the exception of a Ca+ channel blocker.<br>6. Subject has Systolic BP > 190 or Diastolic BP > 120 documented within the six months prior to visit.<br>7. Subject has a regular alcohol intake of greater than 21 units per week in the past 6 months<br>8. Subject has smoked greater than two packs of cigarettes (total) or equivalent nicotine intake in the past 6 months.<br>9. Subject has an anticipated survival less than 12 months.<br>10. Any other reason that the subject is inappropriate for study enrollment in the opinion of the Investigator. |
| Primary Study Objective: | To assess the relationship between the drug therapy class/combination of therapy classes that resulted in the best blood pressure control for a patient vs. what the Geneticure high blood pressure panel would have predicted. |
| Secondary Study Objectives: | To assess the clinical time to achieve optimal blood pressure treatment. To assess the number of office visits required to achieve optimal blood pressure treatment. |

1 Introduction

Hypertension (high blood pressure) is one of the most important preventable contributors to disease and death in the United States and represents the most common condition seen in the primary care setting (The sixth report of the Joint National Committee on prevention, detection, evaluation, and treatment of high blood pressure. Arch Intern Med. 157(21):2413-2446 (1997); Chobanian et al. JAMA 289(19): 2560-2572 (2003)). According to the American Heart Association, approximately 78 million adults (1 in 3) living in the United States have hypertension with more than 5 million new diagnoses made each year (American Heart Association. Heart and Stroke Statistics—2004 Update. Paper presented at: Dallas: American Heart Association (2004); Roger et al. Circulation. 125(1):e2-e220 (2012)). Of these individuals, 82% are aware they have it, 75% are currently being treated for it, but only 52% have their blood pressure under control. Thus, about 48% of individuals with hypertension do not have adequate blood pressure control. Hypertension is known to lead to myocardial infarction (heart attack), stroke, renal failure, and death if not detected early and treated appropriately. In fact, in 2009, high blood pressure was listed as a primary or contributing cause of death in ~350,000 of the ~2.4 million U.S. deaths (14% of all deaths). From 1999-2009 the number of deaths attributable to hypertension increased by 44%.

Refractory (or resistant) hypertension is defined as blood pressure that remains above clinical guideline goals in spite of concurrent use of three antihypertensive agents of different classes (Akpunonu et al., Disease-a-month: DM. October 1996; 42(10):609-722). Critically, refractory hypertension is noted in approximately 25-30% of all individuals being treated for hypertension. Refractory hypertension is a common clinical problem which contributes to the high levels of morbidity and mortality. The inability to gain control of blood pressure in these individuals may be related to the pharmacogenetics of the individual coupled with the specific classes of drugs and/or combination of classes chosen for that individual (Calhoun et al. Circulation 117 (25):e510-526 (2008); Johnson & Turner, Curr Opin Mol Ther 7(3):218-225 (2005)). In 2009, the direct and indirect economic burden on the United States health care system associated with hypertension was estimated at $51 billion. With the advent of improved diagnostic techniques, increased rates of health care utilization and screening, and the increasing age of the population, a continual upward trend in this expenditure is expected.

Globally, nearly 1 billion individuals have been diagnosed with hypertension with an estimate of an additional 400 million living with undiagnosed hypertension. Hypertension is the leading cause of premature death and the leading cause of cardiovascular disease worldwide. Similar to the continued upward trend in prevalence as seen in the United States, it is estimated that in 2025 approximately 1.56 billion adults will be living with hypertension. Because nearly two-thirds of the people living with hypertension worldwide reside in developing countries, providing optimal treatment at the lowest cost is critically important.

Unfortunately, despite a significant impulse in the medical community to move towards an "individualized medicine" approach to patient centered treatment, the current clinical treatment strategy is based on a set algorithm which does not take into account individual patient differences. Rather, physicians are guided to choose a drug (one out of many options) in a given class of drugs and use that specific drug as a "first line therapy" (typically initiating with the diuretic class) and titrate that specific drug of choice to therapeutic dosage regardless of efficacy (Chobanian et al. JAMA 289(19):2560-2572 (2003)). It is only after a prolonged course of treatment with that specific class of drug that clinical efficacy is determined (typically three months). At this stage, if clinical guideline goals for blood pressure have not been met, it is often recommended that the patient remain on the "first line therapy" whilst an additional drug from a different class of drugs (typically an Angiotensin converting enzyme inhibitor (ACE inhibitor) or Angiotensin II receptor blocker (ARB)) is added to the pharmacologic regimen. Again, this drug is titrated to recommended therapeutic dosage and another prolonged course of treatment is initiated before clinical efficacy is determined (an additional three months—six months since initiation of treatment). If at this point, clinical guideline goals for blood pressure have not been met, a third drug from a third class of drugs (typically a beta-blocker) is added and the process is repeated (another three months—nine months from initiation of treatment). Further, if clinical guideline goals have continued to be elusive, the diagnosis of refractory hypertension is added and the process is reinitiated with a different combination of drugs, different classes of drugs, different drug options within a given class of drugs, different dosages, or all of the above. Thus, from the time of initial diagnosis and the start of treatment to the point in which blood pressure is adequately controlled may take anywhere from three months to well over one year. This trial-and-error standard of care is clearly not optimal.

The blood pressure panel created by Geneticure has been created to comprehensively assess fourteen common genetic variants in the cardiac, vascular, and renal systems that can improve therapeutic guidance for the clinician based on known functional alterations of the protein through these genetic changes, as well as demonstrated effects of certain drug classes on these various genotypes. Based on this information, a clinician can guide therapy with knowledge specific to their patient, rather than "trial-and-error" based on population data and using drugs with least side effects initially.

1.1 Investigational Device: Geneticure Pharmacogenetic Testing Kit

The Geneticure pharmacogenetic testing kit contains two buccal swabs with two buffer solution vials to stabilize DNA. These buccal swabs are used for DNA collection which is then extracted for analysis of genes important in high blood pressure.

The Geneticure Pharmacogenetic Testing Kit is a pharmacogenomic treatment decision support product that tests for clinically important genetic variants affecting a patient's response to antihypertensive medications.

1.2 Genetic Analysis

Each sample can be analyzed for fourteen common genetic variants using 3 different methodologies, the Sequenom MassArray genotyping platform, Sanger sequencing using the ABI 3730xl genomic analyzer from Applied Biosystems, and classical PCR and gel sizing to determine insertion/deletion status (see, FIGS. 3A-3B).

2 Methodology 2.1 Study Design and Protocol Overview

This is a post-hoc association study of patients who have been diagnosed with high blood pressure and have been stable on medication treatment for at least 6 months. The purpose of this study is to evaluate the relationship between optimal medication therapy (or the therapy that has resulted in the most stable blood pressure for that particular patient) and the predicted optimal medication therapy based on a patient's genetic profile.

Chart reviews for the patient's history of antihypertensive therapy can be coupled with buccal swabs and blood pressure readings collected from eligible patients who have provided informed consent. The swab can be analyzed for fourteen genetic variants that are associated with antihypertensive therapy response (efficacy, side-effects).

2.2 Study Objective

To assess the relationship between the drug therapy class/combination of therapy classes that resulted in the best blood pressure control for a patient vs. what the Geneticure high blood pressure panel would have predicted.

2.3 Secondary Objectives

The secondary objectives are as follows:
To assess the clinical time to achieve optimal blood pressure treatment.
To assess the number of office visits required to achieve optimal blood pressure treatment.

3 Investigational Study Center

This study will be conducted at up to 5 study centers within the United States that have adequate resources for trial responsibilities.

4 Study Population

To be enrolled in this study, subjects must meet ALL of the inclusion criteria and NONE of the exclusion criteria:

4.1 Inclusion Criteria
1. Subject is able and willing to provide informed consent
2. Subject is ≥30 and ≤70 years of age
3. Subject with diagnosis of Hypertension for a minimum of 1 year
4. Subject has been on the same class/classes of blood pressure medication for a minimum of 6 months. Note: A change in dosage, frequency, or specific medication is acceptable as long as there have been no changes to the class/classes of medications prescribed.
5. Subject with a Body Mass Index (BMI) ≥19 and ≤35
6. Subject is currently prescribed and taking one of the following classes of medications alone or in combination with each other or a $Ca^+$ channel blocker.
   Diuretics
   ACE Inhibitors
   Angiotensin Receptor Blocker (ARB)
   Beta-blockers

4.2 Exclusion Criteria
1. Subject has clinically significant kidney disease as determined by the investigator.
2. Subject has clinically significant cardiac disease as determined by the investigator.
3. Subject has clinically significant vascular disease as determined by the investigator.
4. Subject has a diagnosis of secondary hypertension or is experiencing a complication of pregnancy.
5. Subject is currently prescribed and taking any additional class of medication(s) for high blood pressure not included in the list above, with the exception of a Ca+ channel blocker.
6. Subject has Systolic BP>190 or Diastolic BP>120 documented within the six months prior to visit.
7. Subject has a regular alcohol intake of greater than 21 units per week in the past 6 months
8. Subject has smoked greater than two packs of cigarettes (total) or equivalent nicotine intake in the past 6 months.
9. Subject has an anticipated survival less than 12 months.
10. Any other reason that the subject is inappropriate for study enrollment in the opinion of the Investigator.

5 Informed Consent

The investigator will prepare an informed consent form in accordance with this study protocol and all regulatory requirements (21 CFR Part 50) using the template informed consent form provided by the sponsor. The informed consent form must be submitted to the IRB and a copy of the final IRB-approved consent form must be submitted to the Study Management Center prior to the start of the study at that investigational site.

Prior to any study procedures, all subjects must document their consent for study participation and authorization for use and disclosure of health information by signing the IRB-approved Informed Consent Form. As part of the consent process, the subject will have the opportunity to ask questions of, and receive answers from the personnel conducting the study.

The investigator will notify the Study Management Center and the IRB within 5 working days if device use occurs without subject informed consent.

6 Study Assessments and Data Management

6.1 Screening
Identify Potential Study Subjects. Refer to the Inclusion and Exclusion Criteria sections of this protocol for a complete list of eligibility criteria.

Obtain Written Informed Consent. Each potential study participant must be given time to review the IRB-approved informed consent form, have his/her questions answered to their satisfaction and sign the form prior to any study procedures being performed. A subject will be given a copy of the informed consent form.

Review Inclusion/Exclusion Criteria. The investigator and/or designee will review all criteria to determine if the subject is eligible for enrollment. Eligibility of all subjects must personally be confirmed by the Investigator and will be documented on the CRF.

6.2 Enrollment
Assign Identification Number to Eligible Subjects. See Protocol section 6.3.

Record Demographics, Antihypertensive Medical History and current Blood Pressure. Data will be documented in the source document and recorded on the CRF, including but not limited to the following:
Age
Height
Weight
Race
Ethnicity
Length of Hypertension diagnosis
Previously and currently prescribed antihypertensive medications
Blood pressure measurements

6.3 Specimen Collection
Collect Buccal Specimen.
Using the collection kit consisting of two buccal swabs and two uniquely barcoded tubes the investigator or designee will remove the first buccal brush and scrape the brush end across a Subject's right cheek repeatedly (for five seconds). The investigator/designee will place the brush end over the open buffer vial and press the opposite end of the swab stick to release the brush into the buffer and then close the vial. The process can be repeated on the left cheek. Each of the right and left cheek vial numbers must be recorded on the CRF and accountability log as right (R), or left (L).
Adverse Event Recording
Perform Product Accountability

6.4 Subject Numbering
Subjects meeting the criteria for enrollment (and their specimens) can be identified by unique numbers that can be assigned sequentially by order of enrollment. The pre-assigned investigational site number can be prefixed to the identification number and separated by a hyphen (e.g., site 01 would number their subjects sequentially as 01-001, 01-002, 01-003, etc.). Throughout the descriptions within the protocol the A swab will be referring to the swab that has originated from the right cheek, while the B swab will be that that has originated from the left cheek. To further clarify, Subject 01-001 can be given two barcoded tubes. These barcode numbers can be recorded for each patient. These can also be recorded as originating from the right check (A) or left check (B).

At no time should any study paperwork or specimens be marked with the subject's name or any other traceable identifier except for the informed consent form, which is signed by the subject and kept at the site. At no time should the original (signed) or a copy of this form be collected by the Sponsor or its representative.

6.5 Subject Completion and Withdrawal

Once subjects undergo the sampling procedure, their study participation is complete. There are no follow-up visits. Subjects will be instructed to notify the Investigator if they experience any symptoms or complications from the sampling procedure.

Subjects are free to withdraw consent and discontinue participation in the study at any time. A subject's participation in the study may be discontinued at any time at the discretion of the Investigator or Geneticure. The following may be justifiable reasons for the Investigator or Geneticure to remove a subject from the study:

The subject was erroneously included in the study or was found to have an exclusion criterion.
The subject was uncooperative.
The subject experienced an AE/SAE during the sample collection procedure that is considered intolerable by the subject or Investigator.

To the extent possible, safety data will be collected on subjects who discontinue participation in the study due to safety reasons.

The following may be justifiable reasons for the Investigator or Geneticure to remove a specimen from the study:

Sample is determined to be of poor or inadequate quality for analysis (e.g., contamination, insufficient material for analysis).
The sample was erroneously included in the study.
The specimen was not collected or processed per protocol procedures.

6.6 Concomitant Medications/Treatment/Procedures

This study protocol does not require change to any existing treatments or those prescribed during the course of the study by the Investigator or any other provider whom the subject sees for any medical reason. Outside of eligibility screening, there are no clinical evaluations as part of this study.

6.7 Data Management

The Investigator is responsible to ensure the accuracy, completeness, and timeliness of reported data.

All data will be sent to Geneticure who will enter it into the study database using a secure, protected Excel spreadsheet. The database will be validated prior to use in the study. All required data will be recorded on CRFs or paper facsimiles.

Data collected within the CRFs will be supported by source documents as appropriate and may be updated to reflect the latest observations on the subjects participating in the study. Corrections to the source documentation can be made in a manner that does not obscure the original entry and will be dated and initialed by the Investigator or assigned designee. It is important for data entry to occur in a timely manner, therefore, data collected on source documents should be transferred into CRFs as soon as possible following study visits.

Study subject data can be reviewed at the investigational site by monitors at regular intervals throughout the study. Information on the CRFs can be compared to information originally recorded on source documents related to the study (i.e. professional notes, study-specific worksheets, etc.)

7 Genomic Core Laboratory

The subjects' cheek vials will be sent to the Geneticure processing center. The vials will then be batched and sent to the Genomic Core laboratory for DNA extraction and genetic analysis. Following analysis, results will be sent to Geneticure for statistical analysis and DNA will be destroyed.

A protocol for the extraction and analysis will be followed to ensure consistency and objectivity.

8 Adverse Events

The procedures outlined in this protocol do not involve significant risk to subject safety. Subjects will be provided the investigator's contact information and will be instructed to notify the investigator of any adverse events they experience during or secondary to the sample collection procedures.

8.1 Definitions
8.1.1 Adverse Event

For the purposes of this study, an adverse event is defined as any undesirable/unusual medical experience that occurs to a subject in conjunction with the use of the product, whether or not considered product related, including (but not limited to) those events that result from the use as stipulated in the protocol.

The following adverse events will not be collected in this study:

Adverse events which, in the opinion of the Investigator, are unrelated to the swab collection procedure, but rather related to the subject's underlying medical conditions or status
Adverse events that may be related to the sample collection procedure but result only in local, mild and transient discomforts.

The Investigator is responsible for documenting all Adverse Events on the Adverse Event CRF, except for those events noted above.

8.1.2 Serious Adverse Event

A Serious adverse event is an adverse event that:
led to death,
led to serious deterioration in the health of a subject that resulted in a life-threatening illness or injury,
resulted in permanent impairment of a body structure or body function,
required inpatient hospitalization or prolongation of existing hospitalization.
resulted in medical or surgical intervention to prevent permanent impairment to a body structure or a body function.
led to fetal distress, fetal death or a congenital anomaly or birth defect.

8.2 Event Reporting

Any AE, or SAE experienced by a subject after signing the informed consent until twenty-four (24) hours following study completion or termination will be recorded in the progress notes and on the CRF. The Investigator and/or designee will continue to monitor the subject with additional assessments until the AE is considered resolved, stabilized, or is lost to follow up.

A full description of an adverse event, including the nature, date and time of onset and resolution, determination of seriousness, frequency, severity, treatment, outcome, and relationship to the study will be recorded on the Adverse Event CRF.

SAEs must be reported to RCRI within 48 hours of the Investigator's first knowledge of the event.

9 Statistical Methods

Following is a summary of the Statistical Analysis Plan for the study. The following objectives have been prospectively defined; however, due to the nature of these data, additional analyses may be conducted or additional subsets may be identified that are not listed in this protocol.

9.1 Sample Size
  Up to 300 subjects may be enrolled at each site. The minimum number of subjects for meaningful statistical analysis is 100 subjects.

9.2 Data Analysis
  All data will be coded for statistical analysis (i.e. drug classes and genotypes will be coded numerically). All data will be analyzed with SPSS v.20. Normality of the data will be assessed using Levene's test prior to statistical analysis and any correction for non-normal data distribution will be used. Descriptive statistics will be computed (average time for blood pressure control, average number of visits to the clinician for blood pressure control, age, height, weight, BMI, etc.).
  Data will be initially analysed following the collection of samples/data from 100 subjects. This will allow for direction for power calculations/etc. for future statistical analysis. Although some of the genes have been analysed individually, no mean or standard deviation data exists to allow for a true a priori power calculation. Data will be analysed again after two months or following 300 subjects for which data has been collected. Statistical tests will be corrected for the number of tests run (preservation of alpha).
  Ordinary least squares regression via univariate modelling will be used to estimate the magnitude of linearity between drug class that yielded the best blood pressure control and genetic profile of the subject. Multiple regression analysis will be performed to determine the impact of confounding variables (height, weight, age, race) on blood pressure control. For all statistical analyses an alpha level of 0.05 will be used to determine statistical significance.

9.3 Other Statistical Considerations
  Justification of Pooling Data across Centers
    There is no need to keep the data from different centers separate for data collection. Primary reasons for not pooling blood pressure data from different centers could include different races (which we are collecting as a demographic and analyzing as a co-variate in a multiple-regression) and different cultures (i.e. southern vs. northern habits of diet, exercise, etc.). The study will take race, height, weight, age into account as co-variates in a multiple regression model, but will not be powered to take into account possible geographic influences on the data.
  Missing Data
    All patients with available data will be included in the analyses of primary and secondary objectives. Because some of the data was not recorded as part of a prospective protocol an unknown amount of data will be permanently missing. No patients will be contacted to retrieve missing data, and no sensitivity analyses will be performed on missing data.

10 Risk Analysis 10.1 Device Description
  The procedures outlined in this protocol do not involve significant risk to subject safety. Subjects will be provided the investigator's contact information and will be instructed to notify the investigator of any adverse events they experience during or secondary to the specimen collection procedures.
  The collection kit includes a small, soft, brush for cheek swabbing and a buffer solution in a small vial, one of each for each cheek, two in total. Once the swab has been placed into the lysis buffer the cells are no longer viable and therefore samples are now considered to be nucleic acids and safe to be shipped via standard mail.

11 Study Materials 11.1 Handling and Storage
  The Investigator must ensure that the investigational product is stored in a controlled location with limited access.

11.2 Product Accountability
  The investigator is responsible for investigational product accountability, reconciliation and record maintenance. The investigator must maintain investigational product accountability records throughout the course of the study.
  Upon completion or termination of the study, all unused product, together with a copy of the product accountability form will be returned to Geneticure or its representative.
  All supplies are to be used only for this protocol and not for any other purpose.

12 Study Administration 12.1 Subject Confidentiality
  All information and data sent to Geneticure, and/or its designees concerning subjects and their participation in this study are considered confidential by Geneticure and it designees (subcontractors or contract research organization). Only authorized Geneticure personnel or approved contracted agents of Geneticure will have access to some portions of these confidential files and will act in accordance with applicable regulations as required by HIPAA. The IRBs and FDA also have the right to inspect and copy all records pertinent to this study. All data used in the reporting of the study will eliminate identifiable reference to the subjects.

12.2 Investigational Center Qualification
  Investigational Center qualification visits or phone calls will be conducted by the Study Management Center prior to acceptance of the site into this study. The site qualification visit will be scheduled to include time with the Principal Investigator and other study personnel as applicable. Areas of discussion include a review of personnel training, investigator qualifications, adequacy of potential subject pool. FDA-regulated study experience, this study's specific requirements for procedures, and a review of staffing availability and appropriateness. A written report of the qualification visit will be drafted by the Study Management Center.

12.3 Site Training
  Study-specific training of study personnel is the responsibility of the Sponsor or Study Management Center and the Principal Investigator. Study training will occur before the first device use. To ensure protocol and regulatory compliance as well as accurate data collection, site training will include a detailed review of the protocol, CRF completion, study specific procedures, monitoring logistics, and regulatory requirements.

12.4 Investigator Responsibilities

The investigator is responsible for ensuring that the study is conducted according to the investigational plan and all applicable FDA regulations, including reporting and record-keeping requirements, and controlling the devices undergoing investigation and HIPAA. In addition, the principal investigator is responsible for ensuring that informed consent is obtained from each subject prior to participating in the study, as well as protecting the rights, safety and welfare of participating subjects. Specific responsibilities are listed in this investigational plan.

Records and reports must remain on file at the investigational site for a minimum of two years after the later of either the completion/termination of the investigational study or the date it is determined the records are no longer required to support submissions to regulatory authorities. They may be discarded only upon approval from Geneticure. The Principal Investigator must contact Geneticure before destroying any records and reports pertaining to the study to ensure that they no longer need to be retained. In addition, Geneticure must be contacted if the investigator plans to leave the investigational site to ensure that arrangements for a new investigator or records transfer are made prior to investigator departure.

12.4.1 Records

Records to be maintained by the investigator in the designated investigational center's study file include:
Investigational plan and all amendments
Signed Financial Disclosure
IRB approval letter including consent and HIPAA authorization form(s)
IRB Membership list or Letter of Assurance
All correspondence relating to the study between the site and Geneticure, and the Study Management Center
CVs and professional licenses for all investigators
Site personnel signature and responsibility list
Clinical monitor sign-in log
Blank set of each version of CRFs
Subject Screening/Enrollment log
Investigational device accountability log including: date, quantity, lot numbers of all devices, identification of all persons the device was used on and final disposition.

The following records are maintained for each subject enrolled in the study:
Signed Consent Form and Authorization for the Use and Disclosure of Health Information
Compete, accurate and current CRFs and DCFs
Adverse event reports and any supporting documentation
Protocol deviations
Complete medical records, including procedure reports, lab reports, professional notes, etc.

Geneticure reserves the right to secure data clarification and additional medical documentation on subjects enrolled in this study at any time.

13 Abbreviations

AE=Adverse Event CRF=Case Report Form
DCF=Data Clarification Form FDA=Food and Drug Administration
HIPAA=Health Insurance Portability and Accountability Act of 1996
IRB/IEC=Institutional Review Board/Independent Ethics Committee
ITT=Intent-to-Treat PP=Per Protocol
SAE=Serious Adverse Event
UADE=Unanticipated Adverse Device Effect Example 7: Results and Summary of Phase I Clinical Study Introduction For this phase-I research study 14 genes within the Geneticure blood pressure (BP) panel were assessed as they relate to time to BP control and absolute BP values in 99 patients with hypertension. The study design utilized a post-hoc patient chart review carried out by two clinical sites through the direction of RCRI (a third-party clinical research firm) exploring genes important in drug metabolism, renal $Na^+$ handling, vascular function, and cardiac output (all of which can result differences in BP and response to BP therapy). Although the primary aim was BP control in response to therapy relative to genetic data, the time on average, it takes patients to achieve BP control without consideration of genetic information was also determined.

In summary, the study demonstrated that the genes in the Geneticure panel were predictive of time to BP control in patients with hypertension. In addition, there was an effect of several of the genes being predictive of BP taken within the clinic at the time of the research study. In addition, mechanistic data was gathered for the genes that encode the alpha subunit of the epithelial $Na^+$ channel (SCNN1A, rs #2228576) and found that SCNN1A was predictive of urinary $Na^+$ concentration and mean arterial BP.

Methods:

The BP history for patients was collected and the current BP levels were measured in patients with controlled hypertension. DNA was collected using a buccal swab and analyzed the genes within the Geneticure panel. The study sought to determine if patients with "functional" genotypes of proteins important in certain drug classes responded better if they were taking the drug that would inhibit the activity of that protein. As an example, the beta-1 adrenergic receptor (ADRB1) is important in heart rate control and patients who are on a beta-blocker can demonstrate a drop in BP because of inhibition of this protein. Therefore, one would hypothesize that if a patient with a functional protein of the ADRB1 is put on a beta-blocker early, they will demonstrate better BP control (because of a greater drop in heart rate and, therefore BP). This was assessed according to 14 genes and 3 major classes of BP drugs (diuretic, vasodilator, beta-blocker) and one drug metabolizing enzyme (CYP2D6).

Results: Subject Characteristics

Demographics (n=99)

| Variable | mean ± SEM |
| --- | --- |
| Age (yrs) | 58 ± 0.8 |
| Sex (% female) | 46 |
| Diabetes (% with) | 28 ± 4 |
| Weight (kg) | 86 ± 1.4 |
| Height (cm) | 169 ± 1 |
| BMI (kg/m$^2$) | 29.9 ± 0.4 |

Results: Blood Pressure Data (n=99)

| Variable | Mean ± SEM |
| --- | --- |
| Initial SBP (mmHg) | 151 ± 2 |
| Initial DBP (mmHg) | 91 ± 1 |
| Initial MAP (mmHg) | 111 ± 1 |
| Lowest SBP in past two years (mmHg) | 115 ± 1 |
| Lowest DBP in past two years (mmHg) | 72 ± 1 |
| Current SBP (mmHg) | 134 ± 2 |
| Current DBP (mmHg) | 82 ± 1 |
| Current MAP (mmHg) | 99 ± 1 |
| Time to BP control (months) | 22 ± 10 |
| Clinic Visits in the Past two years for HTN | 3.6 ± 0.3 |

Results: Current Blood Pressure Therapy Information
Drug Class Usage (n=99)

| Variable | mean ± SEM |
| --- | --- |
| Number of Classes of Drugs for HTN | 1.8 ± 0.08 |
| Diuretic (% taking) | 42 ± 5 |
| ACE Inhibitor (% taking) | 62 ± 5 |
| ARB (% taking) | 27 ± 5 |
| B-Blocker (% taking) | 33 ± 5 |
| $Ca^+$ Channel Blocker (% taking) | 16 ± 4 |

These data describe the number of different drug classes that the patients were taking. In addition, we assessed the percent of subjects who were on drugs within the vasodilator class (ACE-inhibitor and ARB), the cardiac class (B-blocker $Ca^+$ channel blocker), and the renal class (diuretic).

Time to Control According to Drug Class (n=99)

| Drug Class | Months For Control | | Clinic Visits/2Years | |
| --- | --- | --- | --- | --- |
| | On the Drug Class | Not on the Drug Class | On the Drug Class | Not on the Drug Class |
| Diuretic | 39.5 ± 20.4 | 7.9 ± 4.2 | 4.5 ± 0.6 | 3.0 ± 0.4* |
| ACE Inhibitor | 22.27 ± 11.4 | 22.5 ± 16.4 | 3.1 ± 0.4 | 4.5 ± 0.6* |
| Antiotensin Receptor Blocker | 32.8 ± 23.1 | 17.1 ± 9.1 | 3.9 ± 0.6 | 3.5 ± 0.4 |
| B-Blocker | 24.5 ± 16.9 | 21.2 ± 12.0 | 4.9 ± 0.7 | 3.1 ± 0.4* |
| Ca+ Channel Blocker | 9.9 ± 4.5 | 25.0 ± 11.7 | 5.1 ± 0.7 | 3.3 ± 0.4 |

*$p < 0.05$ compared to those patients who were on the class of drugs

These data describe the time it took for BP control according to which class of drugs the patient was taking. While there are no significant differences in months taken for BP control according to drug class, there was an effect of number of clinic visits (specific to hypertension) within the past 2 years according to drug class. Patients using beta-blockade and diuretic therapy to control their BP had fewer clinic visits, when compared to those patients not on these therapies. Patients on an ACE-inhibitor had significantly more clinic visits per year, when compared to patients not on this therapy.

Blood Pressure Control According to Genotypes (n=86)

1. Genes Important in Renal $Na^+$ Handling (and Those that are Differentially Responsive to Diuretic Therapy).

| WNK1 (RS# 1159744) | | | | |
| --- | --- | --- | --- | --- |
| | On Target Therapy (Diuretic) | | | |
| | No | | Yes | |
| | Genotype | | | |
| | GG | C•containing | GG | C•containing |
| n | 26 | 24 | 19 | 15 |
| Systolic Blood Pressure (mmHg) | 133.7 ± 3.2 | 133.5 ± 2.3 | 137.8 ± 4.1 | 132.1 ± 5.2 |
| Diastolic Blood Pressure | 79.7 ± 2.3 | 84.6 ± 2.0 | 88.7 ± 2.7* | 79.5 ± 3.7 |
| Mean Arterial Blood Pressure (mmHg) | 97.7 ± 2.4 | 100.9 ± 1.81 | 105.1 ± 2.7* | 97.1 ± 3.6 |
| Months to BP Control | 3.6 ± 1.4 | 4.8 ± 2.6 | 8.2 ± 5.6 | 16.5 ± 6.2 |

*$P < 0.05$ compared to same genotype not on target therapy.

| SLC12A3 (RS# 1529927) | | | | |
| --- | --- | --- | --- | --- |
| | On Target Therapy (Diuretic) | | | |
| | No | | Yes | |
| | Genotype | | | |
| | GG | C•containing | GG | C•containing |
| n | 45 | 6 | 33 | 2 |
| Systolic Blood Pressure (mm Hg) | 134.2 ± 2.31 | 136.8 ± 5.9 | 136.4 ± 3.4 | 128.0 ± 8 |
| Diastolic Blood Pressure (mm Hg) | 81.8 ± 1.7 | 86.2 ± 2.3 | 85.9 ± 2.5 | 75.0 ± 5.0 |
| Mean Arterial Blood Pressure (mm Hg) | 99.3 ± 1.7 | 103.3 ± 3.1 | 102.7 ± 2.4 | 92.3 ± 6.0 |
| Months to BP Control | 2.5 ± 0.7 | 17.7 ± 7 | 10.5 ± 3.9 | 42 |

| WNK1 (RS# 2107614) | | | | |
| --- | --- | --- | --- | --- |
| | On Target Therapy | | | |
| | No | | Yes | |
| | Genotype | | | |
| | GG | C•containing | G | C•containing |
| n | 9 | 41 | 7 | 27 |
| Systolic Blood Pressure (mm Hg) | 130.3 ± 5.6 | 134.4 ± 2.1 | 147.7 ± 7.9 | 132.1 ± 3.3 |
| Diastolic Diastolic Blood Pressure (mm Hg) | 80.4 ± 4.7 | 82.4 ± 1.6 | 84.6 ± 4 | 84.7 ± 2.8 |
| Mean Arterial Blood Pressure (mm Hg) | 97.1 ± 4.6 | 99.7 ± 1.6 | 106 ± 4.4 | 100.5 ± 2.6 |
| Months to BP Control | 10.5 ± 7.2 | 2.6 ± 0.9 | 10.5 ± 9.5 | 13.1 ± 4.8 |

| Alpha Adducin (RS# 4961) | | | | |
|---|---|---|---|---|
| | On Target Therapy | | | |
| | No | | Yes | |
| | Genotype | | | |
| | GG | T•containing | GG | T•containing |
| n | 40 | 11 | 24 | 11 |
| Systolic Blood Pressure (mm Hg) | 134.2 ± 2.3 | 135.0 ± 5.3 | 135.3 ± 3.9 | 137.4 ± 5.9 |
| Diastolic Blood Pressure (mm Hg) | 83.1 ± 1.8 | 79.7 ± 3.3 | 85.8 ± 2.9 | 84.2 ± 4.3 |
| Mean Arterial Blood Pressure (mm Hg) | 100.2 ± 1.8 | 98.2 ± 3.6 | 102.3 ± 2.7 | 101.9 ± 4.5 |
| Months to BP Control | 4.4 ± 1.6 | 3.6 ± 15.1 | 10.5 ± 5.2 | 15.1 ± 6.7 |

Of the four genes explored in the clinical study RS #1159744 (the gene that encodes cytoplasmic serine-threonine kinase that is expressed in the kidney, WNK-1) was most predictive of response to therapy. Patients with the C genotype of WNK-1 had the best response to therapy demonstrating 8 mmHg lower DBP, when compared to patients with this genotype who were not on diuretic therapy. Subjects who were homozygous for G for this gene actually had a lower blood pressure if they were not on a diuretic, indicating that they may be benefiting from alternate therapy. Although just a trend (due to small sample size of the minor allele) the C polymorphism of SLC12A3 also may be predictive of response to diuretic therapy with patients demonstrating an 11 mmHg drop in DBP with therapy, compared to the G polymorphism which demonstrated a small increase in DBP with therapy.

Figure 8:
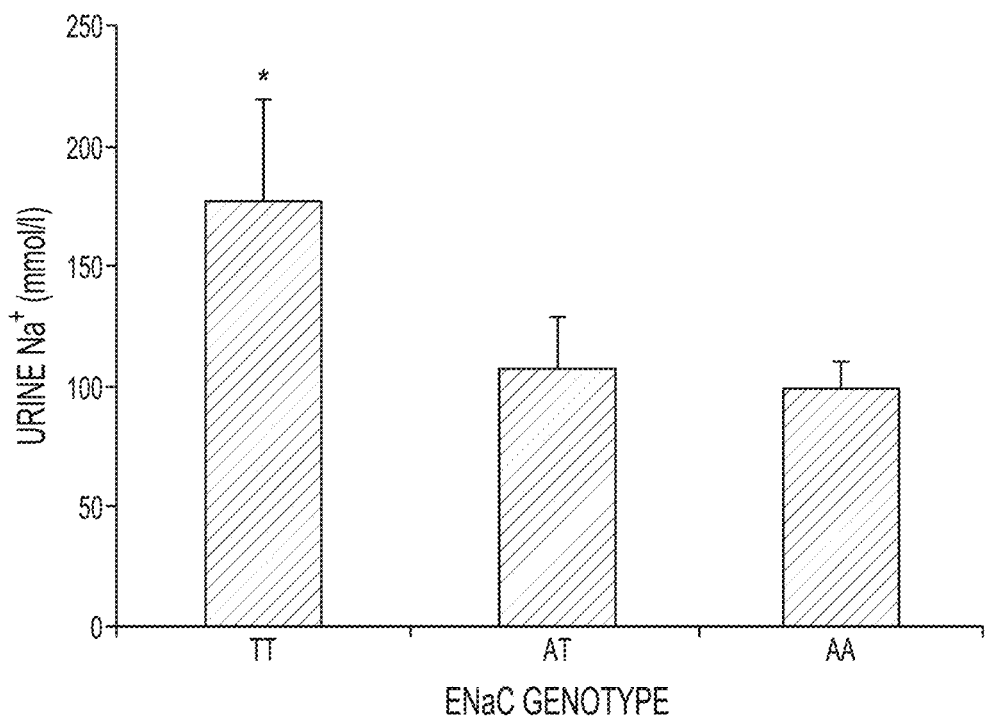
FIG. 8 is a bar graph of urinary sodium output as a function of genetic variation of SCNN1A.
Figure 9:
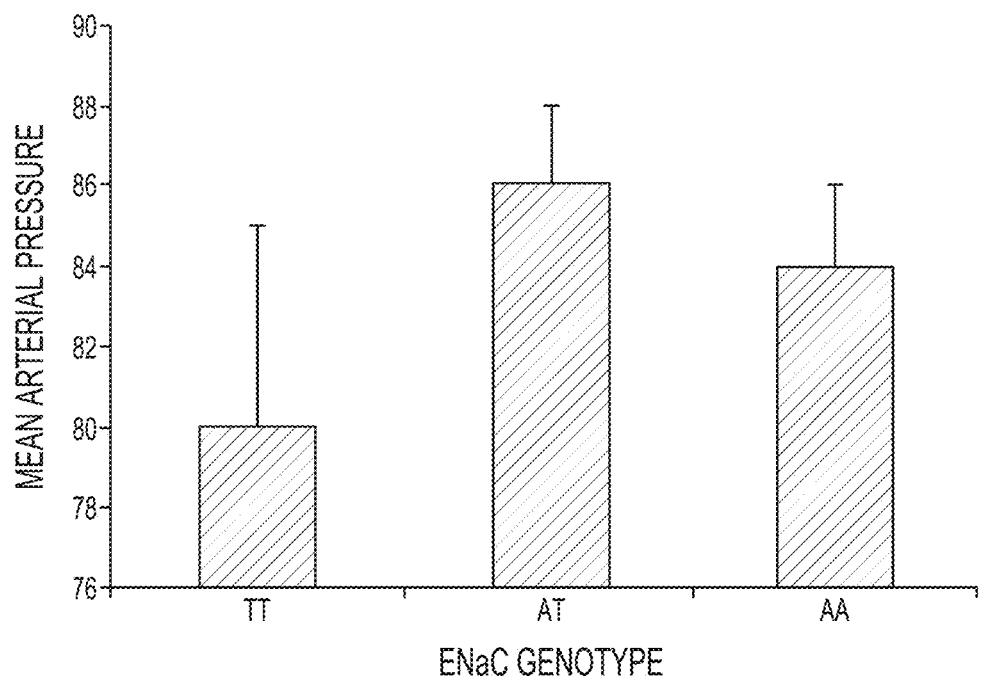
FIG. 9 is a bar graph of mean arterial blood pressure as a function of genetic variation of SCNN1A.

In addition to this clinical BP data 24-hour urinary and resting BP data were gathered according to genetic variation of the alpha sub-unit of the epithelial Na$^+$ channel (SCNN1A, RS #2228576). It was found that subjects homozygous for the T variant of SCNN1A demonstrated more Na$^+$ excretion from the kidneys and they also demonstrated lower mean arterial blood pressure, when compared to genotype groups containing the A variant (See FIGS. 8 and 9).

2. Genes Important in Cardiac Function (and Those that May Respond Differentially to Beta-Blocker Therapy).

The beta-1 adrenergic receptor (ADRB1) is important in controlling heart rate and cardiac contractility.

| Beta-1 Adrenergic Receptor 49 (RS# 1801252) | | | | |
|---|---|---|---|---|
| | On Target Therapy (Beta-Blocker) | | | |
| | No | | Yes | |
| | Genotype | | | |
| | Ser/Ser | Thr•containing | Ser/Ser | Thr•containing |
| n | 1 | 55 | 2 | 28 |
| Systolic Blood Pressure (mm Hg) | 137 | 136.4 ± 2.3 | 136 ± 6 | 132.4 ± 3.2 |
| Diastolic Blood Pressure (mm Hg) | 86 | 85.5 ± 1.7 | 75 ± 3 | 80.3 ± 2.1* |
| Mean Arterial Blood Pressure (mm Hg) | 103 | 102.4 ± 1.7 | 95 ± 0 | 97.7 ± 2.1 |
| Months to BP Control | N/A | 7.0 ± 2.4 | N/A | 9.4 ± 3.8 |

*P < 0.05 compared to same genotype not on target therapy.

| Beta-1 Adrenergic Receptor 389 (RS# 1801253) | | | | |
|---|---|---|---|---|
| | On Target Therapy (Beta-Blocker) | | | |
| | No | | Yes | |
| | Genotype | | | |
| | GG | C•containing | GG | C•containing |
| n | 56 | 0 | 30 | 0 |
| Systolic Blood Pressure (mm Hg) | 136.4 ± 2.3 | | 132.6 ± 3.0 | |
| Diastolic Blood Pressure (mm Hg) | 85.5 ± 1.7 | | 80.0 ± 2.0* | |
| Mean Arterial Blood Pressure (mm Hg) | 102.4 ± 1.7 | | 97.5 ± 1.98 | |
| Months to BP Control | 7.0 ± 2.3 | | 8.8 ± 3.5 | |

*P < 0.05 compared to same genotype not on target therapy.

These data indicate a differential BP response to beta-blocker therapy according to genetic variation at position 49 of the ADRB1. Specifically, the inventors found that subjects with the Ser genotype at position 49 of ADRB1 benefit from beta-blocker therapy with an average drop in DBP of 11 mmHg, compared with a drop of 5 mmHg with Thr at this position. Therefore, although patients with the Thr polymorphism also demonstrated a drop in BP with beta-blocker therapy, the effect was most pronounced in patients with the Ser polymorphism.

The beta-2 adrenergic receptor (ADRB2) is important in cardiac contractility, which controls stroke volume, and can influence BP through differences in cardiac output.

| Beta-2 Adrenergic Receptor 16 (RS# 1042713) | | | | |
|---|---|---|---|---|
| | On Target Therapy (B-Blocker) | | | |
| | No | | Yes | |
| | Genotype | | | |
| | Arg/Arg | Gly-containing | Arg/Arg | Gly-containing |
| n | 5 | 51 | 3 | 27 |
| Systolic Blood Pressure (mmHg) | 143.6 ± 5.9 | 135.7 ± 2.4 | 129 ± 5 | 133.3 ± 3 |
| Diastolic Blood Pressure (mmHg) | 84.0 ± 7.4 | 85.6 ± 1.8 | 80.3 ± 6.6 | 79.9 ± 2.1* |
| Mean Arterial Blood Pressure (mmHg) | 104.0 ± 6.82 | 102.3 ± 1.8 | 96.6 ± 5.9 | 97.6 ± 2.1 |
| Months to BP Control | 7 ± 5 | 7 ± 2.6 | 4.3 ± 3.8 | 9.9 ± 4.3 |

*$P < 0.05$ compared to same genotype not on target therapy.

| Beta-2 Adrenergic Receptor 27 (RS# 1042714) | | | | |
|---|---|---|---|---|
| | On Target Therapy (B-Blocker) | | | |
| | No | | Yes | |
| | Genotype | | | |
| | Gln/Gln | Glu-containing | Gln/Gln | Glu-containing |
| n | 6 | 48 | 4 | 24 |
| Systolic Blood Pressure (mmHg) | 142.0 ± 6.9 | 134.4 ± 2.2 | 125.5 ± 5.9 | 132.7 ± 3.6 |
| Diastolic Blood Pressure (mmHg) | 82.5 ± 2.7 | 85.1 ± 1.8 | 82.5 ± 2.7 | 79.5 ± 2.4 |
| Mean Arterial Blood Pressure (mmHg) | 102.3 ± 4.1 | 101.5 ± 1.8 | 102.3 ± 4.1 | 97.2 ± 2.3 |
| Months to BP Control | 8.5 ± 7.8 | 7 ± 2.8 | 5.3 ± 2.3 | 9.6 ± 4.4 |

These data demonstrate a generally favorable response to beta-blocker therapy with both genotype groups. However, the Gly16 genotype demonstrated a statistically significant difference in BP control if the patients were on a beta-blocker (drop in DBP of 5 mmHg), when compared to patients with the Arg16 genotype. Generally, there is a similar pattern for a greater drop in BP with subjects who have the most functional gene that encodes the ADRB2 (Gly at position 16 and Glu at position 27). There is strong linkage disequilibrium between these two sites (amino acids 16 and 27), so the similar response between the sites is expected.

Observations on Genetic Variation of Cytochrome P450 2D6 (CYP2D6), which is Important in Drug Metabolism, Especially of Particular Beta-Blockers.

| CYP 2D6 (RS#) | | | | |
|---|---|---|---|---|
| | On Target Therapy (B-Blocker) | | | |
| | No | | Yes | |
| | Genotype | | | |
| | CC | T-Containing | CC | T-Containing |
| n | 35 | 22 | 23 | 7 |
| Systolic Blood Pressure (mmHg) | 140.6 ± 2.7 | 128.5 ± 3.1 | 133.4 ± 3.6 | 130.0 ± 5.7 |
| Diastolic Blood Pressure (mmHg) | 86.0 ± 2.4 | 83.2 ± 2.4 | 79.2 ± 2.1* | 82.6 ± 5.3 |
| Mean Arterial Blood Pressure (mmHg) | 104.2 ± 2.3 | 983 ± 2.4 | 97.3 ± 2.2* | 98.4 ± 4.8 |
| Months to BP Control | 7.8 ± 2.9 | 5.08 ± 3.7 | 6.25 ± 3.2 | 16.5 ± 10.8 |

*$P < 0.05$ compared to same genotype not on target therapy

These data demonstrate that the CC homozygous group of CYP2D6 demonstrates the greatest response to beta-blocker therapy, when compared to the CT and TT groups. Patients with the CC polymorphism had demonstrated a 6 mmHg lower DBP and a 7 mmHd lower MAP when on beta-blocker therapy, compared to this genotype not on beta-blocker therapy. In contrast, patients in the T-containing group (those with the CT and TT genotypes) did not respond to beta-blocker therapy.

3. Genes Important in Vascular Function (and Those that May Respond Differentially to Vasodilator Therapy).

The following are observations on the genetic variation of the angiotensin gene (encoding a precursor to angiotensin-II, a potent vasoconstrictor, which is converted via angiotensin converting enzyme, ACE) and the responses to various therapies.

| | Angiotensin (RS# 699) | | | |
|---|---|---|---|---|
| | On Target Therapy (Angiotensin Receptor Blocker) | | | |
| | No | | Yes | |
| | Genotype | | | |
| | CC | T-containing | CC | T-containing |
| n | 15 | 50 | 4 | 17 |
| Systolic Blood Pressure (mmHg) | 135.3 ± 2.6 | 135.1 ± 2.6 | 135.0 ± 7.4 | 135.1 ± 4.5 |
| Diastolic Blood Pressure (mmHg) | 89.5 ± 2.9 | 82.6 ± 1.7 | 77.5 ± 7.8 | 82.7 ± 3.4 |
| Mean Arterial Blood Pressure (mmHg) | 104.7 ± 2.6 | 100.1 ± 1.7 | 96.6 ± 7.5 | 100.2 ± 3.3 |
| Months to BP Control | 2.7 ± 1.3 | 6.7 ± 2.7 | 12 | 12.4 ± 4.8 |

| | Angiotensin (RS# 699) | | | |
|---|---|---|---|---|
| | On Target Therapy (ACE-Inhibitor) | | | |
| | No | | Yes | |
| | Genotype | | | |
| | CC | T-containing | CC | T-containing |
| n | 6 | 24 | 13 | 43 |
| Systolic Blood Pressure (mmHg) | 131.7 ± 5.3 | 133.7 ± 3.5 | 136.8 ± 2.7 | 135.8 ± 2.9 |
| Diastolic Blood Pressure (mmHg) | 78.5 ± 5.0 | 80.4 ± 2.1 | 90.8 ± 3.2* | 83.9 ± 2.0 |
| Mean Arterial Blood Pressure (mmHg) | 96.2 ± 4.7 | 98.2 ± | 106.2 ± 2.8* | 101.1 ± 2.0 |
| Months to BP Control | 6.7 ± 3.1 | 7.7 ± 3.2 | 2.3 ± 1.7 | 9.9 ± 3.8 |

*$P < 0.05$ compared to same genotype not on target therapy

| | All Receptor Type-1 (RS# 5186) | | | |
|---|---|---|---|---|
| | On Target Therapy (Angiotensin Receptor Blocker) | | | |
| | No | | Yes | |
| | Genotype | | | |
| | AA | C-containing | AA | C-containing |
| n | 39 | 28 | 9 | 11 |
| Systolic Blood Pressure (mmHg) | 137.3 ± 2.6 | 131.0 ± 3.1 | 1.363 ± 4.6 | 134.1 ± 6.5 |
| Diastolic Blood Pressure (mmHg) | 85.4 ± 2.1 | 80.9 ± 2.0 | 87.6 ± 3.9 | 77.9 ± 4.5 |
| Mean Arterial Blood Pressure (mmHg) | 102.7 ± 2.0 | 97.6 ± 2.1 | 103.8 ± 2.9 | 96.6 ± 4.9 |
| Months to BP Control | 7.3 ± 2.9 | 3.8 ± 2.5 | 13.4 ± 7.8 | 11.9 ± 5.7 |

These data indicate that patients homozygous for the C genotype of angiotensin may benefit from an angiotensin receptor blocker (ARB). When on an ARB, patients with the CC genotype demonstrated a 12 mmHg lower DBP when compared to patients with this genotype who were not on this therapy. In contrast, patients in the T-containing group (those with the CT or TT genotypes) did not show a response to ARB therapy. Furthermore, inhibition of ACE (which converts angiotensin-I to angiotensin-II) results in higher BP levels, possibly due to a "build-up" of angiotensin. Therefore, these data indicate that patients homozygous for C should be given an angiotensin receptor blocker with an ACE inhibitor.

Angiotensin Converting Enzyme (ACE) Genotype and ACE-Inhibition

| ACE (RS# 1799752) | | | | |
|---|---|---|---|---|
| | On Target Therapy (ACE-Inhibition) | | | |
| | No | | Yes | |
| | Genotype | | | |
| | Ins/Ins | Del•Containing | Ins/Ins | Del•Containing |
| n | 3 | 27 | 12 | 47 |
| Systolic Blood Pressure (mm Hg) | 142.7 ± 11.1 | 132.3 ± 3.1 | 129.5 ± 3.5 | 137.1 ± 2.6 |
| Diastolic Blood Pressure (mm Hg) | 79.6 ± 6.1 | 80.0 ± 2.1 | 80.4 ± 14.4 | 85.7 ± 1.9* |
| Mean Arterial Blood Pressure (mm Hg) | 100.7 ± 7.7 | 97.4 ± 2.1 | 96.8 ± 3.8 | 102.8 ± 1.8 |
| Months to BP Control | 4.7 ± 3.7 | 8.0 ± 3 | 7.4 ± 5.8 | 7.3 ± 3.0 |

*$P < 0.05$ compared to same genotype not on target therapy.

These data indicate that those with the Insertion polymorphism (Ins) of the ACE gene will respond best to ACE-inhibition. Patients with the Del polymorphism actually demonstrated higher DBP with ACE-inhibition, when compared to this patient group not on ACE-inhibitors.

Observations on Renin Genotype and Angiotensin Receptor Blocker

Renin is a precursor to angiotensin and, therefore, patients with a functional genotype of renin may benefit from Angiotensin Receptor Blocker (ARB) therapy because a more functional genotype can lead to greater angiotensin levels which can result in high BP.

| Renin (RS# 12750834) | | | | |
|---|---|---|---|---|
| | On Target Therapy (Angiotensin Receptor Blocker) | | | |
| | No | | Yes | |
| | Genotype | | | |
| | G/G | A•containing | G/G | A•containing |
| n | 48 | 17 | 14 | 7 |
| Systolic Blood Pressure (mm Hg) | 134.8 ± 2.3 | 135.9 ± 4.4 | 136.4 ± 4.6 | 132.2 ± 7.3 |
| Diastolic Blood Pressure (mm Hg) | 83.8 ± 1.7 | 85.1 ± 2.9 | 82.0 ± 2.9 | 81.0 ± 7.4 |
| Mean Arterial Blood Pressure (mm Hg) | 100.8 ± 1.7 | 102.1 ± 2.9 | 100.2 ± 3.2 | 98.1 ± 6.6 |
| Months to BP Control | 4.75 ± 1.9 | 8.0 ± 5.8 | 15.5 ± 5.3* | 1.3 ± 0.7 |

*$P < 0.05$ compared to same genotype not on target therapy.

These data indicate that the functional genotype of renin (A) may benefit from ARB therapy. Specifically, the BP response to therapy was not significant, however, the response to therapy time was pronounced. Patients who have the functional genotype of renin (the AG and AA genotype groups) demonstrate a much shorter time to BP control, when compared to patients within this group who do not take this therapy. In contrast, patients in the GG group demonstrate a longer time to control if they take this therapy, possibly due to greater response to another class of drugs.

Figure 10:
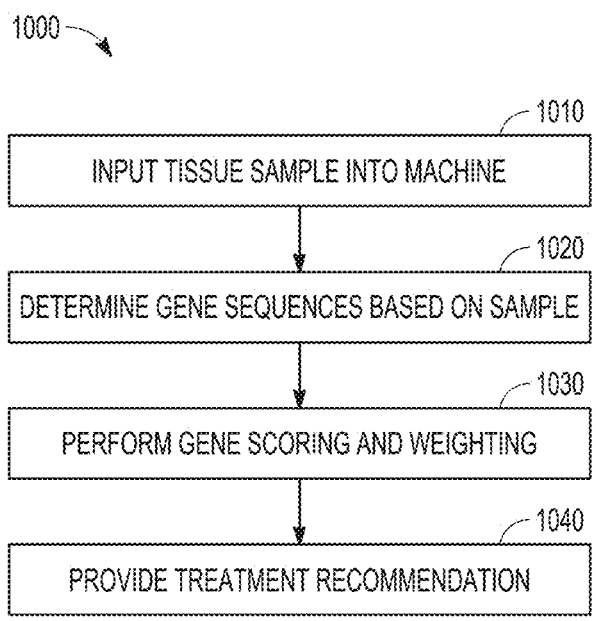
FIG. 10 is a flowchart of a method for providing a hypertension treatment recommendation in accordance with some embodiments.

FIG. 10 is a flowchart of a method 1000 for providing a hypertension treatment recommendation in accordance with some embodiments. In operation 1010, a tissue sample is input into a machine for assay to obtain genotype data. In some examples, patient DNA, primers, reagents and PCR polymerase are loaded into an MJ Tetrad thermoplexer (e.g., a MJ Research Tetrad 2 instrument available from GMI headquartered in Ramsey, Minn.) and the desired genotype SNPs are amplified to yield gene fragment material. This gene fragment material is loaded into, for example an Athena MassArray machine (available from CD Genomics of Shirley, N.Y.), which identifies and quantifies the amplified gene material. This result provides the patient's genotype profile for the 14 SNP sequences of interest.

In operation 1020, gene sequences can be determined. These can include, for example:
1. gene sequences having cardiac effect:
   a. an ADRB2 nucleic acid with a guanine at the variable position of rs1042713 (hereinafter ADRB2_16), which predicts non-selective beta-blocker use;
   b. an ADRB2 nucleic acid with a guanine at the variable position of rs1042714 (hereinafter ADRB2_27), which predicts a non-selective beta-blocker use;
   c. an ADRB1 nucleic acid with an adenine at the variable position of rs1801252 (hereinafter ADRB1_49), which predicts response to a beta blocker;
   d. an ADRB1 nucleic acid with a cytosine at the variable position of rs1801253 (hereinafter ADRB1_389), which predicts response to a beta blocker; and
   e. a CYP2D6 nucleic acid with an adenine at the variable position of Rs3892097 (hereinafter CYP2D6).
2. gene sequences having renal effect:
   a. a WNK1 nucleic acid with a cytosine at the variable position of rs1159744 (hereinafter WNK1(a), which predicts response to thiazide diuretic;

b. a SLC12A3 nucleic acid with a thymine at the variable position of rs1529927 (hereinafter SLC12A3(2));
c. a WNK1 nucleic acid with a cytosine at the variable position of rs2107614 (hereinafter WNK1(b)), which predicts response to thiazide diuretic;
d. a SCNN1A nucleic acid with an adenine at the variable position of rs2228576, which predicts response to diuretic (hereinafter SCNNIA);
e. WNK1(c) at position rs2277869, which predicts response to a thiazide diuretic (hereinafter WNK1(c)); and
f. an ADD1 nucleic acid with a thymine at the variable position of rs4961 (hereinafter Alpha Adducin), which predicts response to diuretic therapy.
3. gene sequences having vascular effect:
a. a renin nucleic acid with a cytosine at the variable position of rs12750834 (hereinafter Renin), which predicts response to vasidilating agents;
b. a first Angiotensin (rs5051, hereinafter Angiotensin (1));
c. an AGT1R nucleic acid with a cytosine at the variable position of rs5186 (hereinafter A-II Receptor);
d. an AGT nucleic acid with a cytosine at the variable position of rs699 (hereinafter Angiotensin(2));
e. an ACE nucleic acid with a deletion in rs1799752 (hereinafter ACE); and
f. a third Angiotensin (rs7079, hereinafter Angiotensin (3)).

Figure 11:
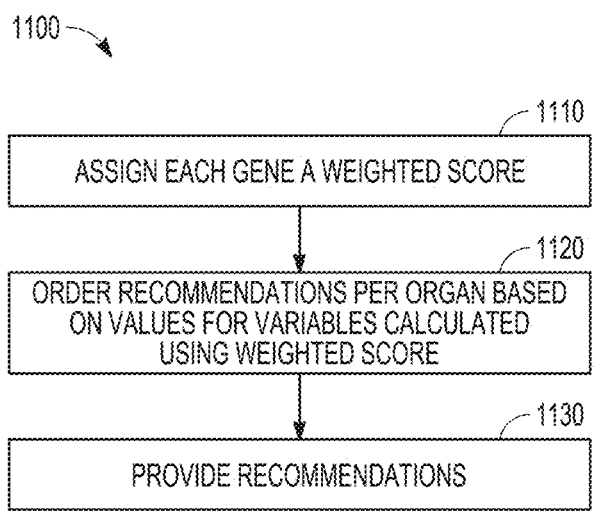
FIG. 11 is a flowchart of an algorithm for providing a hypertension treatment recommendation based on a gene assay in accordance with some embodiments.

In operation 1030 and 1040, SNP scoring and weighting can be performed, and a treatment recommendation can be provided, using the algorithm described with respect to FIG. 11.

FIG. 11 is a flowchart of an algorithm 1100 for providing a hypertension treatment recommendation based on a gene assay in accordance with some embodiments. At least some operations of algorithm 1100 can be performed by machine 1200 (FIG. 12) or by a component thereof such as processing circuitry 1202, or instructions 1224 stored thereon or on main memory 1204, static memory 1206, machine-readable medium 1222, etc.

In operation 1110, each single nucleotide polymorphism (SNP) is assigned a weighted score. It will be appreciated from above that each gene relates to one area or site that corresponds to an organ or system, e.g., cardiac, vascular, and renal. Each single nucleotide polymorphism (SNP) is given a score for functionality ("functional score", or "recommendation score"). This score is on a scale of 1 (not functional) to 10 (very functional) and values are assigned as 1, 5, and 10, as the level of moderate functional cannot be further fine-tuned beyond a score of 5, given the complexity of what is considered somewhat functional. A functional genotype is one that has demonstrated enhanced receptor function, altered drug metabolism, greater protein expression, or higher channel activity, depending on the genotype. In addition, the functional genotype has, in most cases, been shown to be associated with greater drug responsiveness for a given drug class (i.e. if it is a $Na^+$ channel the enhanced drug response is that of a diuretic).

Each gene has a weight that can be based on, for example, the number of scholarly articles related to that gene, the findings of those articles, the quality of those articles (based e.g., on level of review), etc. For example, the inventors have implemented a review that determined that some of the genotypes have considerable scientific alignment with hundreds of studies and almost all studies are in agreement with the degree and direction of functionality for a given genotype. In contrast, some of the genotypes in the panel are more novel and have fewer research studies with some mixed results on degree and direction of functionality. Based on this, the inventors provide a scoring system that aligns the functionality with the number and level of scientific agreement in the previous literature, this is the "weight" score and is on a continuous scale of 1-10.

A weighted score assigned therefore equals a recommendation score times the weight, where example data for assigning each of these weights is shown below in Table 12. This data can be stored remotely or on machine 1200. It will be appreciated that the below is merely example data and embodiments can include additional data (e.g., additional genes, etc.) or different values for the below data (e.g., different weights can be assigned, or other parameters can be provided). It will be noted that "rs" denotes a reference SNP cluster ID (a universal way to identify SNPs), which is the genotype nucleotide fragment with the nucleotide variation that for example generates a trait.

"rs1042713": {"name": "ADRB2_16", "varname": "adrb2_16", "area": "cardiac", "rs": "rs1042713". "weight": 9,},

TABLE 12

| SNP names and weights. |
|---|
| "rs1042714": {"name": "ADRB2_27", "varname": "adrb2_27", "area": "cardiac", "rs": "rs1042714", "weight": 8, }, |
| "rs1801252": {"name": "ADRB1_49", "varname": "adrb1_49", "area": "cardiac", "rs": "rs1801252", "weight": 9.5,}, |
| "rs1801253": {"name": "ADRB1_389", "varname": "adrb1_389", "area": "cardiac", "rs": "rs1801253", "weight": 10, }, |
| "rs3892097": {"name": "CYP2d6", "varname": "metabolism", "area": "cardiac", "rs": "rs3892097", "weight": 9,}, |
| "rs4961": {"name": "Alpha Adducin", "varname": "alpha_adducin", "area": "renal", "rs": "rs4961", "weight": 9}, |
| "rs1159744": {"name": "WNK1(a)", "varname": "wnk1_a", "area": "renal", "rs": "rs1159744","weight": 7,}, |
| "rs1529927": {"name": "SLC12A3(2)","varname": "slc12a3","area": "renal", "rs": "rs1529927","weight": 5,}, |
| "rs2107614": {"name": "WNK1(b)","varname": "wnk1_b", "area": "renal", "rs": "rs2107614","weight": 7,}, |
| "rs2228576": {"name": "SCNN1A", "varname": "scnn1a", "area": "renal","rs": "rs2228576","weight": 5,}, |
| "rs2277869": {"name": "WNK1(c)","varname": "wnk1_c", "area": "renal", "rs": "rs2277869","weight": 8,}, |
| "rs699": {"name": "Angiotensin(2)", "varname": "angiotensin_2", "area": "vascular","rs": "rs699","weight": 7,}, |

TABLE 12-continued

SNP names and weights.

"rs5051": {"name": "Angiotensin(1)","varname": angiotensin_1", "area": "vascular","rs": "rs5051","weight": 7,},
"rs5186": {"name": "A:II Receptor", "varname": "a_ii","area": "vascular","rs": "rs5186","weight": 8,},
"rs7079": {"name": "Angiotensin(3)","varname": "angiotensin_3", "area": "vascular", "rs": "rs7079","weight": 5,},
rs1799752": {"name": "ACE","varname": "ace","area": "vascular","rs": "rs1799752", "weight": 8,},
"rs12750834": {"name": "Renin","varname": "renin","area": "vascular","rs": "rs12750834","weight": 6,}

The recommendation score is calculated based on homozygosity versus heterozygosity: In some examples, individuals who are homozygous for the functional genotype (SNP) are always given a score of 10 for that genotype and individuals who are homozygous for a non-functional genotype are given a score of 1 for that genotype. In some examples, the heterozygous condition is sometimes semi-functional, sometimes non-functional, and sometimes fully-functional. The genotype combinations (at one site, i.e. GC, GG, or CC) may be given a score based on the genetic pair in which non-functional condition (homozygous for the non-functional genotype or heterozygous condition has demonstrated that this is most in-line with the non-functional genotype) is given a score of 1, semi-functional condition (heterozygous and this has demonstrated moderate functionality) is given a score of 5, and the fully-functional condition (homozygous for the functional genotype or heterozygous condition has demonstrated that this is most in-line with the functional genotype) is given a score of 10.

In operation 1120, values are calculated for a number of variables based on the weighted scores generated in operation 1110, to assess which organ system (cardiac, renal, or vascular) is the most functional, and will therefore likely lead to best drug response, based on the average scoring for that organ system (individual genotypes averaged for a given organ system). In some examples, there is a minimum threshold of 40 for an organ system's individual genotype averages that must be met in order for that organ system to default to the top drug class choice. If two or more organ systems have a score greater than 40 then the highest number defaults as the top choice. If no organ system meets the threshold of 40, then individual genotypes and haplotypes (genotype combinations that have been deemed particularly functional) are used to determine drug class choices.

Once a first drug class choice has been selected then a second drug class can be determined using the same algorithm (genotype average >40 but less than first drug class will determine next choice, if not >40 then SNP scoring and haplotype combinations determine next choice). Once a second-choice drug class has been selected, the scoring of the algorithm occurs again for a third, and so on until all drug classes have been selected.

For the cardiac and vascular systems there are two drug class choices (selective vs non-selective 1-blocker for the cardiac, and angiotensin-converting enzyme (ACE) inhibitor vs angiotensin-II receptor blocker for the vascular system). When the cardiac and vascular organ systems are selected as functional, then scoring of the SNPs occurs to determine if a patient will respond to specific drug class within that organ system.

For the cardiac system, the algorithm is used to determine if a patient will respond to a selective vs non-selective β-blocker (based on the functional genotypes of the $β_1$ adrenergic receptor, which directs towards selective, vs $β_2$ adrenergic receptor, which directs towards non-selective). Because calcium channel blockers physiologically act like beta-blockers (decreasing cardiac output), we have written in the algorithm that if a patient is likely to respond to a β-blocker, but has a co-morbidity that would exclude such treatment, that a clinician should consider a calcium-channel blocker. When the vascular system is determined to be the functional organ system the algorithm is used to determine if they will respond best to an ACE inhibitor vs angiotensin-II receptor blocker based on the functional genotypes of ACE and the angiotensin receptor. Within the cardiac system a patient can only be responsive to a selective or a non-selective b-blocker (meaning if one is selected then the other cannot be selected further down the treatment algorithm). In contrast, a patient can have a choice of ACE-inhibitor followed by a choice of angiotensin-II receptor blocker, or vice versa, because these drug classes are more independent.

Some variables include those listed below in Table 13. Variables make reference to SNP varnames provided above in Table 12.

TABLE 13 variable calculations.

{"varname": "cardiac_sum","eval": "$['adrb2_16']['wt'] + $['adrb2_27']['wt'] + $['adrb1_49']['wt'] + $['adrb1_389']['wt'] + $['metabolism']['wt']" },
{"varname": "cardiac_average","eval": "round($['cardiac_sum'] / 5)"},
{"varname": "adrb1_sum","eval": "$['adrb1_49']['wt'] +['adrb1_389']['wt']"},
{"varname": "adrb2_sum","eval": "$['adrb2_16']['wt'] +$['adrb2_27']['wt']"},
{"varname": "adrb1_adrb2_ratio","eval": "($['adrb1_49']['score'] + $['adrb1_389']['score']) / ($['adrb2_16']['score'] + $['adrb2_27']['score'])"},
{"varname": "cardiac_functional_limit","eval": 50},
{"varname": "cardiac_is_functional", "eval": "$['cardiac_average'] > ['cardiac_functional_limit']"},
{"varname": "vascular_sum", "eval": "$['angiotensin_1']['wt'] + ['angiotensin_2']['wt'] + $['angiotensin_3']['wt'] + $['a_ii']['wt'] + $['ace']['wt'] + $['renin']['wt']"},

TABLE 13-continued variable calculations.

```
{"varname": "vascular_average","eval": "round($['vascular_sum'] / 6)"},
{"varname": "angiotensin_sum","eval": "$['angiotensin_1']['wt'] +
$['angiotensin_2']['wt'] + $['angiotensin_3']['wt'],"},
{"varname": "angiotensin_scores_sum","eval": "$['angiotensin_1']['score'] +
$['angiotensin_2']['score'] + $['angiotensin_3']['score']"},
{"varname": "vascular_functional_limit","eval": 50},
{"varname": "vascular_is_functional","eval": "$['vascular_average'] >
$['vascular_functional_limit']"},
{"varname": "renal_sum","eval": "$['alpha_adducin']['wt'] +
$['wnk1_a']['wt'] + $['slc12a3']['wt'] + $['wnk1_b']['wt'] + $['scnn1a']['wt'] +
$['wnk1_c']['wt']"},
{"varname": "renal_average", "eval": "round($['renal_sum'] / 6)"},
{"varname": "wnk_sum","eval": "$['wnk1_a']['wt'] + $['wnk1_b']['wt'] +
$['wnk1_c']['wt']"},
{"varname": "renal_functional_limit","eval": 50},
{"varname": "renal_is_functional","eval": "$[renal_average'] >
$['renal_functional_limit']"},
{"varname": "bb_selective_list","condition": "$['metabolism']['score'] >=
5","eval": "' (metoprolol or nebivolol)'"},
{"varname": "bb_nonselective_list", "condition": "$['metabolism']['score']
>= 5", "eval": "' (timolol, alprenolol, carvedilol, or propranolo)'"},
{"varname": "bb_dose","eval": "['normal', 'moderate',
'low'][round($['metabolism']['score'] / 5)]"}
```

The variables cardiac_average, cardiac_sum, vascular_sum, vascular_average, renal_sum, and renal_average, are calculated so that recommendations can be made based on a descending order of those averages. The variables cardiac_functional_limit, cardiac_is_functional, vascular_functional_limit, vascular_is_functional, renal_functional_limit, and renal_is_functional are calculated to determine whether functional or non-functional recommendations should be provided for that organ. Other variables may be calculated because the inventors have determined that threshold values for those variables indicate that a particular recommendation should be made.

In operation 1130, recommendations are provided. These can be provided on a user display or in a printout, using components of the example machine 1200.

Figure 12:
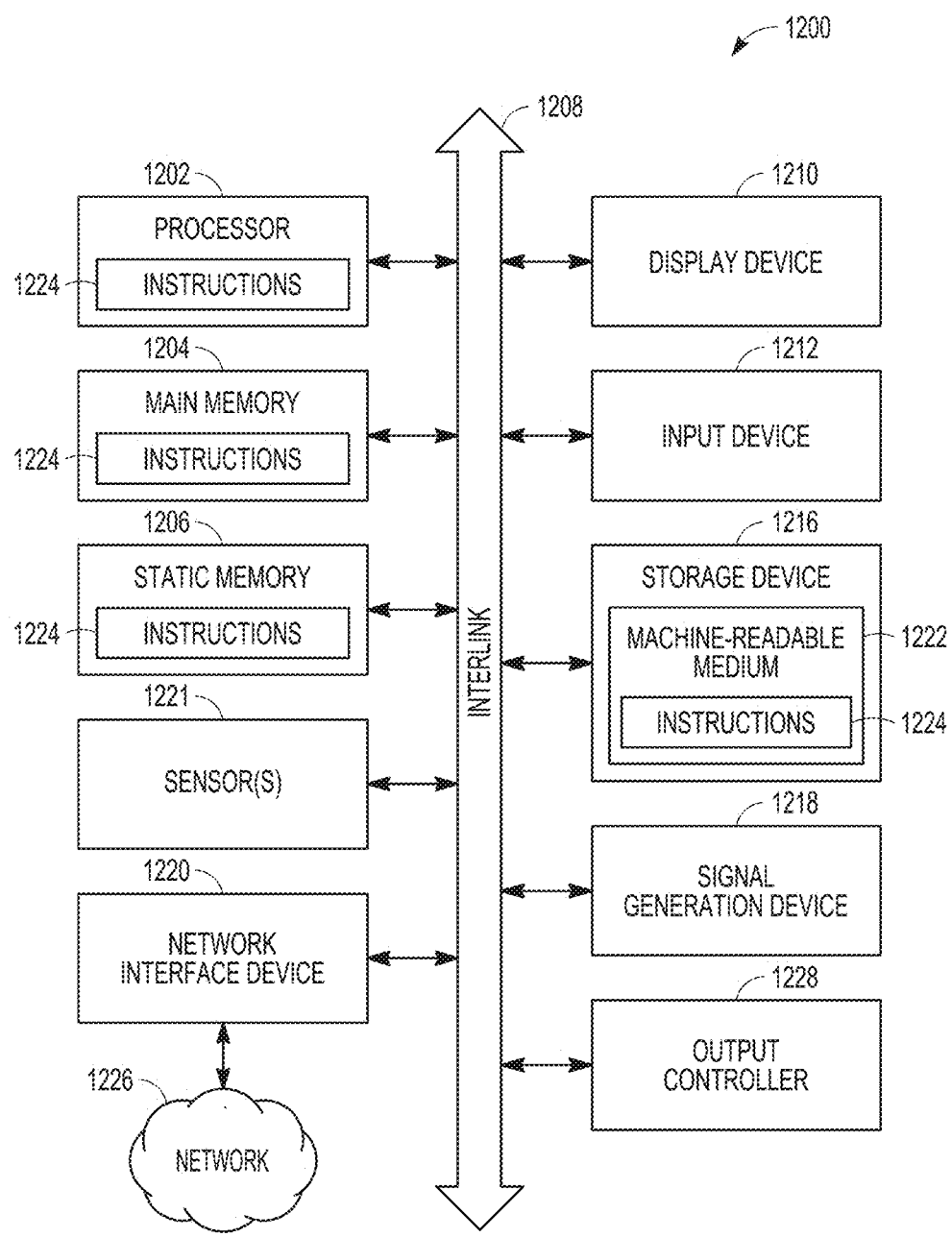
FIG. 12 illustrates a block diagram of an example machine upon which any one or more of the techniques (e.g., methodologies) discussed herein may perform. In alternative aspects, the machine may operate as a standalone device or may be connected (e.g., networked) to other machines.

FIG. 12 illustrates a block diagram of an example machine 1200 upon which any one or more of the techniques (e.g., methodologies) discussed herein may perform. In alternative aspects, the machine 1200 may operate as a standalone device or may be connected (e.g., networked) to other machines. In a networked deployment, the machine 1200 may operate in the capacity of a server machine, a client machine, or both in server-client network environments. In an example, the machine 1200 may act as a peer machine in peer-to-peer (P2P) (or other distributed) network environment. The machine 1200 may be, or be a part of, a communications network device, a cloud service, a personal computer (PC), a tablet PC, a personal digital assistant (PDA), a mobile telephone, a smart phone, or any machine capable of executing instructions (sequential or otherwise) that specify actions to be taken by that machine. In some aspects, the machine 1200 may be configured to implement a portion of the methods discussed herein. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or mechanisms. Modules are tangible entities (e.g., hardware) capable of performing specified operations and may be configured or arranged in a certain manner. In an example, circuits may be arranged (e.g., internally or with respect to external entities such as other circuits) in a specified manner as a module. In an example, the whole or part of one or more computer systems (e.g., a standalone, client or server computer system) or one or more hardware processors may be configured by firmware or software (e.g., instructions, an application portion, or an application) as a module that operates to perform specified operations. In an example, the software may reside on a machine readable medium. In an example, the software, when executed by the underlying hardware of the module, causes the hardware to perform the specified operations.

Accordingly, the term "module" or "engine" is understood to encompass a tangible entity, be that an entity that is physically constructed, specifically configured (e.g., hardwired), or temporarily (e.g., transitorily) configured (e.g., programmed) to operate in a specified manner or to perform part, or all of any operation described herein. Considering examples in which modules are temporarily configured, each of the modules need not be instantiated at any one moment in time.

For example, where the modules comprise a general-purpose hardware processor configured using software, the general-purpose hardware processor may be configured as respective different modules at different times. Software may accordingly configure a hardware processor, for example, to constitute a module at one instance of time and to constitute a different module at a different instance of time. A module or engine can be implemented using processing circuitry configured to perform the operations thereof.

Machine (e.g., computer system) 1200 may include a hardware processing circuitry 1202 (e.g., a central processing unit (CPU), a graphics processing unit (GPU), a hardware processor core, or any combination thereof), a main memory 1204 and a static memory 1206, some or all of which may communicate with each other via an interlink (e.g., bus) 1208. The machine 1200 may further include a display unit 1210, an alphanumeric input device 1212 (e.g., a keyboard), and a user interface (UI) navigation device 1214 (e.g., a mouse). In an example, the display unit 1210, input device 1212 and UI navigation device 1214 may be a touch screen display. The machine 1200 may additionally include a storage device (e.g., drive unit) 1216, a signal generation device 1218 (e.g., a speaker), a network interface device 1220, and one or more sensors 1220, such as a global positioning system (GPS) sensor, compass, accelerometer, or another sensor, or an input for receiving tissues samples as described earlier herein. The machine 1200 may include an output controller 1228, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1216 may include a machine readable medium 1222 on which is stored one or more sets of data structures or instructions 1224 (e.g., software) embodying or utilized by any one or more of the techniques or functions described herein. The instructions 1224 may also reside, completely or at least partially, within the main memory 1204, within static memory 1206, or within the hardware processing circuitry 1202 during execution thereof by the machine 1200. In an example, one or any combination of the hardware processing circuitry 1202, the main memory 1204, the static memory 1206, or the storage device 1216 may constitute machine readable media.

While the machine readable medium 1222 is illustrated as a single medium, the term "machine readable medium" may include a single medium or multiple media (e.g., a centralized or distributed database, and/or associated caches and servers) configured to store the one or more instructions 1224.

The term "machine readable medium" may include any medium that is capable of storing, encoding, or carrying instructions for execution by the machine 1200 and that cause the machine 1200 to perform any one or more of the techniques of the present disclosure, or that is capable of storing, encoding or carrying data structures used by or associated with such instructions. Non-limiting machine-readable medium examples may include solid-state memories, and optical and magnetic media. Specific examples of machine-readable media may include: non-volatile memory, such as semiconductor memory devices (e.g., Electrically Programmable Read-Only Memory (EPROM). Electrically Erasable Programmable Read-Only Memory (EEPROM)) and flash memory devices; magnetic disks, such as internal hard disks and removable disks; magneto-optical disks; Random Access Memory (RAM); Solid State Drives (SSD); and CD-ROM and DVD-ROM disks. In some examples, machine readable media may include non-transitory machine-readable media. In some examples, machine readable media may include machine readable media that is not a transitory propagating signal.

The instructions 1224 may further be transmitted or received over a communications network 1226 using a transmission medium via the network interface device 1220. The machine 1200 may communicate with one or more other machines utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®). IEEE 802.16 family of standards known as WiMax®). IEEE 802.15.4 family of standards, a Long Term Evolution (LTE) family of standards, a Universal Mobile Telecommunications System (UMTS) family of standards, peer-to-peer (P2P) networks, among others. In an example, the network interface device 1220 may include one or more physical jacks (e.g., Ethernet, coaxial, or phone jacks) or one or more antennas to connect to the communications network 1226. In an example, the network interface device 1220 may include a plurality of antennas to wirelessly communicate using at least one of single-input multiple-output (SIMO), multiple-input multiple-output (MIMO), or multiple-input single-output (MISO) techniques. In some examples, the network interface device 1220 may wirelessly communicate using Multiple User MIMO techniques.

REFERENCES

1. Kearney P M, Whelton M. Reynolds K. Muntner P, Whelton P K. He J. Global burden of hypertension: Analysis of worldwide data. *Lancet* 2005; 365:217-223.
2. Brodde O E. The functional importance of beta 1 and beta 2 adrenoceptors in the human heart. *Am J Cardiol* 1988; 62:24C-29C.
3. Snyder E M, Wong E C, Foxx-Lupo W T. Wheatley C M. Cassuto N A, Patanwala A E. Effects of an inhaled beta2-agonist on cardiovascular function and sympathetic activity in healthy subjects. *Pharmacotherapy* 2011; 31:748-756.
4. Johnson J A, Turner S T. Hypertension pharmacogenomics: Current status and future directions. *Curr Opin Mol Ther* 2005; 7:218-225.
5. La Rosee K. Huntgeburth M. Rosenkranz S, Bohm M. Schnabel P. The arg389gly beta1-adrenoceptor gene polymorphism determines contractile response to catecholamines. *Pharmacogenetics* 2004; 14:711-716.
6. Liu J, Liu Z-Q, Tan Z-R, Chen X-P, Wang L-S, Zhou G, Zhou H-H. Gly389arg polymorphism of [beta]1-adrenergic receptor is associated with the cardiovascular response to metoprolol[ast]. *Clin Pharmacol Ther* 2003; 74:372-379.
7. Snyder E M. Beck K C. Dietz N M, Eisenach J H, Joyner M J, Turner S T. Johnson B D. Arg16gly polymorphism of the {beta}2-adrenergic receptor is associated with differences in cardiovascular function at rest and during exercise in humans. *J Physiol* 2006; 571:121-130.
8. Snyder E M, Hulsebus M L, Turner S T. Joyner M J, Johnson B D. Genotype related differences in beta2 adrenergic receptor density and cardiac function. *Med Sci Sports Exerc* 2006; 38:882-886.
9. Snyder E M. Johnson B D, Joyner M J. Genetics of beta2-adrenergic receptors and the cardiopulmonary response to exercise. *Exerc Sport Sci Rev* 2008; 36:98-105.
10. Snyder E M, Joyner M J, Turner S T, Johnson B D. Blood pressure variation in healthy humans: A possible interaction with beta-2 adrenergic receptor genotype and renal epithelial sodium channels. *Med Hypotheses* 2005; 65:296-299.
11. Snyder E M, Turner S T, Joyner M J, Eisenach J H, Johnson B D. The arg16gly polymorphism of the {beta}2-adrenergic receptor and the natriuretic response to rapid saline infusion in humans. *J Physiol* 2006; 574:947-954.
12. Ulgen M S, Ozturk O, Alan S, Kayrak M, Turan Y, Tekes S, Toprak N. The relationship between angiotensin-converting enzyme (insertion/deletion) gene polymorphism and left ventricular remodeling in acute myocardial infarction. *Coron Artery Dis* 2007; 18:153-157.
13. McNamara D M, Holubkov R, Postava L, Janosko K, MacGowan G A, Mathier M, Murali S, Feldman A M, London B. Pharmacogenetic interactions between angiotensin-converting enzyme inhibitor therapy and the angiotensin-converting enzyme deletion polymorphism in patients with congestive heart failure. *J Am Coil Cardiol* 2004; 44:2019-2026.
14. Pilati M, Cicoira M, Zanolla L, Nicoletti I, Muraglia S, Zardini P. The role of angiotensin-converting enzyme polymorphism in congestive heart failure. *Congest Heart Fail* 2004; 10:87-93; quiz 94-85.
15. Pilbrow A P, Palmer B R, Frampton C M, Yandle T G, Troughton R W, Campbell E, Skelton L. Lainchbury J G, Richards A M, Cameron V A. Angiotensinogen m235t and t 174m gene polymorphisms in combination doubles the risk of mortality in heart failure. *Hypertension* 2007; 49:322-327.
16. Tang W. Devereux R B, Rao D C, Oberman A, Hopkins P N, Kitzman D W, Arnett D K. Associations between angiotensinogen gene variants and left ventricular mass and function in the hypergen study. *Am Heart J* 2002; 143:854-860.
17. Miller J A. Thai K, Scholey J W. Angiotensin ii type 1 receptor gene polymorphism predicts response to losartan and angiotensin ii. *Kidney Int* 1999; 56:2173-2180.
18. Baudin B. Angiotensin ii receptor polymorphisms in hypertension. Pharmacogenomic considerations. *Pharmacogenomics* 2002; 3:65-73.
19. Vangjeli C. Clarke N, Quinn U, Dicker P. Tighe O, Ho C. O'Brien E. Stanton A V. Confirmation that the renin gene distal enhancer polymorphism ren-5312c/t is associated with increased blood pressure. *Circulation Cardiovascular genetics* 2010; 3:53-59.
20. Meisler M H, Barrow L L, Canessa C M, Rossier B C. Scnnl, an epithelial cell sodium channel gene in the conserved linkage group on mouse chromosome 6 and human chromosome 12. *Genomics* 1994; 24:185-186.
21. Jin H S. Hong K W. Lim J E, Hwang S Y. Lee S H, Shin C, Park H K, Oh B. Genetic variations in the sodium balance-regulating genes enac, nedd41, ndfip2 and usp2 influence blood pressure and hypertension. *Kidney Blood Press Res* 2010; 33:15-23.
22. Pratt J H. Central role for enac in development of hypertension. *J Am Soc Nephrol* 2005:16:3154-3159.
23. Zhang L N, Ji L D, Fei L J, Yuan F, Zhang Y M. Xu J. Association between polymorphisms of alpha-adducin gene and essential hypertension in chinese population. *BioMed research international* 2013; 2013:451094.
24. Psaty B M. Smith N L. Heckbert S R, Vos H L, Lemaitre R N, Reiner A P, Siscovick D S. Bis J, Lumley T, Longstreth W T. Jr., Rosendaal F R. Diuretic therapy, the alpha-adducin gene variant, and the risk of myocardial infarction or stroke in persons with treated hypertension. *JAMA* 2002; 287:1680-1689.
25. Turner S T, Schwartz G L, Chapman A B, Boerwinkle E. Wnk1 kinase polymorphism and blood pressure response to a thiazide diuretic. *Hypertension* 2005; 46:758-765.
26. The sixth report of the Joint National Committee on prevention, detection, evaluation, and treatment of high blood pressure. *Arch Intern Med.* Nov. 24 1997; 157(21): 2413-2446.
27. Chobanian A V, Bakris G L, Black H R, et al. The Seventh Report of the Joint National Committee on Prevention. Detection, Evaluation, and Treatment of High Blood Pressure: the JNC 7 report. *Jama.* May 21 2003: 289(19):2560-2572.
29. American Heart Association. Heart and Stroke Statistics—2004 Update. Paper presented at: Dallas: American Heart Association 2004.
30. Roger V L, Go A S, Lloyd-Jones D M, et al. Heart disease and stroke statistics—2012 update: a report from the American Heart Association. *Circulation.* Jan. 3 2012; 125(1):e2-e220.
31. Akpunonu B E, Mulrow P J, Hoffman E A. Secondary hypertension: evaluation and treatment. *Disease-a-month: D M.* October 1996; 42(10):609-722.
32. Calhoun D A, Jones D. Textor S. et al. Resistant hypertension: diagnosis, evaluation, and treatment: a scientific statement from the American Heart Association Professional Education Committee of the Council for High Blood Pressure Research. *Circulation.* Jun. 24 2008; 117(25):e510-526.
33. Johnson J A, Turner S T. Hypertension pharmacogenomics: current status and future directions. *Curr Opin Mol Ther.* June 2005; 7(3):218-225.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods, devices, and kits described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acid or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there

What is claimed:

1. A method comprising:

obtaining a test sample from a subject suspected of having high blood pressure;

performing at least one assay to determine that one or more single nucleotide polymorphisms (SNPs) are present within the test sample;

determining, by a computing system including one or more processors and memory, a functional score for individual SNPs of the one or more SNPs based on responsiveness of subjects in which the individual SNPs are present to one or more classes of drugs of subjects;

assigning, by the computing system, weighting values to one or more SNPs detected within the test sample, wherein the weighting values indicate a degree of certainty of the functionality of the one or more SNPs;

determining, by the computing system, a weighted score for the individual SNPs of the one or more SNPs based on the functional score and the weighting values;

analyzing, by the computing system, the one or more weighted scores with respect to a number of organ systems to determine an organ system having a greatest amount of functionality with respect to the subject;

determining, by the computing system, one or more drugs that correspond to the organ system and that are provided to treat high blood pressure;

determining, by the computing system, a treatment recommendation for the subject that includes at least one drug of the one or more drugs based on an amount of functionality of the at least one drug with respect to the one or more SNPs; and presenting, by the computing system, the treatment recommendation in a user interface.

2. The method of claim 1, wherein the weighting values are assigned based on the number and results of medical studies on the effects of the corresponding SNPs.

3. The method of claim 1, comprising:

determining, by the computing system, one or more co-morbidities of the subject;

wherein the treatment recommendation is based on the one or more co-morbidities.

4. The method of claim 1, wherein the functionality of the one or more SNPs corresponds to enhanced receptor function, altered drug metabolism, greater protein expression, or higher channel activity.

5. The method of claim 2, wherein the weighting value is assigned based on the degree to which studies are in agreement concerning functionality of an SNP.

6. The method of claim 1, comprising generating functional score based on the degree of homozygosity versus heterozygosity of the subject for a given functional genotype.

7. The method of claim 6, further comprising: assessing which organ system, of at least a cardiac system, a renal system and a vascular system is most functional and will lead to a highest degree of drug response.

8. A non-transitory computer-readable medium including instructions that, when executed on a processor, cause the processor to:

obtain genetic data of a patient suspected of having high blood pressure assign weighting values to the one or more SNPs detected within the test sample, wherein the weighting values indicate a degree of certainty of the functionality of the one or more SNPs;

determine a weighted score for the individual SNPs of the one or more SNPs based on the functional score and the weighting values;

analyze the one or more weighted scores with respect to a number of organ systems to determine an organ system having a greatest amount of functionality with respect to the subject;

determine one or more drugs that correspond to the organ system and that are provided to treat high blood pressure;

determine a treatment recommendation for the subject that includes at least one drug of the one or more drugs based on an amount of functionality of the at least one drug with respect to the one or more SNPs; and present the treatment recommendation in a user interface.

9. The non-transitory computer-readable medium of claim 8, wherein the weighting values are assigned based on the number and results of medical studies on the effects of the corresponding SNPs.

10. The non-transitory computer-readable medium of claim 8, wherein the SNPs are provided as an assessment of genetic variants in one of a cardiac system, a vascular system, and a renal system of the subject.

11. The non-transitory computer-readable medium of claim 8, wherein the functionality of the one or more SNPs corresponds to enhanced receptor function, altered drug metabolism, greater protein expression, or higher channel activity.

12. The non-transitory computer-readable medium of claim 8, wherein the weighting value is assigned based on the degree to which studies are in agreement concerning functionality of an SNP.

13. The non-transitory computer-readable medium of claim 8, wherein the instructions, when executed on a processor, cause the processor to further generate the functional score for an individual SNP based on the degree of homozygosity versus heterozygosity of the subject for a given functional genotype.

14. The non-transitory computer-readable medium of claim 13, further comprising: assessing which organ system, of at least a cardiac system, a renal system and a vascular system is most functional and will lead to a highest degree of drug response.

15. A device comprising:

memory to store genetic data corresponding to a sample of a patient suspected of having high blood pressure, the genetic data indicating one or more single nucleotide polymorphisms (SNPs) present in the subject; and processing circuitry configured to:

assign weighting values to the one or more SNPs detected within the test sample, wherein the weighting values indicate a degree of certainty of the functionality of the one or more SNPs;

determine a weighted score for the individual SNPs of the one or more SNPs based on the functional score and the weighting values;

analyze the one or more weighted scores with respect to a number of organ systems to determine an organ system having a greatest amount of functionality with respect to the subject;

determine one or more drugs that correspond to the organ system and that are provided to treat high blood pressure;

determine a treatment recommendation for the subject that includes at least one drug of the one or more drugs based on an amount of functionality of the at least one drug with respect to the one or more SNPs; and present the treatment recommendation in a user interface.

16. The device of claim 15 further comprising:

a user interface device for displaying the treatment recommendation.

17. The device of claim 15, further comprising: a network interface to receive data from an assaying machine.

18. The device of claim 15, wherein the processing circuitry is configured to:

determine a first cumulative score for a first organ system of the number of organ systems based on a plurality of first weighted scores that correspond to a plurality of first SNPs related to the first organ system; and determine a second cumulative score for a second organ system of the number of organ systems based on a plurality of second weighted scores that correspond to a plurality of second SNPs related to the second organ system.

19. The device of claim 15, wherein the processing circuitry is configured to:

determine that the first cumulative score is greater than a threshold score; and determine a class of drugs that corresponds to the first organ system;

wherein the at least one drug of the treatment recommendation corresponds to the first organ system system.

20. The device of claim 18, wherein the processing circuitry is configured to:
- determine that the at least one drug is a first line therapy for high blood pressure with respect to the subject;
- determine that the second cumulative score is less than the threshold score;
- determine that a combination of SNPs for the second organ system is present within the subject, the combination of SNPs being functional in relation to using an additional class of drugs to treat high blood pressure; and
- determine that an additional drug of the additional class of drugs is an additional line of therapy for high blood pressure with respect to the subject.

* * * * *